United States Patent
Sciotti et al.

(10) Patent No.: US 9,700,562 B2
(45) Date of Patent: Jul. 11, 2017

(54) TRIAZINE COMPOUNDS AND COMPOSITIONS THEREOF AND METHODS FOR TREATING MALARIA AND CHEMOPROPHYLAXIS

(71) Applicant: The United States of America, as represented by the Secretary of the Army, on behalf of the Walter Reed Army Inst. of Research, Washington, DC (US)

(72) Inventors: Richard J. Sciotti, Olney, MD (US); Gregory A. Reichard, Lovettsville, VA (US); Kristina M. Pannone, Columbia, MD (US); Victor E. Zottig, Bethesda, MD (US)

(73) Assignee: The United States of America, as represented by the Secretary of the Army, on behalf of the Walter Reed Army Institute of Research, Washington, DC (US)

( * ) Notice: Subject to any disclaimer, the term of this patent is extended or adjusted under 35 U.S.C. 154(b) by 0 days.

(21) Appl. No.: 15/090,848

(22) Filed: Apr. 5, 2016

(65) Prior Publication Data
US 2016/0213675 A1    Jul. 28, 2016

Related U.S. Application Data

(63) Continuation of application No. 14/426,275, filed as application No. PCT/US2014/025586 on Mar. 13, 2014, now Pat. No. 9,334,246.

(60) Provisional application No. 61/779,331, filed on Mar. 13, 2013.

(51) Int. Cl.
| | |
|---|---|
| C07D 251/42 | (2006.01) |
| C07D 401/04 | (2006.01) |
| C07D 401/12 | (2006.01) |
| C07D 401/14 | (2006.01) |
| C07D 403/04 | (2006.01) |
| C07D 403/12 | (2006.01) |
| C07D 403/14 | (2006.01) |
| A61K 31/53 | (2006.01) |
| A61P 33/06 | (2006.01) |
| C07D 487/08 | (2006.01) |
| C07D 471/08 | (2006.01) |
| A61K 31/5377 | (2006.01) |
| C07D 251/18 | (2006.01) |
| C07D 251/22 | (2006.01) |
| A61K 45/06 | (2006.01) |
| C07D 491/08 | (2006.01) |

(52) U.S. Cl.
CPC .......... *A61K 31/53* (2013.01); *A61K 31/5377* (2013.01); *A61K 45/06* (2013.01); *C07D 251/18* (2013.01); *C07D 251/22* (2013.01); *C07D 251/42* (2013.01); *C07D 401/04* (2013.01); *C07D 401/12* (2013.01); *C07D 403/12* (2013.01); *C07D 471/08* (2013.01); *C07D 487/08* (2013.01); *C07D 491/08* (2013.01)

(58) Field of Classification Search
CPC .. C07D 401/04; C07D 401/12; C07D 401/14; C07D 403/04; C07D 403/12; C07D 403/14; A61K 31/53; A61K 31/5377
USPC .................................. 544/194, 209; 514/245
See application file for complete search history.

(56) References Cited

U.S. PATENT DOCUMENTS

| | | | |
|---|---|---|---|
| 3,086,855 A | 4/1963 | Knusli | |
| 3,103,512 A | 9/1963 | Welberg | |
| 3,462,430 A | 8/1969 | Heimberger | |
| 3,530,121 A | 9/1970 | Heimberger | |
| 3,534,036 A | 10/1970 | Heimberger | |
| 3,536,708 A | 10/1970 | Heimberger | |
| 3,536,709 A | 10/1970 | Heimberger | |
| 3,549,755 A | 12/1970 | Kodama | |
| 3,549,759 A | 12/1970 | Kodama | |
| 4,098,891 A | 7/1978 | Tocco | |
| 9,334,246 B2 * | 5/2016 | Sciotti | ................. C07D 401/04 |

FOREIGN PATENT DOCUMENTS

| | | |
|---|---|---|
| GB | 767749 A | 2/1957 |
| GB | 767848 A | 2/1957 |

OTHER PUBLICATIONS

Wakabayashi et al Nippon Dojo Hiryogaku Zasshi (1970), 41 (5), 193-200 (Wakabayashi-I); CA 73: 119790, 1970, CAPLUS.
Wakabayashi et al. Nippon Dojo Hiryogaku Zasshi (1970), 41 (4), 133-41 (Wakabayashi-II); CA 73: 108869, 1970, CAPLUS.
Wakabayashi et al. Yuki Gosei Kagaku Kyokaishi (1970), 28(2), 252-60 (Wakabayashi-III); CA 72: 100653, 1970, CAPLUS.
Wakabayashi et al. Yuki Gosei Kagaku Kyokaishi (1969), 27(9), 868-74 (Wakabayashi-IV); CA 72: 3469, 1970, CAPLUS.
Ruiz et al. Toxicology and Applied Pharmacology (1971 ), 18(2), 487-97; CA 74: 74988, 1971, CAPLUS.
International Search Report received in PCT/US2014/025586, mailed Jul. 9, 2014.
"Extended European Search Report received in EP 14772718.4", Jul. 26, 2016.
Genther, et al., "Antifolate Studies. Activities of 40 Potential Antimalarial Compounds against Sensitive Chlorguanide Triazine Resistant Strains of Folate-Requiring . . . ", Jul. 12, 1977, pp. 237-243, vol. 20, No. 2, Publisher: Journal of Medicinal Chemistry.

* cited by examiner

Primary Examiner — Venkataraman Balasubramanian
(74) Attorney, Agent, or Firm — Elizabeth Arwine, Esq.

(57) ABSTRACT

Disclosed herein are triazine compounds and methods of making and using thereof to treat malaria, provide chemoprophylaxis, and/or treat or inhibit infection by one or more *Plasmodium* spp.

18 Claims, No Drawings

TRIAZINE COMPOUNDS AND COMPOSITIONS THEREOF AND METHODS FOR TREATING MALARIA AND CHEMOPROPHYLAXIS

CROSS-REFERENCE TO RELATED APPLICATIONS

This application claims the benefit of U.S. Application No. 61/779,331, filed 13 Mar. 2013, which is herein incorporated by reference in its entirety.

ACKNOWLEDGEMENT OF GOVERNMENT SUPPORT

This invention was made by employees of the U.S. Army Medical Research & Materiel Command. The Government has certain rights in the invention.

NO BIOLOGICAL SEQUENCES

This application refers to chemical names and formulas and does not refer to any biological sequences that require a Sequence Listing.

BACKGROUND OF THE INVENTION

1. Field of the Invention

The present invention relates to novel triazine compounds and compositions and methods of using to treat malaria and/or chemoprophylaxis.

2. Description of the Related Art

Malaria is the number one infectious disease threat for deployed US troops. There is a critical need for the discovery of new classes of anti-malaria drugs due to the therapeutic challenges emanating from the emergence of resistance in many structural classes of current therapies.

SUMMARY OF THE INVENTION

The present invention is directed to novel triazine compounds, compositions, and methods making and using to treat malaria, provide chemoprophylaxis, and/or treat or inhibit infections by one or more *Plasmodium* spp. in subjects.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DETAILED DESCRIPTION OF THE INVENTION

Definitions

For purposes of the present invention, as described and claimed herein, the following terms and phrases are defined as follows:

The term "patient" and "subject" are synonyms and mean all mammals, including humans and animals such as cows, dogs, cats, goats, sheep, pigs, rodents, and rabbits.

A "therapeutically effective amount", unless otherwise indicated, refers to an amount of one or more compounds of the present invention that, when administered to a subject, (i) treats or inhibits the particular disease, condition, or disorder, (ii) attenuates, ameliorates, or eliminates one or more symptoms of the particular disease, condition, or disorder, and/or (iii) inhibits or delays the onset of one or more symptoms of the particular disease, condition, or disorder.

"Treatment", "treating", and the like, unless otherwise indicated, refers to reversing, alleviating, or inhibiting the progress of the particular disease, condition, or disorder to which such term applies, or one or more symptoms of the particular disease, condition, or disorder. These terms also encompass, depending on the condition of the mammal, preventing or inhibiting the onset of the particular disease, condition, or disorder or symptoms thereof. Treatment can refer to prophylactic treatment, i.e., administration of one or more compounds of the present invention to a subject that is not at the time of administration afflicted with the particular disease, condition, or disorder.

As provided herein, a bond is represented by a line, such as "—", or the symbol " $\sim$ ". The line and symbol represent that the bond is the point of attachment between two molecular subunits.

An "alkyl" refers to a straight or branched chain monovalent radical of saturated and/or unsaturated carbon atoms and hydrogen atoms, such as methyl (Me) ethyl (Et) propyl (Pr) isopropyl (i-Pr) butyl (n-Bu) isobutyl (i-Bu) t-butyl (t-Bu) (sec-Bu) ethenyl, pentenyl, butenyl, propenyl, ethynyl, butynyl, propynyl, pentynyl, hexynyl, and the like, which may be unsubstituted (i.e., contain only carbon and hydrogen) or substituted by one or more substituents as defined below (e.g., one or more halogen, such as F, Cl, Br, or I, with F and Cl being preferred). The term "$(C_1-C_6)$alkyl" as used herein refers to a straight or branched hydrocarbon from 1 to 6 carbon atoms and includes methyl, ethyl, n-propyl, isopropyl, n-butyl, sec-butyl, isobutyl, tert-butyl, n-pentyl, n-hexyl, and the like. The $(C_1-C_6)$alkyl group optionally can be substituted with one or more substituents as defined below. The term "$(C_1-C_3)$alkyl" as used herein refers to a straight or branched hydrocarbon of from 1 to 3 carbon atoms and includes methyl, ethyl, n-propyl, isopropyl, and the like. The $(C_1-C_3)$alkyl group optionally can be substituted with one or more of more substituents as defined below.

The term "halo" includes chlorine, fluorine, bromine, and iodine.

The term "haloalkyl" refers to a branched or straight chained alkyl group in which at least one hydrogen atom is replaced with a halogen, e.g., $(C_1-C_6)$haloalkyl=a branched or straight chained alkyl group containing from 1 to 6 carbon atoms, in which at least one hydrogen atom is replaced with a halogen. Examples of haloalkyls include chloromethyl, trichloromethyl, fluoromethyl, trifluoromethyl, and the like.

A "hydroxyl" refers to the radical —OH.

The term "alkoxy" refers to the radical —OR, where R is a straight or branched chain alkyl group. Exemplary alkoxy groups include methoxy, ethoxy, n-propoxy, isopropoxy, n-butoxy, isobutoxy, pentoxy, and the like. A "$(C_1-C_6)$alkoxy" refers to a straight or branched chain alkoxy group containing from 1 to 6 carbon atoms and a "$(C_1-C_3)$alkoxy" refers to a straight or branched chain alkoxy group containing from 1 to 3 carbon atoms.

An "alkoxycarbonyl" refers to the radical —C(O)OR, where R is an alkyl group.

The term "haloalkoxy" refers to a branched or straight chained alkoxy group in which at least one hydrogen atom is replaced with a halogen, e.g., $(C_1-C_6)$haloalkoxy=a branched or straight chained alkoxy group containing from 1 to 6 carbon atoms, in which at least one hydrogen atom is replaced with a halogen. Examples of haloalkoxys include chloromethoxy, trichloromethoxy, fluoromethoxy, trifluoromethoxy, and the like.

A "cycloalkyl" refers to a non-aromatic monovalent monocyclic, bicyclic, or tricyclic radical comprising 3-14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more substituents. The term "$(C_3-C_8)$cycloalkyl" means a hydrocarbon ring containing from 3 to 8 carbon atoms, for example, cyclopropyl, cyclobutyl, cyclopentyl, or cyclohexyl. Where possible, the cycloalkyl group may contain double bonds, for example, 3-cyclohexen-1-yl. The cycloalkyl ring may be unsubstituted or optionally may be substituted by one or more substituents selected from $(C_1-C_6)$alkyl, $(C_1-C_6)$alkoxy, $(C_1-C_6)$thioalkoxy, hydroxy, thiol, halo, formyl, carboxyl, amino, aminoalkyl, —$CO_2(C_1-C_6)$alkyl, —$CO(C_1-C_6)$alkyl, —$C(O)N(C_1-C_6)$alkyl, aryl, and heteroaryl.

The term "aryl" means a cyclic or polycyclic aromatic ring having from 5 to 12 carbon atoms, and may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents.

A "heteroaryl" refers to an aromatic monovalent monocyclic, bicyclic, or tricyclic radical comprising 4-18 ring members, including 1-5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents.

A "heterocycloalkyl" refers to a non-aromatic monovalent monocyclic, bicyclic, or tricyclic radical, which is saturated or unsaturated, comprising 3-18 ring members, which includes 1-5 heteroatoms selected from nitrogen, oxygen, and sulfur, where the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents.

A "heterocycle" refers to a heteroaryl or heterocycloalkyl as defined above.

An "acyl" refers to a —C(O)—R radical, where R is a suitable substituent as defined below.

A "thioacyl" refers to a —C(S)—R radical, where R is a suitable substituent as defined below.

A "sulfonyl" refers to a —$SO_2R$ radical, where R is a suitable substituent as defined below.

The term "amino" refers to —$NH_2$.

The term "alkylamino" refers to an amino moiety substituted with one (i.e., —NHR) or two (i.e., —NRR') $(C_1-C_6)$ alkyl groups which may be the same or different. Examples of such alkylamino groups include aminomethyl, dimethylamino, aminomethylethyl, aminomethylpropyl, and the like.

The term "amino group" refers to amino and alkylamino groups.

An "alkylsulfonyl" refers to the radical —$SO_2R$, where R is an alkyl group.

An "alkylaminocarbonyl" refers to the radical —C(O)NHR, where R is an alkyl group.

A "dialkylaminocarbonyl" refers to the radical —C(O)NRR', where each R may be the same or different alkyl group.

A "mercapto" refers to the radical —SH.

An "alkylthio" refers to the radical —SR, where R is an alkyl group.

A "carboxyl" refers to the radical —C(O)OH.

A "carbamoyl group" refers to the radical $C(O)NH_2$.

An "aryloxyl" refers to the radical —O

A "heteroaryloxyl" refers to the radical —O-HAR, where HAR is a heteroaryl group.

An "arylthio" refers to the radical —S-ARY, where ARY is an aryl group.

A "heteroarylthio" refers to the radical —S-HAR, where HAR is a heteroaryl group.

A "leaving group" (Lv) refers to any suitable group that will be displaced by a substitution reaction. One of ordinary skill in the art will know that any conjugate base of a strong acid can act as a leaving group. Illustrative examples of suitable leaving groups include, but are not limited to, —F, —Cl, —Br, alkyl chlorides, alkyl bromides, alkyl iodides, alkyl sulfonates, alkyl benzenesulfonates, alkyl p-toluenesulfonates, alkyl methanesulfonates, triflate, and any groups having a bisulfate, methyl sulfate, or sulfonate ion.

A "protecting group" is intended to refer to groups that protect one or more inherent functional group from premature reaction. Suitable protecting groups may be routinely selected by those skilled in the art in light of the functionality and particular chemistry used to construct the compound. Examples of suitable protecting groups are described, for example, in Greene and Wuts, Protective Groups in Organic Synthesis, $3^{rd}$ edition, John Wiley and Sons, New York, N.Y. (1999).

The term "suitable organic moiety" refers to any organic moiety recognizable, such as by routine testing, to those skilled in the art as not adversely affecting the inhibitory activity of the inventive compounds. Illustrative examples of suitable organic moieties include, but are not limited to, hydroxyl groups, alkyl groups, oxo groups, cycloalkyl groups, heterocycloalkyl groups, aryl groups, heteroaryl groups, acyl groups, sulfonyl groups, mercapto groups, alkylthio groups, alkoxyl groups, carboxyl groups, amino groups, alkylamino groups, dialkylamino groups, carbamoyl groups, arylthio groups, heteroarylthio groups, and the like.

In general, the various moieties or functional groups for variables in the formulae may be "optionally substituted" by one or more suitable "substituents". The term "substituent" or "suitable substituent" refers to any suitable substituent that may be recognized or selected, such as through routine testing, by those skilled in the art. Illustrative examples of useful substituents are those found in the exemplary compounds that follow, as well as halogen (chloro, iodo, bromo, or fluoro) $(C_1-C_6)$alkyl; $(C_1-C_6)$alkenyl; $(C_1-C_6)$alkynyl; hydroxyl; $(C_1-C_6)$alkoxyl; amino; nitro; thiol; thioether; imine; cyano; amido; phosphonato; phosphine; carboxyl; carbonyl; aminocarbonyl; thiocarbonyl; sulfonyl; sulfonamine; sulfonamide; ketone; aldehyde; ester; oxygen (=O) haloalkyl (e.g., trifluoromethyl) carbocyclic cycloalkyl, which may be monocyclic or fused or non-fused polycyclic (e.g., cyclopropyl, cyclobutyl, cyclopentyl, or cyclohexyl) or a heterocycloalkyl, which may be monocyclic or fused or non-fused polycyclic (e.g., pyrrolidinyl, piperidinyl, piperazinyl, morpholinyl, or thiazinyl) carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl) amino (primary, secondary, or tertiary) nitro; thiol; thioether, O—($C_1$-$C_6$)alkyl; O-aryl, aryl; aryl-($C_1$-$C_6$)alkyl; $CO_2CH_3$; $CONH_2$; $OCH_2CONH_2$; $NH_2$; $SO_2NH_2$; $OCHF_2$; $CF_3$; $OCF_3$; and the like. Such moieties may also be optionally substituted by a fused-ring structure or bridge, for example $OCH_2$—O. All of these substituents may optionally be further substituted with a substituent selected from groups such as hydroxyl groups, halogens, oxo groups, alkyl groups, acyl groups, sulfonyl groups, mercapto groups, alkylthio groups, alkyloxyl groups, cycloalkyl groups, heterocycloalkyl groups, aryl groups, heteroaryl groups, carboxyl groups, amino groups, alkylamino groups, dialkylamino groups, carbamoyl groups, aryloxyl groups, heteroaryloxyl groups, arylthio groups, heteroarylthio groups, and the like.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

A "solvate" refers to a pharmaceutically acceptable solvate form of a specified compound that retains the biological effectiveness of such compound. Examples of solvates include compounds of the invention in combination with water, isopropanol, ethanol, methanol, dimethyl sulfoxide, ethyl acetate, acetic acid, ethanolamine, or acetone. Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of compounds of formula I (including formula A) are within the scope of the invention. It will also be appreciated by those skilled in organic chemistry that many organic compounds can exist in more than one crystalline form. For example, crystalline form may vary from solvate to solvate. Thus, all crystalline forms of the compounds of formula I (including formula A) or the pharmaceutically acceptable solvates thereof are within the scope of the present invention.

The term "pharmaceutically acceptable salts" refers to salt forms that are pharmacologically acceptable and substantially non-toxic to the subject being treated with the compound of the invention. Pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide) those derived from inorganic bases such as alkali or alkaline earth-metal (e.g., sodium, potassium, lithium, calcium, or magnesium) hydroxides, and those derived from non-toxic organic bases such as basic amino acids.

"A pharmaceutically acceptable prodrug" is a compound that may be converted under physiological conditions or by solvolysis to the specified compound or to a pharmaceutically acceptable salt of such compound. "A pharmaceutically active metabolite" refers to a pharmacologically active product produced through metabolism in the body of a specified compound or salt thereof. Prodrugs and active metabolites of a compound may be identified using routine techniques known in the art. See, e.g., Bertolini, G. et al., (1997) J. Med. Chem. 40:2011-2016; Shan, D. et al., J. Pharm. Sci., 86(7):765-767; Bagshawe K., (1995) Drug Dev. Res. 34:220-230; Bodor, N., (1984) Advances in Drug Res. 13:224-331; Bundgaard, H., Design of Prodrugs (Elsevier Press, 1985) and Larsen, I. K., Design and Application of Prodrugs, Drug Design and Development (Krogsgaard-Larsen et al., eds., Harwood Academic Publishers, 1991).

As used herein, some chemical formulas are provided as SMILES using Chem Bio Draw Ultra, Version 13 (PerkinElmer). If necessary, the structural formulas and IUPAC chemical names of such SMILES are herein incorporated by reference.

The present invention provides triazine compounds, compositions, and methods of using thereof to treat malaria, chemoprophylaxis, and/or infections by one or more *Plasmodium* spp. The triazine compounds of the present invention were designed based on exhaustive compound library screening and structure activity relationship (SAR) analysis using in vitro blood stage assays.

A late stage lead compound, described herein as Compound 641, was found to exhibit excellent in vitro potency, desired metabolic stability. Compound 641 produced complete cures (5/5 mice) after a single 160 mg/kg PO dose. Pharmacokinetic (PK) analysis (80 mg/kg dosed PO, mouse) revealed that Compound 641 possesses a long mouse half-life (8 hr) and good exposure. In the rhesus *P. cynomolgi* relapsing model (Deye, G; et. al. Am. J. Trop. Med. Hyg., 86(6), 2012, pp. 931-935) Compound 641 prevented malaria parasitemia as a prophylactic drug when dosed once weekly (65 mg, PO) and was well tolerated at 316 mg/kg. Compound 641 exhibits a possible binding affinity to the voltage gated potassium channel encoded by the human Ether-à-go-go-Related Gene (hERG) since the Cmax exceeded the hERG IC50 (600 nM) in an initial hERG assay. See Sanguinetti M, Mitcheson J (2005) Predicting drug-hERG channel interactions that cause acquired long QT syndrome. Trends in Pharmacological Sciences 26: 119-124. Binding to the hERG channel is a well-established in vitro marker for drug induced Torsades de Pointes (TdP). TdP is a rare arrhythmia that can lead to ventricular fibrillation and sudden death. The hERG channel is a large cylindrical cavity with a high density of flat aromatic and polar residues that are highly symmetric. An evaluation of compounds known to bind the hERG channel revealed a pharmacophore with several aromatic (hydrophobic) residues and a basic amine.

Thus, several strategies were used to design triazine compounds exhibiting antimalarial activity and reduced binding affinity to the hERG channel. One approach was to diminish the binding affinity to the hERG channel by disrupting interactions with the polar groups in the channel. To accomplish this, amines were designed encumbered with bulky groups or were designed to have the basic amine contained in a more rigid framework. Another design strategy was to reduce the basicity of the amine to weaken binding in the hERG channel. Another strategy that was employed was to design molecules that contained a polar group (e.g., a hydroxyl (—OH)) to lower the overall lipophilicity and thereby disrupt the binding to the aromatic non-polar surfaces. One unexpected result was that increased steric hindrance on the aryl substituent resulted in reduced hERG channel binding.

Over 760 substituted triazine compounds were designed and profiled in vitro against different drug resistant strains of *P. falciparum*. Most substituted triazine compounds possessed good in vitro potency (IC50s<500 ng/mL), little evidence of cross-resistance, and a short chemical synthesis (2-4 chemical steps).

Representative compounds were profiled in hERG assays and clear SAR trends were identified with structural modifications that significantly diminish hERG binding, yet have minimal effects on anti-malarial activity. Many compounds in the triazine series of compounds possess an inherently long half-life in animal models, oral efficacy in a Thompson Test (mouse model assay) and may provide effective malaria treatment and prophylaxis at a relatively low cost.

Thus, the compounds of the present invention have the following Formula I:

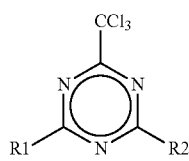

I wherein

R1 is a 5-10 membered aromatic ring having 0-4 ring heteroatoms each independently selected from the group consisting of nitrogen, oxygen, and sulfur, wherein each substitutable ring carbon is independently substituted by -Rc, and wherein each substitutable ring nitrogen is independently substituted by —R, or R1 is benzopyan, branched or unbranched —$(C_1$-$C_6)$alkyl, or

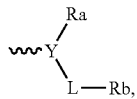

wherein Y is —CH, —CR, or N;

R2 is a nitrogen attached 5-8 membered monocyclic ring or a nitrogen attached 7-8 membered bicyclo ring system, and further having 0-2 ring heteroatoms each independently selected from the group consisting of nitrogen, oxygen, and sulfur, wherein each substitutable ring carbon is independently substituted by -Rc, and wherein and each substitutable ring nitrogen is independently substituted by —R, or R2 is

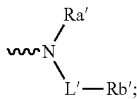

and
wherein:

L and L' are each independently a linker selected from the group consisting of a bond, a substituted or unsubstituted —$(C_1$-$C_6)$alkyl- which may be branched or unbranched, and

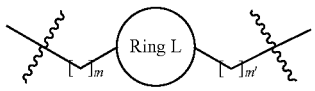

wherein Ring L is a 5-7 membered cyclic or aromatic ring and m and m' are independently 0-3;

Ra and Ra' are each independently H or branched or unbranched —$(C_1$-$C_6)$alkyl;

Rb and Rb' are each independently —$CO_2R$, branched or unbranched —$(C_1$-$C_6)$alkyl, branched or unbranched —$(C_2$-$C_8)$alkyl substituted with an —OR, —NRR', or —N(O)RR' group on one of the C2-C8 carbons, naphthyl, or a 3-7 membered ring having 0-2 ring heteroatoms each independently selected from the group consisting of nitrogen, oxygen, and sulfur, wherein each substitutable ring carbon is independently substituted by -Rc, and wherein each substitutable ring nitrogen is independently substituted by —R;

Rc and Rc' are each independently selected from the group consisting of H, halo, trihalomethyl, trihalomethoxy, branched or unbranched —$(C_1$-$C_6)$alkyl, phenyl, branched or unbranched —$(C_1$-$C_6)$alkyl-OR, —C(=O)R, —$CO_2R$, —$S(O)_2R$, —OR, —$NO_2$, —CN, —$NH_2$, —NRR', —NHC (=O)R, —NHC(OR)=O, —C(O)NRR', —$S(O)_nR$, and —$SO_2NRR'$ (wherein NRR' can form a 4 to 6 member ring), wherein n is 0, 1, or 2; and R and R' are each independently H, branched or unbranched —$(C_1$-$C_6)$alkyl, branched or unbranched —$(C_1$-$C_6)$alkyl alcohol, or —$CO_2$—$(C_1$-$C_6)$alkyl;

wherein where nitrogen is present as a heteroatom, it is at least 2 carbon atoms from any nitrogen atom attached to the triazine ring, and wherein the ring carbons next to a ring nitrogen are not substituted with —OR, —$NO_2$, —NRR', —NHC(O)R, —NHC(O)OR, —$S(O)_nR$, or —$SO_2NRR'$;

or a pharmaceutically acceptable salt thereof.

In some embodiments of Formula I, R1 is a ring structure selected from the group consisting of naphthyl, biphenyl, and a 5-8 membered aromatic ring, said ring structure having 0-4 ring heteroatoms each independently selected from the group consisting of nitrogen, oxygen, and sulfur, wherein each substitutable ring carbon of said ring structure is independently substituted by -Rc, and wherein each substitutable ring nitrogen of said ring structure is independently substituted by —R, or R1 is a branched or unbranched —$(C_1$-$C_6)$alkyl, or

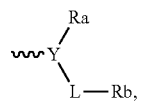

wherein Y is —CH, —CR, or N; R2 is a nitrogen attached 5-8 membered monocyclic ring or a nitrogen attached 7-8 membered bicyclo ring system, and further having 0-2 ring heteroatoms each independently selected from the group consisting of nitrogen, oxygen, and sulfur, wherein each substitutable ring carbon is independently substituted by -Rc, and wherein and each substitutable ring nitrogen is independently substituted by —R, or R2 is

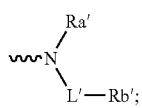

and wherein: L and L' are each independently a linker independently selected from the group consisting of a bond, a substituted or unsubstituted —(C₁-C₆)alkyl- which may be branched or unbranched, and

wherein Ring L is a 5-7 membered cyclic or aromatic ring and m and m' are independently 0-3; Ra and Ra' are each independently H or a branched or unbranched (C₁-C₆)alkyl; Rb and Rb' are each independently a branched —(C₂-C₈) alkyl substituted with an —OR, —NRR', or —N(O)RR' group on one of the C2-C8 carbons, or a 3-7 membered ring having 0-2 ring heteroatoms independently selected from the group consisting of nitrogen, oxygen, and sulfur, wherein each substitutable ring carbon is independently substituted by -Rc, and wherein each substitutable ring nitrogen is independently substituted by —R; wherein where nitrogen is present as a heteroatom, it is at least 2 carbon atoms from the nitrogen atom attached to the triazine ring, and wherein the ring carbons next to a ring nitrogen are not substituted with —OR, —NO₂, —NH₂, —NRR', —NHC(O)R, —NHC(O) OR, —S(O)ₙR, or —SO₂NRR'; or a pharmaceutically acceptable salt thereof. In some of these embodiments, R2 is selected from the group consisting of R2 is selected from the group consisting of

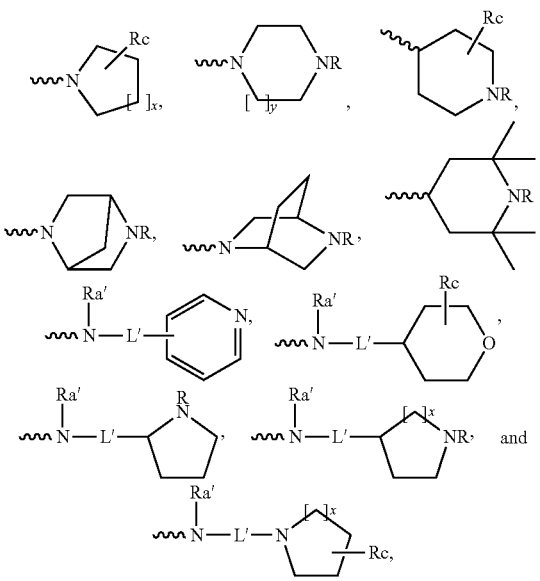

wherein x is 1-3 and y is 1-2. In some of these embodiments, R1 is a 5-8 membered aromatic ring which has at least one substitutable ring carbon substituted with a halo, trihalomethyl, —S(O)₂R, a branched or unbranched —(C₁-C₆)alkyl, or —OR.

In some embodiments of Formula I, R1 is phenyl, naphthyl, biphenyl, pyridyl, quinolinyl, benzopyran,

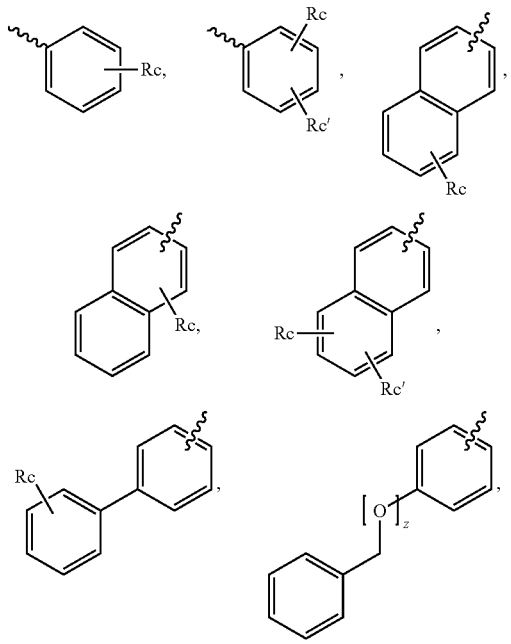

where z is 0 or 1,

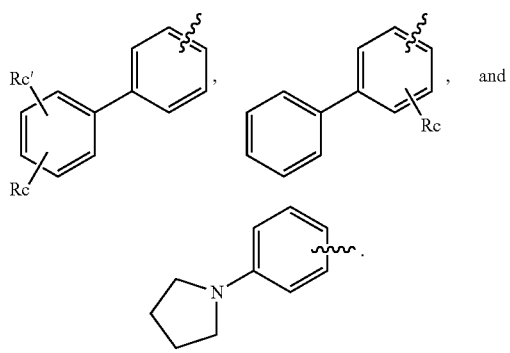

In some embodiments of Formula I, R1 is

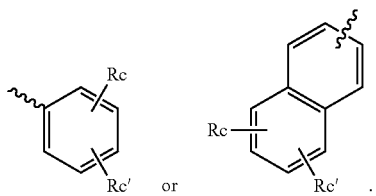

In some embodiments of Formula I, R1 is

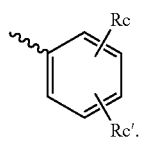

In some embodiments of Formula I, R2 is selected from the group consisting of

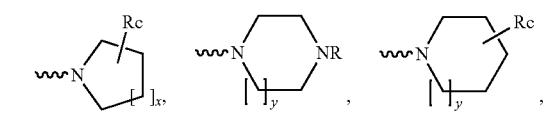
—NCH₂C(NH₂)RR',
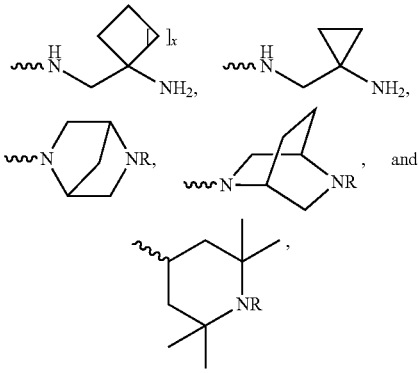
wherein x is 1-3 and y is 1-2.
In some embodiments of Formula I, R1 is
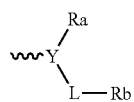
and Rb is selected from the group consisting of
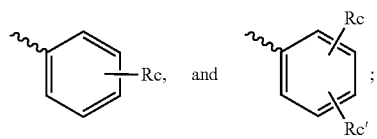
and R2 is
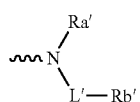
and Rb' is selected from the group consisting of an amine group, —CH₂C(NH₂)RR',
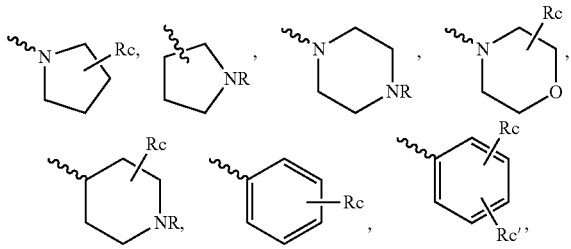
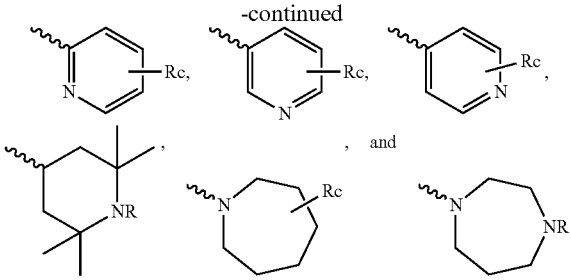
In some embodiments of Formula I, R1 is phenyl, naphthyl, biphenyl, pyridyl,
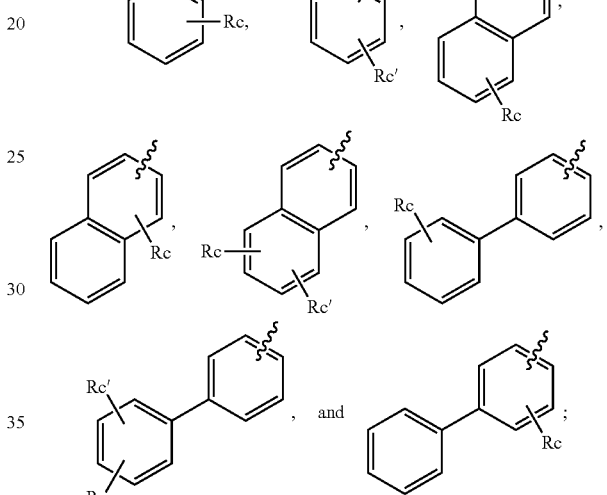
and R2 is selected from the group consisting of
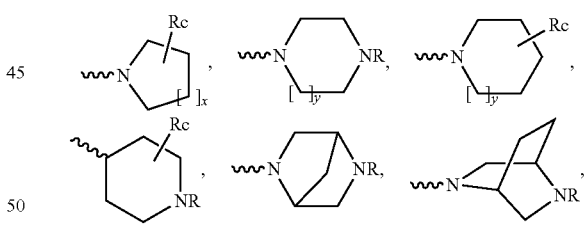
—CH₂C(NH₂)RR',
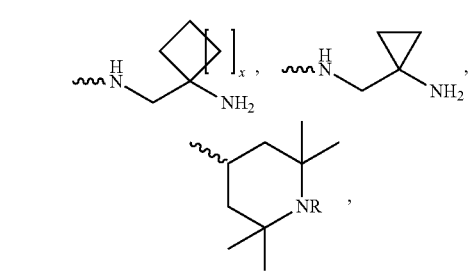
wherein x is 1-3 and y is 1-2.

In some embodiments of Formula I, R1 is

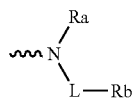

and Rb is selected from the group consisting of an amine group,

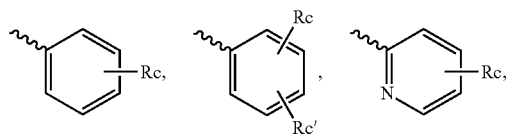

and R2 is selected from the group consisting of

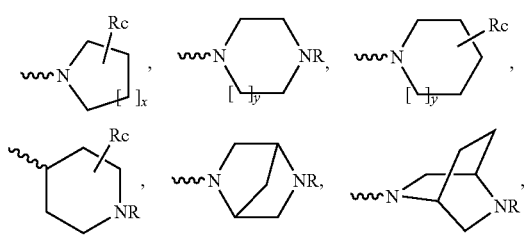

—CH₂C(NH₂)RR',

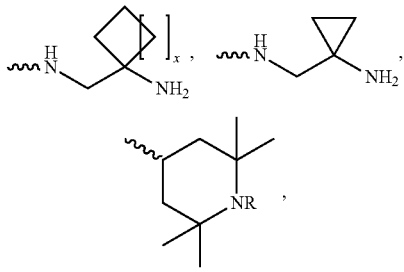

wherein x is 1-3 and y is 1-2.

In some embodiments of Formula I, R1 is

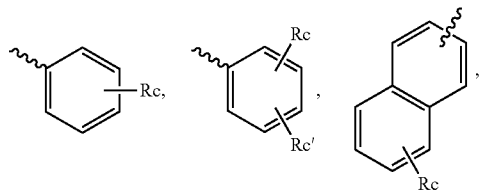

-continued

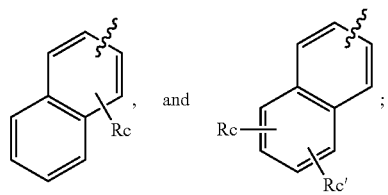

and R2 is

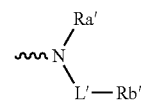

and Rb' is selected from the group consisting of an amine group,

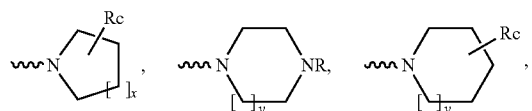

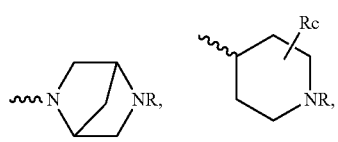 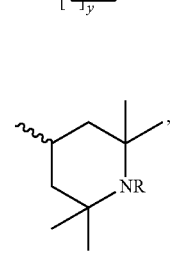

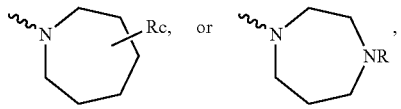

wherein x is 1-3 and y is 1-2.

In some embodiments of Formula I, R2 is —NRR', —C(NH₂)RR', or

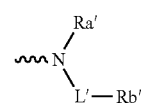

where Rb' is

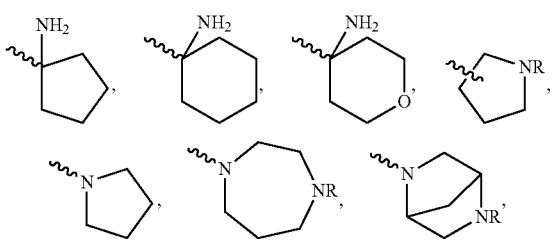

-continued

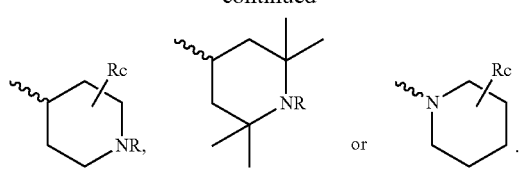

In some embodiments of Formula I, R1 is phenyl, naphthyl, biphenyl, or

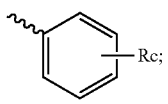

and R2 is —NRR', —C(NH$_2$)RR', or

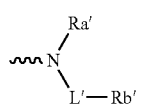

where Rb' is

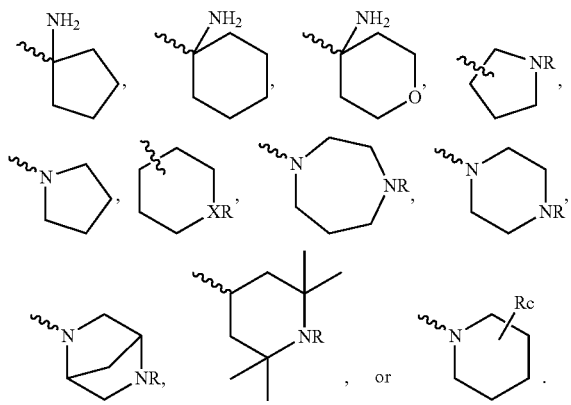

In some embodiments of Formula I, R1 is

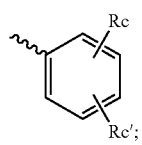

and R2 is —NRR', —C(NH$_2$)RR', or

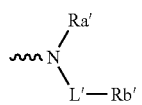

where Rb' is

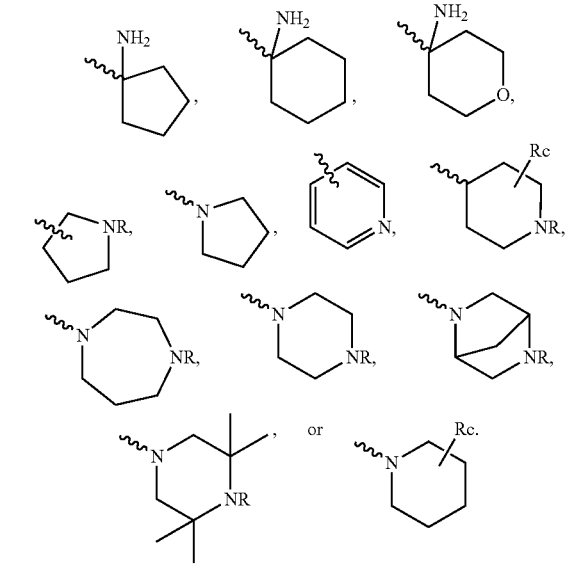

In some embodiments of Formula I, Rc and Rc' are each independently selected from the group consisting of t-butyl, Cl, trichloromethyl, F, trifluoromethyl, —CH$_3$, —NH$_2$, —NO$_2$, —(CH$_2$)NRR', —NHC(OR)=O, —NHC(=O)R, —OR, —SR, —S(O)R, —S(O)$_2$R, —COOH, and —COOR. In some embodiments of Formula I, Rc is methyl, t-butyl, halo, trihalomethyl, —S(O)R, —S(O)$_2$R, —OR, or —COOR. In some embodiments of Formula I, Rc and Rc' of the R1 group are each independently halo, trihalomethyl or —OR.

In some embodiments of Formula I, R and R' are each independently selected from the group consisting of H, —CH$_3$, —C$_2$H$_5$, —C$_2$H$_4$OH, —CH(CH$_3$)$_2$, —CH$_2$CH(CH$_3$)$_2$, and C(=O)OC(CH$_3$)$_3$. In some embodiments of Formula I, R is H, methyl, ethyl, —CH$_2$CH(CH$_3$)$_2$, or —(CH$_2$)OH.

In some embodiments of Formula I, L and L' are each independently selected from the group consisting of a bond, —CH$_2$—, —C$_2$H$_4$—, —CH(CH$_3$)—, —CH$_2$CH(CH$_3$)—, —CH(CH$_3$)CH$_2$—, -benzene-, —CH$_2$-benzene-CH$_2$—, and -benzene-CH$_2$—.

Examples of compounds according to the present invention are provided in Table 13. Thus, in some embodiments, the present invention is directed to a compound selected from the group consisting of Ex 1-16 and Compounds 2-745 of Table 13. In some embodiments, the present invention is directed to a compound set forth in Table 13 that exhibits, in the SYBR Green Assay, IC50's against at least one, preferably two or more, more preferably three or more *Plasmodium* strains, of about 500 ng/mL or less, preferably 150 ng/mL or less, and hERG activity of about 75% inhibition or less, preferably 50% inhibition or less, more preferably about 40% inhibition or less, and most preferably about 30% inhibition or less at 10 μM.

In some embodiments, the present invention is directed to a compound set forth in Table 13 that exhibits, in vivo activity, in the Thompson Test, at 160 mg/kg×3 days, preferably 80 mg/kg×3 days, and more preferably 40 mg/kg×3 days, and hERG activity of about 75% inhibition or less, preferably 50% inhibition or less, more preferably about 40% inhibition or less, and most preferably about 30% inhibition or less at 10 μM.

In some embodiments, the present invention is directed to a compound set forth in Table 13 that exhibits, in the SYBR Green Assay, IC50's against at least one, preferably two or more, more preferably three or more *Plasmodium* strains, of about 500 ng/mL or less, preferably 150 ng/mL or less, and in vivo activity, in the Thompson Test, at 160 mg/kg×3 days, preferably 80 mg/kg×3 days, and more preferably 40 mg/kg×3 days.

In some embodiments, the present invention is directed to a compound set forth in Table 13 that exhibits, in the SYBR Green Assay, IC50's against at least one, preferably two or more, more preferably three or more *Plasmodium* strains, of about 500 ng/mL or less, preferably 150 ng/mL or less, and in vivo activity, in the Thompson Test, at 160 mg/kg×3 days, preferably 80 mg/kg×3 days, and more preferably 40 mg/kg×3 days, and hERG activity of about 75% inhibition or less, preferably 50% inhibition or less, more preferably about 40% inhibition or less, and most preferably about 30% inhibition or less at 10 μM.

In some embodiments, the present invention is directed to a compound set forth in Table 13 that exhibits in vivo activity in the Rhesus assay.

In some embodiments, the present invention is directed to a compound selected from Table 14. 20. In some embodiments, the present invention is directed to a compound selected from Compounds 55, 62, 721, 119, 743, 195, 214, 234, 312, 320, 322, 641, 638, 643, 613, 6, 18, Ex. 7, 46, 52, 728, 57, 719, 72, 722, 79, 96, 97, 724, 648, 99, 102, 103, 108, 113, 117, 127, 166, 193, 227, 228, 229, 235, 274, 659, 661, 666, 672, 694, 313, 314, 328, 559, 569, 585, 365, 376, 380, and 555. In some embodiments, the present invention is directed to a compound selected from Compounds 55, 62, 721, 119, 743, 195, 214, 234, 312, 320, and 322.

In some embodiments, the present invention is directed to a pharmaceutical composition comprising one or more compounds of Formula I and pharmaceutically acceptable excipient. In some embodiments, the present invention is directed to a pharmaceutical composition comprising one or more compounds of Table 13, preferably Table 14, and pharmaceutically acceptable excipient. In some embodiments, the present invention is directed to a pharmaceutical composition comprising one or more compounds selected from Compounds 55, 62, 721, 119, 743, 195, 214, 234, 312, 320, 322, 641, 638, 643, 613, 6, 18, Ex. 7, 46, 52, 728, 57, 719, 72, 722, 79, 96, 97, 724, 648, 99, 102, 103, 108, 113, 117, 127, 166, 193, 227, 228, 229, 235, 274, 659, 661, 666, 672, 694, 313, 314, 328, 559, 569, 585, 365, 376, 380, and 555, and pharmaceutically acceptable excipient. In some embodiments, the present invention is directed to a pharmaceutical composition comprising one or more compounds selected from Compounds 55, 62, 721, 119, 743, 195, 214, 234, 312, 320, and 322, and pharmaceutically acceptable excipient.

It is understood that the structural formulas are intended to represent any configurational form of the depicted compound and is not to be limited merely to a specific compound form depicted by the structural formulas.

Some of the compounds of the present invention may exist as single stereoisomers (i.e., essentially free of other stereoisomers) racemates, or mixtures of enantiomers, diastereomers, or both. All such single stereoisomers, racemates and mixtures thereof are intended to be within the scope of the present invention. Preferably, the inventive compounds that are optically active are used in optically pure form.

Additionally, the structural formulas herein are intended to cover, where applicable, solvated as well as unsolvated forms of the compounds. Also included are miscible formulations of solvate mixtures such as a compound of the invention in combination with an acetone and ethanol mixture. In a preferred embodiment, the solvate includes a compound of the invention in combination with about 20% ethanol and about 80% acetone. Thus, the structural formulas include compounds having the indicated structure, including the hydrated as well as the non-hydrated forms.

Compounds of the present invention that are solids may exist in different crystal or polymorphic forms. Additionally, the compounds of the invention include pharmaceutically acceptable salts, prodrugs, active metabolites, precursors, and salts of such metabolites of the compounds of the present invention.

If the compound of the present invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrvic acid, oxalic acid, glycolic acid, salicylic acid, a pyranosidyl acid, such as glucuronic acid or galacturonic acid, an α-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the present invention is an acid, the desired pharmaceutically acceptable salt may be prepared by any suitable method, for example, treatment of the free acid with an inorganic or organic base, such as an amine (primary, secondary or tertiary) an alkali metal hydroxide or alkaline earth metal hydroxide, or the like. Illustrative examples of suitable salts include organic salts derived from basic amino acids, such as lysine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The compounds of the present invention may be synthesized using the methods and preparations as follows:

Preparation 1: 4-(4,6-bis(trichloromethyl)-1,3,5-triazin-2-yl)morpholine

Dissolved 2-chloro-4,6-bis(trichloromethyl)-1,3,5-triazine (0.1 g, 0.28 mmol) in THF (1.5 mL). Added morpholine (0.24 mL, 0.29 mmol) and N,N-diisopropylethylamine (0.06 mL, 0.34 mmol) and stirred for 18 h at room temperature. Concentrated and purified by silica gel chromatography eluting with $CH_2Cl_2$ to obtain the title compound (0.05 g).

Using a similar procedure, the starting triazine of Preparation 1 was treated with the indicated amine in Table 1 to obtain intermediate compounds 1A-II.

Preparation 2: 2-(p-tolyl)-4,6-bis(trichloromethyl)-1,3,5-triazine

Dissolved aluminum tribromide (1.15 g, 4.3 mmol) and 4-methylbenzonitrile (5.0 g, 43 mmol) in 2,2,2-trichloroacetonitrile (21.5 mL, 215 mmol) and cooled to 0-10° C. under $N_2$. Bubbled in HCl gas for 2 h. Warned slowly to room temperature and stirred for 18 h. Added acetone (150 mL) and water (50 mL). Extracted the mixture with $CH_2Cl_2$ (3×100 mL). Washed the organic layer with saturated NaHCO₃ (60 mL) and saturated NaCl (60 mL) then dried (Na₂SO₄) and concentrated.

Method 1: Triturated crude product with methanol (150 mL). Filtered to result in a solid, washed with cold methanol (2×15 mL). Dried solid in high vacuum to afford title compound (6.1 g) as a white solid.

Method 2: Dissolved crude product mixture (10 g) in CH₂Cl₂:water [5:1] (60 mL). Added NaOH (1.48 g, 1.5 eq) and heated to 30° C. for 16 h. Cooled the reaction mixture to 23° C. Washed the organic layer with saturated NH₄Cl and saturated NaCl, then dry (Na₂SO₄) and concentrated to obtain the title compound (3.4 g) as a white solid.

Using a similar procedure to Preparation 2, the nitriles in Table 2 were treated by the indicated method for isolation to obtain intermediate compounds 2A-2AF.

Preparation 3: 2-(3-(4,6-bis(trichloromethyl)-1,3,5-triazin-2-yl)phenyl)isoindoline-1,3-dione Step 1: Dissolved 3-aminobenzonitrile (1.5 g, 12.7 mmol) in anhydrous dioxane (42 mL) under N₂. Added phthalic anhydride (2.54 g, 17.1 mmol). Affixed Dean-Stark trap and refluxed for 16 h. Cooled to 0° C. and filtered off solid (2-((3-cyanophenyl)carbamoyl)benzoic acid). Concentrated filtrate to afford 3-(1,3-dioxoisoindolin-2-yl)benzonitrile (1.6 g) as a white solid. MS, calc'd=248.06. Obsv'd m/z: 248.91 (M+1).

Step 2: The product of Step 1 was treated in a procedure similar to that described in Preparation 2, Method 1, to obtain the title compound as an off-white solid.

Preparation 4: 4-(4,6-bis(trichloromethyl)-1,3,5-triazin-2-yl)phenyl benzoate

Step 1: Treated a solution of 4-hydroxybenzonitrile (5.0 g, 42 mmol) in DMF (20 mL) with 2M KOH (21 mL, 42 mmol) followed by benzyl chloride (3.46 mL, 42 mmol). Heated in an oil bath at 80° C. for 2 h. Cooled to room temperature and poured onto water (100 mL). Filtered the resulting solid, washed with water (2×25 mL) and dried to obtain 4-benzyloxy-benzonitrile (5.1 g) as a solid.

Step 2: Treated the product of Step 1 in a procedure similar to that described in Preparation 2, Method 2 to afford the title compound as a white solid.

Preparation 5: 2-(4-(methylsulfinyl)phenyl)-4,6-bis(trichloromethyl)-1,3,5-triazine Cooled a solution of the product of Preparation 2G (1.0 g, 2.28 mmol) in CH₂Cl₂ (19.0 mL) to 0° C. and treated with NaHCO₃ (0.38 g, 4.57 mmol). Added mCPBA (77 wt %, 0.56 g, 2.28 mmol) portion-wise. After 20 min at 0° C., added saturated Na₂S₂O₃ (8 mL) and saturated NaHCO₃ (8 mL). Warmed mixture to 23° C. and extract with CH₂Cl₂ (15 mL). Washed the organic layer with saturated NaCl (10 mL) then dried (Na₂SO₄) and concentrated. Purified by flash chromatography (silica gel, eluant: CH₂Cl₂). Combined appropriate fractions and concentrate to give the title compound (0.8 g) as an off-white solid.

Preparation 6: 2-(4-(methylsulfonyl)phenyl)-4, 6-bis(trichloromethyl)-1,3,5-triazine Oxidized the product of Preparation 2G (5.0 g, 11.38 mmol) using a procedure similar to that in Preparation 5 using 4.0 eq. of NaHCO₃ and 2.1 eq. of mCPBA to obtain the title compound as a white solid.

Preparation 7: N-(4-chlorophenyl)-4,6-bis(trichloromethyl)-1,3,5-triazin-2-amine Treated a solution of the product of Preparation 2Z (0.45 g, 1.0 mmol) in THF (3.5 mL) with 4-chloroaniline (0.14 g, 1.14 mmol) and N,N-diisopropylethylamine (0.22 mL, 1.24 mmol). Microwaved solution at 120° C. for 5 min at power of 200 W. Concentrated and purified by silica gel chromatography eluting with hexane followed by CH₂Cl₂ to obtain the title compound (0.3 g).

Using a similar procedure to Preparation 7, the product of Preparation 2Z was treated with the indicated amine in Table 3 to obtain intermediate compounds 7A-7E.

Preparation 8: 2-(tert-butyl)-4,6-dichloro-1,3,5-triazine

Dissolved cyanuric chloride (4.2 g, 22.9 mmol) and CuI (0.22 g, 1.1 mmol) in anhydrous THF (12 mL) and cooled to −10° C. under N₂. Added tert-butylmagnesium chloride (1.0M in THF, 25.4 mL) slowly over 20 min. Added saturated NH₄Cl (5 mL) and warmed reaction to room temperature. Extracted mixture with CH₂Cl₂ (4×75 mL). Washed organic layer with water (35 mL) and saturated NaCl (35 mL) then dried (Na₂SO₄) and concentrated. Purified the product by filtration through a pad of silica gel eluting with CH₂Cl₂ to give the title compound (1.5 g) as a yellow oil.

Table 4 provides a non-limiting list of amines which may be employed to obtain compounds according to the present invention.

EXAMPLE 1 AND COMPOUNDS 2-619

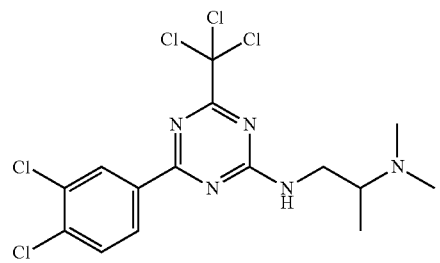 [SMILES: CC(CNc1nc(-c2ccc(Cl)c(Cl)c2)nc(C(Cl)(Cl)Cl)n1)N(C)C]

$N^1$-(4-(3,4-dichlorophenyl)-6-(trichloromethyl)-1,3,5-triazin-2-yl)-$N^2$,$N^2$-dimethylpropane-1,2-diamine Treated a solution of the product of Preparation 2C (0.70 g, 1.5 mmol) in THF (6.0 mL) with $N^2$,$N^2$-dimethylpropane-1,2-diamine (0.18 g, 1.75 mmol). Stirred for 17 h at room temperature. Concentrated and purified by silica gel chromatography eluting with NH₃/MeOH/CH₂Cl₂ mixtures to give the title compound (0.61 g) as a white solid. MS, calc'd=440.98. Obsv'd m/z: 443.10 (M+1).

Using a similar procedure, the appropriate bis-trichloromethyltriazines of Preparations 1-7 were treated with the amines as indicated in Table 5 to obtain Compounds 2-619.

EXAMPLE 2 AND COMPOUNDS 620-635

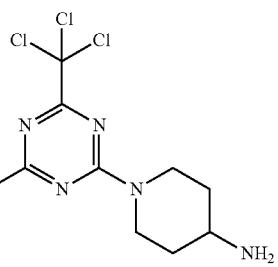

1-(4-(4-fluorophenyl)-6-(trichloromethyl)-1,3,5-triazin-2-yl)piperidin-4-amine

Step 1: Treated the product of Preparation 2Q (0.10 g, 0.24 mmol) with 4-N-Boc-aminopiperidine (0.054 g, 0.27 mmol) using a procedure similar to that described in Example 1.

Step 2: Treated a solution of the product of Step 1 (0.24 g, 0.49 mmol) in $CH_2Cl_2$ (1.6 mL) with concentrated trifluoroacetic acid (1.6 mL). Stirred for 12 h at 23° C. Slowly added saturated $NaHCO_3$ until pH=8. Extracted with $CH_2Cl_2$ (2 mL). Washed organic layer with saturated NaCl (2 mL) then dried ($Na_2SO_4$) and concentrated. Purified by silica gel chromatography eluting with $NH_3/MeOH/CH_2Cl_2$ mixtures to give the title compound (0.05 g) Example 2, as a yellow solid. MS, calc'd=389.04. Obsv'd m/z: 390.27 (M+1).

A procedure similar to that described in Example 2, Steps 1-2, was used with the products of the Preparations as indicated in Table 6 to obtain Compounds 620-635.

EXAMPLE 3

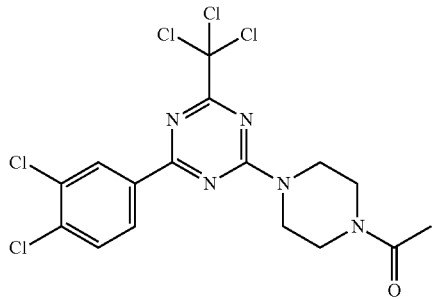 [SMILES: CC(=O)N1CCN(c2nc(-c3ccc(Cl)c(Cl)c3)nc(C(Cl)(Cl)Cl)n2)CC1]

1-(4-(4-(3,4-dichlorophenyl)-6-(trichloromethyl)-1,3,5-triazin-2-yl)piperazin-1-yl)ethan-1-one Step 1: Treated the product of Preparation 2C (0.10 g, 0.22 mmol) with piperazine (0.02 g, 0.24 mmol) using a procedure similar to that described in Example 1.

Step 2: Treated a solution of the product of Step 1 (0.059 g, 0.14 mmol) in $CH_2Cl_2$ (0.5 mL) with triethylamine (0.03 mL, 0.21 mmol) under $N_2$. Cooled to 0° C. and added acetyl chloride (0.010 mL, 0.14 mmol) slowly. Warmed mixture to 23° C. and stirred for 1 h, then added water (1 mL). Extracted with $CH_2Cl_2$ (2×2 mL). Washed organic layer with saturated $NaHCO_3$ (1 mL) saturated NaCl (1 mL) then dried ($Na_2SO_4$) and concentrate. Purified the product by filtration through a pad of silica gel eluting with $CH_2Cl_2$ to give the title compound (0.031 g) as a yellow solid. MS, calc'd=466.96. Obsv'd m/z: (M+1).

EXAMPLE 4 AND COMPOUNDS 636-691

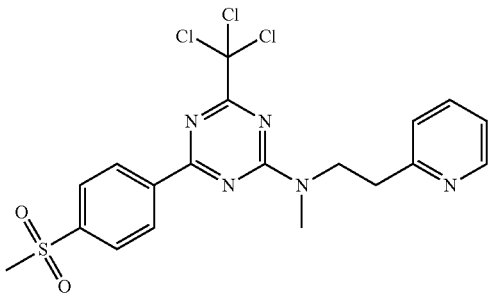 [SMILES: CN(CCc1ccccn1)c1nc(-c2ccc(S(C)(=O)=O)cc2)nc(C(Cl)(Cl)Cl)n1]

N-methyl-4-(4-(methylsulfonyl)phenyl)-N-(2-(pyridin-2-yl)ethyl)-6-(trichloromethyl)-1,3,5-triazin-2-amine Treated a solution of the product of Preparation 6 (0.10 g, 0.21 mmol) in THF (2.1 mL) with N-methyl-2-(pyridin-2-yl)ethanamine (0.35 g, 0.25 mmol) and N,N-diisopropylethylamine (0.05 mL, 0.28 mmol). Stirred for 16 h at room temperature. Concentrated and purified by silica gel chromatography eluting with $NH_3/MeOH/CH_2Cl_2$ mixtures to give the title compound (0.67 g) as a white solid. MS, calc'd=485.02. Obsv'd m/z: 485.94 (M+1).

Using a similar procedure, the product of the specific Preparations were treated with the indicated amine (in place of N-methyl-2-(pyridin-2-yl)ethanamine in Example 4) in Table 7 to obtain Compounds 636-691.

EXAMPLE 5 AND COMPOUNDS 692-704

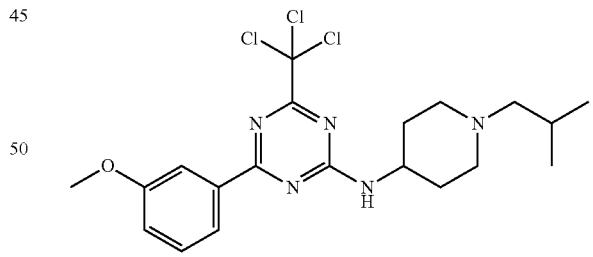

N-(1-isobutylpiperidin-4-yl)-4-(3-methoxyphenyl)-6-(trichloromethyl)-1,3,5-triazin-2-amine Cooled a solution of 1-isobutylpiperidin-4-amine 2,2,2-trifluoroacetate (0.04 g, 0.28 mmol) in anhydrous THF (1.0 mL) to 0° C. under $N_2$ and treated with NaH (60 wt % in mineral oil, 0.17 g, 0.71 mmol). After 5 min at 0° C., the product of preparation 2A (0.10 g, 0.24 mmol) was added and stirred cold for 30 min. Warmed mixture to 23° C. and added saturated $NH_4Cl$ (1 mL) and water (1 mL). Extracted with EtOAc (2×3 mL). Washed organic layer with saturated NaHCO$_3$ (1 mL) saturated NaCl (1.5 mL) then dried (Na$_2$SO$_4$) and concentrate. Purified by silica gel chromatography eluting with NH$_3$/MeOH/CH$_2$Cl$_2$ mixtures to give the title compound (0.021 g) as a gum. MS, calc'd=457.12. Obsv' d m/z: 458.24 (M+1).

Using a similar procedure to Example 5, 1-isobutylpiperidin-4-amine 2,2,2-trifluoroacetate was treated with the indicated Preparation product in Table 8 to obtain Compounds 692-704.

EXAMPLE 6 AND COMPOUNDS 705-715

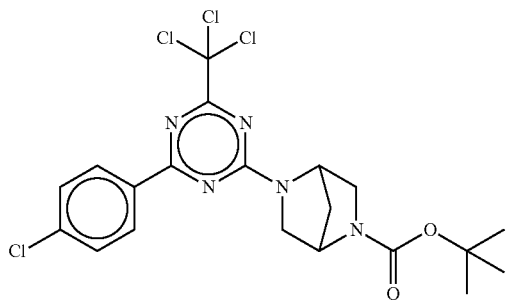

tert-butyl 5-(4-(4-chlorophenyl)-6-(trichloromethyl)-1,3,5-triazin-2-yl)-2,5-diazabicyclo[2.2.1]heptane-2-carboxylate Cooled a solution of (1S,4S)-(−)-2-Boc-2,5-diazabicyclo [2.2.1]-heptane (0.05 g, 0.26 mmol) in anhydrous THF (1.0 mL) to 0° C. under N$_2$ and treat with MeLi (1.7M in hexane, 0.15 mL). After 5 min at 0° C., the product of preparation 2D (0.10 g, 0.24 mmol) was added and stirred cold for 30 min. Warmed mixture to 23° C. and added water (1 mL). Extracted with EtOAc (2×3 mL). Washed organic layer with saturated NaHCO$_3$ (2 mL) saturated NaCl (2 mL) then dried (Na$_2$SO$_4$) and concentrated. Purified by silica gel chromatography eluting with NH$_3$/MeOH/CH$_2$Cl$_2$ mixtures to give the title compound (0.034 g) as an off-white oil. MS, calc'd=503.04. Obsv'd m/z: 504.16 (M+1).

Using a similar procedure, the product of the specific Preparations were treated with the indicated amine in Table 9 to obtain Compounds 705-715.

EXAMPLE 7 AND COMPOUNDS 716-726

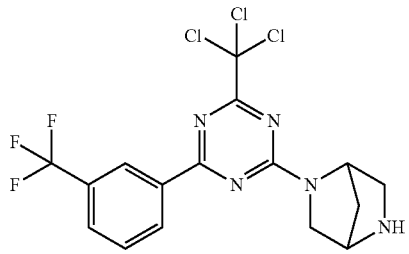 [SMILES: FC(F)(F)c1cccc(-c2nc(N3CC4CC3CN4)nc(C(Cl)(Cl)Cl)n2)c1]

2-(4-(trichloromethyl)-6-(3-(trifluoromethyl)phenyl)-1,3,5-triazin-2-yl)-2,5-diazabicyclo[2.2.1]heptane Step 1: Treated (1S,4S)-(−)-2-Boc-2,5-diazabicyclo [2.2.1]-heptane with the product of Preparation 2F using a procedure similar to Example 6.

Step 2: Deprotected the product of Step 1 using a procedure similar to that described in Example 2, Step 2, to afford the title compound as a yellow solid. MS, calc'd=437.02. Obsv'd m/z: 438.20 (M+1).

Using a similar procedure to Example 7, (1S,4S)-(−)-2-Boc-2,5-diazabicyclo[2.2.1]-heptane was treated with the indicated Preparation product in Table 10 to obtain Compounds 716-726.

EXAMPLE 8 AND COMPOUNDS 727-742

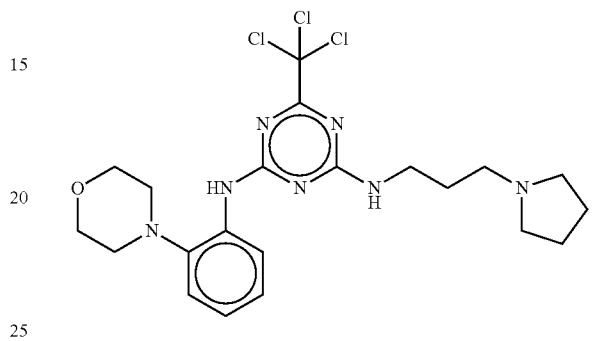

N$^2$-(2-morpholinophenyl)-N$^4$-(3-(pyrrolidin-1-yl) propyl)-6-(trichloromethyl)-1,3,5-triazine-2,4-diamine Treatment a solution of compound 7E (0.08 g, 0.16 mmol) in THF (1.0 mL) with N-(3-aminopropyl)pyrrolidine (0.02 g, 0.18 mmol) and N,N-diisopropylethylamine (0.04 mL, 0.20 mmol). Microwave solution at 120° C. for 5 min at power of 200 W. Concentrated and purified by silica gel chromatography eluting with NH$_3$/MeOH/CH$_2$Cl$_2$ mixtures to give the title compound (0.02 g) as an off-white oil. MS, calc'd=499.14. Obsv'd m/z: 500.18 (M+1).

Using a similar procedure, the products of the specific Preparations were treated with the indicated amines in Table 11 to obtain Compounds 727-742.

EXAMPLE 9 AND COMPOUNDS 743-744

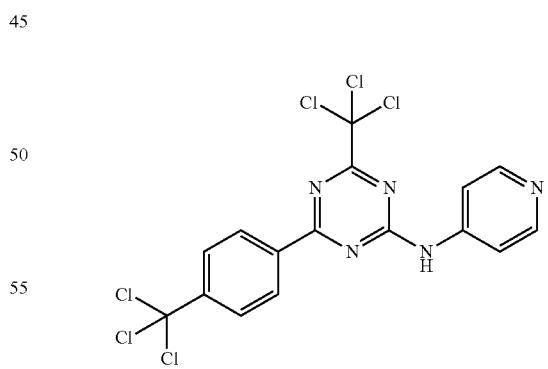

N-(pyridin-4-yl)-4-(trichloromethyl)-6-(4-(trichloromethyl)phenyl)-1,3,5-triazin-2-amine Treated the product of Preparation 2H (0.38 g, 0.73 mmol) using a procedure similar to that in Example 6 using 2.0 eq. of 4-aminopyridine to obtain the title compound (0.37 g) as an off-white solid.

Using a procedure similar to that described in Example 9, 4-aminopyridine was treated with the products of the Preparations in Table 12 to obtain Compounds 743-744.

EXAMPLE 10

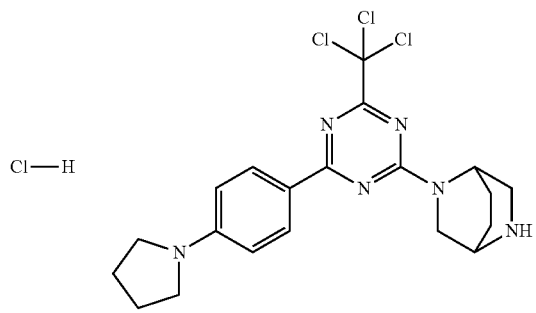 [SMILES: Cl ; ClC(Cl)(Cl)c1nc(-c2ccc(N3CCCC3)cc2)nc(N2CC3CCC2CN3)n1]

2-(4-(4-(pyrrolidin-1-yl)phenyl)-6-(trichloromethyl)-1,3,5-triazin-2-yl)-2,5-diazabicyclo[2.2.2]octane hydrochloride Step 1: Dissolved the product of Preparation 2AA (1.4 g, 3.1 mmol) and 2,5-diazabicyclo[2.2.2]octane-2-carboxylic acid tert butyl ester.HCl (0.76 g, 3.1 mmol) in CH$_3$CN (25 mL) under N$_2$. Added DBU (0.91 mL, 6.1 mmol) stirring for 36 h at room temperature. Concentrated and filtered the resulting solid with CH$_3$CN to afford tert-butyl 5-(4-(4-(pyrrolidin-1-yl)phenyl)-6-(trichloromethyl)-1,3,5-triazin-2-yl)-2,5-diazabicyclo[2.2.2]octane-2-carboxylate (1.1 g) as a yellow solid.

Step 2: Deprotected a solution of the product of Step 1 (1.1 g, 1.98 mmol) in anhydrous CHCl$_3$ (18 mL) with 4N HCl in dioxane (18 mL, 71.6 mmol) under N$_2$. Stirred at room temperature for >18 h, then concentrated. Added diethyl ether (60 mL) and CH$_2$Cl$_2$ (5 mL) and stirred for 1 h. Filtered resulting solid, washed with ether and CH$_2$Cl$_2$, and dried to give the title compound (0.88 g) as a yellow solid. MS, calc'd=452.10. Obsv'd m/z: 453.10 (M+1).

EXAMPLE 11

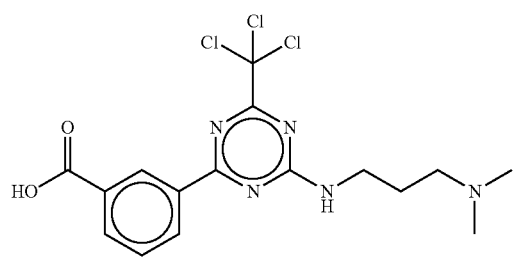

3-(4-((3-(dimethylamino)propyl)amino)-6-(trichloromethyl)-1,3,5-triazin-2-yl)benzoic acid Step 1: Treated the product of Preparation 2AD with N$^1$,N$^1$-dimethylpropane-1,3-diamine using a procedure similar to that described in Example 1.

Step 2: Oxidized the product of Step 1 with 0.1 N HCl in diethyl ether using gradual heating. Concentrated to afford the title compound as a white solid which was then free based. Calc'd for C$_{16}$H$_{18}$Cl$_3$N$_5$O$_2$: C, 45.89; H, 4.33; N, 16.72. Found: C, 45.88; H, 4.32; N, 16.68.

EXAMPLE 12

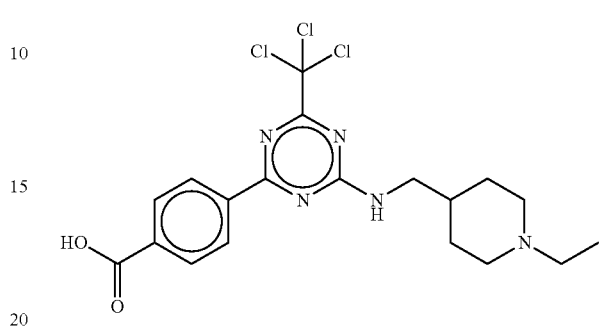

4-(4-(((1-ethylpiperidin-4-yl)methyl)amino)-6-(trichloromethyl)-1,3,5-triazin-2-yl)benzoic acid Step 1: Treated the product of Preparation 2H with (1-ethyl-4-piperidinyl) methanamine using a procedure similar to that described in Example 1.

Step 2: Oxidized the product of Step 1 with aqueous NaOH using gradual heating. Concentrated to afford the title compound as an off-white solid. Calc'd for C$_{19}$H$_{22}$Cl$_3$N$_5$O$_2$: C, 47.86; H, 5.07; N, 14.69; Cl, 22.31. Found: C, 48.38; H, 4.72; N, 14.75; Cl, 22.05.

EXAMPLE 13

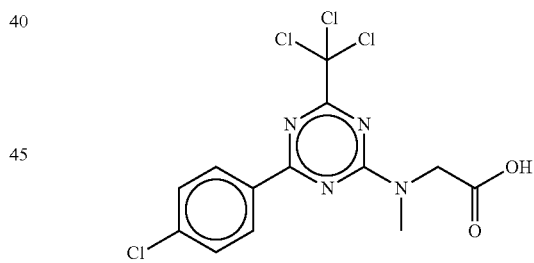

N-(4-(4-chlorophenyl)-6-(trichloromethyl)-1,3,5-triazin-2-yl)-N-methylglycine

Step 1: Treated the product of Preparation 2D (0.10 g, 0.24 mmol) with sarcosine tert-butyl ester hydrochloride (0.05 g, 0.26 mmol) using a procedure similar to that described in Example 4, eluting with CH$_2$Cl$_2$ during chromatography.

Step 2: Saponified a solution of the product of Step 1 (0.05 g) in CH$_2$Cl$_2$ (1.3 mL) with trifluoroacetic acid (0.6 mL) at room temperature. Stirred for 4 h, then concentrated. Added diethyl ether (3 mL). Washed resulting solid with cold diethyl ether (2×2 mL) and dried to afford the title compound (0.03 g) as a white solid. MS, calc'd=393.96. Obsv'd m/z: 394.89 (M+1).

EXAMPLE 14 AND COMPOUND 745

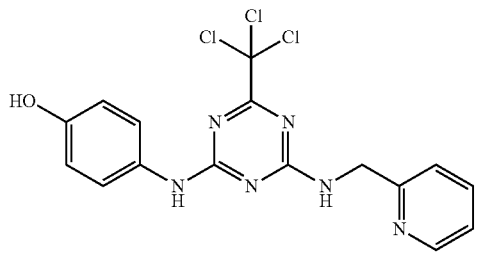 [SMILES: Oc1ccc(Nc2nc(NCc3ccccn3)nc(C(Cl)(Cl)Cl)n2)cc1]

4-((4-((pyridin-2-ylmethyl)amino)-6-(trichloromethyl)-1,3,5-triazin-2-yl)amino)phenol Step 1: Cooled a solution of the product of Preparation 1E (1.0 g, 2.37 mmol) in anhydrous $CH_2Cl_2$ (2.0 mL) to 0° C. under $N_2$ and treated with imidazole (0.34 g, 5.1 mmol). After 5 min at 0° C., tert-butylchlorodimethylsilane (0.39 g, 2.60 mmol) was added slowly and warmed to 23° C. Stirred for 1 h, then added saturated $NaHCO_3$ (1 mL). Extracted with $CH_2Cl_2$ (2×3 mL). Washed organic layer with saturated NaCl (1.5 mL) then dry ($Na_2SO_4$) and concentrated. Purified the product by filtration through a pad of silica gel eluting with hexane to give N-(4-((tert-butyldimethylsilyl)oxy)phenyl)-4,6-bis(trichloromethyl)-1,3,5-triazin-2-amine (1.0 g) as a solid.

Step 2: Treated the product of Step 1 (0.11 g, 0.21 mmol) with 2-(aminomethyl)pyridine (0.02 g, 0.23 mmol) using a procedure similar to that described in Example 1.

Step 3: Cooled a solution of the product of Step 2 (0.1 g, 0.19 mmol) in anhydrous THF (1.0 mL) to 0° C. and deprotected with 1.0 M TBAF in THF (0.4 mL) under $N_2$. Stirred at 0° C. for 5 min, then warmed to room temperature and stirred for 1.5 h. Concentrated and purified by silica gel chromatography eluting with $NH_3/MeOH/CH_2Cl_2$ mixtures to give the title compound (0.06 g) as a solid. MS, calc'd=410.02. Obsv'd m/z: 411.05 (M+1).

Using a procedure similar to that described in Example 14, 2-(aminomethyl)pyridine in Step 2 was substituted with N-(2-aminoethyl)pyrrolidine to obtain 4-((4-((2-(pyrrolidin-1-yl)ethyl)amino)-6-(trichloromethyl)-1,3,5-triazin-2-yl)amino)phenol (Compound 745) as a solid. MS, calc'd=416.07. Obsv'd m/z: 417.04 (M+1).

EXAMPLE 15

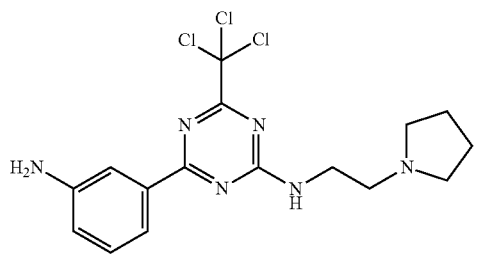 [SMILES: Nc1cccc(-c2nc(NCCN3CCCC3)nc(C(Cl)(Cl)Cl)n2)c1]

4-(3-aminophenyl)-N-(2-(pyrrolidin-1-yl)ethyl)-6-(trichloromethyl)-1,3,5-triazin-2-amine Step 1: Treated the product of Preparation 3 (0.32 g, 0.60 mmol) with N-(2-aminoethyl)pyrrolidine (0.07 g, 0.66 mmol) using a procedure similar to that described in Example 1.

Step 2: Deprotected a solution of the product of Step 1 (0.18 g, 0.34 mmol) in anhydrous EtOH (2.0 mL) with hydrazine monohydrate (0.45 mL, 27 eq.). Stirred vigorously at room temperature for 16 h. Added 10% aqueous $Na_2CO_3$ (1.5 mL). Extracted mixture with $CH_2Cl_2$ (3×5 mL). Washed the organic layer with saturated NaCl (2 mL) dried ($Na_2SO_4$) and concentrated. Purified by silica gel chromatography eluting with $NH_3/MeOH/CH_2Cl_2$ mixtures to give the title compound (0.06 g) as a yellow solid. MS, calc'd=400.07. Obsv'd m/z: 401.19 (M+1).

EXAMPLE 16

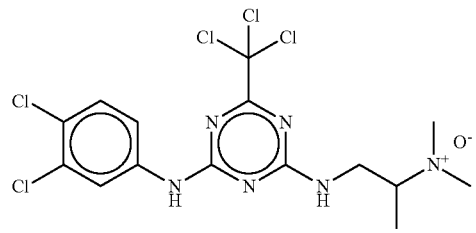

1-((4-((3,4-dichlorophenyl)amino)-6-(trichloromethyl)-1,3,5-triazin-2-yl)amino)-N,N-dimethylpropan-2-amine oxide Step 1: Treated the product of Preparation 2C with $N^2,N^2$-dimethylpropane-1,2-diamine using a procedure similar to that described in Example 1.

Step 2: Oxidized the product of Step 1 with mCPBA using a procedure similar to that described in Preparation 5 to obtain the title compound as a white solid. Calc'd for $C_{15}H_{17}Cl_5N_6O$: C, 37.54; H, 3.59; N, 17.40; Cl, 38.16. Found: C, 37.23; H, 3.71; N, 17.40; Cl, 37.86.

The activities of the compounds of the present invention may be measured by any of the methods available to those skilled in the art, including in vitro and in vivo assays. Examples of suitable assays for activity measurements are provided herein. Properties of the compounds of the present invention may be assessed, for example, by using one or more of the assays set out in the Examples below. Other pharmacological methods may also be used to determine the efficacy of the compounds as antiproliferative, antibacterial, antifungal, and antiprotozoal agents. The compounds of the present invention may be used in combination with or as a substitution for known treatments for malaria, chemoprophylaxis, and/or infection by one or more *Plasmodium* spp.

A compound of the present invention may be administered in a therapeutically effective amount to a subject in need thereof. As used herein, a "subject in need thereof" is one who has or will be exposed to one or more *Plasmodium* spp. or has been diagnosed as having malaria or being infected with one or more *Plasmodium* spp. A therapeutically effective amount of one or more compounds of the present invention will vary depending upon factors such as the given compound(s) the pharmaceutical formulation, route of administration, the type of disease or disorder, the degree of the disease or disorder, and the identity of the subject being treated, but can nevertheless be routinely determined by one skilled in the art. Also, as used herein, a "therapeutically effective amount" of a compound of the present invention is an amount which prevents, inhibits, suppresses, or reduces a given clinical condition in a subject as compared to a control. For example, a "therapeutically effective amount" of a compound of the present invention is an amount which prevents, inhibits, suppresses, or reduces malaria (as determined by clinical symptoms or the amount of *Plasmodium* organisms) in a subject as compared to a control. In some embodiments, a therapeutically effective amount of one or more compounds of the invention ranges from about 0.01 to about 320 mg/kg body weight, preferably about 0.1 to about 160 mg/kg body weight, and more preferably about 0.1 to about 80 mg/kg body weight. The skilled artisan will appreciate that certain factors may influence the dosage required to effectively treat a subject, including but not limited to the severity of the disease or disorder, previous treatments, the general health and/or age of the subject, and other diseases present.

Moreover, treatment of a subject with a therapeutically effective amount of the compound of the present invention may consist of a single administration, or alternatively comprise a series of applications. For example, a subject may be treated with one or more compounds of the present invention at least once. However, the subject may treated with the one or more compounds from about one time per week to about once daily for a given treatment period. The length of the treatment period will depend on a variety of factors such as the severity of the disease or disorder, the concentration and activity of the one or more compounds of the present invention, or a combination thereof. It will also be appreciated that the effective dosage of the one or more compounds used for treatment may increase or decrease over the course of a particular treatment. Changes in dosage may result and become apparent by standard diagnostic assays known in the art. In some instances chronic administration may be required. The compounds of the present invention may be administered before, during, after, or a combination thereof exposure to malaria or *Plasmodium* spp.

The pharmaceutical formulations of the invention comprise one or more compounds of the present invention and may be prepared in a unit-dosage form appropriate for the desired mode of administration. The pharmaceutical formulations of the present invention may be administered for therapy by any suitable route including oral, rectal, nasal, topical (including buccal and sublingual) vaginal, and parenteral (including subcutaneous, intramuscular, intravenous, and intradermal). It will be appreciated that the preferred route will vary with the condition and age of the recipient, the nature of the condition to be treated, and the given compound(s) of the present invention.

It will be appreciated that the actual dosages of the compounds used in the pharmaceutical formulations of this invention will vary according to the particular compound(s) being used, the particular composition formulated, the mode of administration, and the particular site, host, and disease being treated. Optimal dosages for a given set of conditions may be ascertained by those skilled in the art using conventional dosage determination tests in view of the experimental data for a given compound. Administration of prodrugs may be dosed at weight levels that are chemically equivalent to the weight levels of the fully active forms.

The compounds of the present invention can be incorporated into pharmaceutical formulations suitable for administration. Pharmaceutical formulations of this invention comprise a therapeutically effective amount of one or more compounds of the present invention, and an inert, pharmaceutically or cosmetically acceptable carrier or diluent. As used herein the language "pharmaceutically or cosmetically acceptable carrier" is intended to include any and all solvents, dispersion media, coatings, antibacterial, and antifungal agents, isotonic and absorption delaying agents, and the like, compatible with pharmaceutical or cosmetic administration. The pharmaceutical or cosmetic carrier employed may be either a solid or liquid. Exemplary of solid carriers are lactose, sucrose, talc, gelatin, agar, pectin, acacia, magnesium stearate, stearic acid, and the like. Exemplary of liquid carriers are syrup, peanut oil, olive oil, water, and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate, and the like. The use of such media and agents for pharmaceutically or cosmetically active substances is well known in the art.

Except insofar as any conventional media or agent is incompatible with the active compound, use thereof in the formulation is contemplated. Supplementary active compounds can also be incorporated into the formulations. Supplementary active compounds include antibiotics, antiprotozoal agents, antifungal agents, and antiproliferative agents known in the art, analgesics, and other compounds commonly used to treat diseases and disorders associated with cell proliferation, bacterial infection, fungal infection, and protozoal infection.

Antibiotics include penicillin, cloxacillin, dicloxacillin, methicillin, nafcillin, oxacillin, ampicillin, amoxicillin, bacampicillin, azlocillin, carbenicillin, mezlocillin, piperacillin, ticarcillin, azithromycin, clarithromycin, clindamycin, erythromycin, lincomycin, demeclocycline, doxycycline, minocycline, oxytetracycline, tetracycline, quinolone, cinoxacin, nalidixic acid, fluoroquinolone, ciprofloxacin, enoxacin, grepafloxacin, levofloxacin, lomefloxacin, norfloxacin, ofloxacin, sparfloxacin, trovafloxacin, bacitracin, ocolistin, polymyxin B, sulfonamide, trimethoprim-sulfamethoxazole, co-amoxyclav, cephalothin, cefuroxime, ceftriaxone, vancomycin, gentamicin, amikacin, metronidazole, chloramphenicol, nitrofurantoin, co-trimoxazole, rifampicin, isoniazid, pyrazinamide, kirromycin, thiostrepton, micrococcin, fusidic acid, thiolactomycin, fosmidomycin, and the like.

Antiprotozoal agents include chloroquine, doxycycline, mefloquine, metroni dazole, eplornithine, furazolidone, hydroxychloroquine, iodoquinol, pentamidine, mebendazole, piperazine, halofantrine, primaquine, pyrimethamine sulfadoxine, doxycycline, clindamycin, quinine sulfate, quinidine gluconate, quinine dihydrochloride, hydroxychloroquine sulfate, proguanil, quinine, clindamycin, atovaquone, azithromycin, suramin, melarsoprol, eflornithine, nifurtimox, amphotericin B, sodium stibogluconate, pentamidine isethionate, trimethoprim-sulfamethoxazole, pyrimethamine, sulfadiazine, and the like.

Antifungal agents include amphotericin B, fluconazole, itraconazole, ketoconazole, potassium iodide, flucytosine, and the like.

Antiproliferative agents such as altretamine, amifostine, anastrozole, arsenic trioxide, bexarotene, bleomycin, busulfan, capecitabine, carboplatin, carmustine, celecoxib, chlorambucil, cisplatin, cisplatin-epinephrine gel, cladribine, cytarabine liposomal, daunorubicin liposomal, daunorubicin daunomycin, dexrazoxane, docetaxel, doxorubicin, doxorubicin liposomal, epirubicin, estramustine, etoposide phosphate, etoposide VP-16, exemestane, fludarabine, fluorouracil 5-FU, fulvestrant, gemicitabine, gemtuzumab-ozogamicin, goserelin acetate, hydroxyurea, idarubicin, ifosfamide, imatinib mesylate, irinotecan, letrozole, leucovorin, levamisole, liposomal daunorubicin, melphalan L-PAM, mesna, methotrexate, methoxsalen, mitomycin C, mitoxantrone, paclitaxel, pamidronate, pegademase, pentostain, porfimer sodium, streptozocin, talc, tamoxifen, temozolamide, teniposide VM-26, topotecan, toremifene, tretinoin, ATRA, valrubicin, vinorelbine, zoledronate, steroids, and the like.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In Vitro and In Vivo Activity

Various compounds according to the present invention that were synthesized and assayed as described herein and their in vitro and in vivo activities are summarized in Table 13.

SYBR Green Assay In Vitro Assay

The Malaria SYBR Green Fluorescence Assay is a microtiter drug sensitivity assay that uses the intercalation of SYBR Green into malaria DNA as a measure of blood stage *Plasmodium falciparum* parasite proliferation in the presence of antimalarial compounds. See Johnson, J. D., et al. Assessment and Continued Validation of the Malaria SYBR Green I-Based Fluorescence Assay for Use in Malaria Drug Screening. Antimicrob Agents Chemother. 51:1927, 2007. This assay was performed as a dose response (12 two-fold serial dilutions) to obtain a calculated IC50 determination. A variety of culture adapted *P. falciparum* strains with different drug resistance properties (including D6, W2, and C235) from geographically diverse areas were used to assay the compounds disclosed herein.

The columns in Table 13 entitled D6, W2, and C235 set forth the IC50's of the indicated compounds in ng/ml against the given strain. In some embodiments, compounds exhibiting IC50's of one or more, preferably two or more strains, more preferably three strains, of about 500 ng/mL or less are preferred. In some embodiments, compounds exhibiting IC50's of one or more, preferably two or more strains, more preferably three strains, of about 150 ng/mL or less are preferred.

HERG Assay

Compounds according to the present invention were tested in the in vitro electrophysiology patch clamp hERG assay known in the art. See M. H. Bridgland-Taylor et al., (2006). Optimisation and validation of a medium-throughput electrophysiology-based hERG assay using IonWorks HT. Journal of Pharmacological and Toxicological Methods. 54, 189-199. The hERG patch clamp assay is an automated patch-clamp electrophysiology assay for hERG blocking where the membrane potential is controlled across the cell membrane. Compounds were tested to assess their inhibition of current of the hERG potassium ion channel relative to control. The control was quinidine. Results are reported as % inhibition at 10 µM in Table 13. In some embodiments, compounds exhibiting hERG activity of about 75% inhibition or less at 10 µM are preferred. In some embodiments, compounds exhibiting hERG activity of about 50% inhibition or less at 10 µM are preferred. In some embodiments, compounds exhibiting hERG activity of about 40% inhibition or less at 10 µM are preferred. In some embodiments, compounds exhibiting hERG activity of about 30% inhibition or less at 10 µM are preferred.

In Vitro Cytotoxicity Assay

The In vitro Cytotoxicity Assay is a colorimetric microtiter drug toxicity assay that uses the ability of a cell to convert a tetrazolium salt, MTT, (3-(4,5-Dimethylthiazol-2-yl)-2,5-diphenyltetrazolium) to insoluble formazan dyes as a measure of cellular cytotoxicity. See Ferrari, M., et al. MTT colorimetric assay for testing macrophage cytotoxic activity in vitro. J Immunol Methods 1990 Aug. 7; 131(2):165-72. The ability of a cell to reduce MTT is dependent on functioning mitochondria, and toxic compounds affecting mitochondrial function result in impaired production of the reduced purple formazan dye. This assay was conducted as a singlet dose response (11 two-fold serial dilutions) utilizing HepG2 liver cells in the presence of experimental compounds to obtain a calculated IC50 determination.

All compounds tested did not exhibit any significant cytotoxicity.

Thompson Test—In Vivo Mouse Assay

The Modified Thompson mouse malaria assay is an in vivo rodent assay. See Ager, A. L. Experimental models: Rodent Malaria Models (in vivo) p. 225-254. In W. Peters and W. H. G. Richards (ed.) Handbook of experimental pharmacology: Antimalarial Drugs, vol. 68. Springer-Verlag, New York, N.Y. 1984. This assay was used to measure the survivability of mice and parasite clearance following administration of the compounds of the present invention 3 days after a blood stage lethal dose of *P. berghei* was administered on Day 0. Five mice (ICR strain) were used for each compound dose group (dosed on days 3, 4, and 5) and 10 ICR mice were used for controls (vehicle). The percentage of parasitemia was measured routinely throughout the 30-day experiment by a flow cytometry method that measures malaria blood stage parasitemia by intercalation of the fluorescent dye YOYO 1. The survivability of the mice was determined by core body temperature and body weight changes. The endpoints of this assay include no clinical indications of disease and a negative parasitemia on day 31 post-infection, which is designated as a "cure". Untreated control died on Day 7. Compounds extending a subject's lifespan to Day 14 were indicated as suppressive. Typically, 6 dosing groups were used in each experiment, which assess 6 compound dose groups requiring 40 mice per experiment (6 compound dosing groups plus controls).

Not all synthesized compounds were subjected to the Thompson Test. Table 14 summarizes the results of the compounds that were tested. As shown in Table 14, (40×3), (80×3), and (160×3) indicates administration of the given compound at 40 mg/kg for 3 days, 80 mg/kg for 3 days, and 160 mg/kg for 3 days, respectively. Cures indicates mice survive till the end of study (30 days); suppressive, indicates mice survive more than two fold (days) compared to negative control group.

In some embodiments, compounds exhibiting in vivo activity at 160 mg/kg×3, are preferred. In some embodiments, compounds exhibiting in vivo activity at 80 mg/kg× 3, are preferred. In some embodiments, compounds exhibiting in vivo activity at 40 mg/kg×3, are preferred.

Rhesus Assay

The Rhesus Antimalarial Drug Screening model is an in vivo assay which measures liver stage activity of drugs against *P. cynomolgi*, a relapsing primate malaria parasite. The assay system involves establishing a liver stage malaria infection via injection of *P. cynomolgi* sporozoites. Testing of both liver stage activity, radical cure activity, and blood schizonticidal activity is possible in this model with varying dosing schedules and partner drugs. See Deye, G; et. al. Am. J. Trop. Med. Hyg., 86(6), 2012, pp. 931-935. Malaria prophylaxis indicates monkey was free of clinical signs of malaria during testing duration; malaria cures indicate monkeys were free of blood stage parasites at end of treatment regimen.

Due to expense, not all synthesized compounds were subjected to the Rhesus Assay. Table 14 summarizes the results of the compounds that were tested.

In some embodiments, compounds exhibiting in vivo activity in the Rhesus assay are preferred.

In some embodiments, preferred compounds according to the present invention exhibit, in the SYBR Green Assay, IC50's against at least one, preferably two or more, more preferably three or more *Plasmodium* strains, of about 500 ng/mL or less, preferably 150 ng/mL or less, and hERG activity of about 75% inhibition or less, preferably 50% inhibition or less, more preferably about 40% inhibition or less, and most preferably about 30% inhibition or less at 10 μM.

In some embodiments, preferred compounds according to the present invention exhibit in vivo activity, in the Thompson Test, at 160 mg/kg×3, preferably 80 mg/kg×3, and more preferably 40 mg/kg×3, and hERG activity of about 75% inhibition or less, preferably 50% inhibition or less, more preferably about 40% inhibition or less, and most preferably about 30% inhibition or less at 10 μM.

In some embodiments, preferred compounds according to the present invention exhibit, in the SYBR Green Assay, IC50's against at least one, preferably two or more, more preferably three or more *Plasmodium* strains, of about 500 ng/mL or less, preferably 150 ng/mL or less, and in vivo activity, in the Thompson Test, at 160 mg/kg×3, preferably 80 mg/kg×3, and more preferably 40 mg/kg×3.

In some embodiments, preferred compounds according to the present invention exhibit, in the SYBR Green Assay, IC50's against at least one, preferably two or more, more preferably three or more *Plasmodium* strains, of about 500 ng/mL or less, preferably 150 ng/mL or less, and in vivo activity, in the Thompson Test, at 160 mg/kg×3, preferably 80 mg/kg×3, and more preferably 40 mg/kg×3, and hERG activity of about 75% inhibition or less, preferably 50% inhibition or less, more preferably about 40% inhibition or less, and most preferably about 30% inhibition or less at 10 μM.

In some embodiments, preferred compounds according to the present invention exhibit in vivo activity in the Rhesus assay.

In some embodiments, preferred compounds according to the present invention are compounds set forth in Table 14.

In some embodiments, preferred compounds are compounds selected from the group consisting of 55, 62, 721, 119, 743, 195, 214, 234, 312, 320, 322, 641, 638, 643, 613, 6, 18, Ex. 7, 46, 52, 728, 57, 719, 72, 722, 79, 96, 97, 724, 648, 99, 102, 103, 108, 113, 117, 127, 166, 193, 227, 228, 229, 235, 274, 659, 661, 666, 672, 694, 313, 314, 328, 559, 569, 585, 365, 376, 380, and 555. In some embodiments, preferred compounds are compounds selected from the group consisting of 55, 62, 721, 119, 743, 195, 214, 234, 312, 320, and 322.

As provided herein, the compounds of the present invention are useful in the treatment of malaria, chemoprophylaxis, and/or infection by one or more *Plasmodium* spp. In some embodiments, the *Plasmodium* spp. is selected from the group consisting of D6, W2, C235, and C2B. In some embodiments, the *Plasmodium* spp. is a drug resistant strain. In some embodiments, the subject is a mammal, preferably a human. In some embodiments, the subject is a human. In some embodiments, the subject is in need thereof. As used herein, a "subject in need" is one who has been diagnosed as having or suffers from malaria or will likely be exposed to *Plasmodium* spp.

In some embodiments, the subject is administered a therapeutically effective amount of one or more compounds, preferably one or more preferred compounds, according to the present invention, more preferably one or more compounds selected from the group consisting of 55, 62, 721, 119, 743, 195, 214, 234, 312, 320, 322, 641, 638, 643, 613, 6, 18, Ex. 7, 46, 52, 728, 57, 719, 72, 722, 79, 96, 97, 724, 648, 99, 102, 103, 108, 113, 117, 127, 166, 193, 227, 228, 229, 235, 274, 659, 661, 666, 672, 694, 313, 314, 328, 559, 569, 585, 365, 376, 380, and 555, and most preferably one or more compounds selected from the group consisting of 55, 62, 721, 119, 743, 195, 214, 234, 312, 320, and 322. In some embodiments, the subject is treated before, during, and/or after exposure to one or more *Plasmodium* spp.

In some embodiments, the present invention is directed to a method of malaria, providing chemoprophylaxis, and/or treating or inhibiting an infection by one or more *Plasmodium* spp. in a subject which comprises, consists essentially of, or consists of administering a therapeutically effective amount of one or more compounds, preferably one or more preferred compounds according to the present invention, more preferably one or more compounds selected from the group consisting of 55, 62, 721, 119, 743, 195, 214, 234, 312, 320, 322, 641, 638, 643, 613, 6, 18, Ex. 7, 46, 52, 728, 57, 719, 72, 722, 79, 96, 97, 724, 648, 99, 102, 103, 108, 113, 117, 127, 166, 193, 227, 228, 229, 235, 274, 659, 661, 666, 672, 694, 313, 314, 328, 559, 569, 585, 365, 376, 380, and 555, and most preferably one or more compounds selected from the group consisting of 55, 62, 721, 119, 743, 195, 214, 234, 312, 320, and 322, or compositions thereof. In some embodiments, the therapeutically effective amount is administered as a single dose or as multiple doses over a period of time.

In some embodiments, the present invention is directed to the use of one or more compounds, preferably one or more preferred compounds according to the present invention, or compositions thereof for treating malaria, providing chemoprophylaxis, and/or treating or inhibiting an infection by one or more *Plasmodium* spp.

In some embodiments, the present invention is directed to the use of one or more compounds, preferably one or more preferred compounds according to the present invention, or compositions thereof for the manufacture of a medicament for treating malaria, providing chemoprophylaxis, and/or treating or inhibiting an infection by one or more *Plasmodium* spp.

In some embodiments, the present invention is directed to the use of one or more compounds, preferably one or more preferred compounds according to the present invention, or compositions thereof for the manufacture of a medicament for treating malaria, providing chemoprophylaxis, and/or treating or inhibiting an infection by one or more *Plasmodium* spp., wherein the medicament is prepared to be administered in a therapeutically effective amount.

TABLE 1

| Cmpd | SMILES | Amine |
|---|---|---|
| 1A | ClC(C1═NC(NC2═CC═CN═C2OC)═NC(C(Cl)(Cl)Cl)═N1)(Cl)Cl | 2-methoxypyridin-3-amine |
| 1B | ClC(C1═NC(NC2═CC═C(OC)N═C2)═NC(C(Cl)(Cl)Cl)═N1)(Cl)Cl | 6-methoxypyridin-3-amine |
| 1C | ClC(C1═NC(NC2═CC═C(Cl)C(Cl)═C2)═NC(C(Cl)(Cl)Cl)═N1)(Cl)Cl | 3,4-dichloroaniline |
| 1D | FC(F)(F)OC1═CC═C(NC2═NC(C(Cl)(Cl)Cl)═NC(C(Cl)(Cl)Cl)═N2)C═C1 | 4-(trifluoromethoxy)aniline |
| 1E | OC1═CC═C(NC2═NC(C(Cl)(Cl)Cl)═NC(C(Cl)(Cl)Cl)═N2)C═C1 | 4-aminophenol |
| 1F | ClC(C1═NC(NC2═CC(Cl)═CC(Cl)═C2)═NC(C(Cl)(Cl)Cl)═N1)(Cl)Cl | 3,5-dichloroaniline |
| 1G | ClC(C1═NC(NC2═CC═CC═C2)═NC(C(Cl)(Cl)Cl)═N1)(Cl)Cl | aniline |
| 1H | ClC(C1═NC(NC2═CC═C3C═CC═CC3═C2)═NC(C(Cl)(Cl)Cl)═N1)(Cl)Cl | naphthylamine |
| 1I | FC(C1═CC(NC2═NC(C(Cl)(Cl)Cl)═NC(C(Cl)(Cl)Cl)═N2)═CC═C1)(F)F | 3-(trifluoromethyl)aniline |

TABLE 2

| Cmpd | SMILES | Method | Nitrile |
|---|---|---|---|
| 2A | ClC(C1═NC(C2═CC═CC(OC)═C2)═NC(C(Cl)(Cl)Cl)═N1)(Cl)Cl | 1 | 3-methoxybenzonitrile |
| 2B | ClC(C1═NC(C2═CC═C(OC)C═C2)═NC(C(Cl)(Cl)Cl)═N1)(Cl)Cl | 1 | 4-methoxybenzonitrile |
| 2C | ClC(C1═NC(C2═CC═C(Cl)C(Cl)═C2)═NC(C(Cl)(Cl)Cl)═N1)(Cl)Cl | 1 | 3,4-dichlorobenzonitrile |
| 2D | ClC(C1═NC(C2═CC═C(Cl)C═C2)═NC(C(Cl)(Cl)Cl)═N1)(Cl)Cl | 1 | 4-chlorobenzonitrile |
| 2E | ClC(C1═NC(C2═CC═C(C(C)(C)C)C═C2)═NC(C(Cl)(Cl)Cl)═N1)(Cl)Cl | 1 | 4-(tert-butyl)benzonitrile |
| 2F | FC(C1═CC(C2═NC(C(Cl)(Cl)Cl)═NC(C(Cl)(Cl)Cl)═N2)═CC═C1)(F)F | 1 | 3-(trifluoromethyl)benzonitrile |
| 2G | ClC(C1═NC(C2═CC═C(SC)C═C2)═NC(C(Cl)(Cl)Cl)═N1)(Cl)Cl | 1 | 4-(methylthio)benzonitrile |
| 2H | ClC(C1═CC═C(C2═NC(C(Cl)(Cl)Cl)═NC(C(Cl)(Cl)Cl)═N2)C═C1)(Cl)Cl | 1[a] | 4-(trichloromethyl)benzonitrile |
| 2I | ClC(C1═NC(C2═CC═CC═C2)═NC(C(Cl)(Cl)Cl)═N1)(Cl)Cl | 1 | benzonitrile |
| 2J | ClC(C1═NC(C2═CC═C3C═CC═CC3═C2)═NC(C(Cl)(Cl)Cl)═N1)(Cl)Cl | 1[b] | 2-naphthonitrile |
| 2K | ClC(C1═NC(C2═CC═CC═C2C)═NC(C(Cl)(Cl)Cl)═N1)(Cl)Cl | 2 | 2-methylbenzonitrile |
| 2L | ClC(C1═NC(C2═CC(Cl)═CC(Cl)═C2)═NC(C(Cl)(Cl)Cl)═N1)(Cl)Cl | 1 | 3,5-dichlorobenzonitrile |
| 2M | ClC(C1═NC(C2═CC═C(C3═CC═CC═C3)C═C2)═NC(C(Cl)(Cl)Cl)═N1)(Cl)Cl | 1 | [1,1'-biphenyl]-4-carbonitrile |
| 2N | ClC(C1═NC(C2═CC═CC([N+]([O-])═O)═C2)═NC(C(Cl)(Cl)Cl)═N1)(Cl)Cl | 1 | 2-nitrobenzonitrile |
| 2O | ClC(C1═NC(C2═CC═CC═C2C3═CC═C(C)C═C3)═NC(C(Cl)(Cl)Cl)═N1)(Cl)Cl | 1 | 4'-methyl-[1,1'-biphenyl]-2-carbonitrile |
| 2P | ClC(C1═NC(C2═CC═CC(Cl)═C2)═NC(C(Cl)(Cl)Cl)═N1)(Cl)Cl | 2 | 3-chlorobenzonitrile |
| 2Q | ClC(C1═NC(C2═CC═C(F)C═C2)═NC(C(Cl)(Cl)Cl)═N1)(Cl)Cl | 1 | 4-fluorobenzonitrile |
| 2R | ClC(C1═NC(C2═C3C═CC═CC3═C(OC)C═C2)═NC(C(Cl)(Cl)Cl)═N1)(Cl)Cl | 1 | 4-methoxy-1-naphthonitrile |
| 2S | ClC(C1═NC(C2═CC(OC)═C(OC)C═C2)═NC(C(Cl)(Cl)Cl)═N1)(Cl)Cl | 1 | 3,4-dimethoxybenzonitrile |
| 2T | ClC(C1═NC(C2═CC(OC)═CC(OC)═C2)═NC(C(Cl)(Cl)Cl)═N1)(Cl)Cl | 1 | 3,5-dimethoxybenzonitrile |
| 2U | ClC(C1═NC(C2═CC(C═CC(C)(C)O3)═C3C═C2)═NC(C(Cl)(Cl)Cl)═N1)(Cl)Cl | 1 | 2,2-dimethyl-2H-chromene-6-carbonitrile |
| 2V | ClC(C1═NC(C2═CC═CC═C2OC)═NC(C(Cl)(Cl)Cl)═N1)(Cl)Cl | 2 | 2-methoxybenzonitrile |
| 2W | ClC(C1═NC(CC2═CC═CC═C2OC)═NC(C(Cl)(Cl)Cl)═N1)(Cl)Cl | 2 | 2-(2-methoxyphenyl)acetonitrile |
| 2X | ClC(C1═NC(CC2═CC═C(OC)C═C2)═NC(C(Cl)(Cl)Cl)═N1)(Cl)Cl | 2 | 2-(4-methoxyphenyl)acetonitrile |
| 2Y | ClC(C1═NC(CC2═CC═CC(OC)═C2)═NC(C(Cl)(Cl)Cl)═N1)(Cl)Cl | 2 | 2-(3-methoxyphenyl)acetonitrile |
| 2Z | ClC(C1═NC(C(Cl)(Cl)Cl)═NC(C(Cl)(Cl)Cl)═N1)(Cl)Cl | 1 | trichloroacetonitrile |
| 2AA | ClC(C1═NC(C2═CC═C(N3CCCC3)C═C2)═NC(C(Cl)(Cl)Cl)═N1)(Cl)Cl | 1[c] | 4-(pyrrolidin-1-yl)benzonitrile |
| 2AB | O═C(OCC)C1═CC═C(C2═NC(C(Cl)(Cl)Cl)═NC(C(Cl)(Cl)Cl)═N2)C═C1 | 1 | ethyl 4-cyanobenzoate |
| 2AC | FC(C1═CC═C(C2═NC(C(Cl)(Cl)Cl)═NC(C(Cl)(Cl)Cl)═N2)C═C1)(F)F | 2 | 4-(trifluoromethyl)benzonitrile |
| 2AD | ClC(C1═CC═C(C2═NC(C(Cl)(Cl)Cl)═NC(C(Cl)(Cl)Cl)═N2)C═C1)(Cl)Cl | 2 | 3-(trichloromethyl)benzonitrile |
| 2AE | ClC(C1═NC(C2═CC(C(F)(F)F)═CC(C(F)(F)F)═C2)═NC(C(Cl)(Cl)Cl)═N1)(Cl)Cl | 2 | 3,5-bis(trifluoromethyl)benzonitrile |
| 2AF | ClC(C1═NC(C2═CC(C(Cl)(Cl)Cl)═CC(C(Cl)(Cl)Cl)═C2)═NC(C(Cl)(Cl)Cl)═N1)(Cl)Cl | 2 | 3,5-bis(trichloromethyl)benzonitrile |

[a]substitute acetonitrile for methanol
[b]substitute diethyl ether for methanol
[c]substitute CH$_2$Cl$_2$ for methanol

TABLE 3

| Cmpd | SMILES | Amine |
|---|---|---|
| 7A | CC(NC1═CC═CC(NC2═NC(C(Cl)(Cl)Cl)═NC(C(Cl)(Cl)Cl)═N2)═C1)═O | N$^1$-(3-aminophenyl)acetamide |
| 7B | ClC(C1═NC(NC2═CC═C(N3CCN(C)CC3)C═C2)═NC(C(Cl)(Cl)Cl)═N1)(Cl)Cl | 4-(4-methylpiperazino)aniline |
| 7C | ClC(C1═NC(NC2═CC═C(N3N═CC═C3)C═C2)═NC(C(Cl)(Cl)Cl)═N1)(Cl)Cl | 4-(1H-pyrazol-1-yl)aniline |
| 7D | ClC(C1═NC(NC2═CC═CC═C2OC)═NC(C(Cl)(Cl)Cl)═N1)(Cl)Cl | 2-methoxyaniline |
| 7E | ClC(C1═NC(NC2═CC═CC═C2N3CCOCC3)═NC(C(Cl)(Cl)Cl)═N1)(Cl)Cl | 2-morpholinoaniline |

TABLE 4

| Amine | Chemical Name |
|---|---|
| A1 | N-(2-aminoethyl)pyrrolidine |
| A2 | N-(3-aminopropyl)pyrrolidine |
| A3 | 2-(2-aminoethyl)-1-methylpyrrolidine |
| A4 | N,N-diethylethylenediamine |
| A5 | 2-(pyrazin-2-yl)ethanamine |
| A6 | (1S,4S)-(−)-2-Boc-2,5-diazabicyclo[2.2.1]-heptane |
| A7 | homopiperazine |
| A8 | N-methyl-homopiperazine |
| A9 | piperazine |
| A10 | 1-methylpiperazine |
| A11 | 1,2-diamino-2-methylpropane |
| A12 | 4-amino-1-methyl-piperidine |
| A13 | 2-methoxypyridin-3-amine |
| A14 | 4-N-Boc-aminopiperidine |
| A15 | 4-piperidinamine |
| A16 | (1-ethyl-4-piperidinyl)methanamine |
| A17 | 1-ethyl-3-piperidinamine |
| A18 | 4-aminopyridine |
| A19 | N-methyl-2-(pyridin-4-yl)ethanamine |
| A20 | morpholine |
| A21 | 2-(piperazin-1-yl)ethanol |
| A22 | 1-(1-ethylpiperidin-4-yl)ethanamine |
| A23 | 2-(1,4-diazepan-1-yl)ethanol |
| A24 | $N^1,N^1$-dimethylpropane-1,3-diamine |
| A25 | 1-isobutylpiperidin-4-amine |
| A26 | 4-(aminomethyl) oxan-4-amine |
| A27 | 3-(aminomethyl) pentan-3-amine |
| A28 | 1-(aminomethyl) cyclohexan-1-amine dihydrochloride |
| A29 | 1-(aminomethyl) cyclopentan-1-amine dihydrochloride |
| A30 | 1-(aminomethyl) cyclopropan-1-amine dihydrochloride |
| A31 | 4-Amino-2,2,6,6-tetramethylpiperidine |
| A32 | (1-isopropylpiperidin-4-yl)methanamine |
| A33 | (1-methylpiperidin-4-yl)methanamine |
| A34 | 3-N-Boc-amino-azetidine |
| A35 | 4-(aminomethyl)pyridine |
| A36 | 3-picolylamine |
| A37 | 2-(aminomethyl)pyridine |
| A38 | 2-pyridin-4-yl-ethylamine |
| A39 | 3-(2-aminoethyl)pyridine |
| A40 | 2-(2-aminoethyl)pyridine |
| A41 | 2-morpholinoaniline |
| A42 | 4-(1H-pyrazol-1-yl)aniline |
| A43 | 4-(4-methylpiperzino)aniline |
| A44 | $N^1$-(3-aminophenyl)acetamide |
| A45 | 2-((2-aminoethyl)thio)ethanol |
| A46 | (1,3-dimethyl-1H-pyrazol-5-yl)methanamine |
| A47 | N,N-dimethylpyrrolidin-3-amine |
| A48 | 3-(azepan-1-yl)-2,2-dimethylpropan-1-amine |
| A49 | N-methyl-N-(2-pyridin-3-ylbenzyl)amine |
| A50 | 3-aminopyridine |
| A51 | 3,4-dichlorophenylaniline |
| A52 | (3-(pyrrolidin-1-ylmethyl)phenyl)methanamine |
| A53 | piperidine-4-carboxamide |
| A54 | $N^2,N^2$-dimethylpropane-1,2-diamine |
| A55 | $N^1,N^1$-dimethylpropane-1,2-diamine |
| A56 | 2-morpholinoethanamine |
| A57 | ethanolamine |
| A58 | N,N-dimethylpiperidin-3-amine |
| A59 | N-(2-hydroxyethyl)ethylenediamine |
| A60 | cyclohexane-1,2-diamine |
| A61 | sarcosine tert-butyl ester hydrochloride |
| A62 | 5-(Pyrrolidin-1-yl)pentan-1-amine |
| A63 | $N^1,N^1$-Diethylpropane-1,3-diamine |
| A64 | (1-ethylpyrrolidin-3-yl)methanamine |
| A65 | 1-(1-methylpiperidin-2-yl)methanamine |
| A66 | N,N-Dimethylcyclohexane-1,4-diamine |
| A67 | (3-aminobutyl)diethylamine |
| A68 | (2-aminopropyl)diethylamine |
| A69 | 4-Amino-1-diethylaminopentane |
| A70 | N-methyl-2-(pyridin-2-yl)ethanamine |
| A71 | $N^1,N^1$-diethylcyclohexane-1,3-diamine |
| A72 | $N^1,N^1$-dipropylpropane-1,2-diamine |

TABLE 5

| Cmpd | SMILES | Prep | Amine | MS, calc'd | MS, found (M + 1) or mp (° C.) |
|---|---|---|---|---|---|
| 2 | CC(CN(C)C)Nc1nc(nc(n1)C(Cl)(Cl)Cl)c2ccc(Cl)c(Cl)c2 | 2C | A55 | 440.98 | 442.31 |
| 3 | CN(C)C1CCN(C1)c2nc(n2)C(Cl)(Cl)Cl)c3cccc(c3)C(F)(F)F | 2F | A47 | 453.05 | 454.16 |
| 4 | FC(F)(F)c1cccc(c1)c2nc(NCCN3CCOCC3)nc(n2)C(Cl)(Cl)Cl | 2F | A56 | 469.05 | 470.21 |
| 5 | FC(F)(F)c1cccc(c1)c2nc(NCCN3CCCC3)nc(n2)C(Cl)(Cl)Cl | 2F | A1 | 453.05 | 454.41 |
| 6 | COc1cccc(c1)c2nc(NCCCN3CCCC3)nc(n2)C(Cl)(Cl)Cl | 2A | A2 | 429.09 | 430.22 |
| 7 | COc1ccc(cc1)c2nc(NCCCN3CCCC3)nc(n2)C(Cl)(Cl)Cl | 2B | A2 | 429.09 | 430.36 |
| 8 | CN(C)C1CCCN(C1)c2nc(nc(n2)C(Cl)(Cl)Cl)c3cccc(c3)C(F)(F)F | 2F | A58 | 467.07 | 468.17 |
| 9 | COc1ccc(cc1)c2nc(nc(n2)C(Cl)(Cl)Cl)N3CCCC(C3)N(C)C | 2B | A47 | 415.07 | 416.24 |
| 10 | CN(C)C1CCN(C1)c2nc(nc(n2)C(Cl)(Cl)Cl)c3ccc(Cl)cc3 | 2D | A47 | 419.02 | 420.35 |
| 11 | CCOC(=O)c1ccc(cc1)c2nc(NCCN3CCCC3)nc(n2)C(Cl)(Cl)Cl | 2AB | A1 | 457.08 | 458.28 |
| 12 | CCOC(=O)c1ccc(cc1)c2nc(NCCCN3CCCC3)nc(n2)C(Cl)(Cl)Cl | 2AB | A2 | 471.10 | 472.29 |
| 13 | CCOC(=O)c1ccc(cc1)c2nc(nc(n2)C(Cl)(Cl)Cl)N3CCC(C3)N(C)C | 2AB | A47 | 457.08 | 458.21 |
| 14 | CCOC(=O)c1ccc(cc1)c2nc(NCC(C)(C)N)nc(n2)C(Cl)(Cl)Cl | 2AB | A11 | 431.07 | 432.17 |
| 15 | CCOC(=O)c1ccc(cc1)c2nc(NCCN(CC)CC)nc(n2)C(Cl)(Cl)Cl | 2AB | A4 | 459.10 | 460.23 |
| 16 | CCOC(=O)c1ccc(cc1)c2nc(nc(n2)C(Cl)(Cl)Cl)N3CCN(C)CC3 | 2AB | A10 | 443.07 | 444.24 |
| 17 | CCOC(=O)c1ccc(cc1)c2nc(nc(n2)C(Cl)(Cl)Cl)N3CCNCC3 | 2AB | A9 | 429.05 | 430.32 |
| 18 | Clc1cccc(cc1)c2nc(NCCN3CCCC3)nc(n2)C(Cl)(Cl)Cl | 2D | A1 | 419.02 | 420.20 |
| 19 | Clc1cccc(cc1Cl)c2nc(NCCCN3CCCC3)nc(n2)C(Cl)(Cl)Cl | 2D | A1 | 452.98 | 454.32 |
| 20 | CN(C)C1CCN(C1)c2nc(nc(n2)C(Cl)(Cl)Cl)c3ccc(Cl)c(Cl)c3 | 2C | A47 | 452.98 | 454.53 |
| 21 | CC(C)(N)CNc1nc(nc(n1)C(Cl)(Cl)Cl)c2ccc(Cl)c(Cl)c2 | 2C | A11 | 426.97 | 428.27 |
| 22 | CN1CCN(CC1)c2nc(nc(n2)C(Cl)(Cl)Cl)c3ccc(Cl)c(Cl)c3 | 2C | A10 | 438.97 | 440.28 |
| 23 | CN(CCc1ccncc1)c2nc(nc(n2)C(Cl)(Cl)Cl)c3ccc(Cl)c(Cl)c3 | 2C | A19 | 474.97 | |
| 25 | Clc1ccc(cc1Cl)c2nc(nc(n2)C(Cl)(Cl)Cl)N3CCNCC3 | 2C | A9 | 424.95 | |
| 26 | Clc1ccc(cc1)c2nc(NCc3ccncc3)nc(n2)C(Cl)(Cl)Cl | 2C | A35 | 446.94 | |
| 27 | COc1ccc(cc1)c2nc(NCCCN3CCCC3)nc(n2)C(Cl)(Cl)Cl | 2B | A1 | 415.07 | |
| 28 | COc1ccc(cc1)c2nc(nc(n2)C(Cl)(Cl)Cl)N3CCNCC3 | 2B | A9 | 387.04 | 388.22 |
| 29 | CN1CCN(CC1)c2nc(nc(n2)C(Cl)(Cl)Cl)c3ccc(Cl)cc3 | 2D | A10 | 405.01 | 406.00 |
| 30 | OCCSCCNc1nc(nc(n1)C(Cl)(Cl)Cl)c2ccc(Cl)c(Cl)c2 | 2C | A45 | 459.93 | |
| 31 | Clc1ccc(cc1)c2nc(nc(n2)C(Cl)(Cl)Cl)N3CCOCC3 | 2D | A20 | 391.98 | 393.07 |
| 32 | CN1CCN(CC1)c2nc(nc(n2)C(Cl)(Cl)Cl)c3ccc(cc3)C(C)(C)C | 2E | A10 | 427.11 | 428.22 |

TABLE 5-continued

| Cmpd | SMILES | Prep | Amine | MS, calc'd | MS, found (M + 1) or mp (° C.) |
|---|---|---|---|---|---|
| 33 | CCN(CC)CCNc1nc(nc(n1)C(Cl)(Cl)Cl)c2ccc(cc2)C(C)(C)C | 2E | A4 | 443.14 | 444.16 |
| 34 | CC(C)(C)c1ccc(cc1)c2nc(NCCCN3CCCC3)nc(n2)C(Cl)(Cl)Cl | 2E | A2 | 455.14 | 456.29 |
| 35 | ClC(Cl)(Cl)c1nc(NCCCN2CCCC2)nc(n1)c3ccc(OCc4ccccc4)cc3 | 4 | A1 | 491.10 | 492.19 |
| 36 | ClC(Cl)(Cl)c1nc(NCCCN2CCCC2)nc(n1)c3ccc(OCc4ccccc4)cc3 | 4 | A2 | 491.10 | 492.12 |
| 37 | CCN1CCC(CNc2nc(nc(n2)C(Cl)(Cl)Cl)c3ccc(OCc4ccccc4)cc3)CC1 | 4 | A16 | 519.14 | 520.29 |
| 38 | CCN1CCC(CNc2nc(nc(n2)C(Cl)(Cl)Cl)c3ccc(cc3)S(=O)(=O)C)CC1 | 6 | A16 | 491.07 | 492.00 |
| 39 | CS(=O)(=O)c1ccc(cc1)c2nc(NCCCN3CCCC3)nc(n2)C(Cl)(Cl)Cl | 6 | A1 | 463.04 | 464.00 |
| 40 | OCCN1CCN(CC1)c2nc(nc(n2)C(Cl)(Cl)Cl)c3ccc(Cl)cc3 | 2D | A21 | 435.02 | 435.90 |
| 41 | COc1ccc(c1)c2nc(nc(n2)C(Cl)(Cl)Cl)N3CCN(CCO)CC3 | 2A | A21 | 431.07 | 432.15 |
| 42 | OCCN1CCN(CC1)c2nc(nc(n2)C(Cl)(Cl)Cl)c3cccc(c3)C(F)(F)F | 2F | A21 | 469.05 | 470.00 |
| 43 | COc1ccc(c1)c2nc(nc(n2)C(Cl)(Cl)Cl)N3CCN(C)CC3 | 2A | A10 | 401.06 | 402.00 |
| 44 | CSc1ccc(cc1)c2nc(NCCCN3CCCC3)nc(n2)C(Cl)(Cl)Cl | 2G | A2 | 445.07 | 446.29 |
| 45 | CSc1ccc(cc1)c2nc(NCCC3CCCN3C)nc(n2)C(Cl)(Cl)Cl | 2G | A3 | 445.07 | 446.00 |
| 46 | CN1CCCC1CCNc2nc(nc(n2)C(Cl)(Cl)Cl)c3ccc(cc3)C(C)(C)C | 2E | A3 | 455.14 | 456.92 |
| 47 | CSc1ccc(cc1)c2nc(NCCCN3CCCC3)nc(n2)C(Cl)(Cl)Cl | 2G | A1 | 431.05 | 432.18 |
| 48 | CSc1ccc(cc1)c2nc(nc(n2)C(Cl)(Cl)Cl)N3CCN(C)CC3 | 2G | A10 | 449.02 | 450.05 |
| 49 | CCN(CC)CCNc1nc(nc(n1)C(Cl)(Cl)Cl)c2ccc(SC)cc2 | 2G | A4 | 433.07 | 434.12 |
| 50 | Cc1ccc(cc1)c2nc(NCCCN3CCCC3)nc(n2)C(Cl)(Cl)Cl | 2 | A1 | 399.08 | 400.11 |
| 51 | Cc1ccc(cc1)c2nc(NCCCN3CCCC3)nc(n2)C(Cl)(Cl)Cl | 2 | A2 | 413.09 | 414.13 |
| 52 | CN1CCCC1CCNC1=NC(=NC(=N1)C(Cl)(Cl)Cl)C1=CC=C(C)C=C1 | 2 | A3 | 413.09 | 414.49 |
| 53 | CCN(CC)CCNc1nc(nc(n1)C(Cl)(Cl)Cl)c2ccc(C)cc2 | 2 | A4 | 415.02 | 416.15 |
| 54 | CN1CCN(CC1)c2nc(nc(n2)C(Cl)(Cl)Cl)c3ccc(cc3)S(=O)(=O)C | 6 | A10 | 449.02 | 450.07 |
| 55 | CC(C)(N)CNc1nc(nc(n1)C(Cl)(Cl)Cl)c2ccc(cc2)C(Cl)(Cl)Cl | 2H | A11 | 474.95 | 476.22 |
| 56 | CN(C)C1CCN(C1)c2nc(nc(n2)C(Cl)(Cl)Cl)c3ccc(cc3)C(Cl)(Cl)Cl | 2H | A47 | 500.96 | 502.08 |
| 57 | ClC(Cl)(Cl)c1ccc(cc1)c2nc(NCCCN3CCCC3)nc(n2)C(Cl)(Cl)Cl | 2H | A3 | 500.96 | 502.02 |
| 58 | CS(=O)(=O)c1ccc(cc1)c2nc(nc(n2)C(Cl)(Cl)Cl)N3CCOCC3 | 6 | A20 | 435.99 | 437.15 |
| 59 | CCN(CC)CCNc1nc(Cc2ccc(OC)cc2)nc(n1)C(Cl)(Cl)Cl | 2X | A4 | 431.10 | 432.02 |
| 60 | COc1ccc(Cc2nc(NCCCN3CCCC3)nc(n2)C(Cl)(Cl)Cl)cc1 | 2X | A2 | 443.10 | 444.00 |
| 61 | CN1CCC(CC1)Nc2nc(nc(n2)C(Cl)(Cl)Cl)c3ccc(cc3)C(Cl)(Cl)Cl | 2H | A12 | 500.96 | 501.97 |
| 62 | CN1CCCN(CC1)c2nc(nc(n2)C(Cl)(Cl)Cl)c3ccc(cc3)C(Cl)(Cl)Cl | 2H | A8 | 500.96 | 501.89 |
| 63 | COc1ccccc1Nc2nc(NCCC3CCCN3C)nc(n2)C(Cl)(Cl)Cl | 7D | A3 | 444.10 | 446.43 |
| 64 | CN1CCCC1CCNc2nc(Nc3ccccc3N4CCOCC4)nc(n2)C(Cl)(Cl)Cl | 7E | A3 | 499.14 | 500.31 |
| 65 | COc1ccccc1Nc2nc(nc(n2)C(Cl)(Cl)Cl)N3CCN(C)CC3 | 7D | A10 | 416.07 | 418.25 |
| 66 | COc1ccccc1Nc2nc(NCCCN3CCCC3)nc(n2)C(Cl)(Cl)Cl | 7D | A1 | 430.08 | 432.42 |
| 67 | COc1ccccc1Nc2nc(NCCCN3CCCC3)nc(n2)C(Cl)(Cl)Cl | 7D | A2 | 444.10 | 446.38 |
| 68 | COc1ccccc1Cc2nc(NCCCN3CCCC3)nc(n2)C(Cl)(Cl)Cl | 2W | A2 | 443.10 | 444.02 |
| 69 | COc1ccccc1Cc2nc(nc(n2)C(Cl)(Cl)Cl)N3CCN(C)CC3 | 2W | A10 | 415.07 | 415.98 |
| 70 | CCN(CC)CCNc1nc(Cc2ccccc2OC)nc(n1)C(Cl)(Cl)Cl | 2W | A4 | 431.10 | 432.13 |
| 71 | COc1ccccc1Cc2nc(NCCC3CCCN3C)nc(n2)C(Cl)(Cl)Cl | 2W | A3 | 443.10 | 444.04 |
| 72 | CN1CCN(CC1)c2nc(nc(n2)C(Cl)(Cl)Cl)c3ccc(cc3)S(=O) | 5 | A10 | 433.03 | 433.94 |
| 73 | CN1CCCC1CCNc2nc(Nc3ccc(cc3)n4cccn4)nc(n2)C(Cl)(Cl)Cl | 7C | A3 | 480.11 | 481.50 |
| 74 | CCN(CC)CCNc1nc(nc(n1)C(Cl)(Cl)Cl)c2ccc(cc2)S(=O)(=O)C | 6 | A4 | 465.06 | 466.29 |
| 75 | CN1CCCC1CCNc2nc(nc(n2)C(Cl)(Cl)Cl)c3ccc(cc3)S(=O)(=O)C | 6 | A3 | 477.06 | 478.09 |
| 76 | CN1CCCN(CC1)c2nc(nc(n2)C(Cl)(Cl)Cl)c3ccc(cc3)S(=O)(=O)C | 6 | A8 | 463.04 | 464.00 |
| 77 | CN1CCC(CC1)Nc2nc(nc(n2)C(Cl)(Cl)Cl)c3ccc(cc3)S(=O)(=O)C | 6 | A12 | 463.04 | 463.99 |
| 78 | CCN1CCCC(C1)Nc2nc(nc(n2)C(Cl)(Cl)Cl)c3ccccc3 | 2I | A17 | 399.08 | 400.07 |
| 79 | CCN1CCCC(C1)Nc2nc(nc(n2)C(Cl)(Cl)Cl)c3ccc(cc3)C(C)(C)C | 2E | A17 | 455.14 | 456.22 |
| 80 | CCN1CCCC(C1)Nc2nc(nc(n2)C(Cl)(Cl)Cl)c3ccc(C)cc3 | 2 | A17 | 413.09 | 414.05 |
| 81 | CCN1CCCC(C1)Nc2nc(Cc3ccc(OC)cc3)nc(n2)C(Cl)(Cl)Cl | 2X | A17 | 443.10 | 444.02 |
| 82 | COc1ccc(Cc2nc(NCCN3CCCC3)nc(n2)C(Cl)(Cl)Cl)c1 | 2Y | A1 | 429.09 | 430.11 |
| 83 | COc1ccc(Cc2nc(NCCCN3CCCC3)nc(n2)C(Cl)(Cl)Cl)c1 | 2Y | A2 | 443.10 | 444.05 |
| 84 | COc1ccc(Cc2nc(NCCC3CCCN3C)nc(n2)C(Cl)(Cl)Cl)c1 | 2Y | A3 | 443.10 | 444.12 |
| 85 | CCN1CCCC(C1)Nc2nc(Cc3ccc(OC)c3)nc(n2)C(Cl)(Cl)Cl | 2Y | A17 | 443.10 | 444.02 |
| 86 | CCN1CCCC(C1)Nc2nc(Cc3ccc(OC)cc3)nc(n2)C(Cl)(Cl)Cl | 2X | A17 | 443.10 | 444.02 |
| 87 | CCN1CCCC(C1)Nc2nc(nc(n2)C(Cl)(Cl)Cl)c3ccc(cc3)S(=O)(=O)C | 6 | A17 | 477.06 | 477.98 |
| 88 | CCN1CCCC(C1)Nc2nc(nc(n2)C(Cl)(Cl)Cl)c3ccc(SC)cc3 | 2G | A17 | 445.07 | 446.36 |
| 89 | COc1ccc(Cc2nc(NCCCN3CCCC3C)nc(n2)C(Cl)(Cl)Cl)c1 | 2X | A3 | 443.10 | 444.24 |
| 90 | COc1ccc(Cc2nc(NCCCN3CCCC3)nc(n2)C(Cl)(Cl)Cl)cc1 | 2X | A1 | 429.09 | 430.01 |
| 91 | CN1CCCC1CCNc2nc(nc(n2)C(Cl)(Cl)Cl)c3ccc(Cl)cc3 | 2D | A3 | 433.04 | 434.17 |
| 92 | CN1CCCC1CCNc2nc(Nc3cccc(NC(=O)C)c3)nc(n2)C(Cl)(Cl)Cl | 7A | A3 | 471.11 | 472.34 |
| 93 | CS(=O)(=O)c1ccc(cc1)c2nc(Nc3cenec3)nc(n2)C(Cl)(Cl)Cl | 6 | A18 | 442.98 | 444.25 |
| 94 | CCN1CCCC(C1)Nc2nc(Cc3ccccc3OC)nc(n2)C(Cl)(Cl)Cl | 2W | A17 | 443.10 | 444.03 |
| 95 | CS(=O)(=O)c1ccc(cc1)c2nc(NCCCN3CCCC3)nc(n2)C(Cl)(Cl)Cl | 6 | A3 | 477.06 | 478.02 |
| 96 | CS(=O)(=O)c1ccc(cc1)c2nc(nc(n2)C(Cl)(Cl)Cl)N3CCCNCC3 | 6 | A7 | 449.02 | 449.98 |
| 97 | CC(C)(N)CNc1nc(nc(n1)C(Cl)(Cl)Cl)c2ccc(cc2)S(=O)(=O)C | 6 | A11 | 437.02 | 438.11 |
| 98 | CS(=O)(=O)c1ccc(cc1)c2nc(NCCNCCO)nc(n2)C(Cl)(Cl)Cl | 6 | A59 | 453.02 | 453.95 |
| 99 | CN1CCN(CC1)c2nc(nc(n2)C(Cl)(Cl)Cl)c3ccc(cc3)C(Cl)(Cl)Cl | 2H | A10 | 486.95 | 487.86 |
| 100 | COc1ccc(c1)c2nc(nc(n2)C(Cl)(Cl)Cl)N3CCCNCC3 | 2A | A7 | 401.06 | 402.23 |
| 101 | COc1ccc(cc1)c2nc(nc(n2)C(Cl)(Cl)Cl)N3CCCNCC3 | 2B | A7 | 401.06 | 402.28 |
| 102 | Cc1ccc(cc1)c2nc(nc(n2)C(Cl)(Cl)Cl)N3CCCNCC3 | 2 | A7 | 385.06 | 386.06 |
| 103 | Clc1ccc(cc1)c2nc(nc(n2)C(Cl)(Cl)Cl)N3CCCNCC3 | 2C | A7 | 438.97 | 439.99 |
| 104 | COc1ccccc1c2nc(NCCCN3CCCC3)nc(n2)C(Cl)(Cl)Cl | 2V | A1 | 415.07 | 416.11 |
| 105 | COc1ccccc1c2nc(NCCCN3CCCC3)nc(n2)C(Cl)(Cl)Cl | 2V | A2 | 429.09 | 430.31 |
| 106 | COc1ccccc1c2nc(NCCC3CCCN3C)nc(n2)C(Cl)(Cl)Cl | 2V | A3 | 429.09 | 430.08 |

TABLE 5-continued

| Cmpd | SMILES | Prep | Amine | MS, calc'd | MS, found (M + 1) or mp (° C.) |
|---|---|---|---|---|---|
| 107 | CCN(CC)CCNc1nc(nc(n1)C(Cl)(Cl)Cl)c2ccccc2OC | 2V | A4 | 417.09 | 418.08 |
| 108 | FC(F)(F)c1cccc(c1)c2nc(nc(n2)C(Cl)(Cl)Cl)N3CCCNCC3 | 2F | A7 | 439.03 | 440.38 |
| 109 | CN1CCCN(CC1)c2nc(nc(n2)C(Cl)(Cl)Cl)c3cccc(c3)C(F)(F)F | 2F | A8 | 453.05 | 454.12 |
| 110 | COc1cccc(c1)c2nc(nc(n2)C(Cl)(Cl)Cl)N3CCCN(C)CC3 | 2A | A8 | 415.07 | 416.23 |
| 111 | COc1ccc(cc1)c2nc(nc(n2)C(Cl)(Cl)Cl)N3CCCN(C)CC3 | 2B | A8 | 415.07 | 416.19 |
| 112 | CN1CCCN(CC1)c2nc(nc(n2)C(Cl)(Cl)Cl)c3ccc(C)cc3 | 2 | A8 | 399.08 | 400.17 |
| 113 | CN1CCCN(CC1)c2nc(nc(n2)C(Cl)(Cl)Cl)c3ccc(Cl)c(Cl)c3 | 2C | A8 | 452.98 | 454.09 |
| 114 | COc1cccccc1c2nc(NC3CCN(C)CC3)nc(n2)C(Cl)(Cl)Cl | 2V | A12 | 415.07 | 416.12 |
| 115 | CC(C)(C)c1ccc(cc1)c2nc(nc(n2)C(Cl)(Cl)Cl)N3CCCNCC3 | 2E | A9 | 427.11 | 428.10 |
| 116 | CN1CCC(CC1)Nc2nc(nc(n2)C(Cl)(Cl)Cl)c3ccc(cc3)C(C)(C)C | 2E | A12 | 441.13 | 442.41 |
| 117 | CC(C)(C)c1ccc(cc1)c2nc(NCC(C)(C)N)nc(n2)C(Cl)(Cl)Cl | 2E | A11 | 415.11 | 416.55 |
| 118 | CS(=O)(=O)c1ccc(cc1)c2cc(cc(c2)C(Cl)(Cl)Cl)N3CCN(CCO)CC3 | 6 | A21 | 479.04 | 480.05 |
| 119 | OCCN1CCN(c2nc(C(Cl)(Cl)Cl)nc(c3ccc(C(Cl)(Cl)Cl)cc3)n2)CC1 | 2H | A21 | 516.96 | 518.09 |
| 120 | CN1CCCN(CC1)c2nc(nc(n2)C(Cl)(Cl)Cl)c3ccc(cc3)C(C)(C)C | 2E | A8 | 441.13 | 442.16 |
| 121 | Cc1ccccc1c2nc(NCCN3CCCC3)nc(n2)C(Cl)(Cl)Cl | 2K | A1 | 399.08 | 400.03 |
| 122 | CN1CCCCC1CNc2nc(nc(n2)C(Cl)(Cl)Cl)c3ccccc3C | 2K | A3 | 413.09 | 414.06 |
| 123 | CCN(CC)CCNc1nc(nc(n1)C(Cl)(Cl)Cl)c2ccccc2C | 2K | A4 | 401.09 | 402.04 |
| 124 | Cc1ccccc1c2nc(nc(n2)C(Cl)(Cl)Cl)N3CCCNCC3 | 2K | A7 | 385.06 | 386.01 |
| 125 | CN1CCCN(CC1)c2nc(nc(n2)C(Cl)(Cl)Cl)c3ccccc3C | 2K | A8 | 399.08 | 400.04 |
| 126 | CN1CCC(CC1)Nc2nc(nc(n2)C(Cl)(Cl)Cl)c3ccccc3C | 2K | A12 | 399.08 | 400.05 |
| 127 | OCCN1CCCN(CC1)c2nc(nc(n2)C(Cl)(Cl)Cl)c3ccc(cc3)C(Cl)(Cl)Cl | 2H | A23 | 530.97 | 532.08 |
| 128 | Cc1ccccc1c2nc(NCCCN3CCCC3)nc(n2)C(Cl)(Cl)Cl | 2K | A2 | 413.09 | 414.06 |
| 129 | CN(Cc1cccccc1c2cccnc2)c3nc(nc(n3)C(Cl)(Cl)Cl)c4ccc(cc4)S(=O)(=O)C | 6 | A49 | 547.04 | 548.12 |
| 130 | COc1ccc(cc1)c2nc(NCc3ccnc3)nc(n2)C(Cl)(Cl)Cl | 2B | A35 | 409.03 | 410.67 |
| 131 | CC(C)(C)c1nc(NCc2ccncc2)nc(n1)C(Cl)(Cl)Cl | 8 | A35 | 359.05 | |
| 132 | CS(=O)(=O)c1nc(nc(n1)C(Cl)(Cl)Cl)N2CCCN(CCO)CC2 | 6 | A23 | 493.05 | 494.25 |
| 133 | COc1ccccc1C2nc(NCc3ccncc3)nc(n2)C(Cl)(Cl)Cl | 2W | A35 | 423.04 | 424.11 |
| 134 | Cc1ccc(cc1)c2nc(NCc3ccncc3)nc(n2)C(Cl)(Cl)Cl | 2 | A35 | 393.03 | 394.41 |
| 135 | COc1ccccc1c2nc(NCc3ccncc3)nc(n2)C(Cl)(Cl)Cl | 2V | A35 | 409.03 | 410.12 |
| 136 | Clc1ccc(cc1)c2nc(NCc3ccncc3)nc(n2)C(Cl)(Cl)Cl | 2D | A35 | 412.98 | 414.64 |
| 137 | CC(C)(C)c1ccc(cc1)c2nc(NCc3ccncc3)nc(n2)C(Cl)(Cl)Cl | 2E | A35 | 435.08 | 436.25 |
| 138 | FC(F)(F)c1cccc(c1)c2nc(NCc3ccncc3)nc(n2)C(Cl)(Cl)Cl | 2F | A35 | 447.00 | 448.07 |
| 139 | Clc1ccc(cc1)c2nc(NCc3ccncc3)nc(n2)C(Cl)(Cl)Cl | 2D | A38 | 426.99 | 428.01 |
| 140 | Clc1ccc(cc1)c2nc(NCc3ccccn3)nc(n2)C(Cl)(Cl)Cl | 2D | A40 | 426.99 | 428.06 |
| 141 | Clc1ccc(cc1)c2nc(NCc3ccccn3)nc(n2)C(Cl)(Cl)Cl | 2D | A37 | 412.98 | 414.05 |
| 142 | Clc1ccc(cc1)c2nc(NCc3ccncc3)nc(n2)C(Cl)(Cl)Cl | 2D | A36 | 412.98 | 414.07 |
| 143 | Clc1ccc(cc1)c2nc(NCc3cccnc3)nc(n2)C(Cl)(Cl)Cl | 2D | A39 | 426.99 | 428.01 |
| 144 | COc1cccccc1C2nc(NCCc3ccncc3)nc(n2)C(Cl)(Cl)Cl | 2W | A39 | 437.06 | 438.05 |
| 145 | Cc1ccc(cc1)c2nc(NCCc3ccncc3)nc(n2)C(Cl)(Cl)Cl | 2 | A38 | 407.05 | 408.08 |
| 146 | COc1ccccc1c2nc(NCCc3ccncc3)nc(n2)C(Cl)(Cl)Cl | 2V | A38 | 423.04 | 424.17 |
| 147 | COc1ccc(cc1)c2nc(NCCc3ccncc3)nc(n2)C(Cl)(Cl)Cl | 2B | A38 | 423.04 | 424.09 |
| 148 | CC(C)(C)c1ccc(cc1)c2nc(NCCc3ccncc3)nc(n2)C(Cl)(Cl)Cl | 2E | A38 | 449.09 | 446.94 |
| 149 | FC(F)(F)c1cccc(c1)c2nc(NCCc3ccncc3)nc(n2)C(Cl)(Cl)Cl | 2F | A38 | 461.02 | 462.56 |
| 150 | CSc1ccc(cc1)c2nc(NCCc3ccncc3)nc(n2)C(Cl)(Cl)Cl | 2G | A38 | 439.02 | 440.03 |
| 151 | COc1cccc(c1)c2nc(NCCc3ccncc3)nc(n2)C(Cl)(Cl)Cl | 2A | A38 | 423.04 | 424.41 |
| 152 | COc1ccccc1c2nc(NCCc3ccncc3)nc(n2)C(Cl)(Cl)Cl | 2W | A36 | 423.04 | 424.10 |
| 153 | Cc1ccc(cc1)c2nc(NCc3ccncc3)nc(n2)C(Cl)(Cl)Cl | 2 | A36 | 393.03 | 394.21 |
| 154 | COc1ccccc1c2nc(NCc3ccncc3)nc(n2)C(Cl)(Cl)Cl | 2V | A36 | 409.03 | 410.10 |
| 155 | COc1ccccc1c2nc(NCc3ccncc3)nc(n2)C(Cl)(Cl)Cl | 2S | A36 | 409.03 | 410.02 |
| 156 | COc1ccc(cc1)c2nc(NCc3ccncc3)nc(n2)C(Cl)(Cl)Cl | 2B | A36 | 209.03 | 410.04 |
| 157 | Clc1ccc(cc1Cl)c2nc(NCc3ccncc3)nc(n2)C(Cl)(Cl)Cl | 2C | A36 | 446.94 | 448.00 |
| 158 | CC(C)(C)c1ccc(cc1)c2nc(NCc3ccncc3)nc(n2)C(Cl)(Cl)Cl | 2E | A36 | 435.08 | 436.17 |
| 159 | FC(F)(F)c1cccc(c1)c2nc(NCc3ccncc3)nc(n2)C(Cl)(Cl)Cl | 2F | A36 | 447.00 | 448.05 |
| 160 | CSc1ccc(cc1)c2nc(NCc3ccncc3)nc(n2)C(Cl)(Cl)Cl | 2G | A36 | 425.00 | 426.03 |
| 161 | CC(C)(C)c1ccc(cc1)c2nc(nc(n2)C(Cl)(Cl)Cl)N3CCNCC3 | 2E | A9 | 413.09 | 414.12 |
| 162 | ClC(Cl)(Cl)c1ccc(cc1)c2nc(NCCc3cccnc3)nc(n2)C(Cl)(Cl)Cl | 2H | A39 | 508.93 | 509.85 |
| 163 | ClC(Cl)(Cl)c1ccc(cc1)c2nc(NCCc3ccccn3)nc(n2)C(Cl)(Cl)Cl | 2H | A40 | 508.93 | 510.18 |
| 164 | ClC(Cl)(Cl)c1ccc(cc1)c2nc(NCc3ccncc3)nc(n2)C(Cl)(Cl)Cl | 2H | A36 | 494.91 | 496.00 |
| 165 | ClC(Cl)(Cl)c1ccc(cc1)c2nc(NCc3ccccn3)nc(n2)C(Cl)(Cl)Cl | 2H | A37 | 493.92 | 495.96 |
| 166 | ClC(Cl)(Cl)c1ccc(cc1)c2nc(NCCc3ccncc3)nc(n2)C(Cl)(Cl)Cl | 2H | A38 | 508.93 | 509.90 |
| 167 | Cc1ccc(cc1)c2nc(NCc3ccccn3)nc(n2)C(Cl)(Cl)Cl | 2 | A37 | 393.03 | 394.10 |
| 168 | COc1ccc(cc1)c2nc(NCc3ccccn3)nc(n2)C(Cl)(Cl)Cl | 2B | A37 | 409.03 | 410.13 |
| 169 | Clc1ccc(cc1Cl)c2nc(NCc3ccccn3)nc(n2)C(Cl)(Cl)Cl | 2C | A37 | 446.94 | 447.96 |
| 170 | CC(C)(C)c1ccc(cc1)c2nc(NCc3ccccn3)nc(n2)C(Cl)(Cl)Cl | 2E | A37 | 435.08 | 436.18 |
| 171 | FC(F)(F)c1cccc(c1)c2nc(NCc3ccccn3)nc(n2)C(Cl)(Cl)Cl | 2F | A37 | 447.00 | 448.02 |
| 172 | Cc1ccc(cc1)c2nc(NCCc3cccnc3)nc(n2)C(Cl)(Cl)Cl | 2 | A39 | 407.05 | 408.08 |
| 173 | COc1cccc(c1)c2nc(NCCc3cccnc3)nc(n2)C(Cl)(Cl)Cl | 2A | A39 | 423.04 | 424.17 |
| 174 | COc1ccc(cc1)c2nc(NCCc3cccnc3)nc(n2)C(Cl)(Cl)Cl | 2B | A39 | 423.04 | 424.12 |
| 175 | CC(C)(C)c1ccc(cc1)c2nc(NCCc3cccnc3)nc(n2)C(Cl)(Cl)Cl | 2E | A39 | 449.09 | 450.12 |
| 176 | Clc1ccc(cc1Cl)c2nc(NCCc3ccncc3)nc(n2)C(Cl)(Cl)Cl | 2C | A38 | 460.95 | 461.96 |
| 177 | CS(=O)(=O)c1ccc(cc1)c2nc(NCc3ccccn3)nc(n2)C(Cl)(Cl)Cl | 6 | A37 | 456.99 | 458.08 |
| 178 | CS(=O)(=O)c1ccc(cc1)c2nc(NCCc3ccncc3)nc(n2)C(Cl)(Cl)Cl | 6 | A38 | 471.01 | 472.06 |
| 179 | CS(=O)(=O)c1ccc(cc1)c2nc(NCCc3cccnc3)nc(n2)C(Cl)(Cl)Cl | 6 | A39 | 471.01 | 472.04 |
| 180 | CS(=O)(=O)c1ccc(cc1)c2nc(NCCc3ccccn3)nc(n2)C(Cl)(Cl)Cl | 6 | A40 | 471.01 | 472.10 |

TABLE 5-continued

| Cmpd | SMILES | Prep | Amine | MS, calc'd | MS, found (M + 1) or mp (° C.) |
|---|---|---|---|---|---|
| 181 | COc1ccccc1c2nc(NCc3ccccn3)nc(n2)C(Cl)(Cl)Cl | 2V | A37 | 409.03 | 410.07 |
| 182 | COc1ccccc1c2nc(NCCc3ccccn3)nc(n2)C(Cl)(Cl)Cl | 2V | A39 | 423.04 | 424.17 |
| 183 | COc1ccccc1c2nc(NCCc3ccccn3)nc(n2)C(Cl)(Cl)Cl | 2V | A40 | 423.04 | 424.14 |
| 184 | COc1cccc(c1)c2nc(NCCc3ccccn3)nc(n2)C(Cl)(Cl)Cl | 2A | A40 | 423.04 | 424.29 |
| 185 | COc1ccc(cc1)c2nc(NCCc3ccccn3)nc(n2)C(Cl)(Cl)Cl | 2B | A40 | 423.04 | 424.12 |
| 186 | FC(F)(F)c1cccc(c1)c2nc(NCCc3ccccn3)nc(n2)C(Cl)(Cl)Cl | 2F | A40 | 461.02 | 462.03 |
| 187 | CSc1ccc(cc1)c2nc(NCCc3ccccn3)nc(n2)C(Cl)(Cl)Cl | 2G | A40 | 439.02 | 440.12 |
| 188 | ClC(Cl)(Cl)c1nc(NCCc2ccccn2)nc(n1)c3ccccc3 | 2I | A40 | 393.03 | 394.49 |
| 189 | Cc1ccc(cc1)c2nc(NCCc3ccccn3)nc(n2)C(Cl)(Cl)Cl | 2 | A40 | 407.05 | 408.09 |
| 190 | Clc1ccc(ccCl)c2nc(NCCc3ccccn3)nc(n2)C(Cl)(Cl)Cl | 2C | A40 | 460.95 | 462.15 |
| 191 | CC(C)(C)c1ccc(cc1)c2nc(NCCc3ccccn3)nc(n2)C(Cl)(Cl)Cl | 2E | A40 | 449.09 | 450.17 |
| 192 | COc1cccc(c1)c2nc(NCCN3CCCC3)nc(n2)C(Cl)(Cl)Cl | 2A | A1 | 415.07 | 416.18 |
| 193 | COc1cccc(c1)c2nc(NC3CCN(C)CC3)nc(n2)C(Cl)(Cl)Cl | 2A | A12 | 415.07 | 416.12 |
| 194 | CC(C)(C)OC(=O)NC1CCN(CC1)c2nc(nc(n2)C(Cl)(Cl)Cl)c3ccc(cc3)C(Cl)(Cl)Cl | 2H | A14 | 587.00 | 587.83 |
| 195 | CC(C)(N)CNc1nc(nc(n1)C(Cl)(Cl)Cl)c2cc(Cl)cc(Cl)c2 | 2L | A11 | 426.97 | 428.73 |
| 196 | ClC(Cl)(Cl)c1nc(NCCN2CCCC2)nc(n1)c3ccc(cc3)c4ccccc4 | 2M | A1 | 461.09 | 462.80 |
| 197 | ClC(Cl)(Cl)c1nc(NCCCN2CCCC2)nc(n1)c3ccc(cc3)c4ccccc4 | 2M | A2 | 475.11 | 476.51 |
| 198 | ClC(Cl)(Cl)c1nc(nc(n1)c2ccc(cc2)c3ccccc3)N4CCCNCC4 | 2M | A7 | 447.08 | 448.15 |
| 199 | CN1CCCN(CC1)c2nc(nc(n2)C(Cl)(Cl)Cl)c3ccc(cc3)c4ccccc4 | 2M | A8 | 461.09 | 462.76 |
| 200 | CN1CCC(CC1)Nc2nc(nc(n2)C(Cl)(Cl)Cl)c3ccc(cc3)c4ccccc4 | 2M | A10 | 461.09 | 462.27 |
| 201 | CN1CCCC1CCNc2nc(nc(n2)C(Cl)(Cl)Cl)c3ccc(cc3)c4ccccc4 | 2M | A3 | 475.11 | 476.55 |
| 202 | ClC1=CC(=CC(Cl)=C1)C1=NC(NCCN2CCCC2)=NC(=N1)C(Cl)(Cl)Cl | 2L | A1 | 452.98 | 454.60 |
| 203 | Clc1cc(Cl)cc(c1)c2nc(NCCCN3CCCC3)nc(n2)C(Cl)(Cl)Cl | 2L | A2 | 467.00 | 468.05 |
| 204 | ClC1=CC(=CC(Cl)=C1)C1=NC(=NC(=N1)C(Cl)(Cl)Cl)N1CCCNCC1 | 2L | A7 | 438.97 | 440.03 |
| 205 | CN1CCCN(CC1)C1=NC(=NC(=N1)C(Cl)(Cl)Cl)C1=CC(Cl)=CC(Cl)=C1 | 2L | A8 | 452.98 | 454.02 |
| 206 | CN1CCC(CC1)Nc2nc(nc(n2)C(Cl)(Cl)Cl)c3cc(Cl)cc(Cl)c3 | 2L | A12 | 452.98 | 454.07 |
| 207 | CN1CCN(CC1)c2nc(nc(n2)C(Cl)(Cl)Cl)c3cc(Cl)cc(Cl)c3 | 2L | A10 | 438.97 | 440.06 |
| 208 | Clc1cc(Cl)cc(c1)c2nc(NCc3ccncc3)nc(n2)C(Cl)(Cl)Cl | 2L | A35 | 446.94 | 448.09 |
| 209 | Clc1cc(Cl)cc(c1)c2nc(NCc3cccnc3)nc(n2)C(Cl)(Cl)Cl | 2L | A36 | 446.94 | 448.00 |
| 210 | Clc1cc(Cl)cc(c1)c2nc(NCc3ccccn3)nc(n2)C(Cl)(Cl)Cl | 2L | A37 | 446.94 | 447.98 |
| 211 | Clc1cc(Cl)cc(c1)c2nc(NCCc3ccncc3)nc(n2)C(Cl)(Cl)Cl | 2L | A38 | 460.95 | 462.03 |
| 212 | CN1CCC(CC1)Nc2nc(nc(n2)C(Cl)(Cl)Cl)c3ccc(c3)C(F)(F)F | 2F | A12 | 453.05 | |
| 213 | CN1CCN(CC1)c2nc(nc(n2)C(Cl)(Cl)Cl)c3cccc(c3)C(F)(F)F | 2F | A10 | 439.03 | 440.08 |
| 214 | CC(C)(N)CNc1nc(nc(n1)C(Cl)(Cl)Cl)c2cccc(c2)C(F)(F)F | 2F | A11 | 427.03 | 428.14 |
| 215 | CCN1CCCC(C1)Nc2nc(nc(n2)C(Cl)(Cl)Cl)c3ccccc3OC | 2V | A17 | 429.09 | 430.12 |
| 216 | COc1ccccc1c2nc(NCC(C)(C)N)nc(n2)C(Cl)(Cl)Cl N3CCN(C)CC3 | 2V | A10 | 401.06 | 402.12 |
| 217 | COc1ccccc1c2nc(NCC(C)(C)N)nc(n2)C(Cl)(Cl)Cl | 2V | A11 | 389.06 | 390.50 |
| 218 | COc1ccccc1c2nc(nc(n2)C(Cl)(Cl)Cl)N3CCCNCC3 | 2V | A7 | 401.06 | 402.53 |
| 219 | CN1CCN(CC1)c2nc(nc(n2)C(Cl)(Cl)Cl)c3ccc4ccccc4c3 | 2J | A10 | 421.06 | 422.17 |
| 220 | CCN(CC)CCNc1nc(nc(n1)C(Cl)(Cl)Cl)c2ccc3ccccc3c2 | 2J | A4 | 437.09 | 438.22 |
| 221 | CN1CCN(CC1)c2nc(nc(n2)C(Cl)(Cl)Cl)c3ccc(C)cc3 | 2 | A10 | 385.06 | 386.22 |
| 222 | CN1CCC(CC1)Nc2nc(nc(n2)C(Cl)(Cl)Cl)c3ccc(Cl)c(Cl)c3 | 2C | A12 | 452.98 | 456.24 |
| 223 | ClC(Cl)(Cl)c1nc(NCc2ccccn2)nc(n1)c3ccc4ccccc4c3 | 2J | A37 | 429.03 | 430.62 |
| 224 | ClC(Cl)(Cl)c1nc(NCCCN2CCCC2)nc(n1)c3ccc4ccccc4c3 | 2J | A2 | 449.09 | 450.58 |
| 225 | ClC(Cl)(Cl)c1nc(NCCc2ccccn2)nc(n1)c3ccc4ccccc4c3 | 2J | A40 | 443.05 | 444.33 |
| 226 | CN1CCCN(CC1)c2nc(nc(n2)C(Cl)(Cl)Cl)c3ccc4ccccc4c3 | 2J | A8 | 435.08 | 436.70 |
| 227 | ClC(Cl)(Cl)c1nc(nc(n1)c2ccc3ccccc3c2)N4CCCNCC4 | 2J | A7 | 421.06 | 422.21 |
| 228 | ClC(Cl)(Cl)c1nc(NCCN2CCCC2)nc(n1)c3ccc4ccccc4c3 | 2J | A1 | 435.08 | 436.63 |
| 229 | CN1CCCC1CCNc2nc(nc(n2)C(Cl)(Cl)Cl)c3ccc4ccccc4c3 | 2J | A3 | 449.09 | 450.65 |
| 230 | ClC(Cl)(Cl)c1nc(NCCc2ccncc2)nc(n1)c3ccc4ccccc4c3 | 2J | A38 | 443.05 | 444.87 |
| 231 | ClC(Cl)(Cl)c1nc(NCCc2cccnc2)nc(n1)c3ccc4ccccc4c3 | 2J | A39 | 443.05 | 444.55 |
| 232 | ClC(Cl)(Cl)c1nc(NCc2cccnc2)nc(n1)c3ccc4ccccc4c3 | 2J | A36 | 429.03 | 430.11 |
| 233 | ClC(Cl)(Cl)c1nc(NCc2ccncc2)nc(n1)c3ccc4ccccc4c3 | 2J | A35 | 429.03 | 430.64 |
| 234 | CN1CCC(CC1)Nc2nc(nc(n2)C(Cl)(Cl)Cl)c3ccc4ccccc4c3 | 2J | A12 | 435.08 | 436.20 |
| 235 | ClC(Cl)(Cl)c1nc(Nc2ccncc2)nc(n1)c3ccc4ccccc4c3 | 2J | A18 | 415.02 | 416.08 |
| 236 | COc1cccc(c1)c2nc(NCCC3CCCN3C)nc(n2)C(Cl)(Cl)Cl | 2A | A3 | 429.08 | 430.22 |
| 237 | CN1CCC(CC1)Nc2nc(nc(n2)C(Cl)(Cl)Cl)c3ccccc3 | 2I | A12 | 385.06 | 386.12 |
| 238 | COc1cccc(c1)c2nc(NCC(C)(C)N)nc(n2)C(Cl)(Cl)Cl | 2A | A11 | 389.06 | 390.12 |
| 239 | CN1CCN(CC1)c2nc(nc(n2)C(Cl)(Cl)Cl)c3ccccc3 | 2I | A10 | 371.05 | 372.07 |
| 240 | CCN(CC)CCNc1nc(nc(n1)C(Cl)(Cl)Cl)c2ccccc2 | 2I | A4 | 387.08 | 388.15 |
| 241 | CN1CCCC(C1)Nc2nc(nc(n2)C(Cl)(Cl)Cl)c3cccc(OC)c3 | 2A | A17 | 429.09 | 430.14 |
| 242 | CCN(CC)CCNc1nc(nc(n1)C(Cl)(Cl)Cl)c2cccc(OC)c2 | 2A | A4 | 417.09 | 418.18 |
| 243 | CCN(CC)CCNc1nc(Cc2cccc(OC)c2)nc(n1)C(Cl)(Cl)Cl | 2Y | A4 | 431.10 | 432.12 |
| 244 | Cc1ccc(cc1)c2nc(NCC(C)(C)N)nc(n2)C(Cl)(Cl)Cl | 2 | A11 | 373.06 | 374.80 |
| 245 | CN1CCC(CC1)Nc2nc(nc(n2)C(Cl)(Cl)Cl)c3ccc(C)cc3 | 2 | A12 | 399.08 | 400.18 |
| 246 | CC(C)(C)c1ccc(cc1)c2nc(NCCN3CCCC3)nc(n2)C(Cl)(Cl)Cl | 2E | A1 | 441.13 | 442.27 |
| 247 | CCN1CCC(CNc2nc(nc(n2)C(Cl)(Cl)Cl)c3ccc(cc3)C(C)(C)C)CC1 | 2E | A16 | 469.16 | 470.16 |
| 248 | ClC(Cl)(Cl)c1nc(NCc2ccncc2)nc(n1)c3ccc(cc3)c4ccccc4 | 2M | A35 | 455.05 | 456.57 |
| 249 | ClC(Cl)(Cl)c1nc(NCc2cccnc2)nc(n1)c3ccc(cc3)c4ccccc4 | 2M | A36 | 455.05 | 456.29 |
| 250 | ClC(Cl)(Cl)c1nc(NCc2ccccn2)nc(n1)c3ccc(cc3)c4ccccc4 | 2M | A37 | 455.05 | 456.11 |
| 251 | ClC(Cl)(Cl)c1nc(NCCc2ccncc2)nc(n1)c3ccc(cc3)c4ccccc4 | 2M | A38 | 469.06 | 470.12 |
| 252 | ClC(Cl)(Cl)c1nc(NCCc2cccnc2)nc(n1)c3ccc(cc3)c4ccccc4 | 2M | A39 | 469.06 | 470.38 |
| 253 | ClC(Cl)(Cl)c1nc(NCCc2ccccn2)nc(n1)c3ccc(cc3)c4ccccc4 | 2M | A40 | 469.06 | 470.62 |
| 254 | CCN(CC)CCNc1nc(nc(n1)C(Cl)(Cl)Cl)c2ccccc2c3ccc(C)cc3 | 2O | A4 | 477.13 | 478.18 |

TABLE 5-continued

| Cmpd | SMILES | Prep | Amine | MS, calc'd | MS, found (M + 1) or mp (° C.) |
|---|---|---|---|---|---|
| 255 | CN1CCC(CC1)Nc2nc(nc(n2)C(Cl)(Cl)Cl)c3ccccc3c4ccc(C)cc4 | 2O | A12 | 475.11 | 476.35 |
| 256 | CCN1CCCC(C1)Nc2nc(nc(n2)C(Cl)(Cl)Cl)c3ccccc3c4ccc(C)cc4 | 2O | A17 | 489.13 | 491.06 |
| 257 | CCN1CCC(CNc2nc(nc(n2)C(Cl)(Cl)Cl)c3ccc(Cl)c(Cl)c3)CC1 | 2C | A16 | 481.02 | 482.13 |
| 258 | CCN1CCC(CNc2nc(nc(n2)C(Cl)(Cl)Cl)c3cccc(OC)c3)CC1 | 2A | A16 | 443.10 | 444.22 |
| 259 | CCN1CCC(CNc2nc(nc(n2)C(Cl)(Cl)Cl)c3ccccc3c4ccc(C)cc4)CC1 | 2O | A16 | 503.14 | 504.27 |
| 260 | Cc1ccc(cc1)c2ccccc2c3nc(NCC(C)(C)N)nc(n3)C(Cl)(Cl)Cl | 2O | A11 | 449.09 | 450.55 |
| 261 | CSc1ccc(cc1)c2nc(nc(n2)C(Cl)(Cl)Cl)N3CCCN(C)CC3 | 2G | A8 | 431.05 | 432.05 |
| 262 | CSc1ccc(cc1)c2nc(nc(n2)C(Cl)(Cl)Cl)N3CCCNCC3 | 2G | A7 | 417.03 | 417.92 |
| 263 | Cc1ccc(cc1)c2ccccc2c3nc(nc(n3)C(Cl)(Cl)Cl)N4CCCNCC4 | 2O | A2 | 461.09 | 462.01 |
| 264 | Cc1ccc(cc1)c2ccccc2c3nc(NCCCN4CCCC4)nc(n3)C(Cl)(Cl)Cl | 2O | A7 | 489.13 | 490.08 |
| 265 | CCN1CCC(CNc2nc(nc(n2)C(Cl)(Cl)Cl)c3ccc(C)cc3)CC1 | 2 | A16 | 427.11 | 428.06 |
| 266 | Cc1ccc(cc1)c2ccccc2c3nc(NCCN4CCCC4)nc(n3)C(Cl)(Cl)Cl | 2O | A1 | 475.11 | 476.08 |
| 267 | CCN1CCCC(C1)Nc2nc(nc(n2)C(Cl)(Cl)Cl)c3ccc(OC)cc3 | 2B | A17 | 429.09 | 430.13 |
| 268 | CCN(CC)CCNc1nc(nc(n1)C(Cl)(Cl)Cl)c2ccc(OC)cc2 | 2B | A4 | 417.09 | 418.12 |
| 269 | COc1ccc(Cc2nc(nc(n2)C(Cl)(Cl)Cl)N3CCCN(C)CC3)c1 | 2Y | A8 | 429.09 | |
| 270 | CSc1ccc(cc1)c2nc(NC3CCN(C)CC3)nc(n2)C(Cl)(Cl)Cl | 2G | A12 | 431.05 | 431.98 |
| 271 | COc1ccc(cc1)c2nc(NC(C)(C)CN)nc(n2)C(Cl)(Cl)Cl | 2B | A11 | 389.06 | 390.49 |
| 272 | COc1ccc(cc1)c2nc(nc(n2)C(Cl)(Cl)Cl)N3CCN(C)CC3 | 2B | A10 | 401.06 | 402.08 |
| 273 | CCN1CCC(CNc2nc(nc(n2)C(Cl)(Cl)Cl)c3ccc(SC)cc3)CC1 | 2G | A16 | 459.08 | 460.17 |
| 274 | CCN1CCC(CNc2nc(nc(n2)C(Cl)(Cl)Cl)c3ccc(OC)cc3)CC1 | 2B | A16 | 443.10 | 444.55 |
| 275 | COc1ccc(cc1)c2nc(NC3CCN(C)CC3)nc(n2)C(Cl)(Cl)Cl | 2B | A12 | 415.07 | 416.16 |
| 276 | CC(C)(C)c1ccc(cc1)c2nc(nc(n2)C(Cl)(Cl)Cl)N3CCN(CCO)CC3 | 2E | A21 | 457.12 | 458.26 |
| 277 | CSc1ccc(cc1)c2nc(NC(C)(C)CN)nc(n2)C(Cl)(Cl)Cl | 2G | A11 | 405.03 | 406.14 |
| 278 | COc1ccc(c2nc(NCCN3CCCC3)nc(n2)C(Cl)(Cl)Cl)c4ccccc14 | 2R | A1 | 465.09 | 466.14 |
| 279 | CCN1CCC(CNc2nc(nc(n2)C(Cl)(Cl)Cl)c3ccc(OC)c4ccccc34)CC1 | 2R | A16 | 493.12 | 494.20 |
| 280 | CCN1CCCC(C1)Nc2nc(nc(n2)C(Cl)(Cl)Cl)c3ccc(OC)c4ccccc34 | 2R | A7 | 479.10 | 480.13 |
| 281 | COc1ccc(c2nc(nc(n2)C(Cl)(Cl)Cl)N3CCCNCC3)c4ccccc14 | 2R | A17 | 451.07 | 452.09 |
| 282 | Clc1ccc(cc1)c2nc(nc(n2)C(Cl)(Cl)Cl)N3CCCNCC3 | 2D | A7 | 405.01 | 406.02 |
| 283 | CCN1CCC(CNc2nc(nc(n2)C(Cl)(Cl)Cl)c3ccc(Cl)cc3)CC1 | 2D | A16 | 447.06 | 448.12 |
| 284 | CC(C)(N)CNc1nc(nc(n1)C(Cl)(Cl)Cl)c2ccc(Cl)cc2 | 2D | A11 | 393.01 | 394.05 |
| 285 | CN1CCC(CC1)Nc2nc(nc(n2)C(Cl)(Cl)Cl)c3ccc(Cl)cc3 | 2D | A12 | 419.02 | 420.08 |
| 286 | CCN(CC)CCNc1nc(nc(n1)C(Cl)(Cl)Cl)c2ccc(Cl)cc2 | 2D | A4 | 421.04 | 422.07 |
| 287 | CN1CCCN(CC1)c2nc(nc(n2)C(Cl)(Cl)Cl)c3ccc(Cl)cc3 | 2D | A8 | 419.02 | 420.09 |
| 288 | COc1cccc(Cc2nc(nc(n2)C(Cl)(Cl)Cl)N3CCN(C)CC3)c1 | 2Y | A10 | 415.07 | 416.38 |
| 289 | COC1=CC=CC=C1CC1=NC(=NC(=N1)C(Cl)(Cl)Cl)N1CCCN(C)CC1 | 2W | A8 | 429.09 | 430.32 |
| 290 | COC1=CC=CC=C1CC1=NC(=N1)C(Cl)(Cl)Cl)N1CCCNCC1 | 2W | A7 | 415.07 | 416.48 |
| 291 | COC1=CC=CC=C1CC1=NC(NC2CCN(C)CC2)=NC(=N1)C(Cl)(Cl)Cl | 2W | A12 | 429.09 | 430.22 |
| 292 | COC1=CC=CC=C1CC1=NC(NCC(C)(C)N)=NC(=N1)C(Cl)(Cl)Cl | 2W | A11 | 403.07 | 404.25 |
| 293 | CCN1CCC(CNC2=NC(CC3=CC=CC=C3OC)=NC(=N2)C(Cl)(Cl)Cl)CC1 | 2W | A16 | 457.12 | 458.25 |
| 294 | COC1=CC=CC=C1CC1=NC(NCCN2CCCC2)=NC(=N1)C(Cl)(Cl)Cl | 2W | A1 | 429.09 | 430.39 |
| 295 | CN1CCCC1CCNC1=NC(NC2=CC=C(OC(F)(F)F)C=C2)=NC(=N1)C(Cl)(Cl)Cl | 1D | A3 | 498.07 | 499.17 |
| 296 | CC(C)(N)CNC1=NC(NC2=CC=C(OC(F)(F)F)C=C2)=NC(=N1)C(Cl)(Cl)Cl | 1D | A11 | 458.04 | 459.14 |
| 297 | CCN1CCCC(C1)NC1=NC(=NC(=N1)C1=CC=C(C=C1)C1=CC=CC=C1)C(Cl)(Cl)Cl | 2M | A17 | 475.11 | 476.16 |
| 298 | CN1CCN(CC1)C1=NC(=NC(=N1)C1=CC=C(C=C1)C1=CC=CC=C1)C(Cl)(Cl)Cl | 2M | A10 | 447.08 | 448.23 |
| 299 | CC1=CC=C(C=C1)C1=C(C=CC=C1)C1=NC(NCC2=CC=NC=C2)=NC(=N1)-C(Cl)(Cl)Cl | 2O | A35 | 469.06 | 471.17 |
| 300 | COC1=C2C=CC=CC2=C(C=C1)C1=NC(NCC2=CC=NC=C2)=NC(=N1)C(Cl)(Cl)Cl | 2R | A35 | 459.04 | 460.32 |
| 301 | CCN1CCC(CNC2=NC(NC3=CC=C(OC(F)(F)F)C=C3)=NC(=N2)C(Cl)(Cl)Cl)CC1 | 1D | A16 | 512.09 | 513.31 |
| 302 | OCCN1CCN(CC1)C1=NC(NC2=CC=C(OC(F)(F)F)C=C2)=NC(=N1)C(Cl)(Cl)Cl | 1D | A21 | 500.05 | 501.02 |
| 303 | NC1(CNC2=NC(NC3=CC=C(OC(F)(F)F)C=C3)=NC(=N2)C(Cl)(Cl)Cl)CCOCC1 | 1D | A26 | 500.05 | 501.07 |
| 304 | OCCN1CCN(CC1)C1=NC(=NC(=N1)C(Cl)(Cl)Cl)C1=CC(Cl)=C(Cl)C=C1)C(Cl)(Cl)Cl | 2C | A23 | 468.98 | 472.23 |
| 305 | OCCN1CCN(CC1)C1=NC(=NC(=N1)C(Cl)(Cl)Cl)C1=CC=C2C=CC=CC2=C1 | 2J | A21 | 451.07 | 452.14 |
| 306 | CCN1CCC(CNC2=NC(=NC(=N2)C(Cl)(Cl)Cl)C2=CC=C(C=C2)C2=CC=CC=C2)CC1 | 2M | A16 | 489.13 | 490.25 |
| 307 | CCN1CCC(CNC2=NC(=NC(=N2)C2=CC=C3C=CC=CC3=C2)C(Cl)(Cl)Cl)CC1 | 2J | A16 | 463.11 | 464.25 |
| 308 | OCCN1CCN(CC1)C1=NC(=NC(=N1)C(Cl)(Cl)Cl)C1=CC=C(C=C1)C1=CC=CC=C1 | 2M | A21 | 477.09 | 478.67 |
| 309 | CSC1=CC=C(C=C1)C1=NC(=NC(=N1)N1CCN(CCO)CC1)C(Cl)(Cl)Cl | 2G | A21 | 447.05 | 448.16 |
| 310 | CCN1CCCC(C1)NC1=NC(=NC(=N1)C(Cl)(Cl)Cl)C1=CC=C2C=CC=CC2=C1 | 2J | A17 | 449.09 | 450.19 |
| 311 | NC1(CNC2=NC(=NC(=N2)C2=CC=C(C=C2)C(Cl)(Cl)Cl)C(Cl)(Cl)Cl)CCOCC1 | 2H | A26 | 516.96 | 518.05 |
| 312 | CC(C)(N)CNC1=NC(=NC(=N1)C1=CC=CC=C1)C(Cl)(Cl)Cl | 2I | A11 | 359.05 | 360.13 |
| 313 | NC1(CNC2=NC(=NC(=N2)C2=CC=CC=C2)C(Cl)(Cl)Cl)CCOCC1 | 2I | A26 | 401.06 | 402.13 |
| 314 | CC(C)C(C)C1=CC=C(C=C1)C1=NC(NCC2(N)CCOCC2)=NC(=N1)C(Cl)(Cl)Cl | 2E | A26 | 457.12 | 458.62 |
| 315 | NC1(CNC2=NC(=NC(=N2)C2=CC=C(C=C2)C(F)(F)F)C(Cl)(Cl)Cl)CCOCC1 | 2F | A26 | 469.05 | 470.15 |
| 316 | CS(=O)(=O)C1=CC=C(C=C1)C1=NC(NCC2(N)CCOCC2)=NC(=N1)C(Cl)(Cl)Cl | 6 | A26 | 479.04 | 480.14 |
| 317 | NC1(CNC2=NC(=NC(=N2)C2=CC3=C(C=CC=C3)C=C2)C(Cl)(Cl)Cl)CCOCC1 | 2J | A26 | 451.07 | 452.26 |
| 318 | COC1=C2C=CC=CC2=C(C=C1)C1=NC(NCC2(N)CCOCC2)=NC(=N1)C(Cl)(Cl)Cl | 2R | A26 | 481.08 | 482.37 |
| 319 | COC1=C(OC=C(C=C1)C1=NC(NCC2(N)CCOCC2)=NC(=N1)C(Cl)(Cl)Cl | 2S | A26 | 461.08 | 462.35 |
| 320 | CC1(C)CC(CC(C)(C)N1)NC1=NC(=NC(=N1)C1=CC=C(C=C1)C(Cl)(Cl)Cl | 2I | A31 | 427.11 | 428.22 |
| 321 | CC(C)(C)C1=CC=C(C=C1)C1=NC(NC2CC(C)(C)NC(C)(C)C2)=NC(=N1)C(Cl)(Cl)Cl | 2E | A31 | 483.17 | 484.28 |
| 322 | CC1(C)CC(CC(C)(C)N1)NC1=NC(=NC(=N1)C1=CC=C(C=C1)C(F)(F)F)C(Cl)(Cl)Cl | 2F | A31 | 495.10 | 496.17 |
| 323 | CSC1=CC=C(C=C1)C1=NC(NC2CC(C)(C)NC(C)(C)C2)=NC(=N1)C(Cl)(Cl)Cl | 2G | A31 | 473.10 | 474.27 |
| 324 | CC1(C)CC(CC(C)(C)N1)NC1=NC(=NC(=N1)C1=CC=C(C=C1)S(=O)(=O)C)C(Cl)(Cl)Cl | 6 | A31 | 505.09 | 506.20 |
| 325 | CC1(C)CC(CC(C)(C)N1)NC1=NC(=NC(=N1)C1=CC=C(C=C1)C(Cl)(Cl)Cl)C(Cl)(Cl)Cl | 2H | A31 | 543.01 | 544.14 |
| 326 | CC1(C)CC(CC(C)(C)N1)NC1=NC(=NC(=N1)C1=CC2=C(C=CC=C2)C=C1)C(Cl)(Cl)Cl | 2J | A31 | 477.13 | 478.26 |
| 327 | CC1(C)CC(CC(C)(C)N1)NC1=NC(=NC(=N1)C1=CC=C(C=C1)C1=CC=CC=C1)- | 2M | A31 | 503.14 | 504.27 |

TABLE 5-continued

| Cmpd | SMILES | Prep | Amine | MS, calc'd | MS, found (M + 1) or mp (° C.) |
|---|---|---|---|---|---|
| | C(Cl)(Cl)Cl | | | | |
| 328 | COC1=C(OC)C=C(C=C1)C1=NC(NC2CC(C)(C)NC(C)(C)C2)=NC(=N1)C(Cl)(Cl)Cl | 2S | A31 | 487.13 | 488.22 |
| 329 | CC(C)(N)CNC1=NC(=NC(=N1)C(Cl)(Cl)Cl)C1=CC2=C(C=CC=C2)C=C1 | 2J | A11 | 409.06 | 410.13 |
| 330 | CC1(C)CC(CC(C(C)(C)N1)NC1=NC(=NC(=N1)C1=CC=C(Cl)C=C1)C(Cl)(Cl)Cl | 2D | A31 | 461.07 | 462.18 |
| 331 | CC(C)(N)CNC1=NC(=NC(=N1)C1=CC=C(C=C1)C1=CC=CC=C1)C(Cl)(Cl)Cl | 2M | A11 | 435.08 | 436.23 |
| 332 | NC1(CNC2=NC(=NC(=N2)C2=CC=C(C=C2)C2=CC=CC=C2)C(Cl)(Cl)Cl)CCOCC1 | 2M | A26 | 477.09 | 478.18 |
| 333 | NC1(CNC2=NC(=NC(=N2)C2=CC=C(Cl)C=C2)C(Cl)(Cl)Cl)CCOCC1 | 2D | A26 | 435.02 | 436.16 |
| 334 | ClC1=CC=CC(=C1)C1=NC(NCCN2CCCC2)=NC(=N1)C(Cl)(Cl)Cl | 2P | A1 | 419.02 | 420.07 |
| 335 | CN1CCCC1CCNC1=NC(=NC(=N1)C1=CC(Cl)=CC=C1)C(Cl)(Cl)Cl | 2P | A3 | 433.04 | 434.26 |
| 336 | ClC1=CC=CC(=C1)C1=NC(=NC(=N1)C(Cl)(Cl)Cl)N1CCCNCC1 | 2P | A7 | 405.01 | 406.23 |
| 337 | CN1CCC(CC1)NC1=NC(=NC(=N1)C1=CC(Cl)=CC=C1)C(Cl)(Cl)Cl | 2P | A12 | 419.02 | 420.36 |
| 338 | CCN1CCCC(C1)NC1=NC(=NC(=N1)C1=CC(Cl)=CC=C1)C(Cl)(Cl)Cl | 2P | A17 | 433.04 | 434.18 |
| 339 | CCN1CCC(CNC2=NC(=NC(=N2)C2=CC(Cl)=CC=C2)C(Cl)(Cl)Cl)CC1 | 2P | A16 | 447.06 | 448.20 |
| 340 | CSC1=CC=C(C=C1)C1=NC(NCC2(N)CCOCC2)=NC(=N1)C(Cl)(Cl)Cl | 2G | A26 | 447.05 | 448.17 |
| 341 | COC1=CC=C(NC2=NC(NCCC3CCCN3C)=NC(=N2)C(Cl)(Cl)Cl)C=N1 | 1B | A3 | 445.10 | 446.19 |
| 342 | CCN(CC)CCNC1=NC(=NC(NC2=CC=C(OC)N=C2)=N1)C(Cl)(Cl)Cl | 1B | A4 | 433.10 | 434.17 |
| 343 | COC1=CC=C(NC2=NC(=NC(=N2)C(Cl)(Cl)Cl)N2CCCNCC2)C=N1 | 1B | A7 | 417.06 | 418.15 |
| 344 | CCN1CCCC(C1)NC1=NC(=NC(NC2=CC=C(OC)N=C2)=N1)C(Cl)(Cl)Cl | 1B | A1 | 7445.10 | 446.22 |
| 345 | COC1=CC=C(NC2=NC(=NC(=N2)C(Cl)(Cl)Cl)N2CCN(C)CC2)C=N1 | 1B | A10 | 417.06 | 418.13 |
| 346 | COC1=C(NC2=NC(NCCC3CCCN3C)=NC(=N2)C(Cl)(Cl)Cl)C=CC=N1 | 1A | A3 | 445.10 | 446.17 |
| 347 | CCN(CC)CCNC1=NC(=NC(NC2=C(OC)N=CC=C2)=N1)C(Cl)(Cl)Cl | 1A | A4 | 433.10 | 434.19 |
| 348 | COC1=C(NC2=NC(NC3CC(C)(C)NC(C)(C)C3)=NC(=N2)C(Cl)(Cl)Cl)C=CC=N1 | 1A | A31 | 473.13 | 474.24 |
| 349 | COC1=NC=C(NC2=NC(NC3CCN(C)CC3)=NC(=N2)C(Cl)(Cl)Cl)C=C1 | 1B | A12 | 431.08 | 432.19 |
| 350 | COC1=C(NC2=NC(NCCN3CCCC3)=NC(=N2)C(Cl)(Cl)Cl)C=CC=N1 | 1A | A1 | 431.08 | 432.25 |
| 351 | COC1=C(NC2=NC(NCCCN3CCCC3)=NC(=N2)C(Cl)(Cl)Cl)C=CC=N1 | 1A | A2 | 445.10 | 446.27 |
| 352 | CCN1CCC(CNC2=NC(=NC(NC3=C(OC)N=CC=C3)=N2)C(Cl)(Cl)Cl)CC1 | 1A | A16 | 459.11 | 460.27 |
| 353 | COC1=C(NC2=NC(=NC(=N2)C(Cl)(Cl)Cl)N2CCN(C)CC2)C=CC=N1 | 1A | A10 | 417.06 | 418.20 |
| 354 | COC1=C(NC2=NC(NC3CCN(C)CC3)=NC(=N2)C(Cl)(Cl)Cl)C=CC=N1 | 1A | A12 | 431.08 | 432.17 |
| 355 | CCN1CCCC(C1)NC1=NC(=NC(NC2=C(OC)N=CC=C2)=N1)C(Cl)(Cl)Cl | 1A | A17 | 445.10 | 446.21 |
| 356 | CCC(N)(CC)CNC1=NC(=NC(=N1)C1=CC=C(Cl)C=C1)C(Cl)(Cl)Cl | 2D | A27 | 421.04 | 422.19 |
| 357 | CCC(N)(CC)CNC1=NC(=NC(=N1)C1=CC=C(C=C1)C(F)(F)F)C(Cl)(Cl)Cl | 2F | A27 | 455.07 | 456.23 |
| 358 | CCC(N)(CC)CNC1=NC(=NC(=N1)C1=CC(OC)=C(OC)C=C1)C(Cl)(Cl)Cl | 2S | A27 | 447.10 | 448.25 |
| 359 | CCC(N)(CC)CNC1=NC(=NC(=N1)C1=CC(F)=C1)C(Cl)(Cl)Cl | 2Q | A27 | 405.07 | 406.54 |
| 360 | CCC(N)(CC)CNC1=NC(=NC(=N1)C1=CC=C(SC)C=C1)C(Cl)(Cl)Cl | 2G | A27 | 433.07 | 434.58 |
| 361 | CCC(N)(CC)CNC1=NC(=NC(=N1)C1=CC=C(C=C1)C(Cl)(Cl)Cl)C(Cl)(Cl)Cl | 2H | A27 | 502.98 | 504.19 |
| 362 | CCC(N)(CC)CNC1=NC(=NC(=N1)C1=CC=C(C=C1)C(C)(C)C)C(Cl)(Cl)Cl | 2E | A27 | 443.14 | 444.34 |
| 363 | CCC(N)(CC)CNC1=NC(=NC(=N1)C1=CC(Cl)=CC(Cl)=C1)C(Cl)(Cl)Cl | 2L | A27 | 455.00 | 456.40 |
| 364 | CCC(N)(CC)CNC1=NC(=NC(=N1)C1=CC=C(C=C1)C1=CC=CC=C1)C(Cl)(Cl)Cl | 2M | A27 | 463.11 | 464.24 |
| 365 | CCC(N)(CC)CNC1=NC(=NC(=N1)C1=CC=C(C=C1)S(C)(=O)=O)C(Cl)(Cl)Cl | 6 | A27 | 465.06 | 466.12 |
| 366 | ClC(Cl)(Cl)C1=NC(NCCN2CCCC2)=NC(=N1)C1=CC=C1N1CCCC1 | 2AA | A1 | 454.12 | 455.23 |
| 367 | COC1=CC=C(NC2=NC(NCCCN3CCCC3)=NC(=N2)C(Cl)(Cl)Cl)C=N1 | 1B | A2 | 445.10 | 446.16 |
| 368 | ClC(Cl)(Cl)C1=NC(NCCCN2CCCC2)=NC(=N1)C1=CC=C(C=C1)N1CCCC1 | 2AA | A2 | 468.14 | 469.28 |
| 369 | COC1=CC=C(NC2=NC(NCCN3CCCC3)=NC(=N2)C(Cl)(Cl)Cl)C=N1 | 1B | A1 | 431.08 | 432.15 |
| 370 | CN1CCCC1CCNC1=NC(=NC(=N1)C(Cl)(Cl)Cl)C1=CC=C(C=C1)N1CCCC1 | 2AA | A3 | 468.14 | 469.28 |
| 371 | CN1CCCN(CC1)C1=NC(=NC(=N1)C(Cl)(Cl)Cl)C1=CC=C(C=C1)N1CCCC1 | 2AA | A8 | 454.12 | 455.22 |
| 372 | CN1CCC(CC1)NC1=NC(=NC(=N1)C(Cl)(Cl)Cl)C1=CC=C(C=C1)N1CCCC1 | 2AA | A12 | 454.12 | 455.26 |
| 373 | CC(C)(N)CNC1=NC(=NC(=N1)C(Cl)(Cl)Cl)C1=CC=C(C=C1)N1CCCC1 | 2AA | A11 | 428.10 | 429.22 |
| 374 | CCN(CC)CCNC1=NC(NC2=CC=C(OC(F)(F)F)C=C2)=NC(=N1)C(Cl)(Cl)Cl | 1D | A4 | 486.07 | 487.18 |
| 375 | CN1CCN(CC1)C1=NC(NC2=CC=C(OC(F)(F)F)C=C2)=NC(=N1)C(Cl)(Cl)Cl | 1D | A10 | 470.04 | 471.25 |
| 376 | CCC(N)(CC)CNC1=NC(=NC(=N1)C1=CC=CC=C1)C(Cl)(Cl)Cl | 2I | A27 | 387.08 | 388.60 |
| 377 | CCC(N)(CC)CNC1=NC(=NC(=N1)C1=CC2=C(C=CC=C2)C=C1)C(Cl)(Cl)Cl | 2J | A27 | 437.09 | 438.35 |
| 378 | COC1=C(NC2=NC(=NC(=N2)C(Cl)(Cl)Cl)N2CCCNCC2)C=CC=N1 | 1A | A7 | 417.06 | 418.18 |
| 379 | COC1=C(NC2=NC(=NC(=N2)C(Cl)(Cl)Cl)N2CCCN(C)CC2)C=CC=N1 | 1A | A8 | 431.08 | 432.21 |
| 380 | FC1=CC=C(C=C1)C1=NC(NCCN2CCCC2)=NC(=N1)C(Cl)(Cl)Cl | 2Q | A1 | 403.05 | 404.15 |
| 381 | FC1=CC=C(C=C1)C1=NC(NCCCN2CCCC2)=NC(=N1)C(Cl)(Cl)Cl | 2Q | A2 | 417.07 | 418.19 |
| 382 | CN1CCCC1CCNC1=NC(=NC(=N1)C1=CC=C(F)C=C1)C(Cl)(Cl)Cl | 2Q | A3 | 417.07 | 418.20 |
| 383 | CCN(CC)CCNC1=NC(=NC(=N1)C1=CC=C(F)C=C1)C(Cl)(Cl)Cl | 2Q | A4 | 405.05 | 406.21 |
| 384 | CN1CCCN(CC1)C1=NC(=NC(=N1)C1=CC=C(F)C=C1)C(Cl)(Cl)Cl | 2Q | A8 | 403.05 | 404.25 |
| 385 | CN1CCC(CC1)NC1=NC(=NC(=N1)C1=CC=C(F)C=C1)C(Cl)(Cl)Cl | 2Q | A12 | 403.05 | 404.14 |
| 386 | CCN1CCC(CNC2=NC(=NC(=N2)C2=CC=C(F)C=C2)C(Cl)(Cl)Cl)CC1 | 2Q | A16 | 431.08 | 432.28 |
| 387 | CCN1CCCC(C1)NC1=NC(=NC(=N1)C1=CC=C(F)C=C1)C(Cl)(Cl)Cl | 2Q | A17 | 417.07 | 418.21 |
| 388 | CCC(N)(CC)CNC1=NC(=NC(=N1)C1=CC=C(Cl)C(Cl)=C1)C(Cl)(Cl)Cl | 2C | A27 | 455.00 | 456.16 |
| 389 | CC(C)(N)CNC1=NC(=NC(=N1)C1=CC=C(F)C=C1)C(Cl)(Cl)Cl | 2Q | A11 | 377.04 | 378.10 |
| 390 | CN1CCN(CC1)C1=NC(=NC(=N1)C1=CC=C(F)C=C1)C(Cl)(Cl)Cl | 2Q | A10 | 389.04 | 390.15 |
| 391 | CC1(C)CC(CC(C(C)(C)N1)NC1=NC(=NC(=N1)C1=CC=C(F)C=C1)C(Cl)(Cl)Cl | 2Q | A31 | 445.10 | 446.21 |
| 392 | COC1=C(OC)C=C(C=C1)C1=NC(NCCN2CCCC2)=NC(=N1)C(Cl)(Cl)Cl | 2S | A1 | 445.08 | 446.23 |
| 393 | COC1=C(OC)C=C(C=C1)C1=NC(NCCCN2CCCC2)=NC(=N1)C(Cl)(Cl)Cl | 2S | A2 | 459.10 | 460.23 |
| 394 | COC1=C(OC)C=C(C=C1)C1=NC(NCCC2CCCN2C)=NC(=N1)C(Cl)(Cl)Cl | 2S | A3 | 459.10 | 460.23 |
| 395 | CCN(CC)CCNC1=NC(=NC(=N1)C1=CC(OC)=C(OC)C=C1)C(Cl)(Cl)Cl | 2S | A11 | 447.10 | 448.25 |
| 396 | COC1=C(OC)C=C(C=C1)C1=NC(NCC(C)(C)N)=NC(=N1)C(Cl)(Cl)Cl | 2S | A4 | 419.07 | 420.19 |
| 397 | COC1=C(OC)C=C(C=C1)C1=NC(=NC(=N1)C(Cl)(Cl)Cl)N1CCCNCC1 | 2S | A7 | 431.07 | 432.19 |
| 398 | COC1=C(OC)C=C(C=C1)C1=NC(=NC(=N1)C(Cl)(Cl)Cl)N1CCCN(C)CC1 | 2S | A8 | 445.08 | 446.20 |
| 399 | COC1=C(OC)C=C(C=C1)C1=NC(NC2CCN(C)CC2)=NC(=N1)C(Cl)(Cl)Cl | 2S | A12 | 445.08 | 446.28 |
| 400 | COC1=C(OC)C=C(C=C1)C1=NC(=NC(=N1)C(Cl)(Cl)Cl)N1CCN(C)CC1 | 2S | A10 | 431.07 | 432.22 |

TABLE 5-continued

| Cmpd | SMILES | Prep | Amine | MS, calc'd | MS, found (M + 1) or mp (° C.) |
|---|---|---|---|---|---|
| 401 | CCN1CCC(CNC2=NC(=NC(=N2)C2=CC(OC)=C(OC)C=C2)C(Cl)(Cl)Cl)CC1 | 2S | A16 | 473.12 | 474.27 |
| 402 | CCN1CCCC(C1)NC1=NC(=N1)C1=CC(OC)=C(OC)C=C1)C(Cl)(Cl)Cl | 2S | A17 | 459.10 | 460.23 |
| 403 | COC1=NC=C(NC2=NC(NCC(C)(C)N)=NC(=N2)C(Cl)(Cl)Cl)C=C1 | 1B | A11 | 405.06 | 406.13 |
| 404 | COC1=C(NC2=NC(NCC(C)(C)N)=NC(=N2)C(Cl)(Cl)Cl)C=CC=N1 | 1A | A11 | 405.06 | 406.15 |
| 405 | ClC(Cl)(Cl)C1=NC(=NC(NCCN2CCCC2)=N1)C1=CC=CC=C1 | 2I | A1 | 385.06 | 386.21 |
| 406 | ClC(Cl)(Cl)C1=NC(=NC(NCCCN2CCCC2)=N1)C1=CC=CC=C1 | 2I | A2 | 399.08 | 400.27 |
| 407 | CN1CCCC1CCNC1=NC(=NC(=N1)C1=CC=CC=C1)C(Cl)(Cl)Cl | 2I | A3 | 399.08 | 400.29 |
| 408 | ClC(Cl)(Cl)C1=NC(=NC(=N1)N1CCCNCC1)C1=CC=CC=C1 | 2I | A7 | 371.05 | 372.16 |
| 409 | CN1CCCN(CC1)C1=NC(=NC(=N1)C1=CC=CC=C1)C(Cl)(Cl)Cl | 2I | A8 | 385.06 | 386.19 |
| 410 | CCN1CCC(CNC2=NC(=NC(=N2)C2=CC=CC=C2)C(Cl)(Cl)Cl)CC1 | 2I | A16 | 413.09 | 414.34 |
| 411 | CCN(CC)CCNC1=NC(=NC(=N1)C1=C2C=CC=CC2=C(OC)C=C1)C(Cl)(Cl)Cl | 2R | A4 | 467.10 | 468.30 |
| 412 | CCN(CC)CCCNC1=NC(=NC(=N1)C(Cl)(Cl)Cl)C1=CC=C(C=C1)N1CCCC1 | 2AA | A4 | 456.14 | 457.27 |
| 413 | COC1=C2C=CC=CC2=C(C=C1)C1=NC(=NC(=N1)C(Cl)(Cl)Cl)N1CCCN(C)CC1 | 2R | A7 | 465.09 | 466.55 |
| 414 | COC1=C2C=CC=CC2=C(C=C1)C1=NC(=NC(=N1)C(Cl)(Cl)Cl)N1CCN(C)CC1 | 2R | A8 | 451.07 | 452.22 |
| 415 | COC1=C2C=CC=CC2=C(C=C1)C1=NC(=NC(NCC(C)(C)N)=NC(=N1)C(Cl)(Cl)Cl | 2R | A11 | 439.07 | 440.19 |
| 416 | CC1=CC=C(C=C1)C1=NC(=NC(=N1)C(Cl)(Cl)Cl)N1CCN(CCO)CC1 | 2 | A21 | 415.07 | 416.26 |
| 417 | OCCN1CCN(CC1)C1=NC(=NC(=N1)C1=CC=CC=C1)C(Cl)(Cl)Cl | 2I | A21 | 401.06 | 402.18 |
| 418 | OCCN1CCN(CC1)C1=NC(=NC(=N1)C1=CC(Cl)=CC(Cl)=C1)C(Cl)(Cl)Cl | 2L | A21 | 468.98 | 470.15 |
| 419 | CC1=CC=C(C=C1)C1=NC=CC=C1C1=NC(=NC(=N1)C(Cl)(Cl)Cl)N1CCN(CCO)CC1 | 2O | A21 | 491.10 | 492.28 |
| 420 | OCCN1CCN(CC1)C1=NC(=NC(=N1)C1=CC(Cl)=CC=C1)C(Cl)(Cl)Cl | 2P | A21 | 435.02 | 436.16 |
| 421 | OCCN1CCN(CC1)C1=NC(=NC(=N1)C1=CC=C(F)C=C1)C(Cl)(Cl)Cl | 2Q | A21 | 419.05 | 420.15 |
| 422 | COC1=C2C=CC=CC2=C(C=C1)C1=NC(=NC(=N1)C(Cl)(Cl)Cl)N1CCN(CCO)CC1 | 2R | A21 | 481.08 | 482.65 |
| 423 | COC1=C(OC)C=C(C=C1)C1=NC(=NC(=N1)C(Cl)(Cl)Cl)N1CCN(CCO)CC1 | 2S | A21 | 461.08 | 462.19 |
| 424 | COC1=C2C=CC=CC2=C(C=C1)C1=NC(NCCCN2CCCC2)=NC(=N1)C(Cl)(Cl)Cl | 2R | A2 | 479.10 | 480.63 |
| 425 | COC1=C2C=CC=CC2=C(C=C1)C1=NC(NCCC2CCCN2C)=NC(=N1)C(Cl)(Cl)Cl | 2R | A3 | 479.10 | 480.23 |
| 426 | COC1=C2C=CC=CC2=C(C=C1)C1=NC(NC2CCN(C)CC2)=NC(=N1)C(Cl)(Cl)Cl | 2R | A12 | 465.09 | 466.34 |
| 427 | CN1CCN(CC1)C1=NC(=NC(=N1)C(Cl)(Cl)Cl)C1=CC=C(C=C1)N1CCCC1 | 2AA | A10 | 440.10 | 441.33 |
| 428 | ClC(Cl)(Cl)C1=NC(=NC(=N1)C1=CC=C(C=C1)N1CCCC1)N1CCCNCC1 | 2AA | A7 | 440.10 | 441.33 |
| 429 | CCN1CCCC(C1)NC1=NC(=NC(=N1)C(Cl)(Cl)Cl)C1=CC=C(C=C1)N1CCCC1 | 2AA | A17 | 468.14 | 469.28 |
| 430 | CCN1CCC(CNC2=NC(=NC(=N2)C(Cl)(Cl)Cl)C2=CC=C(C=C2)N2CCCC2)CC1 | 2AA | A16 | 482.15 | 483.33 |
| 431 | OCCN1CCN(CC1)C1=NC(=NC(=N1)C(Cl)(Cl)Cl)C1=CC=C(C=C1)N1CCCC1 | 2AA | A21 | 470.12 | 471.33 |
| 432 | NC1(CNC2=NC(=NC(=N2)C(Cl)(Cl)Cl)C2=CC=C(C=C2)N2CCCC2)CCOCC1 | 2AA | A26 | 470.12 | 471.22 |
| 433 | ClC1=CC=CC(=C1)C1=NC(NCCCN2CCCC2)=NC(=N1)C(Cl)(Cl)Cl | 2P | A2 | 433.04 | 434.16 |
| 434 | CCN(CC)CCNC1=NC(=NC(=N1)C1=CC(Cl)=CC=C1)C(Cl)(Cl)Cl | 2P | A4 | 421.04 | 422.17 |
| 435 | CN1CCCN(CC1)C1=NC(=NC(=N1)C1=CC(Cl)=CC=C1)C(Cl)(Cl)Cl | 2P | A8 | 419.02 | 420.15 |
| 436 | CN1CCN(CC1)C1=NC(=NC(=N1)C1=CC(Cl)=CC=C1)C(Cl)(Cl)Cl | 2P | A10 | 405.01 | 406.15 |
| 437 | CC(C)(N)CNC1=NC(=NC(=N1)C1=CC(Cl)=CC=C1)C(Cl)(Cl)Cl | 2P | A11 | 393.01 | 394.09 |
| 438 | CC1(C)CC(CC(C)(C)N1)NC1=NC(=NC(=N1)C1=CC(Cl)=CC=C1)C(Cl)(Cl)Cl | 2P | A31 | 461.07 | 462.34 |
| 439 | CN(C)CCCNC1=NC(=NC(=N1)C1=CC=C(C)C=C1)C(Cl)(Cl)Cl | 2 | A24 | 387.08 | 388.58 |
| 440 | CN(C)CCCNC1=NC(=NC(=N1)C1=CC=C(C(C)(C)C)C=C1)C(Cl)(Cl)Cl | 2E | A24 | 429.13 | 430.25 |
| 441 | CSC1=CC=C(C=C1)C1=NC(NCCCN(C)C)=NC(=N1)C(Cl)(Cl)Cl | 2G | A24 | 419.05 | 420.21 |
| 442 | CN(C)CCCNC1=NC(=NC(=N1)C1=CC=C(C=C1)S(C)(=O)=O)C(Cl)(Cl)Cl | 6 | A24 | 451.04 | 452.39 |
| 443 | CN(C)CCCNC1=NC(=NC(=N1)C1=CC=CC=C1)C(Cl)(Cl)Cl | 2I | A24 | 373.06 | 374.24 |
| 444 | CN(C)CCCNC1=NC(=NC(=N1)C1=CC2=C(C=C1)C2)C(Cl)(Cl)Cl | 2J | A24 | 423.08 | 424.21 |
| 445 | CN(C)CCCNC1=NC(=NC(=N1)C1=CC=C(C=C1)C1=CC=CC=C1)C(Cl)(Cl)Cl | 2M | A24 | 449.09 | 450.01 |
| 446 | CN(C)CCCNC1=NC(=NC(=N1)C1=CC=C(C1)C1=CC=C(C)C=C1)C(Cl)(Cl)Cl | 2O | A24 | 463.11 | 464.65 |
| 447 | CN(C)CCCNC1=NC(=NC(=N1)C1=CC(Cl)=CC=C1)C(Cl)(Cl)Cl | 2P | A24 | 407.02 | 408.18 |
| 448 | CN(C)CCCNC1=NC(=NC(=N1)C1=CC=C(F)C=C1)C(Cl)(Cl)Cl | 2Q | A24 | 391.05 | 392.33 |
| 449 | COC1=CC=C(C2=NC(NCCCN(C)C)=NC(=N2)C(Cl)(Cl)Cl)C2=C1C=CC=C2 | 2R | A24 | 453.09 | 454.29 |
| 450 | COC1=CC=C(C=C1OC)C1=NC(NCCCN(C)C)=NC(=N1)C(Cl)(Cl)Cl | 2S | A24 | 433.08 | 434.37 |
| 451 | OCCN1CCCN(CC1)C1=NC(=NC(=N1)C(Cl)(Cl)Cl)C1=CC=C(C=C1)C1=CC=CC=C1 | 2M | A23 | 491.10 | 492.22 |
| 452 | [O-][N+](=O)C1=CC=CC=C1C1=NC(NCCN2CCCC2)=NC(=N1)C(Cl)(Cl)Cl | 2N | A1 | 430.05 | 431.52 |
| 453 | CC1=CC=C(C=C1)C1=NC(=NC(=N1)N1CCCN(CCO)C1)C(Cl)(Cl)Cl | 2 | A23 | 429.10 | 430.27 |
| 454 | OCCN1CCCN(CC1)C1=NC(=NC(=N1)C(Cl)(Cl)Cl)C1=CC(Cl)=C(Cl)C=C1 | 2C | A23 | 483.00 | 484.17 |
| 455 | OCCN1CCCN(CC1)C1=NC(=NC(=N1)C(Cl)(Cl)Cl)C1=CC=C(Cl)C=C1 | 2D | A23 | 449.03 | 450.17 |
| 456 | OCCN1CCCN(CC1)C1=NC(=NC(=N1)C(Cl)(Cl)Cl)C1=CC=C(C=C1)C(F)(F)F | 2G | A23 | 483.06 | 484.20 |
| 457 | CSC1=CC=C(C=C1)C1=NC(=NC(=N1)N1CCCN(CCO)CC1)C(Cl)(Cl)Cl | 6 | A23 | 461.06 | 462.26 |
| 458 | OCCN1CCCN(CC1)C1=NC(=NC(=N1)C(Cl)(Cl)Cl)C1=CC=CC=C1 | 2I | A23 | 415.07 | 416.18 |
| 459 | OCCN1CCCN(CC1)C1=NC(=NC(=N1)C(Cl)(Cl)Cl)C1=CC2=C(C=CC=C2)C=C1 | 2J | A23 | 465.09 | 466.20 |
| 460 | OCCN1CCCN(CC1)C1=NC(=NC(=N1)C(Cl)(Cl)Cl)C1=CC(Cl)=CC(Cl)=C1 | 2L | A23 | 483.00 | 484.16 |
| 461 | OCCN1CCCN(CC1)C1=NC(=NC(=N1)C(Cl)(Cl)Cl)C1=CC(Cl)=CC=C1 | 2P | A23 | 449.03 | 450.13 |
| 462 | OCCN1CCCN(CC1)C1=NC(=NC(=N1)C(Cl)(Cl)Cl)C1=CC=C(F)C=C1 | 2Q | A23 | 433.06 | 434.17 |
| 463 | COC1=C2C=CC=CC2=C(C=C1)C1=NC(=NC(=N1)N1CCCN(CCO)CC1)C(Cl)(Cl)Cl | 2R | A23 | 495.10 | 496.20 |
| 464 | COC1=C(OC)C=C(C=C1)C1=NC(=NC(=N1)N1CCCN(CCO)CC1)C(Cl)(Cl)Cl | 2S | A23 | 475.09 | 476.30 |
| 465 | OCCN1CCCN(CC1)C1=NC(=NC(=N1)C(Cl)(Cl)Cl)C1=CC=C(C=C1)N1CCCC1 | 2AA | A23 | 484.13 | 485.35 |
| 466 | CCN1CCCC(C1)NC1=NC(=NC(=N1)C1=C(C=CC=C1)[N+]([O-])=O)C(Cl)(Cl)Cl | 2N | A17 | 444.06 | 445.23 |
| 467 | CC(C)(N)CNC1=NC(=NC(=N1)C1=CC=CC=C1)[N+]([O-])=O)C(Cl)(Cl)Cl | 2N | A11 | 404.03 | 407.28 |
| 468 | OCCN1CCCN(CC1)C1=NC(NC2=CC=C(OC(F)(F)F)C=C2)=NC(=N1)C(Cl)(Cl)Cl | 1D | A23 | 514.07 | 515.34 |
| 469 | ClC1=CC=C(C=C1Cl)C1=NC(NCCC2=CN=CC=N2)=NC(=N1)C(Cl)(Cl)Cl | 2D | A5 | 427.99 | 429.11 |
| 470 | ClC1=CC=C(C=C1Cl)C1=NC(=NC(NCCC2=CN=CC=N2)=N1)C(Cl)(Cl)Cl | 2C | A5 | 461.95 | 463.09 |
| 471 | ClC1=CC(=CC(Cl)=C1)C1=NC(=NC(NCCC2=CN=CC=N2)=N1)C(Cl)(Cl)Cl | 2L | A5 | 461.95 | 463.16 |
| 472 | ClC1=CC=CC(=C1)C1=NC(=NC(NCCC2=CN=CC=N2)=N1)C(Cl)(Cl)Cl | 2P | A5 | 427.99 | 429.14 |
| 473 | CN(CCC1=NC=CC=C1)C1=NC(=NC(=N1)C(Cl)(Cl)Cl)C1=CC=C(Cl)C=C1 | 2D | A19 | 441.01 | 442.14 |
| 474 | CN(CCC1=NC=CC=C1)C1=NC(=NC(=N1)C(Cl)(Cl)Cl)C1=CC(Cl)=CC(Cl)=C1 | 2L | A19 | 474.97 | 476.14 |

TABLE 5-continued

| Cmpd | SMILES | Prep | Amine | MS, calc'd | MS, found (M + 1) or mp (° C.) |
|---|---|---|---|---|---|
| 475 | CN(CCC1=NC=CC=C1)C1=NC(=NC(=N1)C(Cl)(Cl)Cl)C1=CC=CC(Cl)=C1 | 2P | A19 | 441.01 | 442.18 |
| 476 | COC1=CC=CC(=CC(OC)=C1)C1=NC(=NC(NCCN2CCCC2)=N1)C(Cl)(Cl)Cl | 2T | A1 | 445.08 | 446.29 |
| 477 | COC1=CC=CC(=CC(OC)=C1)C1=NC(=NC(NCCCN2CCCC2)=N1)C(Cl)(Cl)Cl | 2T | A2 | 459.10 | 460.25 |
| 478 | COC1=CC=CC(=CC(OC)=C1)C1=NC(=NC(NCCC2CCCN2C)=N1)C(Cl)(Cl)Cl | 2T | A3 | 459.10 | 460.27 |
| 479 | CCN(CC)CCNC1=NC(=NC(=N1)C(Cl)(Cl)Cl)C1=CC(OC)=CC(OC)=C1 | 2T | A4 | 447.10 | 448.21 |
| 480 | COC1=CC=CC(=CC(OC)=C1)C1=NC(=NC(=N1)N1CCCN(C)CC1)C(Cl)(Cl)Cl | 2T | A8 | 445.08 | 446.19 |
| 481 | COC1=CC=CC(=CC(OC)=C1)C1=NC(=NC(NCC(C)(C)N)=N1)C(Cl)(Cl)Cl | 2T | A11 | 419.07 | 420.17 |
| 482 | COC1=CC=CC(=CC(OC)=C1)C1=NC(=NC(=N1)N1CCN(C)CC1)C(Cl)(Cl)Cl | 2T | A10 | 431.07 | 432.21 |
| 483 | COC1=CC=CC(=CC(OC)=C1)C1=NC(=NC(=N1)N1CCCN(CCO)CC1)C(Cl)(Cl)Cl | 2T | A23 | 475.09 | 476.22 |
| 484 | CC(C)N1CCC(CNC2=NC(=NC(=N2)C2=CC=C(C)C=C2)C(Cl)(Cl)Cl)CC1 | 2 | A32 | 441.12 | 442.28 |
| 485 | COC1=CC=CC(=C1)C1=NC(NCC2CCN(CC2)C(C)C)=NC(=N1)C(Cl)(Cl)Cl | 2A | A32 | 457.12 | 458.27 |
| 486 | CC(C)N1CCC(CNC2=NC(=NC(=N2)C2=CC(Cl)=C(Cl)C=C2)C(Cl)(Cl)Cl)CC1 | 2C | A32 | 495.03 | 496.31 |
| 487 | CC(C)N1CCC(CNC2=NC(=NC(=N2)C2=CC=C(Cl)C=C2)C(Cl)(Cl)Cl)CC1 | 2D | A32 | 461.07 | 462.22 |
| 488 | CC(C)N1CCC(CNC2=NC(=NC(=N2)C2=CC=C(C=C2)C(C)(C)C)C(Cl)(Cl)Cl)CC1 | 2E | A32 | 483.17 | 484.36 |
| 489 | CC(C)N1CCC(CNC2=NC(=NC(=N2)C2=CC=C(C=C2)C(F)(F)F)C(Cl)(Cl)Cl)CC1 | 2F | A32 | 495.10 | 496.32 |
| 490 | CSC1=CC=C(C=C1)C1=NC(NCC2CCN(CC2)C(C)C)=NC(=N1)C(Cl)(Cl)Cl | 2G | A32 | 473.10 | 474.27 |
| 491 | CC(C)N1CCC(CNC2=NC(=NC(=N2)C2=CC=C(C=C2)S(C)(=O)=O)C(Cl)(Cl)Cl)CC1 | 6 | A32 | 505.09 | 506.25 |
| 492 | CC(C)N1CCC(CNC2=NC(=NC(=N2)C2=CC=C(C=C2)C(Cl)(Cl)Cl)C(Cl)(Cl)Cl)CC1 | 2H | A32 | 543.01 | 544.12 |
| 493 | CC(C)N1CCC(CNC2=NC(=NC(=N2)C2=CC=CC=C2)C(Cl)(Cl)Cl)CC1 | 2I | A32 | 427.11 | 428.44 |
| 494 | CC(C)N1CCC(CNC2=NC(=NC(=N2)C2=CC3=C(C=CC=C3)C=C2)C(Cl)(Cl)Cl)CC1 | 2J | A32 | 479.14 | 478.24 |
| 495 | CC(C)N1CCC(CNC2=NC(=NC(=N2)C2=CC(Cl)=CC(Cl)=C2)C(Cl)(Cl)Cl)CC1 | 2L | A32 | 495.03 | 496.23 |
| 496 | CC(C)N1CCC(CNC2=NC(=NC(=N2)C2=CC=C(C=C2)C2=CC=CC=C2)C(Cl)(Cl)Cl)CC1 | 2M | A32 | 503.14 | 504.34 |
| 497 | CC(C)N1CCC(CNC2=NC(=NC(=N2)C2=CC=C(C=C2)[N+]([O-])=O)C(Cl)(Cl)Cl)CC1 | 2N | A32 | 472.09 | 473.18 |
| 498 | COC1=CC=C(C2=NC(NCC3CCN(CC3)C(C)C)=NC(=N2)C(Cl)(Cl)Cl)C2=C1C=CC=C2 | 2R | A32 | 507.14 | 508.29 |
| 499 | CC(C)N1CCC(CNC2=NC(=NC(=N2)C2=CC(Cl)=CC=C2)C(Cl)(Cl)Cl)CC1 | 2P | A32 | 461.07 | 462.21 |
| 500 | CC(C)N1CCC(CNC2=NC(=NC(=N2)C2=CC=C(F)C=C2)C(Cl)(Cl)Cl)CC1 | 2Q | A32 | 445.10 | 446.25 |
| 501 | COC1=C(OC)C=C(C=C1)C1=NC(NCC2CCN(CC2)C(C)C)=NC(=N1)C(Cl)(Cl)Cl | 2S | A32 | 487.13 | 488.36 |
| 502 | COC1=CC=CC(=CC(OC)=C1)C1=NC(NCC2CCN(CC2)C(C)C)=NC(=N1)C(Cl)(Cl)Cl | 2T | A32 | 487.13 | 488.27 |
| 503 | CN1CCC(CNC2=NC(=NC(=N2)C2=CC=C(C)C=C2)C(Cl)(Cl)Cl)CC1 | 2 | A33 | 413.09 | 414.34 |
| 504 | COC1=CC=CC(=C1)C1=NC(NCC2CCN(C)CC2)=NC(=N1)C(Cl)(Cl)Cl | 2A | A33 | 429.09 | 430.26 |
| 505 | CN1CCC(CNC2=NC(=NC(=N2)C2=CC(Cl)=C(Cl)C=C2)C(Cl)(Cl)Cl)CC1 | 2C | A33 | 467.00 | 468.17 |
| 506 | CN1CCC(CNC2=NC(=NC(=N2)C2=CC=C(Cl)C=C2)C(Cl)(Cl)Cl)CC1 | 2D | A33 | 433.04 | 434.22 |
| 507 | CN1CCC(CNC2=NC(=NC(=N2)C2=CC=C(C=C2)C(C)(C)C)C(Cl)(Cl)Cl)CC1 | 2E | A33 | 455.14 | 456.31 |
| 508 | CN1CCC(CNC2=NC(=NC(=N2)C2=CC=C(C=C2)C(F)(F)F)C(Cl)(Cl)Cl)CC1 | 2F | A33 | 467.07 | 468.46 |
| 509 | CSC1=CC=C(C=C1)C1=NC(NCC2CCN(C)CC2)=NC(=N1)C(Cl)(Cl)Cl | 2G | A33 | 445.07 | 446.37 |
| 510 | CN1CCC(CNC2=NC(=NC(=N2)C2=CC=C(C=C2)S(C)(=O)=O)C(Cl)(Cl)Cl)CC1 | 6 | A33 | 477.06 | 478.18 |
| 511 | CN1CCC(CNC2=NC(=NC(=N2)C2=CC=C(C=C2)C(Cl)(Cl)Cl)C(Cl)(Cl)Cl)CC1 | 2H | A33 | 514.98 | 516.08 |
| 512 | CN1CCC(CNC2=NC(=NC(=N2)C2=CC=CC=C2)C(Cl)(Cl)Cl)CC1 | 2I | A33 | 399.08 | 400.49 |
| 513 | CN1CCC(CNC2=NC(=NC(=N2)C2=CC3=C(C=CC=C3)C=C2)C(Cl)(Cl)Cl)CC1 | 2J | A33 | 449.09 | 450.25 |
| 514 | CN1CCC(CNC2=NC(=NC(=N2)C2=CC(Cl)=CC(Cl)=C2)C(Cl)(Cl)Cl)CC1 | 2L | A33 | 467.00 | 468.25 |
| 515 | CN1CCC(CNC2=NC(=NC(=N2)C2=CC=C(C=C2)C2=CC=CC=C2)C(Cl)(Cl)Cl)CC1 | 2M | A33 | 475.11 | 476.28 |
| 516 | CN1CCC(CNC2=NC(=NC(=N2)C2=CC=C(C=C2)[N+]([O-])=O)C(Cl)(Cl)Cl)CC1 | 2N | A33 | 444.06 | 445.19 |
| 517 | COC1=CC=C(C2=NC(NCC3CCN(C)CC3)=NC(=N2)C(Cl)(Cl)Cl)C2=C1C=CC=C2 | 2R | A33 | 479.10 | 480.29 |
| 518 | CN1CCC(CNC2=NC(=NC(=N2)C2=CC(Cl)=CC=C2)C(Cl)(Cl)Cl)CC1 | 2P | A33 | 433.04 | 434.19 |
| 519 | CN1CCC(CNC2=NC(=NC(=N2)C2=CC=C(F)C=C2)C(Cl)(Cl)Cl)CC1 | 2Q | A33 | 417.07 | 418.21 |
| 520 | COC1=C(OC)C=C(C=C1)C1=NC(NCC2CCN(C)CC2)=NC(=N1)C(Cl)(Cl)Cl | 2S | A33 | 459.10 | 460.24 |
| 521 | COC1=CC=CC(=CC(OC)=C1)C1=NC(NCC2CCN(C)CC2)=NC(=N1)C(Cl)(Cl)Cl | 2T | A33 | 459.10 | 460.25 |
| 522 | [O-][N+](=O)C1=CC=C(C=C1)C1=NC(NCCCN2CCCC2)=NC(=N1)C(Cl)(Cl)Cl | 2N | A2 | 444.06 | 445.21 |
| 523 | CCN(CC)CCNC1=NC(=NC(=N1)C1=CC(=CC=C1)[N+]([O-])=O)C(Cl)(Cl)Cl | 2N | A4 | 432.06 | 433.18 |
| 524 | CN1CCCC1CCNC1=NC(=NC(=N1)C1=C(C=CC=C1)[N+]([O-])=O)C(Cl)(Cl)Cl | 2N | A3 | 444.06 | 445.22 |
| 525 | COC1=CC=CC(=CC(OC)=C1)C1=NC(=NC(=N1)N1CCCNCC1)C(Cl)(Cl)Cl | 2T | A7 | 431.07 | 432.16 |
| 526 | COC1=CC=CC(=CC(OC)=C1)C1=NC(=NC(=N1)N1CCN(CCO)CC1)C(Cl)(Cl)Cl | 2T | A21 | 461.08 | 462.18 |
| 527 | COC1=CC=CC(=CC(OC)=C1)C1=NC(=NC(NC2CC(C)(C)NC(C)(C)C2)=N1)C(Cl)(Cl)Cl | 2T | A31 | 487.13 | 488.25 |
| 528 | CCN1CCCC(C1)NC1=NC(=NC(=N1)C(Cl)(Cl)Cl)C1=CC(OC)=CC(OC)=C1 | 2T | A17 | 459.10 | 460.27 |
| 529 | COC1=CC=CC(=CC(OC)=C1)C1=NC(=NC(NCC2(N)CCOCC2)=N1)C(Cl)(Cl)Cl | 2T | A26 | 461.08 | 462.19 |
| 530 | COC1=CC=CC(=CC(OC)=C1)C1=NC(=NC(NCC2(N)CCCC2)=N1)C(Cl)(Cl)Cl | 2T | A28 | 445.08 | 446.72 |
| 531 | COC1=CC=CC(=CC(OC)=C1)C1=NC(=NC(NCCCN(C)C)=N1)C(Cl)(Cl)Cl | 2T | A24 | 433.08 | 434.19 |
| 532 | CN(C)CCCNC1=NC(=NC(=N1)C1=CC=CC=C1[N+]([O-])=O)C(Cl)(Cl)Cl | 2N | A24 | 418.05 | 419.10 |
| 533 | COC1=CC=CC(=CC=C1)C1=NC(NCCCN(C)C)=NC(=N1)C(Cl)(Cl)Cl | 2 | A24 | 403.07 | 404.16 |
| 534 | CN(CCC1=NC=CC=C1)C1=NC(=NC(=N1)C(Cl)(Cl)Cl)C1=CC=C(C=C1)C(Cl)(Cl)Cl | 2H | A19 | 522.95 | 524.08 |
| 535 | CC1=CC=C(C=C1)C1=NC(=NC(NCCC2=CN=CC=N2)=N1)C(Cl)(Cl)Cl | 2 | A5 | 408.04 | 409.18 |
| 536 | COC1=CC=C(C=C1)C1=NC=NC(NCCC2=CN=CC=N2)=N1)C(Cl)(Cl)Cl | 2A | A5 | 424.04 | 425.17 |
| 537 | COC1=CC=C(C=C1)C1=NC(=NC(NCCC2=CN=CC=N2)=N1)C(Cl)(Cl)Cl | 2B | A5 | 424.04 | 425.38 |
| 538 | CC(C)(C)C1=CC=C(C=C1)C1=NC(=NC(NCCC2=CN=CC=N2)=N1)C(Cl)(Cl)Cl | 2E | A5 | 450.09 | 451.20 |
| 539 | FC(F)(F)C1=CC=C(C=C1)C1=NC(=NC(NCCC2=CN=CC=N2)=N1)C(Cl)(Cl)Cl | 2F | A5 | 462.01 | 463.24 |
| 540 | ClC(Cl)(Cl)C1=NC(NCCC2=CN=CC=N2)=NC(=N1)C1=CC=CC=C1 | 2I | A5 | 394.03 | 395.18 |
| 541 | ClC(Cl)(Cl)C1=NC(NCCC2=CN=CC=N2)=NC(=N1)C1=CC=C2C=CC=CC2=C1 | 2J | A5 | 444.04 | 445.19 |
| 542 | ClC(Cl)(Cl)C1=NC(NCCC2=CN=CC=N2)=NC(=N1)C1=CC=C(C=C1)C1=CC=CC=C1 | 2M | A5 | 470.06 | 471.18 |
| 543 | CSC1=CC=C(C=C1)C1=NC(NCCC2=CN=CC=N2)=NC(=N1)C(Cl)(Cl)Cl | 2G | A5 | 440.01 | 441.13 |
| 544 | [O-][N+](=O)C1=CC=C(C=C1)C1=NC(=NC(NCCC2=CN=CC=N2)=N1)C(Cl)(Cl)Cl | 2N | A5 | 439.01 | 440.21 |
| 545 | CC1(C)OC2=C(C=C1)C=C(C=C2)C1=NC(=NC(NCCC2=CN=CC=N2)=N1)C(Cl)(Cl)Cl | 2U | A5 | 476.07 | 477.25 |
| 546 | COC1=CC=C(C2=C1C=CC=C2)C1=NC(=NC(NCCC2=CN=CC=N2)=N1)C(Cl)(Cl)Cl | 2R | A5 | 474.05 | 475.16 |
| 547 | FC1=CC=C(C=C1)C1=NC(=NC(NCCC2=CN=CC=N2)=N1)C(Cl)(Cl)Cl | 2Q | A5 | 412.07 | 413.16 |
| 548 | CN1CCCN(CC1)C1=NC(=NC(=N1)C1=C(C=CC=C1)[N+]([O-])=O)C(Cl)(Cl)Cl | 2N | A8 | 430.05 | 431.24 |

TABLE 5-continued

| Cmpd | SMILES | Prep | Amine | MS, calc'd | MS, found (M + 1) or mp (° C.) |
|---|---|---|---|---|---|
| 549 | CN1CCN(CC1)C1=NC(=NC(=N1)C1=C(C=CC=C1)[N+]([O-])=O)C(Cl)(Cl)Cl | 2N | A10 | 416.03 | 417.21 |
| 550 | CN1CCC(CC1)NC1=NC(=NC(=N1)C1=C(C=CC=C1)[N+]([O-])=O)C(Cl)(Cl)Cl | 2N | A12 | 430.05 | 431.16 |
| 551 | CCN1CCC(CNC2=NC(=NC(=N2)C2=C(C=CC=C2)[N+]([O-])=O)C(Cl)(Cl)Cl)CC1 | 2N | A16 | 458.08 | 459.23 |
| 552 | OCCN1CCCN(CC1)C1=NC(=NC(=N1)C1=C(C=CC=C1)[N+]([O-])=O)C(Cl)(Cl)Cl | 2N | A23 | 460.06 | 461.20 |
| 553 | CC1(C)OC2=C(C=C1)C=C(C=C2)C1=NC(NCCN2CCCC2)=NC(=N1)C(Cl)(Cl)Cl | 2U | A1 | 467.10 | 468.90 |
| 554 | CC1(C)CC(CC(C)(C)N1)NC1=NC(=NC(=N1)C1=CC(=C)C=C1)C(Cl)(Cl)Cl | 2C | A31 | 495.03 | 496.36 |
| 555 | CC(C)(N)CNC1=NC(=NC(NC2=CC(=CC=C2)C(F)(F)F)=N1)C(Cl)(Cl)Cl | 1I | A11 | 442.05 | 443.31 |
| 556 | CC(C)(N)CNC1=NC(=NC(NC2=CC(Cl)=CC(Cl)=C2)=N1)C(Cl)(Cl)Cl | 1F | A11 | 441.98 | 443.60 |
| 557 | CC(C)(N)CNC1=NC(NC2=CC=CC=C2)=NC(=N1)C(Cl)(Cl)Cl | 1G | A11 | 374.06 | 375.65 |
| 558 | Clc1ccc(cc1)c2nc(NCCCN3CCCC3)nc(n2)C(Cl)(Cl)Cl | 2D | A2 | | 94-97 |
| 559 | CCN1CCCC(C1)Nc2nc(nc(n2)C(Cl)(Cl)Cl)c3ccc(Cl)cc3 | 2D | A17 | | 132-135 |
| 560 | ClC(Cl)(Cl)c1nc(NCCCCCN2CCCC2)nc(n1)C(Cl)(Cl)Cl | 2D | A24 | | 129-131 |
| 561 | CN(C)CCCNc1nc(nc(n1)C(Cl)(Cl)Cl)c2ccc(Cl)cc2 | 2D | A62 | | 103-106 |
| 562 | CN(C)CCCNc1nc(nc(n1)C(Cl)(Cl)Cl)c2cccc(c2)C(F)(F)F | 2F | A24 | | 97-99 |
| 563 | CN(C)CCCNc1nc(nc(n1)C(Cl)(Cl)Cl)c2ccc(cc2)C(F)(F)F | 2AC | A24 | | 98-100 |
| 564 | FC(F)(F)c1ccc(cc1)c2nc(NCCCN3CCCC3)nc(n2)C(Cl)(Cl)Cl | 2AC | A3 | | 92-94 |
| 565 | CN(CCCNC1=NC(C2=CC=C(C(Cl)(Cl)Cl)C=C2)=NC(C(Cl)(Cl)Cl)=N1)C | 2H | A24 | | 120-123 |
| 566 | CN(CCCNC1=NC(C2=CC=CC(C(Cl)(Cl)Cl)C=C2)=NC(C(Cl)(Cl)Cl)=N1)C | 2AD | A24 | | 107-109 |
| 567 | CCN(CC)CCNC1=NC(=NC(C(Cl)(Cl)Cl)=N1)C1=CC=C(C=C1)C(Cl)(Cl)Cl | 2AD | A4 | | 89-92 |
| 568 | CCN(CCN)CNC1=NC(C2=CC=C(C(Cl)(Cl)Cl)C=C2)=NC(C(Cl)(Cl)Cl)=N1)CC | 2H | A4 | | 84-87 |
| 569 | CCN1CCCC(C1)Nc2nc(nc(n2)C(Cl)(Cl)Cl)c3ccc(cc3)C(Cl)(Cl)Cl | 2H | A17 | | 134-136 |
| 570 | ClC(Cl)(Cl)c1ccc(cc1)c2nc(NCCCN3CCCC3)nc(n2)C(Cl)(Cl)Cl | 2H | A2 | | 215-218 |
| 571 | ClC(Cl)(Cl)c1ccc(cc1)c2nc(NCCCN3CCCC3)nc(n2)C(Cl)(Cl)Cl | 2AD | A2 | | 102-105 |
| 572 | CCN(CC)CCNc1nc(nc(n1)C(Cl)(Cl)Cl)c2cccc(c2)C(F)(F)F | 2F | A4 | | 158-160 |
| 573 | CN(C)CCCNc1nc(nc(n1)C(Cl)(Cl)Cl)c2cc(cc(c2)C(F)(F)F)C(F)(F)F | 2AE | A24 | | 113-115 |
| 574 | FC(F)(F)c1cccc(c1)c2nc(NCCCN3CCCC3)nc(n2)C(Cl)(Cl)Cl | 2F | A2 | | 80-82 |
| 575 | FC(F)(F)c1cc(cc(c1)C(F)(F)F)c2nc(NCCCN3CCCC3)nc(n2)C(Cl)(Cl)Cl | 2AE | A2 | | 125-127 |
| 576 | CCN(CC)CCNc1nc(nc(n1)C(Cl)(Cl)Cl)c2cc(cc(c2)C(F)(F)F)C(F)(F)F | 2AE | A4 | | 86-89 |
| 577 | CCN1CCCC(C1)Nc2nc(nc(n2)C(Cl)(Cl)Cl)c3ccc(c(Cl)c3 | 2C | A17 | | 151-153 |
| 578 | CCN1CCCC(C1)Nc2nc(nc(n2)C(Cl)(Cl)Cl)c3cccc(c3)C(F)(F)F | 2F | A17 | | 126-128 |
| 579 | CCN1CCCC(C1)Nc2nc(nc(n2)C(Cl)(Cl)Cl)c3ccc(cc3)C(F)(F)F | 2AC | A17 | | 139-140 |
| 580 | CCN1CCCC(C1)Nc2nc(nc(n2)C(Cl)(Cl)Cl)c3cc(cc(c3)C(F)(F)F)C(F)(F)F | 2AE | A17 | | 102-104 |
| 581 | CCN(CC)CCNc1nc(nc(n1)C(Cl)(Cl)Cl)c2ccc(c(Cl)c2 | 2C | A4 | | 107-108 |
| 582 | CCN(CC)CCNc1nc(nc(n1)C(Cl)(Cl)Cl)c2ccc(cc2)C(F)(F)F | 2AC | A4 | | 90-92 |
| 583 | Clc1ccc(cc1Cl)c2nc(NCCCN3CCCC3)nc(n2)C(Cl)(Cl)Cl | 2C | A2 | | 138-139 |
| 584 | CN(C)CCCNc1nc(nc(n1)C(Cl)(Cl)Cl)c2cc(cc(c2)C(Cl)(Cl)Cl)C(Cl)(Cl)Cl | 2AF | A24 | | 141-143 |
| 585 | CN1CCCC1CCNc2nc(nc(n2)C(Cl)(Cl)Cl)c3ccc(cc3)C(Cl)(Cl)Cl | 2H | A3 | | 98-101 |
| 586 | CC(CNc1nc(nc(n1)C(Cl)(Cl)Cl)c2cccc(c2)C(Cl)(Cl)Cl)N(C)C | 2H | A54 | | 138-140 |
| 587 | CCN(CC)CCCNc1nc(nc(n1)C(Cl)(Cl)Cl)c2cccc(c2)C(Cl)(Cl)Cl | 2AD | A63 | | 152.5-157.5 |
| 588 | ClC(Cl)(Cl)c1cc(cc(c1)C(Cl)(Cl)Cl)c2nc(NCCCN3CCCC3)nc(n2)C(Cl)(Cl)Cl | 2AF | A2 | | 132-135 |
| 589 | CN1CCCC1CCNc2nc(nc(n2)C(Cl)(Cl)Cl)c3cccc(c3)C(Cl)(Cl)Cl | 2AD | A3 | | 134-136 |
| 590 | CC(CN(C)C)Nc1nc(nc(n1)C(Cl)(Cl)Cl)c2cccc(c2)C(Cl)(Cl)Cl | 2AD | A55 | | 93-96 |
| 591 | CCN1CCC(CNc2nc(nc(n2)C(Cl)(Cl)Cl)c3cccc(c3)C(Cl)(Cl)Cl | 2AD | A64 | | 104-107 |
| 592 | CN1CCCCC1CNc2nc(nc(n2)C(Cl)(Cl)Cl)c3cccc(c3)C(Cl)(Cl)Cl | 2AD | A65 | | 109-112 |
| 593 | CC(CNc1nc(nc(n1)C(Cl)(Cl)Cl)c2cccc(c2)C(Cl)(Cl)Cl)N(C)C | 2AD | A54 | | 115-117 |
| 594 | CCOC(=O)c1ccc(cc1)c2nc(NCC3CCN(CC)C3)nc(n2)C(Cl)(Cl)Cl | 2AB | A64 | | 147-150 |
| 595 | CCOC(=O)c1ccc(cc1)c2nc(NCC3CCCCCN3C)nc(n2)C(Cl)(Cl)Cl | 2AB | A65 | | 105-108 |
| 596 | CCN1CCC(CNc2nc(nc(n2)C(Cl)(Cl)Cl)c3ccc(cc3)C(Cl)(Cl)Cl)C1 | 2H | A64 | | 136-140 |
| 597 | CN(C)C1CCC(CC1)Nc2nc(nc(n2)C(Cl)(Cl)Cl)c3ccc(cc3)C(Cl)(Cl)Cl | 2H | A66 | 528.99 | |
| 598 | CCOC(=O)c1ccc(cc1)c2nc(NCCCN(C)C)nc(n2)C(Cl)(Cl)Cl | 2AB | A24 | | 110-112 |
| 599 | CCN(CC)CCNc1nc(nc(n1)C(Cl)(Cl)Cl)c2ccc(Cl)c(Cl)c2•ClC(Cl)(Cl)c1ccc(cc1)C(Cl)(Cl)Cl | 2C | A4 | | |
| 600 | CCN(CC)CCNc1nc(nc(n1)C(Cl)(Cl)Cl)c2ccc(cc2)C(F)(F)F•ClC(Cl)(Cl)c1ccc(cc1)C(Cl)(Cl)Cl | 2AC | A4 | | |
| 601 | CCN(CC)CCNc1nc(nc(n1)C(Cl)(Cl)Cl)c2ccc(cc2)C(Cl)(Cl)Cl•ClC(Cl)(Cl)c1ccc(cc1)-C(Cl)(Cl)Cl | 2H | A4 | | |
| 602 | FC(F)(F)c1cccc(c1)c2nc(NCCCN3CCCC3)nc(n2)C(Cl)(Cl)Cl•ClC(Cl)(Cl)c1ccc(cc1)-C(Cl)(Cl)Cl | 2F | A2 | | |
| 603 | CCN(CC)CCC(C)Nc1nc(nc(n1)C(Cl)(Cl)Cl)c2cccc(c2)C(Cl)(Cl)Cl | 2AD | A67 | | 115-120 |
| 604 | CN(C)CCCNc1nc(nc(n1)C(Cl)(Cl)Cl)C(Cl)(Cl)Cl•ClC(Cl)(Cl)c1ccc(cc1)C(Cl)(Cl)Cl | 1I | A24 | | |
| 605 | CN1CCCC1CCNc2nc(nc(n2)C(Cl)(Cl)Cl)c3ccc(Cl)c(Cl)c3 | 2C | A3 | | 117-120 |
| 606 | CN(C)CCCNc1nc(nc(n1)C(Cl)(Cl)Cl)c2ccc(Cl)c(Cl)c2 | 2C | A24 | | 124.5-128 |
| 607 | FC(F)(F)c1ccc(cc1)c2nc(NCCCN3CCCC3)nc(n2)C(Cl)(Cl)Cl•ClC(Cl)(Cl)c1ccc(cc1)-C(Cl)(Cl)Cl | 2AC | A2 | | |
| 608 | CN1CCCCC1CNc2nc(nc(n2)C(Cl)(Cl)Cl)c3ccc(Cl)c(Cl)c3 | 2C | A65 | | 165.5-169 |
| 609 | CN1CCCC1CCNc2nc(nc(n2)C(Cl)(Cl)Cl)c3cc(Cl)cc(Cl)c3 | 2L | A3 | | 111-113 |
| 610 | CC(CN(C)C)Nc1nc(nc(n1)C(Cl)(Cl)Cl)c2cc(Cl)cc(Cl)c2 | 2L | A55 | | 131-133 |
| 611 | CN(C)CCCNc1nc(nc(n1)C(Cl)(Cl)Cl)c2cc(Cl)cc(Cl)c2 | 2L | A24 | | 207-212 |
| 612 | CCN(CC)CCNc1nc(nc(n1)C(Cl)(Cl)Cl)c2cc(Cl)cc(Cl)c2 | 2L | A4 | | 233-234 |
| 613 | CCN1CCC(CC1)C(C)Nc2nc(nc(n2)C(Cl)(Cl)Cl)c3ccc(Cl)c(Cl)c3 | 2C | A22 | | 136-139 |
| 614 | CCN1CCCC(C1)Nc2nc(nc(n2)C(Cl)(Cl)Cl)c3cc(Cl)cc(Cl)c3 | 2L | A17 | | 195.5-198.5 |
| 615 | CCN(CC)CCNc1nc(nc(n1)C(Cl)(Cl)Cl)c2ccc(cc2)S(=O)C | 5 | A4 | 449.06 | 450.11 |
| 616 | CS(=O)c1ccc(cc1)c2nc(NCCCN3CCCC3)nc(n2)C(Cl)(Cl)Cl | 5 | A2 | 461.06 | 462.28 |
| 617 | CCN(CC)C1CCCC(C1)Nc2nc(nc(n2)C(Cl)(Cl)Cl)c3ccc(c3)C(Cl)(Cl)Cl | 2AD | A71 | | 145-150 |

TABLE 5-continued

| Cmpd | SMILES | Prep | Amine | MS, calc'd | MS, found (M + 1) or mp (° C.) |
|---|---|---|---|---|---|
| 618 | CN(C)CCNc1nc(nc(n1)C(Cl)(Cl)Cl)c2ccc(Cl)c(Cl)c2 | 2C | A63 | | 124.5-128 |
| 619 | CCCN(CCC)CC(C)Nc1nc(Nc2cc(Cl)cc(Cl)c2)nc(n1)C(Cl)(Cl)Cl | 1F | A72 | | 108.5-112.5 |

TABLE 6

| Cmpd | SMILES | Preparation | MS, calc'd | MS, found (M + 1) |
|---|---|---|---|---|
| 620 | COC1=CC=C(C2=NC(=NC(=N2)C(Cl)(Cl)Cl)N2CCC(N)CC2)C2=C1C=CC=C2 | 2R | 451.07 | 452.56 |
| 621 | NC1CCN(CC1)C1=NC(=NC(=N1)C1=CC=CC=C1)C(Cl)(Cl)Cl | 2I | 371.08 | 372.43 |
| 622 | NC1CCN(CC1)C1=NC(=NC(=N1)C(Cl)(Cl)Cl)C1=CC=C(Cl)C(Cl)=C1 | 2C | 438.97 | 440.08 |
| 623 | CC1=CC=C(C=C1)C1=NC(=NC(=N1)C(Cl)(Cl)Cl)N1CCC(N)CC1 | 2 | 385.06 | 386.25 |
| 624 | CC(C)(C)C1=CC=C(C=C1)C1=NC(=NC(=N1)C(Cl)(Cl)Cl)N1CCC(N)CC1 | 2E | 427.11 | 428.32 |
| 625 | NC1CCN(CC1)C1=NC(=NC(=N1)C1=CC=CC=C1)C(F)(F)F)C(Cl)(Cl)Cl | 2F | 439.03 | 440.15 |
| 626 | CSC1=CC=C(C=C1)C1=NC(=NC(=N1)C(Cl)(Cl)Cl)N1CCC(N)CC1 | 2G | 417.03 | 418.15 |
| 627 | CS(=O)(=O)C1=CC=C(C=C1)C1=NC(=NC(=N1)C(Cl)(Cl)Cl)N1CCC(N)CC1 | 6 | 449.02 | 450.09 |
| 628 | NC1CCN(CC1)C1=NC(=NC(=N1)C1=CC2=C(C=CC=C2)C=C1)C(Cl)(Cl)Cl | 2J | 421.05 | 422.19 |
| 629 | COC1=CC(=CC=C1)C1=NC(=NC(=N1)C(Cl)(Cl)Cl)N1CCC(N)CC1 | 2A | 401.06 | 402.20 |
| 630 | NC1CCN(CC1)C1=NC(=NC(=N1)C(Cl)(Cl)Cl)C1=CC=C(Cl)C=C1 | 2D | 405.01 | 407.00 |
| 631 | NC1CCN(CC1)C1=NC(=NC(=N1)C(Cl)(Cl)Cl)C1=CC(Cl)=CC(Cl)=C1 | 2L | 438.97 | 440.07 |
| 632 | NC1CCN(CC1)C1=NC(=NC(=N1)C(Cl)(Cl)Cl)C1=C(C=CC=C1)[N+]([O-])=O | 2N | 416.03 | 417.17 |
| 633 | NC1CCN(CC1)C1=NC(=NC(=N1)C(Cl)(Cl)Cl)C1=CC(Cl)=CC=C1 | 2P | 405.01 | 406.13 |
| 634 | NC1CCN(CC1)C1=NC(=NC(=N1)C1=CC=C(C=C1)C1=CC=CC=C1)C(Cl)(Cl)Cl | 2M | 447.08 | 448.34 |
| 635 | COC1=CC(=CC(OC)=C1)C1=NC(=NC(=N1)C(Cl)(Cl)Cl)N1CCC(N)CC1 | 2T | 431.07 | 432.57 |

TABLE 7

| Cmpd | SMILES | Prep. | Amine | MS, calc'd | MS, found (M + 1) or mp (° C.) |
|---|---|---|---|---|---|
| 636 | CN(C)CCCNc1nc(Nc2ccc(Cl)cc2)nc(n1)C(Cl)(Cl)Cl | 7 | A24 | | 226-228 |
| 637 | CN(C)CCCNc1nc(Nc2ccc(Cl)c(Cl)c2)nc(n1)C(Cl)(Cl)Cl | 1F | A24 | | 215-217 |
| 638 | CCN1CCCC(C1)Nc2nc(Nc3cc(Cl)cc(Cl)c3)nc(n2)C(Cl)(Cl)Cl | 1F | A17 | | 198-202 |
| 639 | CC(CN(C)C)Nc1nc(Nc2cc(Cl)cc(Cl)c2)nc(n1)C(Cl)(Cl)Cl | 1F | A55 | | 168-172 |
| 640 | CC(CN(C)C)Nc1nc(Nc2ccc(Cl)c(Cl)c2)nc(n1)C(Cl)(Cl)Cl | 1C | A55 | | 153-155.5 |
| 641 | CC(CNc1nc(Nc2ccc(Cl)c(Cl)c2)nc(n1)C(Cl)(Cl)Cl)N(C)C | 1C | A54 | | 255-255.5 |
| 642 | CCN(CC)CC(C)Nc1nc(Nc2ccc(Cl)c(Cl)c2)nc(n1)C(Cl)(Cl)Cl | 1C | A68 | | 180-183.5 |
| 643 | CCN1CCC(CC1)C(C)Nc2nc(Nc3ccc(Cl)c(Cl)c3)nc(n2)C(Cl)(Cl)Cl | 1C | A22 | | 105-109 |
| 644 | CCN(CC)CC(C)Nc1nc(Nc2cc(Cl)cc(Cl)c2)nc(n1)C(Cl)(Cl)Cl | 1F | A68 | | 218-220 |
| 645 | CCN1CCC(CC1)C(C)Nc2nc(Nc3cc(Cl)cc(Cl)c3)nc(n2)C(Cl)(Cl)Cl | 1F | A22 | | 235-238 |
| 646 | CCN(CC)CCCCNc1nc(Nc2ccc(Cl)c(Cl)c2)nc(n1)C(Cl)(Cl)Cl | 1C | A69 | | 98-102 |
| 647 | ClC(C1=NC(NCCO)=NC(C2=CC(C(F)(F)F)=CC=C2)=N1)(Cl)Cl | 2F | A57 | 399.99 | 401.06 |
| 648 | CN1CCN(CC1)c2ccc(Nc3nc(nc(n3)C(Cl)(Cl)Cl)c4ccc(cc4)S(=O)(=O)C)cc2 | 6 | A43 | 540.67 | 541.38 |
| 649 | CC(C)CNc1nc(nc(n1)C(Cl)(Cl)Cl)c2ccc(cc2)S(=O)(=O)C)CN3CCCCCC3 | 6 | A48 | 533.12 | 534.04 |
| 650 | CS(=O)(=O)c1ccc(cc1)c2nc(NCc3ccncc3)nc(n2)C(Cl)(Cl)Cl | 6 | A35 | 456.99 | 458.34 |
| 651 | COc1nccnc1Nc2nc(N)C(Cl)(Cl)Cl)c3ccc(cc3)S(=O)(=O)C | 6 | A13 | 472.99 | 473.94 |
| 652 | ClC(Cl)(Cl)c1ccc(cc1)c2nc(NCc3ccncc3)nc(n2)C(Cl)(Cl)Cl | 2H | A35 | 494.91 | 496.02 |
| 653 | CN(Cc1ccccc1c2ccccc2)c3nc(nc(n3)C(Cl)(Cl)Cl)c4ccc(cc4)C(Cl)(Cl)Cl | 2H | A49 | 570.95 | |
| 654 | CS(=O)(=O)c1ccc(cc1)c2nc(Nc3ccnc3)nc(n2)C(Cl)(Cl)Cl | 6 | A50 | 442.98 | 444.01 |
| 655 | CCN1CCCC(C1)NC1=NC(NC2=CC=C(OC(F)(F)F)C=C2)=NC(=N1)C(Cl)(Cl)Cl | 1D | A17 | 498.07 | 499.12 |
| 656 | FC(F)(F)OC1=CC=C(NC2=NC(=NC(NCCCN3CCCC3)=N2)C(Cl)(Cl)Cl)C=C1 | 1D | A1 | 484.06 | 485.14 |
| 657 | FC(F)(F)OC1=CC=C(NC2=NC(=NC(NCCCCN3CCCC3)=N2)C(Cl)(Cl)Cl)C=C1 | 1D | A2 | 498.07 | 499.10 |
| 658 | CN1CCCN(CC1)C1=NC(NC2=CC=C(OC(F)(F)F)C=C2)=NC(=N1)C(Cl)(Cl)Cl | 1D | A8 | 484.06 | 485.07 |
| 659 | FC(F)(F)OC1=CC=C(NC2=NC(=NC(=N2)N2CCCNCC2)C(Cl)(Cl)Cl)C=C1 | 1D | A7 | 470.04 | 471.07 |
| 660 | CC1=CC=C(C=C1)C1=NC(NCC2(N)CCCCC2)=NC(=N1)C(Cl)(Cl)Cl | 2 | A28 | 413.09 | 414.16 |
| 661 | COC1=CC=CC(=C1)C1=NC(NCC2(N)CCCCC2)=NC(=N1)C(Cl)(Cl)Cl | 2A | A28 | 429.09 | 430.12 |
| 662 | CC(C)(C)C1=CC=C(C=C1)C1=NC(NCC2(N)CCCCC2)=NC(=N1)C(Cl)(Cl)Cl | 2E | A28 | 455.14 | 456.22 |
| 663 | NC1(CNC2=NC(=NC(=N2)C2=CC=C(C2)C(F)(F)F)C(Cl)(Cl)Cl)CCCCC1 | 2F | A28 | 467.07 | 468.14 |
| 664 | CSC1=CC=C(C=C1)C1=NC(NCC2(N)CCCCC2)=NC(=N1)C(Cl)(Cl)Cl | 2G | A28 | 445.07 | 446.11 |
| 665 | CS(=O)(=O)C1=CC=C(C=C1)C1=NC(NCC2(N)CCCCC2)=NC(=N1)C(Cl)(Cl)Cl | 6 | A28 | 477.06 | 478.16 |
| 666 | NC1(CNC2=NC(=NC(=N2)C2=CC=C(C=C2)C(Cl)(Cl)Cl)C(Cl)(Cl)Cl)CCCCC1 | 2H | A28 | 514.98 | 516.03 |
| 667 | NC1(CNC2=NC(=NC(=N2)C2=CC3=C(C=CC=C3)C=C2)C(Cl)(Cl)Cl)CCCCC1 | 2J | A28 | 449.09 | 450.17 |
| 668 | COC1=C2C=CC=CC2=C(C=C1)C1=NC(NCC2(N)CCCCC2)=NC(=N1)C(Cl)(Cl)Cl | 2R | A28 | 479.10 | 480.23 |
| 669 | COC1=C(OC)C=C(C=C1)C1=NC(NCC2(N)CCCCC2)=NC(=N1)C(Cl)(Cl)Cl | 2S | A28 | 459.10 | 460.78 |
| 670 | NC1(CNC2=NC(=NC(=N2)C2=CC(Cl)=C(Cl)C=C2)C(Cl)(Cl)Cl)CCCCC1 | 2C | A28 | 467.00 | 468.03 |
| 671 | NC1(CNC2=NC(=NC(=N2)C2=CC=C(C=C2)C(Cl)(Cl)Cl)C(Cl)(Cl)Cl)CCCCC1 | 2H | A29 | 500.96 | 501.94 |
| 672 | NC1(CNC2=NC(=NC(=N2)C2=CC=C(C=C2)C2=CC=CC=C2)C(Cl)(Cl)Cl)CCCCC1 | 2M | A29 | 435.08 | 436.12 |

TABLE 7-continued

| Cmpd | SMILES | Prep. | Amine | MS, calc'd | MS, found (M + 1) or mp (° C.) |
|---|---|---|---|---|---|
| 673 | COC1=C2C=CC=CC2=C(C=C1)C1=NC(NCC2(N)CCCC2)=NC(=N1)C(Cl)(Cl)Cl | 2R | A29 | 465.09 | 466.18 |
| 674 | COC1=C(OC)C=C(C=C1)C1=NC(NCC2(N)CCCC2)=NC(=N1)C(Cl)(Cl)Cl | 2S | A29 | 445.08 | 446.17 |
| 675 | COC1=CC=CC(=C1)C1=NC(NCC2(N)CCCC2)=NC(=N1)C(Cl)(Cl)Cl | 2A | A29 | 415.07 | 416.15 |
| 676 | CN1CCC(CC1)NC1=NC(NC2=CC=C(OC(F)(F)F)C=C2)=NC(=N1)C(Cl)(Cl)Cl | 1D | A12 | 484.06 | 484.91 |
| 677 | NC1(CNC2=NC(=NC(=N2)C2=CC=CC=C2)C(Cl)(Cl)Cl)CC1 | 2I | A30 | 357.03 | 358.14 |
| 678 | NC1(CNC2=NC(=NC(=N2)C2=CC=C(Cl)C=C2)C(Cl)(Cl)Cl)CC1 | 2D | A30 | 390.99 | 392.10 |
| 679 | NC1(CNC2=NC(=NC(=N2)C2=CC=C(C=C2)C(Cl)(Cl)C(Cl)(Cl)Cl)CC1 | 2H | A30 | 472.93 | 474.08 |
| 680 | NC1(CNC2=NC(=NC(=N2)C2=CC(Cl)=CC=C2)C(Cl)(Cl)Cl)CC1 | 2P | A30 | 390.99 | 392.12 |
| 681 | CC1=CC=C(C=C1)C1=NC(NCC2(N)CC2)=NC(=N1)C(Cl)(Cl)Cl | 2 | A30 | 371.05 | 372.09 |
| 682 | NC1(CNC2=NC(=NC(=N2)C2=CC(=CC=C2)C(F)(F)F)C(Cl)(Cl)Cl)CC1 | 2F | A30 | 425.02 | 426.57 |
| 683 | NC1(CNC2=NC(=NC(=N2)C2=CC(Cl)=CC(Cl)=C2)C(Cl)(Cl)Cl)CC1 | 2L | A30 | 424.95 | 426.08 |
| 684 | CC(C)CN1CCC(CC1)NC1=NC(=NC(=N1)C(Cl)(Cl)Cl)C1=C(C=CC=C1)[N+]([O-])=O | 2N | A25 | 472.09 | 473.27 |
| 685 | COC1=CC=C(C=C1)C1=NC(=NC(NCC2(N)CCCC2)=N1)C(Cl)(Cl)Cl | 2T | A28 | 459.10 | 460.19 |
| 686 | ClC(Cl)(Cl)C1=NC(NCCN2CCCC2)=NC(NC2=CC3=C(C=CC=C3)C=C2)=N1 | 1H | A1 | 450.09 | 451.31 |
| 687 | CN(CC(=O)OC(C)(C)C)c1nc(nc(n1)C(Cl)(Cl)Cl)c2ccc(Cl)cc2 | 2D | A61 | 450.02 | 451.29 |
| 688 | NC(=O)C1CCN(CC1)c2nc(nc(n2)C(Cl)(Cl)Cl)c3ccc(cc3)C(Cl)(Cl)Cl | 2H | A53 | 514.94 | 516.08 |
| 689 | CS(=O)(=O)c1ccc(cc1)c2nc(Nc3ccc(cc3)n4cccn4)nc(n2)C(Cl)(Cl)Cl | 6 | A42 | 508.00 | 510.95 |
| 690 | CS(=O)(=O)c1ccc(cc1)c2nc(nc(n2)C(Cl)(Cl)Cl)N3CCC(CC3)C(=O)N | 6 | A53 | 477.02 | 478.21 |
| 691 | CC(=O)Nc1cccc(Nc2nc(nc(n2)C(Cl)(Cl)Cl)c3ccc(cc3)S(=O)(=O)C)c1 | 6 | A44 | 499.00 | |

TABLE 8

| Cmpd | SMILES | Prep. | MS, calc'd | MS, found (M + 1) |
|---|---|---|---|---|
| 692 | CC(C)CN1CCC(CC1)NC1=NC(=NC(=N1)C(Cl)(Cl)Cl)C1=CC=C(Cl)C(Cl)=C1 | 2C | 495.03 | 496.17 |
| 693 | CC(C)CN1CCC(CC1)NC1=NC(=NC(=N1)C(Cl)(Cl)Cl)C1=CC=C(Cl)C=C1 | 2D | 461.07 | 462.21 |
| 694 | CC(C)CN1CCC(CC1)NC1=NC(=NC(=N1)C(Cl)(Cl)Cl)C1=CC=C(C=C1)C(C)(C)C | 2E | 483.17 | 484.47 |
| 695 | CSC1=CC=C(C=C1)C1=NC(=NC(NC2CCN(CC(C)C)CC2)=N1)C(Cl)(Cl)Cl | 2G | 473.10 | 474.22 |
| 696 | COC1=CC=C(C=C1)C1=NC(NC2CCN(CC(C)C)CC2)=NC(=N1)C(Cl)(Cl)Cl | 2B | 457.12 | 458.23 |
| 697 | CC(C)CN1CCC(CC1)NC1=NC(=NC(=N1)C1=CC=C(C=C1)C(Cl)(Cl)C(Cl)(Cl)Cl | 2H | 543.01 | 544.13 |
| 698 | CC(C)CN1CCC(CC1)NC1=NC(=NC(=N1)C1=CC2=C(C=CC=C2)C=C1)C(Cl)(Cl)Cl | 2J | 477.13 | 478.32 |
| 699 | CC(C)CN1CCC(CC1)NC1=NC(=NC(=N1)C1=CC=C(C=C1)C1=CC=CC=C1)C(Cl)(Cl)Cl | 2M | 503.14 | 504.29 |
| 700 | CC(C)CN1CCC(CC1)NC1=NC(=NC(=N1)C1=CC=CC=C1C(F)(F)F)C(Cl)(Cl)Cl | 2F | 495.10 | 496.26 |
| 701 | CC(C)CN1CCC(CC1)NC1=NC(=NC(=N1)C1=CC(Cl)=CC=C1)C(Cl)(Cl)Cl | 2P | 461.07 | 462.18 |
| 702 | COC1=C(OC)C=C(C=C1)C1=NC(NC2CCN(CC(C)C)CC2)=NC(=N1)C(Cl)(Cl)Cl | 2S | 487.13 | 488.29 |
| 703 | COC1=C2C=CC=CC2=C(C=C1)C1=NC(NC2CCN(CC(C)C)CC2)=NC(=N1)C(Cl)(Cl)Cl | 2R | 507.14 | 508.25 |
| 704 | CC(C)CN1CCC(CC1)NC1=NC(=NC(=N1)C1=CC=CC=C1)C(Cl)(Cl)Cl | 2I | 427.11 | 428.30 |

TABLE 9

| Cmpd | SMILES | Prep. | Amine | MS, calc'd | MS, found (M + 1) |
|---|---|---|---|---|---|
| 705 | CC(C)(C)OC(=O)N1CC2CC1CN2c3nc(nc(n3)C(Cl)(Cl)Cl)c4ccc(Cl)c(Cl)c4 | 2C | A6 | 537.01 | |
| 706 | COc1ccc(cc1)c2nc(nc(n2)C(Cl)(Cl)Cl)N3CC4CC3CN4C(=O)OC(C)(C)C | 2B | A6 | 499.09 | |
| 707 | CC(C)(C)OC(=O)N1CC2CC1CN2c3nc(nc(n3)C(Cl)(Cl)Cl)c4cccc(c4)C(F)(F)F | 2F | A6 | 537.07 | |
| 708 | Clc1cc(CNc2nc(nc(n2)C(Cl)(Cl)Cl)c3ccc(Cl)c(Cl)c3)n(C)n1 | 2C | A46 | 463.96 | |
| 709 | Clc1ccc(Nc2nc(nc(n2)C(Cl)(Cl)Cl)N3CCOCC3)cc1Cl | 1 | A51 | 440.95 | 442.12 |
| 710 | CSc1ccc(cc1)c2nc(nc(n2)C(Cl)(Cl)Cl)N3CC4CC3CN4C(=O)OC(C)(C)C | 2G | A6 | 515.07 | 515.87 |
| 711 | Cc1ccc(cc1)c2nc(nc(n2)C(Cl)(Cl)Cl)N3CC4CC3CN4C(=O)OC(C)(C)C | 2B | A6 | 483.10 | 484.01 |
| 712 | CC(C)(C)OC(=O)N1CC2CC1CN2c3nc(nc(n3)C(Cl)(Cl)Cl)c4ccc(cc4)C(C)(C)C | 2E | A6 | 525.15 | 525.99 |
| 713 | CC(C)(C)OC(=O)N1CC2CC1CN2c3nc(nc(n3)C(Cl)(Cl)Cl)c4ccc(cc4)C(Cl)(Cl)Cl | 2H | A6 | 584.98 | 586.14 |
| 714 | CC(C)(C)OC(=O)N1CC2CC1CN2c3nc(nc(n3)C(Cl)(Cl)Cl)c4ccccc4 | 2I | A6 | 469.08 | 469.96 |
| 715 | CC(C)(C)OC(=O)N1CC2CC1CN2c3nc(nc(n3)C(Cl)(Cl)Cl)c4ccc(cc4)S(=O)(=O)C | 6 | A6 | 547.06 | 548.11 |

TABLE 10

| Cmpd | SMILES | Prep. | MS, calc'd | MS, found (M + 1) |
|---|---|---|---|---|
| 716 | Clc1ccc(cc1Cl)c2nc(nc(n2)C(Cl)(Cl)Cl)N3CC4CC3CN4 | 2C | 436.95 | |
| 717 | Clc1ccc(cc1)c2nc(nc(n2)C(Cl)(Cl)Cl)N3CC4CC3CN4 | 2D | 402.99 | |
| 718 | COc1ccc(cc1)c2nc(nc(n2)C(Cl)(Cl)Cl)N3CC4CC3CN4 | 2B | 399.04 | 400.25 |
| 719 | Cc1ccc(cc1)c2nc(nc(n2)C(Cl)(Cl)Cl)N3CC4CC3CN4 | 2 | 383.05 | 384.03 |
| 720 | ClC(Cl)(Cl)c1nc(nc(n1)c2ccccc2)N3CC4CC3CN4 | 2I | 369.03 | 370.01 |
| 721 | CC(C)c1ccc(cc1)c2nc(nc(n2)C(Cl)(Cl)Cl)N3CC4CC3CN4 | 2E | 425.09 | 426.30 |
| 722 | ClC(Cl)(Cl)c1ccc(cc1)c2nc(nc(n2)C(Cl)(Cl)Cl)N3CC4CC3CN4 | 2H | 484.93 | 486.08 |

TABLE 10-continued

| Cmpd | SMILES | Prep. | MS, calc'd | MS, found (M + 1) |
|---|---|---|---|---|
| 723 | CSc1ccc(cc1)c2nc(nc(n2)C(Cl)(Cl)Cl)N3CC4CC3CN4 | 2G | 415.02 | 416.02 |
| 724 | CS(=O)(=O)c1ccc(cc1)c2nc(nc(n2)C(Cl)(Cl)Cl)N3CC4CC3CN4 | 6 | 447.01 | 448.00 |
| 725 | FC(F)(F)OC1=CC=C(NC2=NC(=NC(=N2)C(Cl)(Cl)Cl)N2CC3CC2CN3)C=C1 | 1D | 468.02 | 469.20 |
| 726 | ClC(Cl)(Cl)C1=NC(=NC(=N1)C1=CC=C(C=C1)N1CCCC1)N1CC2CC1CN2 | 2AA | 438.09 | 439.30 |

TABLE 11

| Cmpd | SMILES | Prep. | Amine | MS, calc'd | MS, found (M + 1) |
|---|---|---|---|---|---|
| 727 | CC(=O)Nc1cccc(Nc2nc(nc(n2)C(Cl)(Cl)Cl)C(Cl)(Cl)Cl)c1 | 2Z | A44 | 460.89 | 461.99 |
| 728 | ClC(Cl)(Cl)c1nc(NCCCN2CCCC2)nc(Nc3ccc(cc3)n4cccn4)n1 | 7C | A2 | 480.11 | 481.20 |
| 729 | ClC(Cl)(Cl)c1nc(Nc2ccccc2N3CCOCC3)nc(n1)C(Cl)(Cl)Cl | 2Z | A41 | 488.93 | 490.08 |
| 730 | COc1ccccc1Nc2nc(nc(n2)C(Cl)(Cl)Cl)C(Cl)(Cl)Cl | 2Z | A13 | 433.88 | 436.09 |
| 731 | CN1CCN(CC1)c2ccc(Nc3nc(nc(n3)C(Cl)(Cl)Cl)C(Cl)(Cl)Cl)cc2 | 2Z | A43 | 501.96 | 503.11 |
| 732 | ClC(Cl)(Cl)c1nc(Nc2cccc(cc2)n3cccn3)nc(n1)C(Cl)(Cl)Cl | 2Z | A42 | 469.89 | 471.09 |
| 733 | CN1CCN(CC1)c2ccc(Nc3nc(NCCN4CCCC4)nc(n3)C(Cl)(Cl)Cl)cc2 | 7B | A1 | 498.16 | 499.10 |
| 734 | CC(C)(C)c1ccc(cc1)c2nc(nc(n2)C(Cl)(Cl)Cl)N3CCOCC3 | 2E | A20 | 414.08 | 415.57 |
| 735 | CC(C)(C)c1ccc(cc1)c2nc(NCc3cccc(CN4CCCC4)c3)nc(n2)C(Cl)(Cl)Cl | 2E | A52 | 517.16 | 518.18 |
| 736 | CN(CCc1ccccn1)c2nc(nc(n2)C(Cl)(Cl)Cl)c3ccc(cc3)C(C)(C)C | 2E | A19 | 463.11 | 464.23 |
| 737 | CC(C)(C)c1ccc(cc1)c2nc(NCC(C)(C)CN3CCCCCC3)nc(n2)C(Cl)(Cl)Cl | 2E | A48 | 511.20 | 512.22 |
| 738 | CC(C)(C)c1ccc(cc1)c2nc(nc(n2)C(Cl)(Cl)Cl)N3CCCN(CCO)CC3 | 2E | A23 | 471.14 | 472.18 |
| 739 | CC(C)(C)c1ccc(cc1)c2nc(Nc3ccncc3)nc(n2)C(Cl)(Cl)Cl | 2E | A15 | 421.06 | 422.23 |
| 740 | NC1CCCC1NC1=NC(=NC(=N1)C1=CC(Cl)=C(Cl)C=Cl)C(Cl)(Cl)Cl | 2C | A60 | 452.98 | 456.27 |
| 741 | CC1(C)CC(CC(C)(C)N1)NC1=NC(NC2=CC=CC=C2)=NC(=N1)C(Cl)(Cl)Cl | 1G | A31 | 442.12 | 443.41 |
| 742 | CN1CCC(CC1)NC1=NC(NC2=CC3=C(C=CC=C3)C=C2)=NC(=N1)C(Cl)(Cl)Cl | 1H | A12 | 450.09 | 451.76 |

TABLE 12

| Cmpd | SMILES | Prep. | MS, calc'd | MS, found (M + 1) |
|---|---|---|---|---|
| 743 | NC1CCN(CC1)c2nc(nc(n2)C(Cl)(Cl)Cl)c3ccc(cc3)C(Cl)(Cl)Cl | 2H | 486.95 | 488.34 |
| 744 | ClC(Cl)(Cl)C1=NC(NC2=CC=NC=C2)=NC(=N1)C1=CC=C(C=C1)N1CCCC1 | 2AA | 434.06 | 435.20 |

TABLE 13

| Cmpd | IUPAC Name | D6 | W2 | C235 | hERG |
|---|---|---|---|---|---|
| 2 | (2-{[4-(3,4-dichlorophenyl)-6-(trichloromethyl)-1,3,5-triazin-2-yl]amino}propyl)dimethylamine | 162 | 103 | 119 | |
| 3 | N,N-dimethyl-1-[4-(trichloromethyl)-6-[3-(trifluoromethyl)phenyl]-1,3,5-triazin-2-yl]pyrrolidin-3-amine | 198 | 93 | 139 | 100 |
| 4 | N-[2-(morpholin-4-yl)ethyl]-4-(trichloromethyl)-6-[3-(trifluoromethyl)phenyl]-1,3,5-triazin-2-amine | 328 | 173 | 385 | 85 |
| 5 | N-[2-(pyrrolidin-1-yl)ethyl]-4-(trichloromethyl)-6-[3-(trifluoromethyl)phenyl]-1,3,5-triazin-2-amine | 58 | 54 | 62 | 99 |
| 6 | 4-(3-methoxyphenyl)-N-[3-(pyrrolidin-1-yl)propyl]-6-(trichloromethyl)-1,3,5-triazin-2-amine | 33 | 26 | 44 | 96 |
| 7 | 4-(4-methoxyphenyl)-N-[3-(pyrrolidin-1-yl)propyl]-6-(trichloromethyl)-1,3,5-triazin-2-amine | 105 | 80 | 103 | 100 |
| 8 | N,N-dimethyl-N-[4-(trichloromethyl)-6-[3-(trifluoromethyl)phenyl]-1,3,5-triazin-2-yl]piperidin-3-amine | 307 | 97 | 313 | 75 |
| 9 | 1-[4-(4-methoxyphenyl)-6-(trichloromethyl)-1,3,5-triazin-2-yl]-N,N-dimethylpyrrolidin-3-amine | 36 | 41 | 261 | 59 |
| 10 | 1-[4-(4-chlorophenyl)-6-(trichloromethyl)-1,3,5-triazin-2-yl]-N,N-dimethylpyrrolidin-3-amine | | | | |
| 11 | ethyl 4-(4-{[2-(pyrrolidin-1-yl)ethyl]amino}-6-(trichloromethyl)-1,3,5-triazin-2-yl)benzoate | 588 | 475 | 592 | |
| 12 | ethyl 4-(4-{[3-(pyrrolidin-1-yl)propyl]amino}-6-(trichloromethyl)-1,3,5-triazin-2-yl)benzoate | 1000 | 1000 | 1000 | |
| 13 | ethyl 4-(4-{[3-(dimethylamino)pyrrolidin-1-yl]-6-(trichloromethyl)-1,3,5-triazin-2-yl)benzoate | 1000 | 1000 | 1000 | |
| 14 | ethyl 4-{4-[(2-amino-2-methylpropyl)amino]-6-(trichloromethyl)-1,3,5-triazin-2-yl}benzoate | 37 | 24 | 36 | 11 |
| 15 | ethyl 4-(4-{[2-(diethylamino)ethyl]amino}-6-(trichloromethyl)-1,3,5-triazin-2-yl)benzoate | 52 | 39 | 48 | 84 |
| 16 | ethyl 4-[4-(4-methylpiperazin-1-yl)-6-(trichloromethyl)-1,3,5-triazin-2-yl]benzoate | 1000 | 1000 | 1000 | 46 |
| 17 | ethyl 4-[4-(piperazin-1-yl)-6-(trichloromethyl)-1,3,5-triazin-2-yl]benzoate | 1000 | 833.3 | 1000 | 35.9 |
| 18 | 4-(4-chlorophenyl)-N-[2-(pyrrolidin-1-yl)ethyl]-6-(trichloromethyl)-1,3,5-triazin-2-amine | 43 | 37 | 46 | 102 |
| 19 | 4-(3,4-dichlorophenyl)-N-[2-(pyrrolidin-1-yl)ethyl]-6-(trichloromethyl)-1,3,5-triazin-2-amine | | | | 92 |
| 20 | 1-[4-(3,4-dichlorophenyl)-6-(trichloromethyl)-1,3,5-triazin-2-yl]-N,N-dimethylpyrrolidin-3-amine | | | | 50 |
| 21 | N-(2-amino-2-methylpropyl)-4-(3,4-dichlorophenyl)-6-(trichloromethyl)-1,3,5-triazin-2-amine | | | | 37 |
| 22 | 2-(3,4-dichlorophenyl)-4-(4-methylpiperazin-1-yl)-6-(trichloromethyl)-1,3,5-triazine | | | | 33 |
| 23 | 4-(3,4-dichlorophenyl)-N-methyl-N-[2-(pyridin-2-yl)ethyl]-6-(trichloromethyl)-1,3,5-triazin-2-amine | | | | 77 |
| 25 | 2-(3,4-dichlorophenyl)-4-(piperazin-1-yl)-6-(trichloromethyl)-1,3,5-triazine | | | | 10 |
| 26 | 4-(3,4-dichlorophenyl)-N-(pyridin-4-ylmethyl)-6-(trichloromethyl)-1,3,5-triazin-2-amine | 246 | 173 | 479 | 10 |
| 27 | 4-(4-methoxyphenyl)-N-[2-(pyrrolidin-1-yl)ethyl]-6-(trichloromethyl)-1,3,5-triazin-2-amine | 41 | 37 | 50 | 94 |
| 28 | 2-(4-methoxyphenyl)-4-(piperazin-1-yl)-6-(trichloromethyl)-1,3,5-triazine | 586 | 268 | 523 | 32 |
| 29 | 2-(4-chlorophenyl)-4-(4-methylpiperazin-1-yl)-6-(trichloromethyl)-1,3,5-triazine | 307 | 173 | 351 | 5 |
| 30 | 2-[(2-{[4-(3,4-dichlorophenyl)-6-(trichloromethyl)-1,3,5-triazin-2-yl]amino}ethyl)sulfanyl]ethan-1-ol | 744 | 205 | 573 | 42.7 |
| 31 | 2-(4-chlorophenyl)-4-(morpholin-4-yl)-6-(trichloromethyl)-1,3,5-triazine | | | | 12 |

TABLE 13-continued

| Cmpd | IUPAC Name | D6 | W2 | C235 | hERG |
|---|---|---|---|---|---|
| 32 | 2-(4-tert-butylphenyl)-4-(4-methylpiperazin-1-yl)-6-(trichloromethyl)-1,3,5-triazine | 1000 | 167 | 408 | 33 |
| 33 | (2-{[4-(4-tert-butylphenyl)-6-(trichloromethyl)-1,3,5-triazin-2-yl]amino}ethyl)diethylamine | 151 | 138 | 142 | 41 |
| 34 | 4-(4-tert-butylphenyl)-N-[3-(pyrrolidin-1-yl)propyl]-6-(trichloromethyl)-1,3,5-triazin-2-amine | 152 | 141 | 152 | 80.9 |
| 35 | 4-[4-(benzyloxy)phenyl]-N-[2-(pyrrolidin-1-yl)ethyl]-6-(trichloromethyl)-1,3,5-triazin-2-amine | 194 | 125 | 186 | 56 |
| 36 | 4-[4-(benzyloxy)phenyl]-N-[3-(pyrrolidin-1-yl)propyl]-6-(trichloromethyl)-1,3,5-triazin-2-amine | 1000 | 563 | 679 | |
| 37 | 4-[4-(benzyloxy)phenyl]-N-[(1-ethylpiperidin-4-yl)methyl]-6-(trichloromethyl)-1,3,5-triazin-2-amine | 266 | 205 | 314 | |
| 38 | N-[(1-ethylpiperidin-4-yl)methyl]-4-(4-methanesulfonylphenyl)-6-(trichloromethyl)-1,3,5-triazin-2-amine | 163 | 50 | 122 | 81.4 |
| 39 | 4-(4-methanesulfonylphenyl)-N-[2-(pyrrolidin-1-yl)ethyl]-6-(trichloromethyl)-1,3,5-triazin-2-amine | 85 | 45 | 92 | 90 |
| 40 | 2-{4-[4-(4-chlorophenyl)-6-(trichloromethyl)-1,3,5-triazin-2-yl]piperazin-1-yl}ethan-1-ol | 359 | 175 | 405 | |
| 41 | 2-{4-[4-(3-methoxyphenyl)-6-(trichloromethyl)-1,3,5-triazin-2-yl]piperazin-1-yl}ethan-1-ol | 33 | 102 | 290 | 7.7 |
| 42 | 2-{4-[4-(trichloromethyl)-6-[3-(trifluoromethyl)phenyl]-1,3,5-triazin-2-yl]piperazin-1-yl}ethan-1-ol | 1000 | 416 | 1000 | |
| 43 | 2-(3-methoxyphenyl)-4-(4-methylpiperazin-1-yl)-6-(trichloromethyl)-1,3,5-triazine | 1000 | 1000 | 1000 | |
| 44 | 4-[4-(methylsulfanyl)phenyl]-N-[3-(pyrrolidin-1-yl)propyl]-6-(trichloromethyl)-1,3,5-triazin-2-amine | 462 | 204 | 638 | |
| 45 | N-[2-(1-methylpyrrolidin-2-yl)ethyl]-4-[4-(methylsulfanyl)phenyl]-6-(trichloromethyl)-1,3,5-triazin-2-amine | 43 | 91 | 74 | 38 |
| 46 | 4-(4-tert-butylphenyl)-N-[2-(1-methylpyrrolidin-2-yl)ethyl]-6-(trichloromethyl)-1,3,5-triazin-2-amine | 47 | 56 | 69 | 25 |
| 47 | 4-[4-(methylsulfanyl)phenyl]-N-[2-(pyrrolidin-1-yl)ethyl]-6-(trichloromethyl)-1,3,5-triazin-2-amine | | | | 95 |
| 48 | 2-(4-methylpiperazin-1-yl)-4-[4-(methylsulfanyl)phenyl]-6-(trichloromethyl)-1,3,5-triazine | 449 | 231 | 778 | |
| 49 | diethyl[2-({4-[4-(methylsulfanyl)phenyl]-6-(trichloromethyl)-1,3,5-triazin-2-yl}amino)ethyl]amine | 118 | 134 | 379 | |
| 50 | 4-(4-methylphenyl)-N-[2-(pyrrolidin-1-yl)ethyl]-6-(trichloromethyl)-1,3,5-triazin-2-amine | | | | |
| 51 | 4-(4-methylphenyl)-N-[3-(pyrrolidin-1-yl)propyl]-6-(trichloromethyl)-1,3,5-triazin-2-amine | 1000 | 725 | 1000 | |
| 52 | 4-(4-methylphenyl)-N-[2-(1-methylpyrrolidin-2-yl)ethyl]-6-(trichloromethyl)-1,3,5-triazin-2-amine | 32 | 22 | 36 | 83 |
| 53 | diethyl(2-{[4-(4-methylphenyl)-6-(trichloromethyl)-1,3,5-triazin-2-yl]amino}ethyl)amine | 394 | 228 | 396 | |
| 54 | 2-(4-methanesulfonylphenyl)-4-(4-methylpiperazin-1-yl)-6-(trichloromethyl)-1,3,5-triazine | 432 | 356 | 632 | |
| 55 | N-(2-amino-2-methylpropyl)-4-(trichloromethyl)-6-[4-(trichloromethyl)phenyl]-1,3,5-triazin-2-amine | 46 | 30 | 89 | 17 |
| 56 | N,N-dimethyl-1-[4-(trichloromethyl)-6-[4-(trichloromethyl)phenyl]-1,3,5-triazin-2-yl]pyrrolidin-3-amine | 1000 | 1000 | 1000 | |
| 57 | N-[2-(pyrrolidin-1-yl)ethyl]-4-(trichloromethyl)-6-[4-(trichloromethyl)phenyl]-1,3,5-triazin-2-amine | 10 | 6 | 22 | 25 |
| 58 | 2-(4-methanesulfonylphenyl)-4-(morpholin-4-yl)-6-(trichloromethyl)-1,3,5-triazine | 1000 | 665 | 1000 | |
| 59 | diethyl[2-({4-[(4-methoxyphenyl)methyl]-6-(trichloromethyl)-1,3,5-triazin-2-yl}amino)ethyl]amine | 290 | 153 | 288 | 100 |
| 60 | 4-[(4-methoxyphenyl)methyl]-N-[3-(pyrrolidin-1-yl)propyl]-6-(trichloromethyl)-1,3,5-triazin-2-amine | 525 | 232 | 491 | |
| 61 | N-(1-methylpiperidin-4-yl)-4-(trichloromethyl)-6-[4-(trichloromethyl)phenyl]-1,3,5-triazin-2-amine | 570 | 376 | 556 | |
| 62 | 1-methyl-4-[4-(trichloromethyl)-6-[4-(trichloromethyl)phenyl]-1,3,5-triazin-2-yl]-1,4-diazepane | 9 | 5 | 9 | 31 |
| 63 | 2-N-(2-methoxyphenyl)-4-N-[2-(1-methylpyrrolidin-2-yl)ethyl]-6-(trichloromethyl)-1,3,5-triazine-2,4-diamine | 603 | 794 | 540 | |
| 64 | 2-N-[2-(1-methylpyrrolidin-2-yl)ethyl]-4-N-[2-(morpholin-4-yl)phenyl]-6-(trichloromethyl)-1,3,5-triazine-2,4-diamine | 140 | 75 | 121 | 100 |
| 65 | N-(2-methoxyphenyl)-4-(4-methylpiperazin-1-yl)-6-(trichloromethyl)-1,3,5-triazin-2-amine | 32 | 32 | 31 | 83 |
| 66 | 2-N-(2-methoxyphenyl)-4-N-[2-(pyrrolidin-1-yl)ethyl]-6-(trichloromethyl)-1,3,5-triazine-2,4-diamine | 549 | 542 | 380 | |
| 67 | 2-N-(2-methoxyphenyl)-4-N-[3-(pyrrolidin-1-yl)propyl]-6-(trichloromethyl)-1,3,5-triazine-2,4-diamine | 1000 | 1000 | 1000 | |
| 68 | 4-[(2-methoxyphenyl)methyl]-N-[3-(pyrrolidin-1-yl)propyl]-6-(trichloromethyl)-1,3,5-triazin-2-amine | 1000 | 1000 | 1000 | |
| 69 | 2-[(2-methoxyphenyl)methyl]-4-(4-methylpiperazin-1-yl)-6-(trichloromethyl)-1,3,5-triazine | 1000 | 1000 | 1000 | |
| 70 | diethyl[2-({4-[(2-methoxyphenyl)methyl]-6-(trichloromethyl)-1,3,5-triazin-2-yl}amino)ethyl]amine | 6 | 6 | 6 | 100 |
| 71 | 4-[(2-methoxyphenyl)methyl]-N-[2-(1-methylpyrrolidin-2-yl)ethyl]-6-(trichloromethyl)-1,3,5-triazin-2-amine | 6 | 6 | 6 | 117 |
| 72 | 2-(4-methanesulfinylphenyl)-4-(4-methylpiperazin-1-yl)-6-(trichloromethyl)-1,3,5-triazine | 33 | 33 | 27 | 41 |
| 73 | 2-N-[2-(1-methylpyrrolidin-2-yl)ethyl]-4-N-[4-(1H-pyrazol-1-yl)phenyl]-6-(trichloromethyl)-1,3,5-triazine-2,4-diamine | 1000 | 1000 | 1000 | |
| 74 | diethyl(2-{[4-(4-methanesulfonylphenyl)-6-(trichloromethyl)-1,3,5-triazin-2-yl]amino}ethyl)amine | 1000 | 1000 | 1000 | |
| 75 | 4-(4-methanesulfonylphenyl)-N-[2-(1-methylpyrrolidin-2-yl)ethyl]-6-(trichloromethyl)-1,3,5-triazin-2-amine | 635 | 1000 | 1000 | |
| 76 | 1-[4-(4-methanesulfonylphenyl)-6-(trichloromethyl)-1,3,5-triazin-2-yl]-4-methyl-1,4-diazepane | 1000 | 1000 | 1000 | |
| 77 | 4-(4-methanesulfonylphenyl)-N-(1-methylpiperidin-4-yl)-6-(trichloromethyl)-1,3,5-triazin-2-amine | 92 | 53 | 131 | 72 |
| 78 | N-(1-ethylpiperidin-3-yl)-4-phenyl-6-(trichloromethyl)-1,3,5-triazin-2-amine | 70 | 50 | 90 | 103 |
| 79 | 4-(4-tert-butylphenyl)-N-(1-ethylpiperidin-3-yl)-6-(trichloromethyl)-1,3,5-triazin-2-amine | 26 | 25 | 36 | 51 |
| 80 | N-(1-ethylpiperidin-3-yl)-4-(4-methylphenyl)-6-(trichloromethyl)-1,3,5-triazin-2-amine | 135 | 90 | 129 | 97 |
| 81 | 1-{4-[(4-ethoxyphenyl)methyl]piperazin-1-yl}-3-[4-(3-{4-[(4-ethoxyphenyl)methyl]piperazin-1-yl}-2-hydroxypropoxy)phenoxy]propan-2-ol | 633 | 601 | 992 | |
| 82 | 4-[(3-methoxyphenyl)methyl]-N-[2-(pyrrolidin-1-yl)ethyl]-6-(trichloromethyl)-1,3,5-triazin-2-amine | 1000 | 805 | 1000 | |
| 83 | 4-[(3-methoxyphenyl)methyl]-N-[3-(pyrrolidin-1-yl)propyl]-6-(trichloromethyl)-1,3,5-triazin-2-amine | 103 | 68 | 133 | 117 |
| 84 | 4-[(3-methoxyphenyl)methyl]-N-[2-(1-methylpyrrolidin-2-yl)ethyl]-6-(trichloromethyl)-1,3,5-triazin-2-amine | 1000 | 1000 | 1000 | |
| 85 | N-(1-ethylpiperidin-3-yl)-4-[(3-methoxyphenyl)methyl]-6-(trichloromethyl)-1,3,5-triazin-2-amine | 1000 | 1000 | 1000 | |
| 86 | N-(1-ethylpiperidin-3-yl)-4-[(4-methoxyphenyl)methyl]-6-(trichloromethyl)-1,3,5-triazin-2-amine | 623 | 600 | 991 | |
| 87 | N-(1-ethylpiperidin-3-yl)-4-(4-methanesulfonylphenyl)-6-(trichloromethyl)-1,3,5-triazin-2-amine | 43 | 32 | 57 | |
| 88 | N-(1-ethylpiperidin-3-yl)-4-[4-(methylsulfanyl)phenyl]-6-(trichloromethyl)-1,3,5-triazin-2-amine | 79 | 69 | 77 | |
| 89 | 4-[(4-methoxyphenyl)methyl]-N-[2-(2-methylpyrrolidin-1-yl)ethyl]-6-(trichloromethyl)-1,3,5-triazin-2-amine | 805 | 718 | 991 | 50 |
| 90 | 4-[(4-methoxyphenyl)methyl]-N-[2-(pyrrolidin-1-yl)ethyl]-6-(trichloromethyl)-1,3,5-triazin-2-amine | 1000 | 1000 | 1000 | |
| 91 | 4-(4-chlorophenyl)-N-[2-(1-methylpyrrolidin-2-yl)ethyl]-6-(trichloromethyl)-1,3,5-triazin-2-amine | 31 | 19 | 32 | 79 |
| 92 | N-{3-[(4-{[2-(1-methylpyrrolidin-2-yl)ethyl]amino}-6-(trichloromethyl)-1,3,5-triazin-2-yl)amino]phenyl}acetamide | 122 | 106 | 164 | |
| 93 | 4-(4-methanesulfonylphenyl)-N-(pyridin-4-yl)-6-(trichloromethyl)-1,3,5-triazin-2-amine | 1000 | 995 | 1000 | |
| 94 | N-(1-ethylpiperidin-3-yl)-4-[(2-methoxyphenyl)methyl]-6-(trichloromethyl)-1,3,5-triazin-2-amine | 396 | 173 | 456 | |
| 95 | 4-(4-methanesulfonylphenyl)-N-[3-(pyrrolidin-1-yl)propyl]-6-(trichloromethyl)-1,3,5-triazin-2-amine | 163 | 86 | 178 | |
| 96 | 1-[4-(4-methanesulfonylphenyl)-6-(trichloromethyl)-1,3,5-triazin-2-yl]-1,4-diazepane | 70 | 51 | 96 | 65 |

TABLE 13-continued

| Cmpd | IUPAC Name | D6 | W2 | C235 | hERG |
|---|---|---|---|---|---|
| 97 | N-(2-amino-2-methylpropyl)-4-(4-methanesulfonylphenyl)-6-(trichloromethyl)-1,3,5-triazin-2-amine | 26 | 20 | 33 | 35 |
| 98 | 2-[(2-{[4-(4-methanesulfonylphenyl)-6-(trichloromethyl)-1,3,5-triazin-2-yl]amino}ethyl)amino]ethan-1-ol | 448 | 366 | 554 | |
| 99 | 2-(4-methylpiperazin-1-yl)-4-(trichloromethyl)-6-[4-(trichloromethyl)phenyl]-1,3,5-triazine | 59 | 12 | 21 | 16 |
| 100 | 1-[4-(3-methoxyphenyl)-6-(trichloromethyl)-1,3,5-triazin-2-yl]-1,4-diazepane | 112 | 69 | 88 | 38 |
| 101 | 1-[4-(4-methoxyphenyl)-6-(trichloromethyl)-1,3,5-triazin-2-yl]-1,4-diazepane | 182 | 117 | 158 | |
| 102 | 1-[4-(4-methylphenyl)-6-(trichloromethyl)-1,3,5-triazin-2-yl]-1,4-diazepane | 58 | 44 | 48 | 47 |
| 103 | 1-[4-(3,4-dichlorophenyl)-6-(trichloromethyl)-1,3,5-triazin-2-yl]-1,4-diazepane | 24 | 20 | 16 | 34 |
| 104 | 4-(2-methoxyphenyl)-N-[2-(pyrrolidin-1-yl)ethyl]-6-(trichloromethyl)-1,3,5-triazin-2-amine | 115 | 53 | 82 | |
| 105 | 4-(2-methoxyphenyl)-N-[3-(pyrrolidin-1-yl)propyl]-6-(trichloromethyl)-1,3,5-triazin-2-amine | 145 | 73 | 93 | |
| 106 | 4-(2-methoxyphenyl)-N-[2-(1-methylpyrrolidin-2-yl)ethyl]-6-(trichloromethyl)-1,3,5-triazin-2-amine | 162 | 79 | 106 | |
| 107 | diethyl(2-{[4-(2-methoxyphenyl)-6-(trichloromethyl)-1,3,5-triazin-2-yl]amino}ethyl)amine | 212 | 95 | 158 | |
| 108 | 1-[4-(trichloromethyl)-6-[3-(trifluoromethyl)phenyl]-1,3,5-triazin-2-yl]-1,4-diazepane | 70 | 47 | 82 | 28 |
| 109 | 1-methyl-4-[4-(trichloromethyl)-6-[3-(trifluoromethyl)phenyl]-1,3,5-triazin-2-yl]-1,4-diazepane | 100 | 52 | 114 | |
| 110 | 1-[4-(3-methoxyphenyl)-6-(trichloromethyl)-1,3,5-triazin-2-yl]-4-methyl-1,4-diazepane | 243 | 142 | 303 | |
| 111 | 1-[4-(4-methoxyphenyl)-6-(trichloromethyl)-1,3,5-triazin-2-yl]-4-methyl-1,4-diazepane | 191 | 103 | 232 | |
| 112 | 1-methyl-4-[4-(4-methylphenyl)-6-(trichloromethyl)-1,3,5-triazin-2-yl]-1,4-diazepane | 168 | 107 | 209 | |
| 113 | 1-[4-(3,4-dichlorophenyl)-6-(trichloromethyl)-1,3,5-triazin-2-yl]-4-methyl-1,4-diazepane | 33 | 23 | 35 | 64 |
| 114 | 4-(2-methoxyphenyl)-N-(1-methylpiperidin-4-yl)-6-(trichloromethyl)-1,3,5-triazin-2-amine | 70 | 41 | 72 | 95 |
| 115 | 1-[4-(4-tert-butylphenyl)-6-(trichloromethyl)-1,3,5-triazin-2-yl]-1,4-diazepane | 357 | 242 | 360 | |
| 116 | 4-(4-tert-butylphenyl)-N-(1-methylpiperidin-4-yl)-6-(trichloromethyl)-1,3,5-triazin-2-amine | 59 | 61 | 73 | 22 |
| 117 | N-(2-amino-2-methylpropyl)-4-(4-tert-butylphenyl)-6-(trichloromethyl)-1,3,5-triazin-2-amine | 55 | 44 | 70 | 14 |
| 118 | 2-(4-(4'-(methylsulfonyl)-5-(trichloromethyl)-[1,1'-biphenyl]-3-yl)piperazin-1-yl)ethan-1-ol | 618 | 399 | 784 | |
| 119 | 2-{4-[4-(trichloromethyl)-6-[4-(trichloromethyl)phenyl]-1,3,5-triazin-2-yl]piperazin-1-yl}ethan-1-ol | 29 | 12 | 46 | 18 |
| 120 | 1-[4-(4-tert-butylphenyl)-6-(trichloromethyl)-1,3,5-triazin-2-yl]-4-methyl-1,4-diazepane | 123 | 82 | 112 | 15 |
| 121 | 4-(2-methylphenyl)-N-[2-(pyrrolidin-1-yl)ethyl]-6-(trichloromethyl)-1,3,5-triazin-2-amine | 70 | 42 | 84 | 103 |
| 122 | 4-(2-methylphenyl)-N-[2-(1-methylpyrrolidin-2-yl)ethyl]-6-(trichloromethyl)-1,3,5-triazin-2-amine | 172 | 80 | 219 | |
| 123 | diethyl(2-{[4-(2-methylphenyl)-6-(trichloromethyl)-1,3,5-triazin-2-yl]amino}ethyl)amine | 57 | 31 | 67 | |
| 124 | 1-[4-(2-methylphenyl)-6-(trichloromethyl)-1,3,5-triazin-2-yl]-1,4-diazepane | 108 | 73 | 142 | |
| 125 | 1-methyl-4-[4-(2-methylphenyl)-6-(trichloromethyl)-1,3,5-triazin-2-yl]-1,4-diazepane | 180 | 68 | 224 | |
| 126 | 4-(2-methylphenyl)-N-(1-methylpiperidin-4-yl)-6-(trichloromethyl)-1,3,5-triazin-2-amine | 22 | 7 | 22 | |
| 127 | 2-{4-[4-(trichloromethyl)-6-[4-(trichloromethyl)phenyl]-1,3,5-triazin-2-yl]-1,4-diazepan-1-yl}ethan-1-ol | 5 | 3 | 9 | 25 |
| 128 | 4-(2-methylphenyl)-N-[3-(pyrrolidin-1-yl)propyl]-6-(trichloromethyl)-1,3,5-triazin-2-amine | 181 | 80 | 204 | |
| 129 | 4-(4-methanesulfonylphenyl)-N-methyl-N-{[2-(pyridin-3-yl)phenyl]methyl}-6-(trichloromethyl)-1,3,5-triazin-2-amine | 170 | 102 | 233 | |
| 130 | 4-(4-methoxyphenyl)-N-(pyridin-4-ylmethyl)-6-(trichloromethyl)-1,3,5-triazin-2-amine | 12 | 5 | 24 | 20 |
| 131 | 4-(tert-butyl)-N-(pyridin-4-ylmethyl)-6-(trichloromethyl)-1,3,5-triazin-2-amine | 302 | 443 | 1000 | |
| 132 | 2-{4-[4-(4-methanesulfonylphenyl)-6-(trichloromethyl)-1,3,5-triazin-2-yl]-1,4-diazepan-1-yl}ethan-1-ol | 64 | 103 | 200 | |
| 133 | 4-[(2-methoxyphenyl)methyl]-N-(pyridin-4-ylmethyl)-6-(trichloromethyl)-1,3,5-triazin-2-amine | 1000 | 784 | 1000 | |
| 134 | 4-(4-methylphenyl)-N-(pyridin-4-ylmethyl)-6-(trichloromethyl)-1,3,5-triazin-2-amine | 521 | 453 | 1000 | |
| 135 | 4-(2-methoxyphenyl)-N-(pyridin-4-ylmethyl)-6-(trichloromethyl)-1,3,5-triazin-2-amine | 765 | 461 | 1000 | |
| 136 | 4-(4-chlorophenyl)-N-(pyridin-4-ylmethyl)-6-(trichloromethyl)-1,3,5-triazin-2-amine | 378 | 212 | 852 | |
| 137 | 4-(4-tert-butylphenyl)-N-(pyridin-4-ylmethyl)-6-(trichloromethyl)-1,3,5-triazin-2-amine | 246 | 228 | 287 | |
| 138 | N-(pyridin-4-ylmethyl)-4-(trichloromethyl)-6-[3-(trifluoromethyl)phenyl]-1,3,5-triazin-2-amine | 241 | 118 | 407 | |
| 139 | 4-(4-chlorophenyl)-N-[2-(pyridin-4-yl)ethyl]-6-(trichloromethyl)-1,3,5-triazin-2-amine | 202 | 81 | 320 | |
| 140 | 4-(4-chlorophenyl)-N-[2-(pyridin-2-yl)ethyl]-6-(trichloromethyl)-1,3,5-triazin-2-amine | 106 | 32 | 136 | 11 |
| 141 | 4-(4-chlorophenyl)-N-(pyridin-2-ylmethyl)-6-(trichloromethyl)-1,3,5-triazin-2-amine | 556 | 237 | 652 | |
| 142 | 4-(4-chlorophenyl)-N-(pyridin-3-ylmethyl)-6-(trichloromethyl)-1,3,5-triazin-2-amine | 306 | 112 | 469 | |
| 143 | 4-(4-chlorophenyl)-N-[2-(pyridin-3-yl)ethyl]-6-(trichloromethyl)-1,3,5-triazin-2-amine | 424 | 150 | 513 | |
| 144 | 4-[(2-methoxyphenyl)methyl]-N-[2-(pyridin-3-yl)ethyl]-6-(trichloromethyl)-1,3,5-triazin-2-amine | 472 | 252 | 563 | |
| 145 | 4-(4-methylphenyl)-N-[2-(pyridin-4-yl)ethyl]-6-(trichloromethyl)-1,3,5-triazin-2-amine | 168 | 94 | 344 | |
| 146 | 4-(2-methoxyphenyl)-N-[2-(pyridin-4-yl)ethyl]-6-(trichloromethyl)-1,3,5-triazin-2-amine | 539 | 246 | 804 | |
| 147 | 4-(4-methoxyphenyl)-N-[2-(pyridin-4-yl)ethyl]-6-(trichloromethyl)-1,3,5-triazin-2-amine | 155 | 77 | 233 | |
| 148 | 4-(4-tert-butylphenyl)-N-[2-(pyridin-4-yl)ethyl]-6-(trichloromethyl)-1,3,5-triazin-2-amine | 621 | 151 | 671 | |
| 149 | N-[2-(pyridin-4-yl)ethyl]-4-(trichloromethyl)-6-[3-(trifluoromethyl)phenyl]-1,3,5-triazin-2-amine | 326 | 108 | 380 | |
| 150 | 4-[4-(methylsulfanyl)phenyl]-N-[2-(pyridin-4-yl)ethyl]-6-(trichloromethyl)-1,3,5-triazin-2-amine | 380 | 109 | 394 | |
| 151 | 4-(3-methoxyphenyl)-N-[2-(pyridin-4-yl)ethyl]-6-(trichloromethyl)-1,3,5-triazin-2-amine | 346 | 133 | 549 | |
| 152 | 4-[(2-methoxyphenyl)methyl]-N-(pyridin-3-ylmethyl)-6-(trichloromethyl)-1,3,5-triazin-2-amine | 1000 | 615.8 | 1000 | |
| 153 | 4-(4-methylphenyl)-N-(pyridin-3-ylmethyl)-6-(trichloromethyl)-1,3,5-triazin-2-amine | 199 | 87 | 249 | |
| 154 | 4-(2-methoxyphenyl)-N-(pyridin-3-ylmethyl)-6-(trichloromethyl)-1,3,5-triazin-2-amine | 1000 | 477 | 1000 | |
| 155 | 4-(3-methoxyphenyl)-N-(pyridin-3-ylmethyl)-6-(trichloromethyl)-1,3,5-triazin-2-amine | 318 | 145 | 614 | |
| 156 | 4-(4-methoxyphenyl)-N-(pyridin-3-ylmethyl)-6-(trichloromethyl)-1,3,5-triazin-2-amine | 1000 | 560 | 1000 | |
| 157 | 4-(3,4-dichlorophenyl)-N-(pyridin-3-ylmethyl)-6-(trichloromethyl)-1,3,5-triazin-2-amine | 298 | 80 | 343 | |
| 158 | 4-(4-tert-butylphenyl)-N-(pyridin-3-ylmethyl)-6-(trichloromethyl)-1,3,5-triazin-2-amine | 260 | 92 | 324 | |
| 159 | N-(pyridin-3-ylmethyl)-4-(trichloromethyl)-6-[3-(trifluoromethyl)phenyl]-1,3,5-triazin-2-amine | 603 | 191 | 635 | |
| 160 | 4-[4-(methylsulfanyl)phenyl]-N-(pyridin-3-ylmethyl)-6-(trichloromethyl)-1,3,5-triazin-2-amine | 789 | 238 | 896 | |
| 161 | 2-(4-tert-butylphenyl)-4-(piperazin-1-yl)-6-(trichloromethyl)-1,3,5-triazine | 88 | 32 | 98 | 15 |
| 162 | N-[2-(pyridin-3-yl)ethyl]-4-(trichloromethyl)-6-[4-(trichloromethyl)phenyl]-1,3,5-triazin-2-amine | 69 | 30 | 90 | 14 |
| 163 | N-[2-(pyridin-2-yl)ethyl]-4-(trichloromethyl)-6-[4-(trichloromethyl)phenyl]-1,3,5-triazin-2-amine | 50 | 20 | 61 | 5 |
| 164 | N-(pyridin-3-ylmethyl)-4-(trichloromethyl)-6-[4-(trichloromethyl)phenyl]-1,3,5-triazin-2-amine | 99 | 33 | 145 | |
| 165 | N-(pyridin-2-ylmethyl)-4-(trichloromethyl)-6-[4-(trichloromethyl)phenyl]-1,3,5-triazin-2-amine | 82 | 29 | 90 | 20 |
| 166 | N-[2-(pyridin-4-yl)ethyl]-4-(trichloromethyl)-6-[4-(trichloromethyl)phenyl]-1,3,5-triazin-2-amine | 43 | 13 | 40 | 12 |
| 167 | 4-(4-methylphenyl)-N-(pyridin-2-ylmethyl)-6-(trichloromethyl)-1,3,5-triazin-2-amine | 1000 | 423 | 1000 | |
| 168 | 4-(4-methoxyphenyl)-N-(pyridin-2-ylmethyl)-6-(trichloromethyl)-1,3,5-triazin-2-amine | 755 | 338 | 898 | |
| 169 | 4-(3,4-dichlorophenyl)-N-(pyridin-2-ylmethyl)-6-(trichloromethyl)-1,3,5-triazin-2-amine | 640 | 211 | 626 | |
| 170 | 4-(4-tert-butylphenyl)-N-(pyridin-2-ylmethyl)-6-(trichloromethyl)-1,3,5-triazin-2-amine | 1000 | 313 | 1000 | |

TABLE 13-continued

| Cmpd | IUPAC Name | D6 | W2 | C235 | hERG |
|---|---|---|---|---|---|
| 171 | N-(pyridin-2-ylmethyl)-4-(trichloromethyl)-6-[3-(trifluoromethyl)phenyl]-1,3,5-triazin-2-amine | 390 | 183 | 547 | |
| 172 | 4-(4-methylphenyl)-N-[2-(pyridin-3-yl)ethyl]-6-(trichloromethyl)-1,3,5-triazin-2-amine | 209 | 106 | 346 | |
| 173 | 4-(3-methoxyphenyl)-N-[2-(pyridin-3-yl)ethyl]-6-(trichloromethyl)-1,3,5-triazin-2-amine | 302 | 127 | 552 | |
| 174 | 4-(4-methoxyphenyl)-N-[2-(pyridin-3-yl)ethyl]-6-(trichloromethyl)-1,3,5-triazin-2-amine | 430 | 181 | 641 | |
| 175 | 4-(4-tert-butylphenyl)-N-[2-(pyridin-3-yl)ethyl]-6-(trichloromethyl)-1,3,5-triazin-2-amine | 110 | 54 | 165 | |
| 176 | 4-(3,4-dichlorophenyl)-N-[2-(pyridin-4-yl)ethyl]-6-(trichloromethyl)-1,3,5-triazin-2-amine | 204 | 80 | 293 | |
| 177 | 4-(4-methanesulfonylphenyl)-N-(pyridin-2-ylmethyl)-6-(trichloromethyl)-1,3,5-triazin-2-amine | 355 | 186 | 565 | |
| 178 | 4-(4-methanesulfonylphenyl)-N-[2-(pyridin-4-yl)ethyl]-6-(trichloromethyl)-1,3,5-triazin-2-amine | 392 | 162 | 518 | |
| 179 | 4-(4-methanesulfonylphenyl)-N-[2-(pyridin-3-yl)ethyl]-6-(trichloromethyl)-1,3,5-triazin-2-amine | 471 | 201 | 680 | |
| 180 | 4-(4-methanesulfonylphenyl)-N-[2-(pyridin-2-yl)ethyl]-6-(trichloromethyl)-1,3,5-triazin-2-amine | 819 | 478 | 1000 | |
| 181 | 4-(2-methoxyphenyl)-N-(pyridin-2-ylmethyl)-6-(trichloromethyl)-1,3,5-triazin-2-amine | 1000 | 471 | 1000 | |
| 182 | 4-(2-methoxyphenyl)-N-[2-(pyridin-3-yl)ethyl]-6-(trichloromethyl)-1,3,5-triazin-2-amine | 659 | 256 | 1000 | |
| 183 | 4-(2-methoxyphenyl)-N-[2-(pyridin-2-yl)ethyl]-6-(trichloromethyl)-1,3,5-triazin-2-amine | 1055 | 344 | 1000 | |
| 184 | 4-(3-methoxyphenyl)-N-[2-(pyridin-2-yl)ethyl]-6-(trichloromethyl)-1,3,5-triazin-2-amine | 263 | 114 | 434 | |
| 185 | 4-(4-methoxyphenyl)-N-[2-(pyridin-2-yl)ethyl]-6-(trichloromethyl)-1,3,5-triazin-2-amine | 185 | 63 | 244 | |
| 186 | N-[2-(pyridin-2-yl)ethyl]-4-(trichloromethyl)-6-[3-(trifluoromethyl)phenyl]-1,3,5-triazin-2-amine | 494 | 115 | 499 | |
| 187 | 4-[4-(methylsulfanyl)phenyl]-N-[2-(pyridin-2-yl)ethyl]-6-(trichloromethyl)-1,3,5-triazin-2-amine | 317 | 73 | 478 | |
| 188 | 4-phenyl-N-[2-(pyridin-2-yl)ethyl]-6-(trichloromethyl)-1,3,5-triazin-2-amine | 176 | 42 | 197 | |
| 189 | 4-(4-methylphenyl)-N-[2-(pyridin-2-yl)ethyl]-6-(trichloromethyl)-1,3,5-triazin-2-amine | 213 | 147 | 263 | |
| 190 | 4-(3,4-dichlorophenyl)-N-[2-(pyridin-2-yl)ethyl]-6-(trichloromethyl)-1,3,5-triazin-2-amine | 347 | 264 | 551 | |
| 191 | 4-(4-tert-butylphenyl)-N-[2-(pyridin-2-yl)ethyl]-6-(trichloromethyl)-1,3,5-triazin-2-amine | 238 | 159 | 287 | |
| 192 | 4-(3-methoxyphenyl)-N-[2-(pyrrolidin-1-yl)ethyl]-6-(trichloromethyl)-1,3,5-triazin-2-amine | 18 | 13 | 12 | 100 |
| 193 | 4-(3-methoxyphenyl)-N-(1-methylpiperidin-4-yl)-6-(trichloromethyl)-1,3,5-triazin-2-amine | 29 | 22 | 17 | 93 |
| 194 | tert-butyl N-{1-[4-(trichloromethyl)-6-[4-(trichloromethyl)phenyl]-1,3,5-triazin-2-yl]piperidin-4-yl}carbamate | 138 | 79 | 132 | |
| 195 | N-(2-amino-2-methylpropyl)-4-(3,5-dichlorophenyl)-6-(trichloromethyl)-1,3,5-triazin-2-amine | 6 | 6 | 3 | 3 |
| 196 | 4-(4-phenylphenyl)-N-[2-(pyrrolidin-1-yl)ethyl]-6-(trichloromethyl)-1,3,5-triazin-2-amine | 31 | 25 | 30 | 53 |
| 197 | 4-(4-phenylphenyl)-N-[3-(pyrrolidin-1-yl)propyl]-6-(trichloromethyl)-1,3,5-triazin-2-amine | 128 | 105 | 137 | |
| 198 | 1-[4-(4-phenylphenyl)-6-(trichloromethyl)-1,3,5-triazin-2-yl]-1,4-diazepane | 64 | 40 | 70 | |
| 199 | 1-methyl-4-[4-(4-phenylphenyl)-6-(trichloromethyl)-1,3,5-triazin-2-yl]-1,4-diazepane | | | | |
| 200 | N-(1-methylpiperidin-4-yl)-4-(4-phenylphenyl)-6-(trichloromethyl)-1,3,5-triazin-2-amine | | | | |
| 201 | N-[2-(1-methylpyrrolidin-2-yl)ethyl]-4-(4-phenylphenyl)-6-(trichloromethyl)-1,3,5-triazin-2-amine | 1000 | 845 | 1000 | |
| 202 | 4-(3,5-dichlorophenyl)-N-[2-(pyrrolidin-1-yl)ethyl]-6-(trichloromethyl)-1,3,5-triazin-2-amine | 7 | 10 | 7 | 51 |
| 203 | 4-(3,5-dichlorophenyl)-N-[3-(pyrrolidin-1-yl)propyl]-6-(trichloromethyl)-1,3,5-triazin-2-amine | 50 | 59 | 43 | 83 |
| 204 | 1-[4-(3,5-dichlorophenyl)-6-(trichloromethyl)-1,3,5-triazin-2-yl]-1,4-diazepane | 231 | 78 | 214 | |
| 205 | 1-[4-(3,5-dichlorophenyl)-6-(trichloromethyl)-1,3,5-triazin-2-yl]-4-methyl-1,4-diazepane | 23 | 7 | 26 | 20 |
| 206 | 4-(3,5-dichlorophenyl)-N-(1-methylpiperidin-4-yl)-6-(trichloromethyl)-1,3,5-triazin-2-amine | | | | |
| 207 | 2-(3,5-dichlorophenyl)-4-(4-methylpiperazin-1-yl)-6-(trichloromethyl)-1,3,5-triazine | | | | |
| 208 | 4-(3,5-dichlorophenyl)-N-(pyridin-4-ylmethyl)-6-(trichloromethyl)-1,3,5-triazin-2-amine | 137 | 62 | 150 | |
| 209 | 4-(3,5-dichlorophenyl)-N-(pyridin-3-ylmethyl)-6-(trichloromethyl)-1,3,5-triazin-2-amine | 122 | 67 | 112 | |
| 210 | 4-(3,5-dichlorophenyl)-N-(pyridin-2-ylmethyl)-6-(trichloromethyl)-1,3,5-triazin-2-amine | 112 | 72 | 78 | |
| 211 | 4-(3,5-dichlorophenyl)-N-[2-(pyridin-4-yl)ethyl]-6-(trichloromethyl)-1,3,5-triazin-2-amine | 314 | 148 | 303 | |
| 212 | N-(1-methylpiperidin-4-yl)-4-(trichloromethyl)-6-[3-(trifluoromethyl)phenyl]-1,3,5-triazin-2-amine | 45 | 16 | 25 | 80 |
| 213 | 2-(4-methylpiperazin-1-yl)-4-(trichloromethyl)-6-[3-(trifluoromethyl)phenyl]-1,3,5-triazine | 314 | 94 | 186 | |
| 214 | N-(2-amino-2-methylpropyl)-4-(trichloromethyl)-6-[3-(trifluoromethyl)phenyl]-1,3,5-triazin-2-amine | 19 | 11 | 10 | 42 |
| 215 | N-(1-ethylpiperidin-3-yl)-4-(2-methoxyphenyl)-6-(trichloromethyl)-1,3,5-triazin-2-amine | 426 | 132 | 248 | |
| 216 | 2-(2-methoxyphenyl)-4-(4-methylpiperazin-1-yl)-6-(trichloromethyl)-1,3,5-triazine | 709 | 244 | 547 | |
| 217 | N-(2-amino-2-methylpropyl)-4-(2-methoxyphenyl)-6-(trichloromethyl)-1,3,5-triazin-2-amine | 43 | 20 | 20 | 62 |
| 218 | 1-[4-(2-methoxyphenyl)-6-(trichloromethyl)-1,3,5-triazin-2-yl]-1,4-diazepane | 104 | 38 | 73 | |
| 219 | 2-(4-methylpiperazin-1-yl)-4-(naphthalen-2-yl)-6-(trichloromethyl)-1,3,5-triazine | 75 | 19 | 49 | |
| 220 | diethyl(2-{[4-(naphthalen-2-yl)-6-(trichloromethyl)-1,3,5-triazin-2-yl]amino}ethyl)amine | 40 | 8 | 12 | 66 |
| 221 | 2-(4-methylphenyl)-4-(4-methylpiperazin-1-yl)-6-(trichloromethyl)-1,3,5-triazine | | | | |
| 222 | 4-(3,4-dichlorophenyl)-N-(1-methylpiperidin-4-yl)-6-(trichloromethyl)-1,3,5-triazin-2-amine | 22 | 2 | 8 | 68 |
| 223 | 4-(naphthalen-2-yl)-N-(pyridin-2-ylmethyl)-6-(trichloromethyl)-1,3,5-triazin-2-amine | 371 | 43 | 233 | |
| 224 | 4-(naphthalen-2-yl)-N-[3-(pyrrolidin-1-yl)propyl]-6-(trichloromethyl)-1,3,5-triazin-2-amine | 33 | 9 | 12 | 41 |
| 225 | 4-(naphthalen-2-yl)-N-[2-(pyridin-2-yl)ethyl]-6-(trichloromethyl)-1,3,5-triazin-2-amine | | | | |
| 226 | 1-methyl-4-[4-(naphthalen-2-yl)-6-(trichloromethyl)-1,3,5-triazin-2-yl]-1,4-diazepane | | | | |
| 227 | 1-[4-(naphthalen-2-yl)-6-(trichloromethyl)-1,3,5-triazin-2-yl]-1,4-diazepane | 29 | 10 | 12 | 18 |
| 228 | 4-(naphthalen-2-yl)-N-[2-(pyrrolidin-1-yl)ethyl]-6-(trichloromethyl)-1,3,5-triazin-2-amine | 26 | 6 | 7 | 77 |
| 229 | N-[2-(1-methylpyrrolidin-2-yl)ethyl]-4-(naphthalen-2-yl)-6-(trichloromethyl)-1,3,5-triazin-2-amine | 31 | 6 | 11 | 55 |
| 230 | 4-(naphthalen-2-yl)-N-[2-(pyridin-4-yl)ethyl]-6-(trichloromethyl)-1,3,5-triazin-2-amine | 246 | 59 | 212 | |
| 231 | 4-(naphthalen-2-yl)-N-[2-(pyridin-3-yl)ethyl]-6-(trichloromethyl)-1,3,5-triazin-2-amine | 127 | 57 | 83 | |
| 232 | 4-(naphthalen-2-yl)-N-(pyridin-3-ylmethyl)-6-(trichloromethyl)-1,3,5-triazin-2-amine | 238 | 132 | 239 | |
| 233 | 4-(naphthalen-2-yl)-N-(pyridin-4-ylmethyl)-6-(trichloromethyl)-1,3,5-triazin-2-amine | 323 | 149 | 196 | |
| 234 | N-(1-methylpiperidin-4-yl)-4-(naphthalen-2-yl)-6-(trichloromethyl)-1,3,5-triazin-2-amine | 24 | 15 | 14 | 29 |
| 235 | 4-(naphthalen-2-yl)-N-(pyridin-4-yl)-6-(trichloromethyl)-1,3,5-triazin-2-amine | 14 | 8 | 10 | |
| 236 | 4-(3-methoxyphenyl)-N-[2-(1-methylpyrrolidin-2-yl)ethyl]-6-(trichloromethyl)-1,3,5-triazin-2-amine | 52 | 50 | 60 | |
| 237 | N-(1-methylpiperidin-4-yl)-4-phenyl-6-(trichloromethyl)-1,3,5-triazin-2-amine | 47 | 32 | 31 | 107 |
| 238 | N-(2-amino-2-methylpropyl)-4-(3-methoxyphenyl)-6-(trichloromethyl)-1,3,5-triazin-2-amine | 570 | 464 | 399 | |
| 239 | 2-(4-methylpiperazin-1-yl)-4-phenyl-6-(trichloromethyl)-1,3,5-triazine | 192 | 125 | 158 | |
| 240 | diethyl(2-{[4-phenyl-6-(trichloromethyl)-1,3,5-triazin-2-yl]amino}ethyl)amine | 221 | 163 | 149 | |
| 241 | N-(1-ethylpiperidin-3-yl)-4-(3-methoxyphenyl)-6-(trichloromethyl)-1,3,5-triazin-2-amine | 1000 | 1000 | 963 | |
| 242 | diethyl(2-{[4-(3-methoxyphenyl)-6-(trichloromethyl)-1,3,5-triazin-2-yl]amino}ethyl)amine | 64 | 47 | 36 | |
| 243 | diethyl[2-({4-[(3-methoxyphenyl)methyl]-6-(trichloromethyl)-1,3,5-triazin-2-yl}amino)ethyl]amine | 199 | 123 | 128 | |
| 244 | N-(2-amino-2-methylpropyl)-4-(4-methylphenyl)-6-(trichloromethyl)-1,3,5-triazin-2-amine | | | | |
| 245 | 4-(4-methylphenyl)-N-(1-methylpiperidin-4-yl)-6-(trichloromethyl)-1,3,5-triazin-2-amine | 441 | 304 | 289 | |
| 246 | 4-(4-tert-butylphenyl)-N-[2-(pyrrolidin-1-yl)ethyl]-6-(trichloromethyl)-1,3,5-triazin-2-amine | 48 | 59 | 35 | |
| 247 | 4-(4-tert-butylphenyl)-N-[(1-ethylpiperidin-4-yl)methyl]-6-(trichloromethyl)-1,3,5-triazin-2-amine | 139 | 131 | 94 | |

TABLE 13-continued

| Cmpd | IUPAC Name | D6 | W2 | C235 | hERG |
|---|---|---|---|---|---|
| 248 | 4-(4-phenylphenyl)-N-(pyridin-4-ylmethyl)-6-(trichloromethyl)-1,3,5-triazin-2-amine | 1000 | 674 | 920 | |
| 249 | 4-(4-phenylphenyl)-N-(pyridin-3-ylmethyl)-6-(trichloromethyl)-1,3,5-triazin-2-amine | 1000 | 545 | 755 | |
| 250 | 4-(4-phenylphenyl)-N-(pyridin-2-ylmethyl)-6-(trichloromethyl)-1,3,5-triazin-2-amine | 1000 | 721 | 858 | |
| 251 | 4-(4-phenylphenyl)-N-[2-(pyridin-4-yl)ethyl]-6-(trichloromethyl)-1,3,5-triazin-2-amine | 1000 | 1000 | 1000 | |
| 252 | 4-(4-phenylphenyl)-N-[2-(pyridin-3-yl)ethyl]-6-(trichloromethyl)-1,3,5-triazin-2-amine | 1000 | 1000 | 1000 | |
| 253 | 4-(4-phenylphenyl)-N-[2-(pyridin-2-yl)ethyl]-6-(trichloromethyl)-1,3,5-triazin-2-amine | 1000 | 1000 | 1000 | |
| 254 | diethyl[2-({4-[2-(4-methylphenyl)phenyl]-6-(trichloromethyl)-1,3,5-triazin-2-yl}amino)ethyl]amine | 632 | 492 | 462 | |
| 255 | 4-[2-(4-methylphenyl)phenyl]-N-(1-methylpiperidin-4-yl)-6-(trichloromethyl)-1,3,5-triazin-2-amine | 217 | 159 | 146 | |
| 256 | N-(1-ethylpiperidin-3-yl)-4-[2-(4-methylphenyl)phenyl]-6-(trichloromethyl)-1,3,5-triazin-2-amine | 306 | 194 | 220 | |
| 257 | 4-(3,4-dichlorophenyl)-N-[(1-ethylpiperidin-4-yl)methyl]-6-(trichloromethyl)-1,3,5-triazin-2-amine | 54 | 45 | 29 | |
| 258 | N-[(1-ethylpiperidin-4-yl)methyl]-4-(3-methoxyphenyl)-6-(trichloromethyl)-1,3,5-triazin-2-amine | 50 | 29 | 26 | |
| 259 | N-[(1-ethylpiperidin-4-yl)methyl]-4-[2-(4-methylphenyl)phenyl]-6-(trichloromethyl)-1,3,5-triazin-2-amine | 162 | 105 | 113 | |
| 260 | N-(2-amino-2-methylpropyl)-4-[2-(4-methylphenyl)phenyl]-6-(trichloromethyl)-1,3,5-triazin-2-amine | 85 | 71 | 56 | 62 |
| 261 | 1-methyl-4-{4-[4-(methylsulfanyl)phenyl]-6-(trichloromethyl)-1,3,5-triazin-2-yl}-1,4-diazepane | 1000 | 1000 | 1000 | |
| 262 | 1-{4-[4-(methylsulfanyl)phenyl]-6-(trichloromethyl)-1,3,5-triazin-2-yl}-1,4-diazepane | 1000 | 1000 | 1000 | |
| 263 | 1-{4-[2-(4-methylphenyl)phenyl]-6-(trichloromethyl)-1,3,5-triazin-2-yl}-1,4-diazepane | 1000 | 960 | 763 | |
| 264 | 4-[2-(4-methylphenyl)phenyl]-N-[3-(pyrrolidin-1-yl)propyl]-6-(trichloromethyl)-1,3,5-triazin-2-amine | 71 | 57 | 57 | 37 |
| 265 | N-[(1-ethylpiperidin-4-yl)methyl]-4-(4-methylphenyl)-6-(trichloromethyl)-1,3,5-triazin-2-amine | 803 | 714 | 672 | |
| 266 | 4-[2-(4-methylphenyl)phenyl]-N-[2-(pyrrolidin-1-yl)ethyl]-6-(trichloromethyl)-1,3,5-triazin-2-amine | 654 | 474 | 530 | |
| 267 | N-(1-ethylpiperidin-3-yl)-4-(4-methoxyphenyl)-6-(trichloromethyl)-1,3,5-triazin-2-amine | 1000 | 1000 | 1000 | |
| 268 | diethyl(2-{[4-(4-methoxyphenyl)-6-(trichloromethyl)-1,3,5-triazin-2-yl]amino}ethyl)amine | 309 | 259 | 282 | |
| 269 | 1-(4-(3-methoxybenzyl)-6-(trichloromethyl)-1,3,5-triazin-2-yl)-4-methyl-1,4-diazepane | 835 | 286 | 627 | |
| 270 | N-(1-methylpiperidin-4-yl)-4-[4-(methylsulfanyl)phenyl]-6-(trichloromethyl)-1,3,5-triazin-2-amine | 46 | 43 | 43 | |
| 271 | N-(1-amino-2-methylpropan-2-yl)-4-(4-methoxyphenyl)-6-(trichloromethyl)-1,3,5-triazin-2-amine | 19 | 10 | 32 | |
| 272 | 2-(4-methoxyphenyl)-4-(4-methylpiperazin-1-yl)-6-(trichloromethyl)-1,3,5-triazine | 1000 | 1000 | 1000 | |
| 273 | N-[(1-ethylpiperidin-4-yl)methyl]-4-[4-(methylsulfanyl)phenyl]-6-(trichloromethyl)-1,3,5-triazin-2-amine | 319 | 304 | 282 | |
| 274 | N-[(1-ethylpiperidin-4-yl)methyl]-4-(4-methoxyphenyl)-6-(trichloromethyl)-1,3,5-triazin-2-amine | 19 | 19 | 17 | 88 |
| 275 | 4-(4-methoxyphenyl)-N-(1-methylpiperidin-4-yl)-6-(trichloromethyl)-1,3,5-triazin-2-amine | 1000 | 618 | 699 | |
| 276 | 2-{4-[4-(4-tert-butylphenyl)-6-(trichloromethyl)-1,3,5-triazin-2-yl]piperazin-1-yl}ethan-1-ol | 1000 | 1000 | 1000 | |
| 277 | N-(1-amino-2-methylpropan-2-yl)-4-[4-(methylsulfanyl)phenyl]-6-(trichloromethyl)-1,3,5-triazin-2-amine | 406 | 364 | 312 | |
| 278 | 4-(4-methoxynaphthalen-1-yl)-N-[2-(pyrrolidin-1-yl)ethyl]-6-(trichloromethyl)-1,3,5-triazin-2-amine | 35 | 17 | 48 | |
| 279 | N-[(1-ethylpiperidin-4-yl)methyl]-4-(4-methoxynaphthalen-1-yl)-6-(trichloromethyl)-1,3,5-triazin-2-amine | 66 | 20 | 77 | |
| 280 | N-(1-ethylpiperidin-3-yl)-4-(4-methoxynaphthalen-1-yl)-6-(trichloromethyl)-1,3,5-triazin-2-amine | 138 | 76 | 193 | |
| 281 | 1-[4-(4-methoxynaphthalen-1-yl)-6-(trichloromethyl)-1,3,5-triazin-2-yl]-1,4-diazepane | 148 | 66 | 205 | |
| 282 | 1-[4-(4-chlorophenyl)-6-(trichloromethyl)-1,3,5-triazin-2-yl]-1,4-diazepane | 154 | 67 | 247 | |
| 283 | 4-(4-chlorophenyl)-N-[(1-ethylpiperidin-4-yl)methyl]-6-(trichloromethyl)-1,3,5-triazin-2-amine | 97 | 34 | 146 | |
| 284 | N-(2-amino-2-methylpropyl)-4-(4-chlorophenyl)-6-(trichloromethyl)-1,3,5-triazin-2-amine | 12 | 3 | 18 | |
| 285 | 4-(4-chlorophenyl)-N-(1-methylpiperidin-4-yl)-6-(trichloromethyl)-1,3,5-triazin-2-amine | 799 | 567 | 993 | |
| 286 | (2-{[4-(4-chlorophenyl)-6-(trichloromethyl)-1,3,5-triazin-2-yl]amino}ethyl)diethylamine | 5 | 2 | 10 | |
| 287 | 1-[4-(4-chlorophenyl)-6-(trichloromethyl)-1,3,5-triazin-2-yl]-4-methyl-1,4-diazepane | 143 | 60 | 232 | |
| 288 | 2-[(3-methoxyphenyl)methyl]-4-(4-methylpiperazin-1-yl)-6-(trichloromethyl)-1,3,5-triazine | 859 | 197 | 509 | |
| 289 | 1-{4-[(2-methoxyphenyl)methyl]-6-(trichloromethyl)-1,3,5-triazin-2-yl}-4-methyl-1,4-diazepane | 810 | 311 | 1000 | |
| 290 | 1-{4-[(2-methoxyphenyl)methyl]-6-(trichloromethyl)-1,3,5-triazin-2-yl}-1,4-diazepane | 138 | 87 | 206 | |
| 291 | 4-[(2-methoxyphenyl)methyl]-N-(1-methylpiperidin-4-yl)-6-(trichloromethyl)-1,3,5-triazin-2-amine | 231 | 66 | 328 | |
| 292 | N-(2-amino-2-methylpropyl)-4-[(2-methoxyphenyl)methyl]-6-(trichloromethyl)-1,3,5-triazin-2-amine | 77 | 34 | 103 | |
| 293 | N-[(1-ethylpiperidin-4-yl)methyl]-4-[(2-methoxyphenyl)methyl]-6-(trichloromethyl)-1,3,5-triazin-2-amine | 48 | 13 | 70 | |
| 294 | 4-[(2-methoxyphenyl)methyl]-N-[2-(pyrrolidin-1-yl)ethyl]-6-(trichloromethyl)-1,3,5-triazin-2-amine | 82 | 41 | 167 | |
| 295 | 2-N-[2-(1-methylpyrrolidin-2-yl)ethyl]-6-(trichloromethyl)-4-N-[4-(trifluoromethoxy)phenyl]-1,3,5-triazine-2,4-diamine | 10 | 10 | 23 | |
| 296 | 2-N-(2-amino-2-methylpropyl)-6-(trichloromethyl)-4-N-[4-(trifluoromethoxy)phenyl]-1,3,5-triazine-2,4-diamine | 302 | 318 | 460 | |
| 297 | N-(1-ethylpiperidin-3-yl)-4-(4-phenylphenyl)-6-(trichloromethyl)-1,3,5-triazin-2-amine | 16 | 13 | 28 | 38 |
| 298 | 2-(4-methylpiperazin-1-yl)-4-(4-phenylphenyl)-6-(trichloromethyl)-1,3,5-triazine | 62 | 33 | 87 | 10 |
| 299 | 4-[2-(4-methylphenyl)phenyl]-N-(pyridin-4-ylmethyl)-6-(trichloromethyl)-1,3,5-triazin-2-amine | 195 | 148 | 311 | |
| 300 | 4-(4-methoxynaphthalen-1-yl)-N-(pyridin-4-ylmethyl)-6-(trichloromethyl)-1,3,5-triazin-2-amine | 97 | 82 | 359 | |
| 301 | 2-N-[(1-ethylpiperidin-4-yl)methyl]-6-(trichloromethyl)-4-N-[4-(trifluoromethoxy)phenyl]-1,3,5-triazine-2,4-diamine | 1000 | 1000 | 1000 | |
| 302 | 2-{4-[4-(trichloromethyl)-6-{[4-(trifluoromethoxy)phenyl]amino}-1,3,5-triazin-2-yl]piperazin-1-yl}ethan-1-ol | 166 | 107 | 299 | |
| 303 | 2-N-[(4-aminooxan-4-yl)methyl]-6-(trichloromethyl)-4-N-[4-(trifluoromethoxy)phenyl]-1,3,5-triazine-2,4-diamine | 43 | 61 | 65 | |
| 304 | 2-{4-[4-(3,4-dichlorophenyl)-6-(trichloromethyl)-1,3,5-triazin-2-yl]piperazin-1-yl}ethan-1-ol | 80 | 41 | 201 | |
| 305 | 2-{4-[4-(naphthalen-2-yl)-6-(trichloromethyl)-1,3,5-triazin-2-yl]piperazin-1-yl}ethan-1-ol | 35 | 23 | 68 | |
| 306 | N-[(1-ethylpiperidin-4-yl)methyl]-4-(4-phenylphenyl)-6-(trichloromethyl)-1,3,5-triazin-2-amine | 54 | 30 | 87 | 38 |
| 307 | N-[(1-ethylpiperidin-4-yl)methyl]-4-(naphthalen-2-yl)-6-(trichloromethyl)-1,3,5-triazin-2-amine | 21 | 10 | 34 | |
| 308 | 2-{4-[4-(4-phenylphenyl)-6-(trichloromethyl)-1,3,5-triazin-2-yl]piperazin-1-yl}ethan-1-ol | 52 | 24 | 126 | |
| 309 | 2-(4-{4-[4-(methylsulfanyl)phenyl]-6-(trichloromethyl)-1,3,5-triazin-2-yl}piperazin-1-yl)ethan-1-ol | 188 | 122 | 438 | |
| 310 | N-(1-ethylpiperidin-3-yl)-4-(naphthalen-2-yl)-6-(trichloromethyl)-1,3,5-triazin-2-amine | 13 | 9 | 24 | |
| 311 | N-[(4-aminooxan-4-yl)methyl]-4-(trichloromethyl)-6-[4-(trichloromethyl)phenyl]-1,3,5-triazin-2-amine | 81 | 47 | 169 | |
| 312 | N-(2-amino-2-methylpropyl)-4-phenyl-6-(trichloromethyl)-1,3,5-triazin-2-amine | 8 | 3 | 18 | 65 |
| 313 | N-[(4-aminooxan-4-yl)methyl]-4-phenyl-6-(trichloromethyl)-1,3,5-triazin-2-amine | 7 | 2 | 14 | |

TABLE 13-continued

| Cmpd | IUPAC Name | D6 | W2 | C235 | hERG |
|---|---|---|---|---|---|
| 314 | N-[(4-aminooxan-4-yl)methyl]-4-(4-tert-butylphenyl)-6-(trichloromethyl)-1,3,5-triazin-2-amine | 7 | 2 | 16 | 5 |
| 315 | N-[(4-aminooxan-4-yl)methyl]-4-(trichloromethyl)-6-[3-(trifluoromethyl)phenyl]-1,3,5-triazin-2-amine | 3 | 1 | 8 | 36 |
| 316 | N-[(4-aminooxan-4-yl)methyl]-4-(4-methanesulfonylphenyl)-6-(trichloromethyl)-1,3,5-triazin-2-amine | 11 | 12 | 23 | 38 |
| 317 | N-[(4-aminooxan-4-yl)methyl]-4-(naphthalen-2-yl)-6-(trichloromethyl)-1,3,5-triazin-2-amine | 3 | 2 | 8 | 20 |
| 318 | N-[(4-aminooxan-4-yl)methyl]-4-(4-methoxynaphthalen-1-yl)-6-(trichloromethyl)-1,3,5-triazin-2-amine | 7 | 2 | 17 | 23 |
| 319 | N-[(4-aminooxan-4-yl)methyl]-4-(3,4-dimethoxyphenyl)-6-(trichloromethyl)-1,3,5-triazin-2-amine | 16 | 10 | 34 | |
| 320 | 4-phenyl-N-(2,2,6,6-tetramethylpiperidin-4-yl)-6-(trichloromethyl)-1,3,5-triazin-2-amine | 11 | 2 | 20 | |
| 321 | 4-(4-tert-butylphenyl)-N-(2,2,6,6-tetramethylpiperidin-4-yl)-6-(trichloromethyl)-1,3,5-triazin-2-amine | 6 | 3 | 11 | 11 |
| 322 | N-(2,2,6,6-tetramethylpiperidin-4-yl)-4-(trichloromethyl)-6-[3-(trifluoromethyl)phenyl]-1,3,5-triazin-2-amine | 63 | 57 | 103 | 30 |
| 323 | 4-[4-(methylsulfanyl)phenyl]-N-(2,2,6,6-tetramethylpiperidin-4-yl)-6-(trichloromethyl)-1,3,5-triazin-2-amine | 20 | 17 | 51 | |
| 324 | 4-(4-methanesulfonylphenyl)-N-(2,2,6,6-tetramethylpiperidin-4-yl)-6-(trichloromethyl)-1,3,5-triazin-2-amine | 208 | 166 | 391 | |
| 325 | N-(2,2,6,6-tetramethylpiperidin-4-yl)-4-(trichloromethyl)-6-[4-(trichloromethyl)phenyl]-1,3,5-triazin-2-amine | 123 | 82 | 269 | |
| 326 | 4-(naphthalen-2-yl)-N-(2,2,6,6-tetramethylpiperidin-4-yl)-6-(trichloromethyl)-1,3,5-triazin-2-amine | | | | |
| 327 | 4-(4-phenylphenyl)-N-(2,2,6,6-tetramethylpiperidin-4-yl)-6-(trichloromethyl)-1,3,5-triazin-2-amine | 33 | 33 | 63 | 20 |
| 328 | 4-(3,4-dimethoxyphenyl)-N-(2,2,6,6-tetramethylpiperidin-4-yl)-6-(trichloromethyl)-1,3,5-triazin-2-amine | 64 | 40 | 84 | 31 |
| 329 | N-(2-amino-2-methylpropyl)-4-(naphthalen-2-yl)-6-(trichloromethyl)-1,3,5-triazin-2-amine | 561 | 357 | 652 | |
| 330 | 4-(4-chlorophenyl)-N-(2,2,6,6-tetramethylpiperidin-4-yl)-6-(trichloromethyl)-1,3,5-triazin-2-amine | | | | |
| 331 | N-(2-amino-2-methylpropyl)-4-(4-phenylphenyl)-6-(trichloromethyl)-1,3,5-triazin-2-amine | 36 | 23 | 41 | |
| 332 | N-[(4-aminooxan-4-yl)methyl]-4-(4-phenylphenyl)-6-(trichloromethyl)-1,3,5-triazin-2-amine | 46 | 36 | 45 | |
| 333 | N-[(4-aminooxan-4-yl)methyl]-4-(4-chlorophenyl)-6-(trichloromethyl)-1,3,5-triazin-2-amine | 26 | 15 | 40 | |
| 334 | 4-(3-chlorophenyl)-N-[2-(pyrrolidin-1-yl)ethyl]-6-(trichloromethyl)-1,3,5-triazin-2-amine | 9 | 2 | 15 | |
| 335 | 4-(3-chlorophenyl)-N-[2-(1-methylpyrrolidin-2-yl)ethyl]-6-(trichloromethyl)-1,3,5-triazin-2-amine | 15 | 14 | 32 | 99 |
| 336 | 1-[4-(3-chlorophenyl)-6-(trichloromethyl)-1,3,5-triazin-2-yl]-1,4-diazepane | 74 | 38 | 83 | |
| 337 | 4-(3-chlorophenyl)-N-(1-methylpiperidin-4-yl)-6-(trichloromethyl)-1,3,5-triazin-2-amine | | | | |
| 338 | 4-(3-chlorophenyl)-N-(1-ethylpiperidin-3-yl)-6-(trichloromethyl)-1,3,5-triazin-2-amine | 97 | 56 | 111 | |
| 339 | 4-(3-chlorophenyl)-N-[(1-ethylpiperidin-4-yl)methyl]-6-(trichloromethyl)-1,3,5-triazin-2-amine | 34 | 14 | 41 | |
| 340 | N-[(4-aminooxan-4-yl)methyl]-4-[4-(methylsulfanyl)phenyl]-6-(trichloromethyl)-1,3,5-triazin-2-amine | 11 | 8 | 17 | |
| 341 | 2-N-(6-methoxypyridin-3-yl)-4-N-[2-(1-methylpyrrolidin-2-yl)ethyl]-6-(trichloromethyl)-1,3,5-triazine-2,4-diamine | 7 | 5 | 10 | |
| 342 | 2-N-[2-(diethylamino)ethyl]-4-N-(6-methoxypyridin-3-yl)-6-(trichloromethyl)-1,3,5-triazine-2,4-diamine | 335 | 149 | 398 | |
| 343 | 4-(1,4-diazepan-1-yl)-N-(6-methoxypyridin-3-yl)-6-(trichloromethyl)-1,3,5-triazin-2-amine | 3 | 3 | 7 | |
| 344 | 2-N-(1-ethylpiperidin-3-yl)-4-N-(6-methoxypyridin-3-yl)-6-(trichloromethyl)-1,3,5-triazine-2,4-diamine | 80 | 34 | 98 | |
| 345 | N-(6-methoxypyridin-3-yl)-4-(4-methylpiperazin-1-yl)-6-(trichloromethyl)-1,3,5-triazin-2-amine | 267 | 199 | 1100 | |
| 346 | 2-N-(2-methoxypyridin-3-yl)-4-N-[2-(1-methylpyrrolidin-2-yl)ethyl]-6-(trichloromethyl)-1,3,5-triazine-2,4-diamine | 62 | 52 | 116 | |
| 347 | 2-N-[2-(diethylamino)ethyl]-4-N-(2-methoxypyridin-3-yl)-6-(trichloromethyl)-1,3,5-triazine-2,4-diamine | 975 | 896 | 1000 | |
| 348 | 2-N-(2-methoxypyridin-3-yl)-4-N-(2,2,6,6-tetramethylpiperidin-4-yl)-6-(trichloromethyl)-1,3,5-triazine-2,4-diamine | 11 | 9 | 18 | 96 |
| 349 | 2-N-(6-methoxypyridin-3-yl)-4-N-(1-methylpiperidin-4-yl)-6-(trichloromethyl)-1,3,5-triazine-2,4-diamine | 124 | 129 | 296 | |
| 350 | 2-N-(2-methoxypyridin-3-yl)-4-N-[2-(pyrrolidin-1-yl)ethyl]-6-(trichloromethyl)-1,3,5-triazine-2,4-diamine | 560 | 467 | 900 | |
| 351 | 2-N-(2-methoxypyridin-3-yl)-4-N-[3-(pyrrolidin-1-yl)propyl]-6-(trichloromethyl)-1,3,5-triazine-2,4-diamine | 188 | 131 | 327 | |
| 352 | 2-N-[(1-ethylpiperidin-4-yl)methyl]-4-N-(2-methoxypyridin-3-yl)-6-(trichloromethyl)-1,3,5-triazine-2,4-diamine | 790.8 | 637.2 | 1000 | |
| 353 | N-(2-methoxypyridin-3-yl)-4-(4-methylpiperazin-1-yl)-6-(trichloromethyl)-1,3,5-triazin-2-amine | 101 | 80 | 211 | |
| 354 | 2-N-(2-methoxypyridin-3-yl)-4-N-(1-methylpiperidin-4-yl)-6-(trichloromethyl)-1,3,5-triazine-2,4-diamine | 682 | 611 | 1000 | |
| 355 | 2-N-(1-ethylpiperidin-3-yl)-4-N-(2-methoxypyridin-3-yl)-6-(trichloromethyl)-1,3,5-triazine-2,4-diamine | 38 | 31 | 76 | |
| 356 | N-(2-amino-2-ethylbutyl)-4-(4-chlorophenyl)-6-(trichloromethyl)-1,3,5-triazin-2-amine | 3 | 3 | 7 | 44 |
| 357 | N-(2-amino-2-ethylbutyl)-4-(trichloromethyl)-6-[3-(trifluoromethyl)phenyl]-1,3,5-triazin-2-amine | 2 | 2 | 5 | 34 |
| 358 | N-(2-amino-2-ethylbutyl)-4-(3,4-dimethoxyphenyl)-6-(trichloromethyl)-1,3,5-triazin-2-amine | 301 | 296 | 554 | |
| 359 | N-(2-amino-2-ethylbutyl)-4-(4-fluorophenyl)-6-(trichloromethyl)-1,3,5-triazin-2-amine | 45 | 51 | 95 | |
| 360 | N-(2-amino-2-ethylbutyl)-4-[4-(methylsulfanyl)phenyl]-6-(trichloromethyl)-1,3,5-triazin-2-amine | 4 | 4 | 9 | |
| 361 | N-(2-amino-2-ethylbutyl)-4-(trichloromethyl)-6-[4-(trichloromethyl)phenyl]-1,3,5-triazin-2-amine | 1000 | 1000 | 1000 | |
| 362 | N-(2-amino-2-ethylbutyl)-4-(4-tert-butylphenyl)-6-(trichloromethyl)-1,3,5-triazin-2-amine | 4 | 10 | 10 | 28 |
| 363 | N-(2-amino-2-ethylbutyl)-4-(3,5-dichlorophenyl)-6-(trichloromethyl)-1,3,5-triazin-2-amine | 11 | 14 | 17 | 52 |
| 364 | N-(2-amino-2-ethylbutyl)-4-(4-phenylphenyl)-6-(trichloromethyl)-1,3,5-triazin-2-amine | 3 | 4 | 6 | 25 |
| 365 | N-(2-amino-2-ethylbutyl)-4-(4-methanesulfonylphenyl)-6-(trichloromethyl)-1,3,5-triazin-2-amine | 5 | 5 | 10 | 69 |
| 366 | N-[2-(pyrrolidin-1-yl)ethyl]-4-[4-(pyrrolidin-1-yl)phenyl]-6-(trichloromethyl)-1,3,5-triazin-2-amine | 605 | 632 | 775 | |
| 367 | 2-N-(6-methoxypyridin-3-yl)-4-N-[3-(pyrrolidin-1-yl)propyl]-6-(trichloromethyl)-1,3,5-triazine-2,4-diamine | 69 | 82 | 175 | |
| 368 | 4-[4-(pyrrolidin-1-yl)phenyl]-N-[3-(pyrrolidin-1-yl)propyl]-6-(trichloromethyl)-1,3,5-triazin-2-amine | 404 | 392 | 624 | |

TABLE 13-continued

| Cmpd | IUPAC Name | D6 | W2 | C235 | hERG |
|---|---|---|---|---|---|
| 369 | 2-N-(6-methoxypyridin-3-yl)-4-N-[2-(pyrrolidin-1-yl)ethyl]-6-(trichloromethyl)-1,3,5-triazine-2,4-diamine | 64 | 82 | 134 | |
| 370 | N-[2-(1-methylpyrrolidin-2-yl)ethyl]-4-[4-(pyrrolidin-1-yl)phenyl]-6-(trichloromethyl)-1,3,5-triazin-2-amine | 846 | 1000 | 1000 | |
| 371 | 1-methyl-4-{4-[4-(pyrrolidin-1-yl)phenyl]-6-(trichloromethyl)-1,3,5-triazin-2-yl}-1,4-diazepane | 1000 | 1000 | 1000 | |
| 372 | N-(1-methylpiperidin-4-yl)-4-[4-(pyrrolidin-1-yl)phenyl]-6-(trichloromethyl)-1,3,5-triazin-2-amine | 1000 | 1000 | 1000 | |
| 373 | N-(2-amino-2-methylpropyl)-4-[4-(pyrrolidin-1-yl)phenyl]-6-(trichloromethyl)-1,3,5-triazin-2-amine | 409 | 837 | 1000 | |
| 374 | 2-N-[2-(diethylamino)ethyl]-6-(trichloromethyl)-4-N-[4-(trifluoromethoxy)phenyl]-1,3,5-triazine-2,4-diamine | 2 | 5 | 5 | 109 |
| 375 | 4-(4-methylpiperazin-1-yl)-6-(trichloromethyl)-N-[4-(trifluoromethoxy)phenyl]-1,3,5-triazin-2-amine | 75 | 107 | 184 | |
| 376 | N-(2-amino-2-ethylbutyl)-4-phenyl-6-(trichloromethyl)-1,3,5-triazin-2-amine | 3 | 8 | 11 | 89 |
| 377 | N-(2-amino-2-ethylbutyl)-4-(naphthalen-2-yl)-6-(trichloromethyl)-1,3,5-triazin-2-amine | 2 | 6 | 8 | 25 |
| 378 | 4-(1,4-diazepan-1-yl)-N-(2-methoxypyridin-3-yl)-6-(trichloromethyl)-1,3,5-triazin-2-amine | 50 | 59 | 98 | |
| 379 | N-(2-methoxypyridin-3-yl)-4-(4-methyl-1,4-diazepan-1-yl)-6-(trichloromethyl)-1,3,5-triazin-2-amine | 66 | 92 | 159 | |
| 380 | 4-(4-fluorophenyl)-N-[2-(pyrrolidin-1-yl)ethyl]-6-(trichloromethyl)-1,3,5-triazin-2-amine | 19 | 21 | 36 | 108 |
| 381 | 4-(4-fluorophenyl)-N-[3-(pyrrolidin-1-yl)propyl]-6-(trichloromethyl)-1,3,5-triazin-2-amine | 5 | 9 | 14 | 106 |
| 382 | 4-(4-fluorophenyl)-N-[2-(1-methylpyrrolidin-2-yl)ethyl]-6-(trichloromethyl)-1,3,5-triazin-2-amine | 17 | 20 | 36 | 105 |
| 383 | diethyl(2-{[4-(4-fluorophenyl)-6-(trichloromethyl)-1,3,5-triazin-2-yl]amino}ethyl)amine | 15 | 20 | 33 | 102 |
| 384 | 1-[4-(4-fluorophenyl)-6-(trichloromethyl)-1,3,5-triazin-2-yl]-4-methyl-1,4-diazepane | 25 | 29 | 59 | |
| 385 | 4-(4-fluorophenyl)-N-(1-methylpiperidin-4-yl)-6-(trichloromethyl)-1,3,5-triazin-2-amine | 28 | 39 | 57 | |
| 386 | N-[(1-ethylpiperidin-4-yl)methyl]-4-(4-fluorophenyl)-6-(trichloromethyl)-1,3,5-triazin-2-amine | 9 | 12 | 20 | 97 |
| 387 | N-(1-ethylpiperidin-3-yl)-4-(4-fluorophenyl)-6-(trichloromethyl)-1,3,5-triazin-2-amine | 4 | 7 | 13 | 108 |
| 388 | N-(2-amino-2-ethylbutyl)-4-(3,4-dichlorophenyl)-6-(trichloromethyl)-1,3,5-triazin-2-amine | 132 | 98 | 153 | |
| 389 | N-(2-amino-2-methylpropyl)-4-(4-fluorophenyl)-6-(trichloromethyl)-1,3,5-triazin-2-amine | 30 | 13 | 45 | |
| 390 | 2-(4-fluorophenyl)-4-(4-methylpiperazin-1-yl)-6-(trichloromethyl)-1,3,5-triazine | 495 | 143 | 567 | |
| 391 | 4-(4-fluorophenyl)-N-(2,2,6,6-tetramethylpiperidin-4-yl)-6-(trichloromethyl)-1,3,5-triazin-2-amine | 43 | 19 | 46 | |
| 392 | 4-(3,4-dimethoxyphenyl)-N-[2-(pyrrolidin-1-yl)ethyl]-6-(trichloromethyl)-1,3,5-triazin-2-amine | 173 | 69 | 166 | |
| 393 | 4-(3,4-dimethoxyphenyl)-N-[3-(pyrrolidin-1-yl)propyl]-6-(trichloromethyl)-1,3,5-triazin-2-amine | 81 | 37 | 100 | |
| 394 | 4-(3,4-dimethoxyphenyl)-N-[2-(1-methylpyrrolidin-2-yl)ethyl]-6-(trichloromethyl)-1,3,5-triazin-2-amine | 676 | 360 | 642 | |
| 395 | (2-{[4-(3,4-dimethoxyphenyl)-6-(trichloromethyl)-1,3,5-triazin-2-yl]amino}ethyl)diethylamine | 1 | 2 | 2 | |
| 396 | N-(2-amino-2-methylpropyl)-4-(3,4-dimethoxyphenyl)-6-(trichloromethyl)-1,3,5-triazin-2-amine | 86 | 49 | 117 | |
| 397 | 1-[4-(3,4-dimethoxyphenyl)-6-(trichloromethyl)-1,3,5-triazin-2-yl]-1,4-diazepane | 1000 | 1000 | 1000 | |
| 398 | 1-[4-(3,4-dimethoxyphenyl)-6-(trichloromethyl)-1,3,5-triazin-2-yl]-4-methyl-1,4-diazepane | 1000 | 638 | 1000 | |
| 399 | 4-(3,4-dimethoxyphenyl)-N-(1-methylpiperidin-4-yl)-6-(trichloromethyl)-1,3,5-triazin-2-amine | 1000 | 705 | 1000 | |
| 400 | 2-(3,4-dimethoxyphenyl)-4-(4-methylpiperazin-1-yl)-6-(trichloromethyl)-1,3,5-triazine | 564 | 276 | 688 | |
| 401 | 4-(3,4-dimethoxyphenyl)-N-[(1-ethylpiperidin-4-yl)methyl]-6-(trichloromethyl)-1,3,5-triazin-2-amine | 733 | 400 | 726 | |
| 402 | 4-(3,4-dimethoxyphenyl)-N-(1-ethylpiperidin-3-yl)-6-(trichloromethyl)-1,3,5-triazin-2-amine | 428 | 269 | 572 | |
| 403 | 2-N-(2-amino-2-methylpropyl)-4-N-(6-methoxypyridin-3-yl)-6-(trichloromethyl)-1,3,5-triazine-2,4-diamine | 134 | 78 | 203 | |
| 404 | 2-N-(2-amino-2-methylpropyl)-4-N-(2-methoxypyridin-3-yl)-6-(trichloromethyl)-1,3,5-triazine-2,4-diamine | 1000 | 1000 | 1000 | |
| 405 | 4-phenyl-N-[2-(pyrrolidin-1-yl)ethyl]-6-(trichloromethyl)-1,3,5-triazin-2-amine | 27 | 16 | 45 | |
| 406 | 4-phenyl-N-[3-(pyrrolidin-1-yl)propyl]-6-(trichloromethyl)-1,3,5-triazin-2-amine | 77 | 35 | 89 | |
| 407 | N-[2-(1-methylpyrrolidin-2-yl)ethyl]-4-phenyl-6-(trichloromethyl)-1,3,5-triazin-2-amine | 85 | 39 | 94 | |
| 408 | 1-[4-phenyl-6-(trichloromethyl)-1,3,5-triazin-2-yl]-1,4-diazepane | 190 | 84 | 189 | |
| 409 | 1-methyl-4-[4-phenyl-6-(trichloromethyl)-1,3,5-triazin-2-yl]-1,4-diazepane | 118 | 43 | 119 | |
| 410 | N-[(1-ethylpiperidin-4-yl)methyl]-4-phenyl-6-(trichloromethyl)-1,3,5-triazin-2-amine | 103 | 35 | 113 | |
| 411 | diethyl(2-{[4-(4-methoxynaphthalen-1-yl)-6-(trichloromethyl)-1,3,5-triazin-2-yl]amino}ethyl)amine | 232 | 158 | 312 | |
| 412 | diethyl[2-({4-[4-(pyrrolidin-1-yl)phenyl]-6-(trichloromethyl)-1,3,5-triazin-2-yl}amino)ethyl]amine | 1000 | 686 | 1000 | |
| 413 | 1-[4-(4-methoxynaphthalen-1-yl)-6-(trichloromethyl)-1,3,5-triazin-2-yl]-4-methyl-1,4-diazepane | 363 | 171 | 365 | |
| 414 | 2-(4-methoxynaphthalen-1-yl)-4-(4-methylpiperazin-1-yl)-6-(trichloromethyl)-1,3,5-triazine | 388 | 120 | 473 | |
| 415 | N-(2-amino-2-methylpropyl)-4-(4-methoxynaphthalen-1-yl)-6-(trichloromethyl)-1,3,5-triazin-2-amine | 278 | 133 | 261 | |
| 416 | 2-{4-[4-(4-methylphenyl)-6-(trichloromethyl)-1,3,5-triazin-2-yl]piperazin-1-yl}ethan-1-ol | 1000 | 381 | 1000 | |
| 417 | 2-{4-[4-phenyl-6-(trichloromethyl)-1,3,5-triazin-2-yl]piperazin-1-yl}ethan-1-ol | 1000 | 786 | 1000 | |
| 418 | 2-{4-[4-(3,5-dichlorophenyl)-6-(trichloromethyl)-1,3,5-triazin-2-yl]piperazin-1-yl}ethan-1-ol | 327 | 128 | 365 | |
| 419 | 2-(4-{4-[2-(4-methylphenyl)phenyl]-6-(trichloromethyl)-1,3,5-triazin-2-yl}piperazin-1-yl)ethan-1-ol | 1000 | 496 | 1000 | |
| 420 | 2-{4-[4-(3-chlorophenyl)-6-(trichloromethyl)-1,3,5-triazin-2-yl]piperazin-1-yl}ethan-1-ol | 599 | 210 | 676 | |
| 421 | 2-{4-[4-(4-fluorophenyl)-6-(trichloromethyl)-1,3,5-triazin-2-yl]piperazin-1-yl}ethan-1-ol | 1000 | 553 | 1000 | |
| 422 | 2-{4-[4-(4-methoxynaphthalen-1-yl)-6-(trichloromethyl)-1,3,5-triazin-2-yl]piperazin-1-yl}ethan-1-ol | 291 | 73 | 310 | |
| 423 | 2-{4-[4-(3,4-dimethoxyphenyl)-6-(trichloromethyl)-1,3,5-triazin-2-yl]piperazin-1-yl}ethan-1-ol | 765 | 263 | 793 | |
| 424 | 4-(4-methoxynaphthalen-1-yl)-N-[3-(pyrrolidin-1-yl)propyl]-6-(trichloromethyl)-1,3,5-triazin-2-amine | 180 | 91 | 235 | |
| 425 | 4-(4-methoxynaphthalen-1-yl)-N-[2-(1-methylpyrrolidin-2-yl)ethyl]-6-(trichloromethyl)-1,3,5-triazin-2-amine | 289 | 170 | 346 | |
| 426 | 4-(4-methoxynaphthalen-1-yl)-N-(1-methylpiperidin-4-yl)-6-(trichloromethyl)-1,3,5-triazin-2-amine | 239 | 141 | 270 | |
| 427 | 2-(4-methylpiperazin-1-yl)-4-[4-(pyrrolidin-1-yl)phenyl]-6-(trichloromethyl)-1,3,5-triazine | 676 | 459 | 877 | |
| 428 | 1-{4-[4-(pyrrolidin-1-yl)phenyl]-6-(trichloromethyl)-1,3,5-triazin-2-yl}-1,4-diazepane | 1000 | 1000 | 1000 | |
| 429 | N-(1-ethylpiperidin-3-yl)-4-[4-(pyrrolidin-1-yl)phenyl]-6-(trichloromethyl)-1,3,5-triazin-2-amine | 791 | 607 | 912 | |
| 430 | N-[(1-ethylpiperidin-4-yl)methyl]-4-[4-(pyrrolidin-1-yl)phenyl]-6-(trichloromethyl)-1,3,5-triazin-2-amine | 1000 | 1000 | 1000 | |
| 431 | 2-(4-{4-[4-(pyrrolidin-1-yl)phenyl]-6-(trichloromethyl)-1,3,5-triazin-2-yl}piperazin-1-yl)ethan-1-ol | 1000 | 1000 | 1000 | |
| 432 | N-[(4-aminooxan-4-yl)methyl]-4-[4-(pyrrolidin-1-yl)phenyl]-6-(trichloromethyl)-1,3,5-triazin-2-amine | 1000 | 1000 | 1000 | |
| 433 | 4-(3-chlorophenyl)-N-[3-(pyrrolidin-1-yl)propyl]-6-(trichloromethyl)-1,3,5-triazin-2-amine | 76 | 44 | 145 | |
| 434 | (2-{[4-(3-chlorophenyl)-6-(trichloromethyl)-1,3,5-triazin-2-yl]amino}ethyl)diethylamine | 539 | 367 | 636 | |
| 435 | 1-[4-(3-chlorophenyl)-6-(trichloromethyl)-1,3,5-triazin-2-yl]-4-methyl-1,4-diazepane | 1000 | 1000 | 1000 | |
| 436 | 2-(3-chlorophenyl)-4-(4-methylpiperazin-1-yl)-6-(trichloromethyl)-1,3,5-triazine | 155 | 19 | 158 | |

TABLE 13-continued

| Cmpd | IUPAC Name | D6 | W2 | C235 | hERG |
|---|---|---|---|---|---|
| 437 | N-(2-amino-2-methylpropyl)-4-(3-chlorophenyl)-6-(trichloromethyl)-1,3,5-triazin-2-amine | 27 | 16 | 35 | |
| 438 | 4-(3-chlorophenyl)-N-(2,2,6,6-tetramethylpiperidin-4-yl)-6-(trichloromethyl)-1,3,5-triazin-2-amine | 24 | 13 | 46 | |
| 439 | dimethyl(3-{[4-(4-methylphenyl)-6-(trichloromethyl)-1,3,5-triazin-2-yl]amino}propyl)amine | 196 | 82 | 200 | |
| 440 | (3-{[4-(4-tert-butylphenyl)-6-(trichloromethyl)-1,3,5-triazin-2-yl]amino}propyl)dimethylamine | 1000 | 1000 | 1000 | |
| 441 | dimethyl[3-({4-[4-(methylsulfanyl)phenyl]-6-(trichloromethyl)-1,3,5-triazin-2-yl}amino)propyl]amine | 1000 | 1000 | 1000 | |
| 442 | (3-{[4-(4-methanesulfonylphenyl)-6-(trichloromethyl)-1,3,5-triazin-2-yl]amino}propyl)dimethylamine | 2 | 1 | 2 | |
| 443 | dimethyl(3-{[4-phenyl-6-(trichloromethyl)-1,3,5-triazin-2-yl]amino}propyl)amine | 145 | 43 | 161 | |
| 444 | dimethyl(3-{[4-(naphthalen-2-yl)-6-(trichloromethyl)-1,3,5-triazin-2-yl]amino}propyl)amine | 463 | 183 | 403 | |
| 445 | dimethyl(3-{[4-(4-phenylphenyl)-6-(trichloromethyl)-1,3,5-triazin-2-yl]amino}propyl)amine | 151 | 116 | 189 | |
| 446 | dimethyl[3-({4-[2-(4-methylphenyl)phenyl]-6-(trichloromethyl)-1,3,5-triazin-2-yl}amino)propyl]amine | 482 | 223 | 535 | |
| 447 | (3-{[4-(3-chlorophenyl)-6-(trichloromethyl)-1,3,5-triazin-2-yl]amino}propyl)dimethylamine | 591 | 296 | 673 | |
| 448 | (3-{[4-(4-fluorophenyl)-6-(trichloromethyl)-1,3,5-triazin-2-yl]amino}propyl)dimethylamine | 35 | 7 | 40 | |
| 449 | (3-{[4-(4-methoxynaphthalen-1-yl)-6-(trichloromethyl)-1,3,5-triazin-2-yl]amino}propyl)dimethylamine | 194 | 97 | 263 | |
| 450 | (3-{[4-(3,4-dimethoxyphenyl)-6-(trichloromethyl)-1,3,5-triazin-2-yl]amino}propyl)dimethylamine | 239 | 91 | 252 | |
| 451 | 2-{4-[4-(4-phenylphenyl)-6-(trichloromethyl)-1,3,5-triazin-2-yl]-1,4-diazepan-1-yl}ethan-1-ol | 154 | 63 | 179 | |
| 452 | 4-(2-nitrophenyl)-N-[2-(pyrrolidin-1-yl)ethyl]-6-(trichloromethyl)-1,3,5-triazin-2-amine | 192 | 41 | 103 | |
| 453 | 2-{4-[4-(4-methylphenyl)-6-(trichloromethyl)-1,3,5-triazin-2-yl]-1,4-diazepan-1-yl}ethan-1-ol | 173 | 43 | 112 | |
| 454 | 2-{4-[4-(3,4-dichlorophenyl)-6-(trichloromethyl)-1,3,5-triazin-2-yl]-1,4-diazepan-1-yl}ethan-1-ol | 252 | 64 | 118 | |
| 455 | 2-{4-[4-(4-chlorophenyl)-6-(trichloromethyl)-1,3,5-triazin-2-yl]-1,4-diazepan-1-yl}ethan-1-ol | 214 | 65 | 118 | |
| 456 | 2-{4-[4-(trichloromethyl)-6-[3-(trifluoromethyl)phenyl]-1,3,5-triazin-2-yl]-1,4-diazepan-1-yl}ethan-1-ol | 207 | 91 | 136 | |
| 457 | 2-(4-{4-[4-(methylsulfanyl)phenyl]-6-(trichloromethyl)-1,3,5-triazin-2-yl}-1,4-diazepan-1-yl)ethan-1-ol | 328 | 80 | 168 | |
| 458 | 2-{4-[4-phenyl-6-(trichloromethyl)-1,3,5-triazin-2-yl]-1,4-diazepan-1-yl}ethan-1-ol | 172 | 44 | 116 | |
| 459 | 2-{4-[4-(naphthalen-2-yl)-6-(trichloromethyl)-1,3,5-triazin-2-yl]-1,4-diazepan-1-yl}ethan-1-ol | 163 | 108 | 153 | |
| 460 | 2-{4-[4-(3,5-dichlorophenyl)-6-(trichloromethyl)-1,3,5-triazin-2-yl]-1,4-diazepan-1-yl}ethan-1-ol | 594 | 158 | 367 | |
| 461 | 2-{4-[4-(3-chlorophenyl)-6-(trichloromethyl)-1,3,5-triazin-2-yl]-1,4-diazepan-1-yl}ethan-1-ol | 151 | 27 | 80 | |
| 462 | 2-{4-[4-(4-fluorophenyl)-6-(trichloromethyl)-1,3,5-triazin-2-yl]-1,4-diazepan-1-yl}ethan-1-ol | 221 | 43 | 104 | |
| 463 | 2-{4-[4-(4-methoxynaphthalen-1-yl)-6-(trichloromethyl)-1,3,5-triazin-2-yl]-1,4-diazepan-1-yl}ethan-1-ol | 355 | 201 | 306 | |
| 464 | 2-{4-[4-(3,4-dimethoxyphenyl)-6-(trichloromethyl)-1,3,5-triazin-2-yl]-1,4-diazepan-1-yl}ethan-1-ol | 177 | 55 | 144 | |
| 465 | 2-(4-{4-[4-(pyrrolidin-1-yl)phenyl]-6-(trichloromethyl)-1,3,5-triazin-2-yl}-1,4-diazepan-1-yl)ethan-1-ol | 1000 | 222 | 498 | |
| 466 | N-(1-ethylpiperidin-3-yl)-4-(2-nitrophenyl)-6-(trichloromethyl)-1,3,5-triazin-2-amine | 279 | 85 | 179 | |
| 467 | N-(2-amino-2-methylpropyl)-4-(2-nitrophenyl)-6-(trichloromethyl)-1,3,5-triazin-2-amine | 402 | 123 | 256 | |
| 468 | 2-{4-[4-(trichloromethyl)-6-{[4-(trifluoromethoxy)phenyl]amino}-1,3,5-triazin-2-yl]-1,4-diazepan-1-yl}ethan-1-ol | 34 | 16 | 21 | |
| 469 | 4-(4-chlorophenyl)-N-[2-(pyrazin-2-yl)ethyl]-6-(trichloromethyl)-1,3,5-triazin-2-amine | 913 | 176 | 469 | |
| 470 | 4-(3,4-dichlorophenyl)-N-[2-(pyrazin-2-yl)ethyl]-6-(trichloromethyl)-1,3,5-triazin-2-amine | 1000 | 70 | 258 | |
| 471 | 4-(3,5-dichlorophenyl)-N-[2-(pyrazin-2-yl)ethyl]-6-(trichloromethyl)-1,3,5-triazin-2-amine | 1000 | 174 | 1000 | |
| 472 | 4-(3-chlorophenyl)-N-[2-(pyrazin-2-yl)ethyl]-6-(trichloromethyl)-1,3,5-triazin-2-amine | 449 | 51 | 244 | |
| 473 | 4-(4-chlorophenyl)-N-methyl-N-[2-(pyridin-2-yl)ethyl]-6-(trichloromethyl)-1,3,5-triazin-2-amine | | | | |
| 474 | 4-(3,5-dichlorophenyl)-N-methyl-N-[2-(pyridin-2-yl)ethyl]-6-(trichloromethyl)-1,3,5-triazin-2-amine | 65 | 208 | 527 | |
| 475 | 4-(3-chlorophenyl)-N-methyl-N-[2-(pyridin-2-yl)ethyl]-6-(trichloromethyl)-1,3,5-triazin-2-amine | 469 | 86 | 266 | |
| 476 | 4-(3,5-dimethoxyphenyl)-N-[2-(pyrrolidin-1-yl)ethyl]-6-(trichloromethyl)-1,3,5-triazin-2-amine | 57 | 23 | 35 | |
| 477 | 4-(3,5-dimethoxyphenyl)-N-[3-(pyrrolidin-1-yl)propyl]-6-(trichloromethyl)-1,3,5-triazin-2-amine | 77 | 23 | 41 | |
| 478 | 4-(3,5-dimethoxyphenyl)-N-[2-(1-methylpyrrolidin-2-yl)ethyl]-6-(trichloromethyl)-1,3,5-triazin-2-amine | 42 | 14 | 22 | |
| 479 | (2-{[4-(3,5-dimethoxyphenyl)-6-(trichloromethyl)-1,3,5-triazin-2-yl]amino}ethyl)diethylamine | 38 | 12 | 17 | |
| 480 | 1-[4-(3,5-dimethoxyphenyl)-6-(trichloromethyl)-1,3,5-triazin-2-yl]-4-methyl-1,4-diazepane | 307 | 96 | 165 | |
| 481 | N-(2-amino-2-methylpropyl)-4-(3,5-dimethoxyphenyl)-6-(trichloromethyl)-1,3,5-triazin-2-amine | 35 | 12 | 17 | |
| 482 | 2-(3,5-dimethoxyphenyl)-4-(4-methylpiperazin-1-yl)-6-(trichloromethyl)-1,3,5-triazine | 918 | 222 | 485 | |
| 483 | 2-{4-[4-(3,5-dimethoxyphenyl)-6-(trichloromethyl)-1,3,5-triazin-2-yl]-1,4-diazepan-1-yl}ethan-1-ol | 1000 | 200 | 1000 | |
| 484 | 4-(4-methylphenyl)-N-{[1-(propan-2-yl)piperidin-4-yl]methyl}-6-(trichloromethyl)-1,3,5-triazin-2-amine | 65 | 30 | 44 | |
| 485 | 4-(3-methoxyphenyl)-N-{[1-(propan-2-yl)piperidin-4-yl]methyl}-6-(trichloromethyl)-1,3,5-triazin-2-amine | 94 | 24 | 45 | |
| 486 | 4-(3,4-dichlorophenyl)-N-{[1-(propan-2-yl)piperidin-4-yl]methyl}-6-(trichloromethyl)-1,3,5-triazin-2-amine | 25 | 13 | 16 | |
| 487 | 4-(4-chlorophenyl)-N-{[1-(propan-2-yl)piperidin-4-yl]methyl}-6-(trichloromethyl)-1,3,5-triazin-2-amine | 64 | 19 | 33 | |
| 488 | 4-(4-tert-butylphenyl)-N-{[1-(propan-2-yl)piperidin-4-yl]methyl}-6-(trichloromethyl)-1,3,5-triazin-2-amine | 27 | 16 | 20 | |
| 489 | N-{[1-(propan-2-yl)piperidin-4-yl]methyl}-4-(trichloromethyl)-6-[3-(trifluoromethyl)phenyl]-1,3,5-triazin-2-amine | 14 | 8 | 10 | |
| 490 | 4-[4-(methylsulfanyl)phenyl]-N-{[1-(propan-2-yl)piperidin-4-yl]methyl}-6-(trichloromethyl)-1,3,5-triazin-2-amine | 91 | 49 | 67 | |
| 491 | 4-(4-methanesulfonylphenyl)-N-{[1-(propan-2-yl)piperidin-4-yl]methyl}-6-(trichloromethyl)-1,3,5-triazin-2-amine | 48 | 18 | 34 | |
| 492 | N-{[1-(propan-2-yl)piperidin-4-yl]methyl}-4-(trichloromethyl)-6-[4-(trichloromethyl)phenyl]-1,3,5-triazin-2-amine | 95 | 33 | 52 | |
| 493 | 4-phenyl-N-{[1-(propan-2-yl)piperidin-4-yl]methyl}-6-(trichloromethyl)-1,3,5-triazin-2-amine | 33 | 10 | 17 | |
| 494 | 4-(naphthalen-2-yl)-N-{[1-(propan-2-yl)piperidin-4-yl]methyl}-6-(trichloromethyl)-1,3,5-triazin-2-amine | 38 | 18 | 23 | |

TABLE 13-continued

| Cmpd | IUPAC Name | D6 | W2 | C235 | hERG |
|---|---|---|---|---|---|
| 495 | 4-(3,5-dichlorophenyl)-N-{[1-(propan-2-yl)piperidin-4-yl]methyl}-6-(trichloromethyl)-1,3,5-triazin-2-amine | 36 | 10 | 13 | |
| 496 | 4-(4-phenylphenyl)-N-{[1-(propan-2-yl)piperidin-4-yl]methyl}-6-(trichloromethyl)-1,3,5-triazin-2-amine | 29 | 15 | 14 | |
| 497 | 4-(2-nitrophenyl)-N-{[1-(propan-2-yl)piperidin-4-yl]methyl}-6-(trichloromethyl)-1,3,5-triazin-2-amine | 913 | 176 | 469 | |
| 498 | 4-(4-methoxynaphthalen-1-yl)-N-{[1-(propan-2-yl)piperidin-4-yl]methyl}-6-(trichloromethyl)-1,3,5-triazin-2-amine | 247 | 66 | 125 | |
| 499 | 4-(3-chlorophenyl)-N-{[1-(propan-2-yl)piperidin-4-yl]methyl}-6-(trichloromethyl)-1,3,5-triazin-2-amine | 51 | 13 | 20 | |
| 500 | 4-(4-fluorophenyl)-N-{[1-(propan-2-yl)piperidin-4-yl]methyl}-6-(trichloromethyl)-1,3,5-triazin-2-amine | 285 | 113 | 174 | |
| 501 | 4-(3,4-dimethoxyphenyl)-N-{[1-(propan-2-yl)piperidin-4-yl]methyl}-6-(trichloromethyl)-1,3,5-triazin-2-amine | 362 | 94 | 241 | |
| 502 | 4-(3,5-dimethoxyphenyl)-N-{[1-(propan-2-yl)piperidin-4-yl]methyl}-6-(trichloromethyl)-1,3,5-triazin-2-amine | 127 | 28 | 52 | |
| 503 | 4-(4-methylphenyl)-N-[(1-methylpiperidin-4-yl)methyl]-6-(trichloromethyl)-1,3,5-triazin-2-amine | 44 | 14 | 26 | |
| 504 | 4-(3-methoxyphenyl)-N-[(1-methylpiperidin-4-yl)methyl]-6-(trichloromethyl)-1,3,5-triazin-2-amine | 70 | 16 | 32 | |
| 505 | 4-(3,4-dichlorophenyl)-N-[(1-methylpiperidin-4-yl)methyl]-6-(trichloromethyl)-1,3,5-triazin-2-amine | 29 | 17 | 20 | |
| 506 | 4-(4-chlorophenyl)-N-[(1-methylpiperidin-4-yl)methyl]-6-(trichloromethyl)-1,3,5-triazin-2-amine | 31 | 10 | 16 | |
| 507 | 4-(4-tert-butylphenyl)-N-[(1-methylpiperidin-4-yl)methyl]-6-(trichloromethyl)-1,3,5-triazin-2-amine | 43 | 39 | 43 | |
| 508 | N-[(1-methylpiperidin-4-yl)methyl]-4-(trichloromethyl)-6-[3-(trifluoromethyl)phenyl]-1,3,5-triazin-2-amine | 34 | 13 | 22 | |
| 509 | N-[(1-methylpiperidin-4-yl)methyl]-4-[4-(methylsulfanyl)phenyl]-6-(trichloromethyl)-1,3,5-triazin-2-amine | 294 | 98 | 167 | |
| 510 | 4-(4-methanesulfonylphenyl)-N-[(1-methylpiperidin-4-yl)methyl]-6-(trichloromethyl)-1,3,5-triazin-2-amine | 416 | 88 | 273 | |
| 511 | N-[(1-methylpiperidin-4-yl)methyl]-4-(trichloromethyl)-6-[4-(trichloromethyl)phenyl]-1,3,5-triazin-2-amine | 77 | 34 | 56 | |
| 512 | N-[(1-methylpiperidin-4-yl)methyl]-4-phenyl-6-(trichloromethyl)-1,3,5-triazin-2-amine | 103 | 30 | 57 | |
| 513 | N-[(1-methylpiperidin-4-yl)methyl]-4-(naphthalen-2-yl)-6-(trichloromethyl)-1,3,5-triazin-2-amine | 118 | 67 | 78 | |
| 514 | 4-(3,5-dichlorophenyl)-N-[(1-methylpiperidin-4-yl)methyl]-6-(trichloromethyl)-1,3,5-triazin-2-amine | 79 | 26 | 28 | |
| 515 | N-[(1-methylpiperidin-4-yl)methyl]-4-(4-phenylphenyl)-6-(trichloromethyl)-1,3,5-triazin-2-amine | 345 | 235 | 378 | |
| 516 | N-[(1-methylpiperidin-4-yl)methyl]-4-(2-nitrophenyl)-6-(trichloromethyl)-1,3,5-triazin-2-amine | 292 | 83 | 181 | |
| 517 | 4-(4-methoxynaphthalen-1-yl)-N-[(1-methylpiperidin-4-yl)methyl]-6-(trichloromethyl)-1,3,5-triazin-2-amine | 23 | 7 | 12 | |
| 518 | 4-(3-chlorophenyl)-N-[(1-methylpiperidin-4-yl)methyl]-6-(trichloromethyl)-1,3,5-triazin-2-amine | 32 | 11 | 18 | |
| 519 | 4-(4-fluorophenyl)-N-[(1-methylpiperidin-4-yl)methyl]-6-(trichloromethyl)-1,3,5-triazin-2-amine | 14 | 7 | 9 | |
| 520 | 4-(3,4-dimethoxyphenyl)-N-[(1-methylpiperidin-4-yl)methyl]-6-(trichloromethyl)-1,3,5-triazin-2-amine | 82 | 19 | 45 | |
| 521 | 4-(3,5-dimethoxyphenyl)-N-[(1-methylpiperidin-4-yl)methyl]-6-(trichloromethyl)-1,3,5-triazin-2-amine | 45 | 14 | 23 | |
| 522 | 4-(2-nitrophenyl)-N-3-(pyrrolidin-1-yl)propyl)-6-(trichloromethyl)-1,3,5-triazin-2-amine | 312 | 90 | 216 | |
| 523 | diethyl(2-{[4-(2-nitrophenyl)-6-(trichloromethyl)-1,3,5-triazin-2-yl]amino}ethyl)amine | 294 | 79 | 182 | |
| 524 | N-[2-(1-methylpyrrolidin-2-yl)ethyl]-4-(2-nitrophenyl)-6-(trichloromethyl)-1,3,5-triazin-2-amine | 108 | 28 | 70 | |
| 525 | 1-[4-(3,5-dimethoxyphenyl)-6-(trichloromethyl)-1,3,5-triazin-2-yl]-1,4-diazepane | 43 | 33 | 41 | |
| 526 | 2-{4-[4-(3,5-dimethoxyphenyl)-6-(trichloromethyl)-1,3,5-triazin-2-yl]piperazin-1-yl}ethan-1-ol | 250 | 74 | 220 | |
| 527 | 4-(3,5-dimethoxyphenyl)-N-(2,2,6,6-tetramethylpiperidin-4-yl)-6-(trichloromethyl)-1,3,5-triazin-2-amine | 26 | 21 | 24 | |
| 528 | 4-(3,5-dimethoxyphenyl)-N-(1-ethylpiperidin-3-yl)-6-(trichloromethyl)-1,3,5-triazin-2-amine | 35 | 23 | 33 | |
| 529 | N-[(4-aminooxan-4-yl)methyl]-4-(3,5-dimethoxyphenyl)-6-(trichloromethyl)-1,3,5-triazin-2-amine | 59 | 55 | 55 | |
| 530 | N-[(1-aminocyclopentyl)methyl]-4-(3,5-dimethoxyphenyl)-6-(trichloromethyl)-1,3,5-triazin-2-amine | 13 | 14 | 13 | |
| 531 | (3-{[4-(3,5-dimethoxyphenyl)-6-(trichloromethyl)-1,3,5-triazin-2-yl]amino}propyl)dimethylamine | 41 | 22 | 35 | |
| 532 | dimethyl(3-{[4-(2-nitrophenyl)-6-(trichloromethyl)-1,3,5-triazin-2-yl]amino}propyl)amine | 454 | 206 | 355 | |
| 533 | (3-{[4-(3-methoxyphenyl)-6-(trichloromethyl)-1,3,5-triazin-2-yl]amino}propyl)dimethylamine | 129 | 46 | 90 | |
| 534 | N-methyl-N-[2-(pyridin-2-yl)ethyl]-4-(trichloromethyl)-6-[4-(trichloromethyl)phenyl]-1,3,5-triazin-2-amine | 35 | 12 | 38 | |
| 535 | 4-(4-methylphenyl)-N-[2-(pyrazin-2-yl)ethyl]-6-(trichloromethyl)-1,3,5-triazin-2-amine | 465 | 173 | 439 | |
| 536 | 4-(3-methoxyphenyl)-N-[2-(pyrazin-2-yl)ethyl]-6-(trichloromethyl)-1,3,5-triazin-2-amine | 1000 | 362 | 1000 | |
| 537 | 4-(4-methoxyphenyl)-N-[2-(pyrazin-2-yl)ethyl]-6-(trichloromethyl)-1,3,5-triazin-2-amine | 1000 | 297.8 | 1000 | |
| 538 | 4-(4-tert-butylphenyl)-N-[2-(pyrazin-2-yl)ethyl]-6-(trichloromethyl)-1,3,5-triazin-2-amine | 545 | 236.2 | 557 | |
| 539 | N-[2-(pyrazin-2-yl)ethyl]-4-(trichloromethyl)-6-[3-(trifluoromethyl)phenyl]-1,3,5-triazin-2-amine | 325 | 98 | 270 | |
| 540 | 4-phenyl-N-[2-(pyrazin-2-yl)ethyl]-6-(trichloromethyl)-1,3,5-triazin-2-amine | 151 | 88 | 213 | |
| 541 | 4-(naphthalen-2-yl)-N-[2-(pyrazin-2-yl)ethyl]-6-(trichloromethyl)-1,3,5-triazin-2-amine | 1000 | 236 | 761 | |
| 542 | 4-(4-phenylphenyl)-N-[2-(pyrazin-2-yl)ethyl]-6-(trichloromethyl)-1,3,5-triazin-2-amine | 651 | 140 | 594 | |
| 543 | 4-[4-(methylsulfanyl)phenyl]-N-[2-(pyrazin-2-yl)ethyl]-6-(trichloromethyl)-1,3,5-triazin-2-amine | 1000 | 669 | 1000 | |
| 544 | 4-(2-nitrophenyl)-N-[2-(pyrazin-2-yl)ethyl]-6-(trichloromethyl)-1,3,5-triazin-2-amine | 1000 | 530 | 1000 | |
| 545 | 4-(2,2-dimethyl-2H-chromen-6-yl)-N-[2-(pyrazin-2-yl)ethyl]-6-(trichloromethyl)-1,3,5-triazin-2-amine | 338 | 147 | 300 | |
| 546 | 4-(4-methoxynaphthalen-1-yl)-N-[2-(pyrazin-2-yl)ethyl]-6-(trichloromethyl)-1,3,5-triazin-2-amine | 1000 | 361 | 701 | |
| 547 | 4-(4-fluorophenyl)-N-[2-(pyrazin-2-yl)ethyl]-6-(trichloromethyl)-1,3,5-triazin-2-amine | 332 | 90 | 331 | |
| 548 | 1-methyl-4-[4-(2-nitrophenyl)-6-(trichloromethyl)-1,3,5-triazin-2-yl]-1,4-diazepane | 69 | 53 | 70 | |
| 549 | 2-(4-methylpiperazin-1-yl)-4-(2-nitrophenyl)-6-(trichloromethyl)-1,3,5-triazine | 503 | 236 | 663 | |
| 550 | N-(1-methylpiperidin-4-yl)-4-(2-nitrophenyl)-6-(trichloromethyl)-1,3,5-triazin-2-amine | 48.05 | 20.59 | 35.85 | |
| 551 | N-[(1-ethylpiperidin-4-yl)methyl]-4-(2-nitrophenyl)-6-(trichloromethyl)-1,3,5-triazin-2-amine | 70.27 | 35.6 | 56.53 | |
| 552 | 2-{4-[4-(2-nitrophenyl)-6-(trichloromethyl)-1,3,5-triazin-2-yl]-1,4-diazepan-1-yl}ethan-1-ol | 170.4 | 76.05 | 175.6 | |
| 553 | 4-(2,2-dimethyl-2H-chromen-6-yl)-N-[2-(pyrrolidin-1-yl)ethyl]-6-(trichloromethyl)-1,3,5-triazin-2-amine | 18.63 | 15.06 | 15.96 | |

TABLE 13-continued

| Cmpd | IUPAC Name | D6 | W2 | C235 | hERG |
|---|---|---|---|---|---|
| 554 | 4-(3,4-dichlorophenyl)-N-(2,2,6,6-tetramethylpiperidin-4-yl)-6-(trichloromethyl)-1,3,5-triazin-2-amine | | | | |
| 555 | 2-N-(2-amino-2-methylpropyl)-6-(trichloromethyl)-4-N-[3-(trifluoromethyl)phenyl]-1,3,5-triazine-2,4-diamine | 75.55 | 30.79 | 59.58 | |
| 556 | 2-N-(2-amino-2-methylpropyl)-4-N-(3,5-dichlorophenyl)-6-(trichloromethyl)-1,3,5-triazine-2,4-diamine | 24.57 | 15.15 | 19.66 | |
| 557 | 2-N-(2-amino-2-methylpropyl)-4-N-phenyl-6-(trichloromethyl)-1,3,5-triazine-2,4-diamine | | | | |
| 558 | 4-(4-chlorophenyl)-N-[3-(pyrrolidin-1-yl)propyl]-6-(trichloromethyl)-1,3,5-triazin-2-amine | 5 | 4 | 6 | 107 |
| 559 | 4-(4-chlorophenyl)-N-(1-ethylpiperidin-3-yl)-6-(trichloromethyl)-1,3,5-triazin-2-amine | 17 | 9 | 17 | 100 |
| 560 | (3-{[4-(4-chlorophenyl)-6-(trichloromethyl)-1,3,5-triazin-2-yl]amino}propyl)dimethylamine | 20 | 9 | 18 | |
| 561 | 4-(4-chlorophenyl)-N-[5-(pyrrolidin-1-yl)pentyl]-6-(trichloromethyl)-1,3,5-triazin-2-amine | 39.67 | 27.84 | 38.69 | 63 |
| 562 | dimethyl(3-{[4-(trichloromethyl)-6-[3-(trifluoromethyl)phenyl]-1,3,5-triazin-2-yl]amino}propyl)amine | | | | |
| 563 | dimethyl(3-{[4-(trichloromethyl)-6-[4-(trifluoromethyl)phenyl]-1,3,5-triazin-2-yl]amino}propyl)amine | 5 | 2 | 6 | 82 |
| 564 | N-[3-(pyrrolidin-1-yl)propyl]-4-(trichloromethyl)-6-[4-(trifluoromethyl)phenyl]-1,3,5-triazin-2-amine | 24.4 | 16.25 | 22.65 | 102 |
| 565 | dimethyl(3-{[4-(trichloromethyl)-6-[4-(trichloromethyl)phenyl]-1,3,5-triazin-2-yl]amino}propyl)amine | 39 | 23 | 35 | 31 |
| 566 | dimethyl(3-{[4-(trichloromethyl)-6-[3-(trichloromethyl)phenyl]-1,3,5-triazin-2-yl]amino}propyl)amine | 408.4 | 248.5 | 381.5 | |
| 567 | diethyl(2-{[4-(trichloromethyl)-6-[3-(trichloromethyl)phenyl]-1,3,5-triazin-2-yl]amino}ethyl)amine | 182 | 60 | 165 | |
| 568 | diethyl(2-{[4-(trichloromethyl)-6-[4-(trichloromethyl)phenyl]-1,3,5-triazin-2-yl]amino}ethyl)amine | 6 | 4 | 7 | |
| 569 | N-(1-ethylpiperidin-3-yl)-4-(trichloromethyl)-6-[4-(trichloromethyl)phenyl]-1,3,5-triazin-2-amine | 11 | 5 | 12 | 25 |
| 570 | N-[3-(pyrrolidin-1-yl)propyl]-4-(trichloromethyl)-6-[4-(trichloromethyl)phenyl]-1,3,5-triazin-2-amine | | | | |
| 571 | N-[3-(pyrrolidin-1-yl)propyl]-4-(trichloromethyl)-6-[3-(trichloromethyl)phenyl]-1,3,5-triazin-2-amine | 160.4 | 88.28 | 150.4 | |
| 572 | diethyl(2-{[4-(trichloromethyl)-6-[3-(trifluoromethyl)phenyl]-1,3,5-triazin-2-yl]amino}ethyl)amine | 16 | 12 | 16 | 111 |
| 573 | [3-({4-[3,5-bis(trifluoromethyl)phenyl]-6-(trichloromethyl)-1,3,5-triazin-2-yl}amino)propyl]dimethylamine | 10 | 11 | 11 | 33 |
| 574 | N-[3-(pyrrolidin-1-yl)propyl]-4-(trichloromethyl)-6-[3-(trifluoromethyl)phenyl]-1,3,5-triazin-2-amine | 2 | 4 | 5 | 40 |
| 575 | 4-[3,5-bis(trifluoromethyl)phenyl]-N-[3-(pyrrolidin-1-yl)propyl]-6-(trichloromethyl)-1,3,5-triazin-2-amine | 21.2 | 16.86 | 24.22 | 28 |
| 576 | [2-({4-[3,5-bis(trifluoromethyl)phenyl]-6-(trichloromethyl)-1,3,5-triazin-2-yl}amino)ethyl]diethylamine | 7 | 7 | 8 | 27 |
| 577 | 4-(3,4-dichlorophenyl)-N-(1-ethylpiperidin-3-yl)-6-(trichloromethyl)-1,3,5-triazin-2-amine | 1000 | 1000 | 1000 | |
| 578 | N-(1-ethylpiperidin-3-yl)-4-(trichloromethyl)-6-[3-(trifluoromethyl)phenyl]-1,3,5-triazin-2-amine | 62.24 | 36.51 | 59.15 | 23 |
| 579 | N-(1-ethylpiperidin-3-yl)-4-(trichloromethyl)-6-[4-(trichloromethyl)phenyl]-1,3,5-triazin-2-amine | 36.94 | 35.35 | 39.71 | 41 |
| 580 | 4-[3,5-bis(trifluoromethyl)phenyl]-N-(1-ethylpiperidin-3-yl)-6-(trichloromethyl)-1,3,5-triazin-2-amine | 9 | 4 | 9 | 31 |
| 581 | (2-{[4-(3,4-dichlorophenyl)-6-(trichloromethyl)-1,3,5-triazin-2-yl]amino}ethyl)diethylamine | | | | |
| 582 | diethyl(2-{[4-(trichloromethyl)-6-[4-(trifluoromethyl)phenyl]-1,3,5-triazin-2-yl]amino}ethyl)amine | 26.1 | 11.75 | 24.91 | 54 |
| 583 | 4-(3,4-dichlorophenyl)-N-[3-(pyrrolidin-1-yl)propyl]-6-(trichloromethyl)-1,3,5-triazin-2-amine | 83.6 | 30.41 | 69.67 | 92 |
| 584 | [3-({4-[3,5-bis(trichloromethyl)phenyl]-6-(trichloromethyl)-1,3,5-triazin-2-yl}amino)propyl]dimethylamine | 781 | 558 | 877 | |
| 585 | N-[2-(1-methylpyrrolidin-2-yl)ethyl]-4-(trichloromethyl)-6-[4-(trichloromethyl)phenyl]-1,3,5-triazin-2-amine | 3 | 10 | 6 | 42 |
| 586 | dimethyl(1-{[4-(trichloromethyl)-6-[4-(trichloromethyl)phenyl]-1,3,5-triazin-2-yl]amino}propan-2-yl)amine | 10 | 6 | 14 | |
| 587 | diethyl(3-{[4-(trichloromethyl)-6-[3-(trichloromethyl)phenyl]-1,3,5-triazin-2-yl]amino}propyl)amine | 1000 | 1000 | 1000 | |
| 588 | 4-[3,5-bis(trichloromethyl)phenyl]-N-[3-(pyrrolidin-1-yl)propyl]-6-(trichloromethyl)-1,3,5-triazin-2-amine | 16 | 11 | 17 | 20 |
| 589 | N-[2-(1-methylpyrrolidin-2-yl)ethyl]-4-(trichloromethyl)-6-[3-(trichloromethyl)phenyl]-1,3,5-triazin-2-amine | 1000 | 286.1 | 1000 | |
| 590 | dimethyl(2-{[4-(trichloromethyl)-6-[3-(trichloromethyl)phenyl]-1,3,5-triazin-2-yl]amino}propyl)amine | 205.6 | 66.11 | 172.4 | |
| 591 | N-[(1-ethylpyrrolidin-3-yl)methyl]-4-(trichloromethyl)-6-[3-(trichloromethyl)phenyl]-1,3,5-triazin-2-amine | 249 | 123 | 190 | |
| 592 | N-[(1-methylpiperidin-2-yl)methyl]-4-(trichloromethyl)-6-[3-(trichloromethyl)phenyl]-1,3,5-triazin-2-amine | 37.53 | 18.45 | 27.4 | 23 |
| 593 | dimethyl(1-{[4-(trichloromethyl)-6-[3-(trichloromethyl)phenyl]-1,3,5-triazin-2-yl]amino}propan-2-yl)amine | 77 | 23 | 41 | 41 |
| 594 | ethyl 4-(4-{[(1-ethylpyrrolidin-3-yl)methyl]amino}-6-(trichloromethyl)-1,3,5-triazin-2-yl)benzoate | 61 | 40 | 85 | |
| 595 | ethyl 4-(4-{[(1-methylpiperidin-2-yl)methyl]amino}-6-(trichloromethyl)-1,3,5-triazin-2-yl)benzoate | 101 | 72 | 85 | |
| 596 | N-[(1-ethylpyrrolidin-3-yl)methyl]-4-(trichloromethyl)-6-[4-(trichloromethyl)phenyl]-1,3,5-triazin-2-amine | | | | |
| 597 | 1-N,1-N-dimethyl-4-N-[(trichloromethyl)-6-[4-(trichloromethyl)phenyl]-1,3,5-triazin-2-yl]cyclohexane-1,4-diamine | 1000 | 882 | 1000 | |
| 598 | ethyl 4-(4-{[3-(dimethylamino)propyl]amino}-6-(trichloromethyl)-1,3,5-triazin-2-yl)benzoate | 62 | 31 | 72 | |
| 599 | (2-{[4-(3,4-dichlorophenyl)-6-(trichloromethyl)-1,3,5-triazin-2-yl]amino}ethyl)diethylamine; 1,4-bis(trichloromethyl)benzene | 1000 | 1000 | 1000 | |
| 600 | 1,4-bis(trichloromethyl)benzene; diethyl(2-{[4-(trichloromethyl)-6-[4-(trifluoromethyl)phenyl]-1,3,5-triazin-2-yl]amino}ethyl)amine | 1000 | 1000 | 1000 | |
| 601 | 1,4-bis(trichloromethyl)benzene; diethyl(2-{[4-(trichloromethyl)-6-[4-(trichloromethyl)phenyl]-1,3,5-triazin-2-yl]amino}ethyl)amine | 1000 | 1000 | 1000 | |
| 602 | 1,4-bis(trichloromethyl)benzene; N-[3-(pyrrolidin-1-yl)propyl]-4-(trichloromethyl)-6-[3-(trifluoromethyl)phenyl]-1,3,5-triazin-2-amine | 1000 | 853 | 1000 | |
| 603 | diethyl(3-{[4-(trichloromethyl)-6-[3-(trichloromethyl)phenyl]-1,3,5-triazin-2-yl]amino}butyl)amine | 1000 | 1000 | 1000 | |
| 604 | (3-{[bis(trichloromethyl)-1,3,5-triazin-2-yl]amino}propyl)dimethylamine; 1,4-bis(trichloromethyl)benzene | 224 | 363 | 628 | |

TABLE 13-continued

| Cmpd | IUPAC Name | D6 | W2 | C235 | hERG |
|---|---|---|---|---|---|
| 605 | 4-(3,4-dichlorophenyl)-N-[2-(1-methylpyrrolidin-2-yl)ethyl]-6-(trichloromethyl)-1,3,5-triazin-2-amine | 7 | 5 | 5 | 22 |
| 606 | (3-{[4-(3,4-dichlorophenyl)-6-(trichloromethyl)-1,3,5-triazin-2-yl]amino}propyl)dimethylamine | 40 | 16 | 24 | 20 |
| 607 | 1,4-bis(trichloromethyl)benzene; N-[3-(pyrrolidin-1-yl)propyl]-4-(trichloromethyl)-6-[4-(trifluoromethyl)phenyl]-1,3,5-triazin-2-amine | 1000 | 1000 | 1000 | |
| 608 | 4-(3,4-dichlorophenyl)-N-[(1-methylpiperidin-2-yl)methyl]-6-(trichloromethyl)-1,3,5-triazin-2-amine | 62.54 | 20.1 | 51.73 | 44 |
| 609 | 4-(3,4-dichlorophenyl)-N-[2-(1-methylpyrrolidin-2-yl)ethyl]-6-(trichloromethyl)-1,3,5-triazin-2-amine | 264.9 | | 301.9 | |
| 610 | (2-{[4-(3,5-dichlorophenyl)-6-(trichloromethyl)-1,3,5-triazin-2-yl]amino}propyl)dimethylamine | 9 | 7 | 11 | 54 |
| 611 | (3-{[4-(3,5-dichlorophenyl)-6-(trichloromethyl)-1,3,5-triazin-2-yl]amino}propyl)dimethylamine | 8 | 4 | 5 | 48 |
| 612 | (2-{[4-(3,5-dichlorophenyl)-6-(trichloromethyl)-1,3,5-triazin-2-yl]amino}ethyl)diethylamine | 19.5 | 12 | 18 | |
| 613 | 4-(3,4-dichlorophenyl)-N-[1-(1-ethylpiperidin-4-yl)ethyl]-6-(trichloromethyl)-1,3,5-triazin-2-amine | 25 | 8 | 17 | 88 |
| 614 | 4-(3,5-dichlorophenyl)-N-(1-ethylpiperidin-3-yl)-6-(trichloromethyl)-1,3,5-triazin-2-amine | 248 | 161.7 | 275.4 | |
| 615 | diethyl(2-{[4-(4-methanesulfinylphenyl)-6-(trichloromethyl)-1,3,5-triazin-2-yl]amino}ethyl)amine | 1000 | 1000 | 1000 | |
| 616 | 4-(4-methanesulfinylphenyl)-N-[3-(pyrrolidin-1-yl)propyl]-6-(trichloromethyl)-1,3,5-triazin-2-amine | 1000 | 1000 | 1000 | |
| 617 | 1-N,1-N-diethyl-3-N-[4-(trichloromethyl)-6-[3-(trichloromethyl)phenyl]-1,3,5-triazin-2-yl]cyclohexane-1,3-diamine | 211 | 124 | 158 | |
| 618 | (3-{[4-(3,4-dichlorophenyl)-6-(trichloromethyl)-1,3,5-triazin-2-yl]amino}propyl)dimethylamine | 63.08 | 53.09 | 68.23 | 77 |
| 619 | 2-N-(3,5-dichlorophenyl)-4-N-[1-(dipropylamino)propan-2-yl]-6-(trichloromethyl)-1,3,5-triazine-2,4-diamine | 136 | 71 | 132 | |
| 620 | 1-[4-(4-methoxynaphthalen-1-yl)-6-(trichloromethyl)-1,3,5-triazin-2-yl]piperidin-4-amine | 431 | 175 | 409 | |
| 621 | 1-[4-phenyl-6-(trichloromethyl)-1,3,5-triazin-2-yl]piperidin-4-amine | 290 | 101 | 319 | |
| 622 | 1-[4-(3,4-dichlorophenyl)-6-(trichloromethyl)-1,3,5-triazin-2-yl]piperidin-4-amine | 74 | 36 | 59 | |
| 623 | 1-[4-(4-methylphenyl)-6-(trichloromethyl)-1,3,5-triazin-2-yl]piperidin-4-amine | 58 | 21 | 32 | |
| 624 | 1-[4-(4-tert-butylphenyl)-6-(trichloromethyl)-1,3,5-triazin-2-yl]piperidin-4-amine | 91 | 43 | 62 | |
| 625 | 1-[4-(trichloromethyl)-6-[3-(trifluoromethyl)phenyl]-1,3,5-triazin-2-yl]piperidin-4-amine | 47 | 12 | 20 | |
| 626 | 1-{4-[4-(methylsulfanyl)phenyl]-6-(trichloromethyl)-1,3,5-triazin-2-yl}piperidin-4-amine | 18 | 7 | 11 | |
| 627 | 1-[4-(4-methanesulfonylphenyl)-6-(trichloromethyl)-1,3,5-triazin-2-yl]piperidin-4-amine | 85 | 25 | 48 | |
| 628 | 1-[4-(naphthalen-2-yl)-6-(trichloromethyl)-1,3,5-triazin-2-yl]piperidin-4-amine | 42 | 17 | 20 | |
| 629 | 1-[4-(3-methoxyphenyl)-6-(trichloromethyl)-1,3,5-triazin-2-yl]piperidin-4-amine | 21 | 15 | 19 | |
| 630 | 1-[4-(4-chlorophenyl)-6-(trichloromethyl)-1,3,5-triazin-2-yl]piperidin-4-amine | 12 | 10 | 13 | |
| 631 | 1-[4-(3,5-dichlorophenyl)-6-(trichloromethyl)-1,3,5-triazin-2-yl]piperidin-4-amine | 291 | 153 | 219 | |
| 632 | 1-[4-(2-nitrophenyl)-6-(trichloromethyl)-1,3,5-triazin-2-yl]piperidin-4-amine | 64 | 40 | 58 | |
| 633 | 1-[4-(3-chlorophenyl)-6-(trichloromethyl)-1,3,5-triazin-2-yl]piperidin-4-amine | 10 | 8 | 10 | |
| 634 | 1-[4-(4-phenylphenyl)-6-(trichloromethyl)-1,3,5-triazin-2-yl]piperidin-4-amine | 145 | 62 | 88 | |
| 635 | 1-[4-(3,5-dimethoxyphenyl)-6-(trichloromethyl)-1,3,5-triazin-2-yl]piperidin-4-amine | 259 | 135 | 218 | |
| 636 | 2-N-(4-chlorophenyl)-4-N-[3-(dimethylamino)propyl]-6-(trichloromethyl)-1,3,5-triazine-2,4-diamine | 16 | 18 | 40 | |
| 637 | 2-N-(3,4-dichlorophenyl)-4-N-[3-(dimethylamino)propyl]-6-(trichloromethyl)-1,3,5-triazine-2,4-diamine | 17 | 13 | 20 | 103 |
| 638 | 2-N-(3,5-dichlorophenyl)-4-N-(1-ethylpiperidin-3-yl)-6-(trichloromethyl)-1,3,5-triazine-2,4-diamine | 5 | 5 | 5 | 49 |
| 639 | 2-N-(3,5-dichlorophenyl)-4-N-[1-(dimethylamino)propan-2-yl]-6-(trichloromethyl)-1,3,5-triazine-2,4-diamine | 13 | 7 | 9 | 25 |
| 640 | 2-N-(3,4-dichlorophenyl)-4-N-[1-(dimethylamino)propan-2-yl]-6-(trichloromethyl)-1,3,5-triazine-2,4-diamine | 8 | 8 | 10 | 23 |
| 641 | 2-N-(3,4-dichlorophenyl)-4-N-[2-(dimethylamino)propyl]-6-(trichloromethyl)-1,3,5-triazine-2,4-diamine | 15 | 5 | 13 | 117 |
| 642 | 2-N-(3,4-dichlorophenyl)-4-N-[1-(diethylamino)propan-2-yl]-6-(trichloromethyl)-1,3,5-triazine-2,4-diamine | 5 | 3 | 13 | 76 |
| 643 | 2-N-(3,4-dichlorophenyl)-4-N-[1-(1-ethylpiperidin-4-yl)ethyl]-6-(trichloromethyl)-1,3,5-triazine-2,4-diamine | 47 | 33 | 48 | 100 |
| 644 | 2-N-(3,5-dichlorophenyl)-4-N-[1-(diethylamino)propan-2-yl]-6-(trichloromethyl)-1,3,5-triazine-2,4-diamine | 131 | 9 | 14 | 100 |
| 645 | 2-N-(3,5-dichlorophenyl)-4-N-[1-(1-ethylpiperidin-4-yl)ethyl]-6-(trichloromethyl)-1,3,5-triazine-2,4-diamine | 79.11 | 37.5 | 58.86 | 75 |
| 646 | 2-N-(3,4-dichlorophenyl)-4-N-[5-(diethylamino)pentan-2-yl]-6-(trichloromethyl)-1,3,5-triazine-2,4-diamine | 672.7 | 735.4 | 1000 | |
| 647 | 2-{[4-(trichloromethyl)-6-[3-(trifluoromethyl)phenyl]-1,3,5-triazin-2-yl]amino}ethan-1-ol | 35 | 23 | 39 | 100 |
| 648 | 4-(4-methanesulfonylphenyl)-N-[4-(4-methylpiperazin-1-yl)phenyl]-6-(trichloromethyl)-1,3,5-triazin-2-amine | 30 | 18 | 33 | 13 |
| 649 | N-[3-(azepan-1-yl)-2,2-dimethylpropyl]-4-(4-methanesulfonylphenyl)-6-(trichloromethyl)-1,3,5-triazin-2-amine | 338 | 196 | 609 | 72 |
| 650 | 4-(4-methanesulfonylphenyl)-N-(pyridin-4-ylmethyl)-6-(trichloromethyl)-1,3,5-triazin-2-amine | 1000 | 803 | 1000 | |
| 651 | 4-(4-methanesulfonylphenyl)-N-(2-methoxypyridin-3-yl)-6-(trichloromethyl)-1,3,5-triazin-2-amine | 760 | 577 | 1000 | |
| 652 | N-(pyridin-4-ylmethyl)-4-(trichloromethyl)-6-[4-(trichloromethyl)phenyl]-1,3,5-triazin-2-amine | 385 | 301 | 876 | |
| 653 | N-methyl-N-{[2-(pyridin-3-yl)phenyl]methyl}-4-(trichloromethyl)-6-[4-(trichloromethyl)phenyl]-1,3,5-triazin-2-amine | 1000 | 272.1 | 1000 | |
| 654 | 4-(4-methanesulfonylphenyl)-N-(pyridin-3-yl)-6-(trichloromethyl)-1,3,5-triazin-2-amine | 198 | 185 | 271 | |
| 655 | 2-N-(1-ethylpiperidin-3-yl)-6-(trichloromethyl)-4-N-[4-(trifluoromethoxy)phenyl]-1,3,5-triazine-2,4-diamine | 19 | 11 | 28 | |
| 656 | 2-N-[2-(pyrrolidin-1-yl)ethyl]-6-(trichloromethyl)-4-N-[4-(trifluoromethoxy)phenyl]-1,3,5-triazine-2,4-diamine | 3 | 2 | 7 | |
| 657 | 2-N-[3-(pyrrolidin-1-yl)propyl]-6-(trichloromethyl)-4-N-[4-(trifluoromethoxy)phenyl]-1,3,5-triazine-2,4-diamine | 535 | 390 | 731 | |
| 658 | 4-(4-methyl-1,4-diazepan-1-yl)-6-(trichloromethyl)-N-[4-(trifluoromethoxy)phenyl]-1,3,5-triazin-2-amine | 701 | 625 | 875 | |
| 659 | 4-(1,4-diazepan-1-yl)-6-(trichloromethyl)-N-[4-(trifluoromethoxy)phenyl]-1,3,5-triazin-2-amine | 19 | 18 | 38 | 58 |
| 660 | N-[(1-aminocyclohexyl)methyl]-4-(4-methylphenyl)-6-(trichloromethyl)-1,3,5-triazin-2-amine | 8 | 9 | 17 | |
| 661 | N-[(1-aminocyclohexyl)methyl]-4-(3-methoxyphenyl)-6-(trichloromethyl)-1,3,5-triazin-2-amine | 3 | 2 | 8 | 32 |

TABLE 13-continued

| Cmpd | IUPAC Name | D6 | W2 | C235 | hERG |
|---|---|---|---|---|---|
| 662 | N-[(1-aminocyclohexyl)methyl]-4-(4-tert-butylphenyl)-6-(trichloromethyl)-1,3,5-triazin-2-amine | 1000 | 1000 | 1000 | |
| 663 | N-[(1-aminocyclohexyl)methyl]-4-(trichloromethyl)-6-[3-(trifluoromethyl)phenyl]-1,3,5-triazin-2-amine | 729 | 583 | 1000 | |
| 664 | N-[(1-aminocyclohexyl)methyl]-4-[4-(methylsulfanyl)phenyl]-6-(trichloromethyl)-1,3,5-triazin-2-amine | 18 | 21 | 47 | |
| 665 | N-[(1-aminocyclohexyl)methyl]-4-(4-methanesulfonylphenyl)-6-(trichloromethyl)-1,3,5-triazin-2-amine | 76 | 76 | 147 | |
| 666 | N-[(1-aminocyclohexyl)methyl]-4-(trichloromethyl)-6-[4-(trichloromethyl)phenyl]-1,3,5-triazin-2-amine | 3 | 2 | 5 | |
| 667 | N-[(1-aminocyclohexyl)methyl]-4-(naphthalen-2-yl)-6-(trichloromethyl)-1,3,5-triazin-2-amine | 1000 | 1000 | 1000 | |
| 668 | N-[(1-aminocyclohexyl)methyl]-4-(4-methoxynaphthalen-1-yl)-6-(trichloromethyl)-1,3,5-triazin-2-amine | 1000 | 1000 | 1000 | |
| 669 | N-[(1-aminocyclohexyl)methyl]-4-(3,4-dimethoxyphenyl)-6-(trichloromethyl)-1,3,5-triazin-2-amine | 12 | 10 | 23 | |
| 670 | N-[(1-aminocyclohexyl)methyl]-4-(3,4-dichlorophenyl)-6-(trichloromethyl)-1,3,5-triazin-2-amine | 22 | 20 | 38 | |
| 671 | N-[(1-aminocyclopentyl)methyl]-4-(trichloromethyl)-6-[4-(trichloromethyl)phenyl]-1,3,5-triazin-2-amine | 1000 | 1000 | 1000 | |
| 672 | N-[(1-aminocyclopentyl)methyl]-4-(4-phenylphenyl)-6-(trichloromethyl)-1,3,5-triazin-2-amine | 46 | 30 | 68 | 33 |
| 673 | N-[(1-aminocyclopentyl)methyl]-4-(4-methoxynaphthalen-1-yl)-6-(trichloromethyl)-1,3,5-triazin-2-amine | 1000 | 1000 | 1000 | |
| 674 | N-[(1-aminocyclopentyl)methyl]-4-(3,4-dimethoxyphenyl)-6-(trichloromethyl)-1,3,5-triazin-2-amine | 8 | 6 | 18 | |
| 675 | N-[(1-aminocyclopentyl)methyl]-4-(3-methoxyphenyl)-6-(trichloromethyl)-1,3,5-triazin-2-amine | 1000 | 1000 | 1000 | |
| 676 | 2-N-(1-methylpiperidin-4-yl)-6-(trichloromethyl)-4-N-[4-(trifluoromethoxy)phenyl]-1,3,5-triazine-2,4-diamine | 1000 | 1000 | 1000 | |
| 677 | N-[(1-aminocyclopropyl)methyl]-4-phenyl-6-(trichloromethyl)-1,3,5-triazin-2-amine | 1000 | 527 | 910 | |
| 678 | N-[(1-aminocyclopropyl)methyl]-4-(4-chlorophenyl)-6-(trichloromethyl)-1,3,5-triazin-2-amine | 11 | 12 | 20 | |
| 679 | N-[(1-aminocyclopropyl)methyl]-4-(trichloromethyl)-6-[4-(trichloromethyl)phenyl]-1,3,5-triazin-2-amine | 606 | 201 | 1000 | |
| 680 | N-[(1-aminocyclopropyl)methyl]-4-(3-chlorophenyl)-6-(trichloromethyl)-1,3,5-triazin-2-amine | 100 | 35 | 98 | |
| 681 | N-[(1-aminocyclopropyl)methyl]-4-(4-methylphenyl)-6-(trichloromethyl)-1,3,5-triazin-2-amine | 593 | 328 | 750 | |
| 682 | N-[(1-aminocyclopropyl)methyl]-4-(trichloromethyl)-6-[3-(trifluoromethyl)phenyl]-1,3,5-triazin-2-amine | 68 | 31 | 82 | |
| 683 | N-[(1-aminocyclopropyl)methyl]-4-(3,5-dichlorophenyl)-6-(trichloromethyl)-1,3,5-triazin-2-amine | 727 | 503 | 795 | |
| 684 | N-[1-(2-methylpropyl)piperidin-4-yl]-4-(2-nitrophenyl)-6-(trichloromethyl)-1,3,5-triazin-2-amine | 225 | 66 | 155 | |
| 685 | N-[(1-aminocyclohexyl)methyl]-4-(3,5-dimethoxyphenyl)-6-(trichloromethyl)-1,3,5-triazin-2-amine | | | | |
| 686 | 2-N-(naphthalen-2-yl)-4-N-[2-(pyrrolidin-1-yl)ethyl]-6-(trichloromethyl)-1,3,5-triazine-2,4-diamine | | | | |
| 687 | tert-butyl 2-{[4-(4-chlorophenyl)-6-(trichloromethyl)-1,3,5-triazin-2-yl](methyl)amino}acetate | 501 | 501 | 501 | |
| 688 | 1-[4-(trichloromethyl)-6-[4-(trichloromethyl)phenyl]-1,3,5-triazin-2-yl]piperidine-4-carboxamide | 1000 | 1000 | 1000 | |
| 689 | 4-(4-methanesulfonylphenyl)-N-[4-(1H-pyrazol-1-yl)phenyl]-6-(trichloromethyl)-1,3,5-triazin-2-amine | 94 | 58 | 171 | |
| 690 | 1-[4-(4-methanesulfonylphenyl)-6-(trichloromethyl)-1,3,5-triazin-2-yl]piperidine-4-carboxamide | 1000 | 670 | 1000 | |
| 691 | N-(3-{[4-(4-methanesulfonylphenyl)-6-(trichloromethyl)-1,3,5-triazin-2-yl]amino}phenyl)acetamide | 341 | 256 | 705 | |
| 692 | 4-(3,4-dichlorophenyl)-N-[1-(2-methylpropyl)piperidin-4-yl]-6-(trichloromethyl)-1,3,5-triazin-2-amine | 32 | 24 | 43 | |
| 693 | 4-(4-chlorophenyl)-N-[1-(2-methylpropyl)piperidin-4-yl]-6-(trichloromethyl)-1,3,5-triazin-2-amine | 37 | 29 | 69 | |
| 694 | 4-(4-tert-butylphenyl)-N-[1-(2-methylpropyl)piperidin-4-yl]-6-(trichloromethyl)-1,3,5-triazin-2-amine | 24 | 23 | 37 | |
| 695 | N-[1-(2-methylpropyl)piperidin-4-yl]-4-[4-(methylsulfanyl)phenyl]-6-(trichloromethyl)-1,3,5-triazin-2-amine | 582 | 418 | 675 | |
| 696 | 4-(4-methoxyphenyl)-N-[1-(2-methylpropyl)piperidin-4-yl]-6-(trichloromethyl)-1,3,5-triazin-2-amine | 1000 | 1000 | 1000 | |
| 697 | N-[1-(2-methylpropyl)piperidin-4-yl]-4-(trichloromethyl)-6-[4-(trichloromethyl)phenyl]-1,3,5-triazin-2-amine | 1000 | 1000 | 1000 | |
| 698 | N-[1-(2-methylpropyl)piperidin-4-yl]-4-(naphthalen-2-yl)-6-(trichloromethyl)-1,3,5-triazin-2-amine | 1000 | 1000 | 1000 | |
| 699 | N-[1-(2-methylpropyl)piperidin-4-yl]-4-(4-phenylphenyl)-6-(trichloromethyl)-1,3,5-triazin-2-amine | 564 | 430 | 746 | |
| 700 | N-[1-(2-methylpropyl)piperidin-4-yl]-4-(trichloromethyl)-6-[3-(trifluoromethyl)phenyl]-1,3,5-triazin-2-amine | 513 | 368 | 567 | |
| 701 | 4-(3-chlorophenyl)-N-[1-(2-methylpropyl)piperidin-4-yl]-6-(trichloromethyl)-1,3,5-triazin-2-amine | 282 | 195 | 351 | |
| 702 | 4-(3,4-dimethoxyphenyl)-N-[1-(2-methylpropyl)piperidin-4-yl]-6-(trichloromethyl)-1,3,5-triazin-2-amine | 435 | 179 | 480 | |
| 703 | 4-(4-methoxynaphthalen-1-yl)-N-[1-(2-methylpropyl)piperidin-4-yl]-6-(trichloromethyl)-1,3,5-triazin-2-amine | 324 | 237 | 338 | |
| 704 | N-[1-(2-methylpropyl)piperidin-4-yl]-4-phenyl-6-(trichloromethyl)-1,3,5-triazin-2-amine | 867 | 223 | 525 | |
| 705 | tert-butyl 5-[4-(3,4-dichlorophenyl)-6-(trichloromethyl)-1,3,5-triazin-2-yl]-2,5-diazabicyclo[2.2.1]heptane-2-carboxylate | 1000 | 851.8 | 1000 | |
| 706 | tert-butyl 5-[4-(4-methoxyphenyl)-6-(trichloromethyl)-1,3,5-triazin-2-yl]-2,5-diazabicyclo[2.2.1]heptane-2-carboxylate | 1000 | 1000 | 1000 | |
| 707 | tert-butyl 5-[4-(trichloromethyl)-6-[3-(trifluoromethyl)phenyl]-1,3,5-triazin-2-yl]-2,5-diazabicyclo[2.2.1]heptane-2-carboxylate | 1000 | 1000 | 1000 | |
| 708 | 4-(3,4-dichlorophenyl)-N-[(1,3-dimethyl-1H-pyrazol-5-yl)methyl]-6-(trichloromethyl)-1,3,5-triazin-2-amine | 319.7 | 75.2 | 221 | 12.2 |
| 709 | N-(3,4-dichlorophenyl)-4-(morpholin-4-yl)-6-(trichloromethyl)-1,3,5-triazin-2-amine | 1000 | 1000 | 1000 | 6.4 |
| 710 | tert-butyl 5-{4-[4-(methylsulfanyl)phenyl]-6-(trichloromethyl)-1,3,5-triazin-2-yl}-2,5-diazabicyclo[2.2.1]heptane-2-carboxylate | 145 | 281 | 571 | |
| 711 | tert-butyl 5-[4-(4-methylphenyl)-6-(trichloromethyl)-1,3,5-triazin-2-yl]-2,5-diazabicyclo[2.2.1]heptane-2-carboxylate | 812 | 1000 | 1000 | |
| 712 | tert-butyl 5-[4-(4-tert-butylphenyl)-6-(trichloromethyl)-1,3,5-triazin-2-yl]-2,5-diazabicyclo[2.2.1]heptane-2-carboxylate | 1000 | 1000 | 1000 | |
| 713 | tert-butyl 5-[4-(trichloromethyl)-6-[4-(trichloromethyl)phenyl]-1,3,5-triazin-2-yl]-2,5-diazabicyclo[2.2.1]heptane-2-carboxylate | | | | |

TABLE 13-continued

| Cmpd | IUPAC Name | D6 | W2 | C235 | hERG |
|---|---|---|---|---|---|
| 714 | tert-butyl 5-[4-phenyl-6-(trichloromethyl)-1,3,5-triazin-2-yl]-2,5-diazabicyclo[2.2.1]heptane-2-carboxylate | | | | |
| 715 | tert-butyl 5-[4-(4-methanesulfonylphenyl)-6-(trichloromethyl)-1,3,5-triazin-2-yl]-2,5-diazabicyclo[2.2.1]heptane-2-carboxylate | 126 | 63 | 185 | 19 |
| 716 | 2-[4-(3,4-dichlorophenyl)-6-(trichloromethyl)-1,3,5-triazin-2-yl]-2,5-diazabicyclo[2.2.1]heptane | 540.4 | 335.2 | 439.4 | |
| 717 | 2-[4-(4-chlorophenyl)-6-(trichloromethyl)-1,3,5-triazin-2-yl]-2,5-diazabicyclo[2.2.1]heptane | 259 | 163 | 264 | |
| 718 | 2-[4-(4-methoxyphenyl)-6-(trichloromethyl)-1,3,5-triazin-2-yl]-2,5-diazabicyclo[2.2.1]heptane | 278.6 | 77.35 | 139.2 | 23.5 |
| 719 | 2-[4-(4-methylphenyl)-6-(trichloromethyl)-1,3,5-triazin-2-yl]-2,5-diazabicyclo[2.2.1]heptane | 96 | 68 | 114 | 10 |
| 720 | 2-[4-phenyl-6-(trichloromethyl)-1,3,5-triazin-2-yl]-2,5-diazabicyclo[2.2.1]heptane | 56 | 35 | 89 | 84 |
| 721 | 2-[4-(4-tert-butylphenyl)-6-(trichloromethyl)-1,3,5-triazin-2-yl]-2,5-diazabicyclo[2.2.1]heptane | 142 | 69 | 126 | 2 |
| 722 | 2-[4-(trichloromethyl)-6-[4-(trichloromethyl)phenyl]-1,3,5-triazin-2-yl]-2,5-diazabicyclo[2.2.1]heptane | 9 | 5 | 12 | 14 |
| 723 | 2-{4-[4-(methylsulfanyl)phenyl]-6-(trichloromethyl)-1,3,5-triazin-2-yl}-2,5-diazabicyclo[2.2.1]heptane | 128 | 92 | 118 | |
| 724 | 2-[4-(4-methanesulfonylphenyl)-6-(trichloromethyl)-1,3,5-triazin-2-yl]-2,5-diazabicyclo[2.2.1]heptane | 106 | 71 | 110 | 70 |
| 725 | 4-{2,5-diazabicyclo[2.2.1]heptan-2-yl}-6-(trichloromethyl)-N-[4-(trifluoromethoxy)phenyl]-1,3,5-triazin-2-amine | 64 | 53 | 93 | |
| 726 | 2-{4-[4-(pyrrolidin-1-yl)phenyl]-6-(trichloromethyl)-1,3,5-triazin-2-yl}-2,5-diazabicyclo[2.2.1]heptane | 1000 | 1000 | 1000 | |
| 727 | N-(3-{[bis(trichloromethyl)-1,3,5-triazin-2-yl]amino}phenyl)acetamide | 256 | 131 | 319 | |
| 728 | 2-N-[4-(1H-pyrazol-1-yl)phenyl]-4-N-[3-(pyrrolidin-1-yl)propyl]-6-(trichloromethyl)-1,3,5-triazine-2,4-diamine | 77 | 27 | 79 | 116 |
| 729 | N-[2-(morpholin-4-yl)phenyl]-4,6-bis(trichloromethyl)-1,3,5-triazin-2-amine | 1000 | 1000 | 1000 | |
| 730 | N-(2-methoxyphenyl)-4,6-bis(trichloromethyl)-1,3,5-triazin-2-amine | 1000 | 1000 | 1000 | |
| 731 | N-[4-(4-methylpiperazin-1-yl)phenyl]-4,6-bis(trichloromethyl)-1,3,5-triazin-2-amine | 229 | 165 | 263 | |
| 732 | N-[4-(1H-pyrazol-1-yl)phenyl]-4,6-bis(trichloromethyl)-1,3,5-triazin-2-amine | 386 | 160 | 584 | |
| 733 | 2-N-[4-(4-methylpiperazin-1-yl)phenyl]-4-N-[2-(pyrrolidin-1-yl)ethyl]-6-(trichloromethyl)-1,3,5-triazine-2,4-diamine | 117 | 36 | 87 | 55 |
| 734 | 2-(4-tert-butylphenyl)-4-(morpholin-4-yl)-6-(trichloromethyl)-1,3,5-triazine | 1000 | 834 | 1000 | |
| 735 | 4-(4-tert-butylphenyl)-N-{[3-(pyrrolidin-1-ylmethyl)phenyl]methyl}-6-(trichloromethyl)-1,3,5-triazin-2-amine | 207.4 | 60.65 | 257.5 | |
| 736 | 4-(4-tert-butylphenyl)-N-methyl-N-[2-(pyridin-2-yl)ethyl]-6-(trichloromethyl)-1,3,5-triazin-2-amine | 1000 | 445.4 | 1000 | |
| 737 | N-[3-(azepan-1-yl)-2,2-dimethylpropyl]-4-(4-tert-butylphenyl)-6-(trichloromethyl)-1,3,5-triazin-2-amine | 241.3 | 101.3 | 244.2 | |
| 738 | 2-{4-[4-(4-tert-butylphenyl)-6-(trichloromethyl)-1,3,5-triazin-2-yl]-1,4-diazepan-1-yl}ethan-1-ol | 1000 | 60.48 | 239.9 | |
| 739 | 4-(4-tert-butylphenyl)-N-(pyridin-4-yl)-6-(trichloromethyl)-1,3,5-triazin-2-amine | 23 | 24 | 25 | 26 |
| 740 | 1-N-[4-(3,4-dichlorophenyl)-6-(trichloromethyl)-1,3,5-triazin-2-yl]cyclohexane-1,2-diamine | 38 | 11 | 23 | |
| 741 | 2-N-phenyl-4-N-(2,2,6,6-tetramethylpiperidin-4-yl)-6-(trichloromethyl)-1,3,5-triazine-2,4-diamine | | | | |
| 742 | 2-N-(1-methylpiperidin-4-yl)-4-N-(naphthalen-2-yl)-6-(trichloromethyl)-1,3,5-triazine-2,4-diamine | | | | |
| 743 | 1-[4-(trichloromethyl)-6-[4-(trichloromethyl)phenyl]-1,3,5-triazin-2-yl]piperidin-4-amine | 22 | 16 | 14 | 15 |
| 744 | N-(pyridin-4-yl)-4-[4-(pyrrolidin-1-yl)phenyl]-6-(trichloromethyl)-1,3,5-triazin-2-amine | 190 | 188 | 290 | |
| 745 | 4-[(4-{[2-(pyrrolidin-1-yl)ethyl]amino}-6-(trichloromethyl)-1,3,5-triazin-2-yl)amino]phenol | 144 | 80 | 389 | |
| Ex 1 | (1-{[4-(3,4-dichlorophenyl)-6-(trichloromethyl)-1,3,5-triazin-2-yl]amino}propan-2-yl)dimethylamine | 41.56 | 29.43 | 36.75 | 95 |
| Ex 2 | 1-[4-(4-fluorophenyl)-6-(trichloromethyl)-1,3,5-triazin-2-yl]piperidin-4-amine | 137 | 78 | 150 | |
| Ex 3 | 1-{4-[4-(3,4-dichlorophenyl)-6-(trichloromethyl)-1,3,5-triazin-2-yl]piperazin-1-yl}ethan-1-one | 687 | 198.4 | 535.2 | 16.6 |
| Ex 4 | 4-(4-methanesulfonylphenyl)-N-methyl-N-[2-(pyridin-2-yl)ethyl]-6-(trichloromethyl)-1,3,5-triazin-2-amine | 688 | 432 | 1000 | 47 |
| Ex 5 | 4-(3-methoxyphenyl)-N-[1-(2-methylpropyl)piperidin-4-yl]-6-(trichloromethyl)-1,3,5-triazin-2-amine | 190 | 110 | 359 | |
| Ex 6 | tert-butyl 5-[4-(4-chlorophenyl)-6-(trichloromethyl)-1,3,5-triazin-2-yl]-2,5-diazabicyclo[2.2.1]heptane-2-carboxylate | 1000 | 1000 | 1000 | |
| Ex 7 | 2-[4-(trichloromethyl)-6-[3-(trifluoromethyl)phenyl]-1,3,5-triazin-2-yl]-2,5-diazabicyclo[2.2.1]heptane | 106 | 126 | 192 | 29 |
| Ex 8 | 2-N-[2-(morpholin-4-yl)phenyl]-4-N-[3-(pyrrolidin-1-yl)propyl]-6-(trichloromethyl)-1,3,5-triazine-2,4-diamine | 205 | 113 | 160 | |
| Ex 9 | N-(pyridin-4-yl)-4-(trichloromethyl)-6-[4-(trichloromethyl)phenyl]-1,3,5-triazin-2-amine | 7 | 5 | 11 | 5 |
| Ex 10 | 3-(4-{[3-(dimethylamino)propyl]amino}-6-(trichloromethyl)-1,3,5-triazin-2-yl)benzoic acid | | | | |
| Ex 11 | 4-(4-{[(1-ethylpiperidin-4-yl)methyl]amino}-6-(trichloromethyl)-1,3,5-triazin-2-yl)benzoic acid | 1000 | 1000 | 1000 | 15 |
| Ex 12 | 2-{[4-(4-chlorophenyl)-6-(trichloromethyl)-1,3,5-triazin-2-yl](methyl)amino}acetic acid | 5 | 11 | 4 | 39 |
| Ex 13 | 4-({4-[(pyridin-2-ylmethyl)amino]-6-(trichloromethyl)-1,3,5-triazin-2-yl}amino)phenol | 1000 | 1000 | 1000 | |
| Ex 14 | 4-(3-aminophenyl)-N-[2-(pyrrolidin-1-yl)ethyl]-6-(trichloromethyl)-1,3,5-triazin-2-amine | 1000 | 1000 | 1000 | |
| Ex 15 | ethyl 3-(2-nitrophenyl)-2-phenylprop-2-enoate | 69 | 51 | 73 | |
| Ex 16 | 1-((4-((3,4-dichlorophenyl)amino)-6-(trichloromethyl)-1,3,5-triazin-2-yl)amino)-N,N-dimethylpropan-2-amine oxide | | | | |

TABLE 14

| Cmpd | In vivo Results Thompson Assay | Rhesus Results |
|---|---|---|
| 18 | (80 × 3) 3/5 Cures | |
| 46 | (160 × 3) Suppressive | |
| 52 | (80 × 3) Suppressive | |
| 55 | (40 × 3) 3/5 Cures; (80 × 3) 5/5 Cures | Rhesus: (65 mg/kg once weekly, malaria prophylaxis); (65 mg/kg/day × 7 days, malaria cures) |

TABLE 14-continued

| Cmpd | In vivo Results Thompson Assay | Rhesus Results |
|---|---|---|
| 57 | (80 × 3) Suppressive; (160 × 3) 5/5 Cures | |
| 62 | (80 × 3) 2/5 Cures | Rhesus: (65 mg/kg once weekly, malaria prophylaxis); (65 mg/kg/day × 7 days, malaria cures) |
| 72 | (80 × 3) Suppressive | |
| 79 | (80 × 3) Suppressive | |
| 96 | (80 × 3) Suppressive | |
| 97 | (80 × 3) Suppressive; (160 × 3) Suppressive | |
| 99 | (80 × 3) Suppressive | |
| 102 | (80 × 3) Suppressive | |
| 103 | (80 × 3) 1/5 Cures (160 × 3) 5/5 Cures | |
| 108 | (80 × 3) Suppressive | |
| 113 | (80 × 3) Suppressive; (160 × 3) 4/5 Cures | |
| 117 | (80 × 3) Suppressive | |
| 119 | (80 × 3) 4/5 Cures; (40 × 3) 1/5 Cures; | |
| 127 | (80 × 3) 1/5 Cures | |
| 166 | (80 × 3) Suppressive | |
| 193 | (80 × 3) Suppressive | |
| 195 | (40 × 3) 2/5 Cures; (80 × 3) 5/5 Cures; (160 × 3) 5/5 Cures | |
| 214 | (80 × 3) 5/5 Cures; (40 × 3) 2/5 Cures | |
| 227 | (80 × 3) 2/5 Cures | |
| 228 | (80 × 3) 4/5 Cures; (40 × 3) Suppressive | |
| 229 | (80 × 3) 3/5 Cures | |
| 234 | (80 × 3) 4/5 Cures; (40 × 3) Suppressive | |
| 235 | (80 × 3) Suppressive | |
| 274 | (80 × 3) Suppressive | |
| 312 | (80 × 3) 3/3 Cures; (40 × 3) Suppressive | |
| 313 | (80 × 3) 1/5 Cures | |
| 314 | (80 × 3) Suppressive | |
| 320 | (80 × 3) 4/4 Cures; (40 × 3) 1/5 Cures | |
| 322 | (80 × 3) 4/5 Cures; (40 × 3) 4/5 Cures | |
| 328 | (80 × 3) 2/5 Cures | |
| 365 | (80 × 3) Suppressive | |
| 376 | (80 × 3) Suppressive | |
| 380 | (80 × 3) 1/5 Cures | |
| 559 | (160 × 3) 5/5 Cures | |
| 565 | (80 × 3) 5/5 Cures | |
| 569 | (80 × 3) Suppressive | |
| 585 | (160 mpk) 1/5 Cures | |
| 613 | (80 × 3) 4/5 Cures | |
| 638 | (80 × 3) Suppressive | |
| 641 | (80 × 3) 5/5 Cures (160 × 1) 5/5 Cures; (40 × 3) 2/5 Cures | Rhesus: (65 mg/kg once weekly, malaria prophylaxis); (65 mg/kg/day × 7 days, malaria cures) |
| 643 | (80 × 3) 2/5 Cures | |
| 648 | (80 × 3) Suppressive | |
| 659 | (80 × 3) 4/5 Cures | |
| 661 | (80 × 3) Suppressive | |
| 666 | (80 × 3) 2/4 Cures | |
| 672 | (80 × 3) 4/4 Cures | |
| 694 | (80 × 3) Suppressive | |
| 719 | (80 × 3) Suppressive; (160 × 3) Suppressive | |
| 721 | (80 × 3) 2/5 Cures | Rhesus: (65 mg/kg once weekly, malaria prophylaxis); (65 mg/kg/day × 7 days, malaria cures) |
| 722 | (80 × 3) Suppressive; (160 × 3) 5/5 Cures | |
| 724 | (80 × 3) Suppressive | |
| 728 | (80 × 3) Suppressive | |
| 743 | (80 × 3) 3/5 Cures; (40 × 3) Suppressive | |
| Ex.7 | (80 × 3) Suppressive; (160 × 3) 4/5 Cures | |

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A compound of formula I

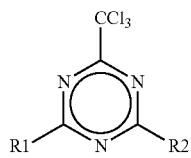

wherein
R1 is

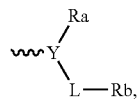

wherein Y is N;
R2 is a nitrogen attached 5-8 membered monocyclic ring or a nitrogen attached 7-8 membered bicyclo ring system, and further having 0-2 ring heteroatoms each independently selected from the group consisting of nitrogen, oxygen, and sulfur, wherein each substitutable ring carbon is independently substituted by -Rc, or R2 is

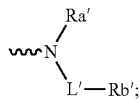

and
wherein:
L and L' are each independently a linker selected from the group consisting of a bond, a substituted or unsubstituted —(C$_1$-C$_6$)alkyl- which may be branched or unbranched, and

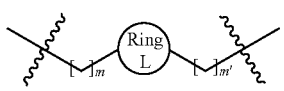

wherein Ring L is a 5-7 membered cyclic or aromatic ring and m and m' are independently 0-3;
Ra and Ra' are each independently H or branched or unbranched —(C$_1$-C$_6$)alkyl;

Rb is naphthyl or a 3-7 membered ring having 0-2 ring heteroatoms each independently selected from the group consisting of nitrogen, oxygen, and sulfur, wherein each substitutable ring carbon is independently substituted by -Rc;

Rb' is —CO$_2$R, branched or unbranched —(C$_1$-C$_6$)alkyl, branched or unbranched —(C$_2$-C$_8$)alkyl substituted with an —OR, —NRR', or —N(O)RR' group on one of the C2-C8 carbons, naphthyl, or a 3-7 membered ring having 0-2 ring heteroatoms each independently selected from the group consisting of nitrogen, oxygen, and sulfur, wherein each substitutable ring carbon is independently substituted by -Rc;

Rc and Rc' are each independently selected from the group consisting of H, halo, trihalomethyl, trihalomethoxy, branched or unbranched —(C$_1$-C$_6$)alkyl, phenyl, branched or unbranched —(C$_1$-C$_6$)alkyl-OR, —C(=O)R, —CO$_2$R, —S(O)$_2$R, —OR, —NO$_2$, —CN, —NH$_2$, —NRR', —NHC(=O)R, —NHC(OR) =O, —C(O)NRR', —S(O)$_n$R, and —SO$_2$NRR' (wherein NRR' can form a 4 to 6 member ring), wherein n is 0, 1, or 2; and R and R' are each independently H, branched or unbranched —(C$_1$-C$_6$)alkyl, branched or unbranched —(C$_1$-C$_6$)alkyl alcohol, or —CO$_2$ —(C$_1$-C$_6$)alkyl;

wherein where nitrogen is present as a heteroatom, it is at least 2 carbon atoms from any nitrogen atom attached to the triazine ring, and wherein the ring carbons next to a ring nitrogen are not substituted with —OR, —NO$_2$, —NH$_2$, —NRR', —NHC(O)R, —NHC(O)OR, —S(O)$_n$R, or —SO$_2$NRR';

or a pharmaceutically acceptable salt thereof.

2. The compound according to claim 1, wherein Rb is selected from the group consisting of

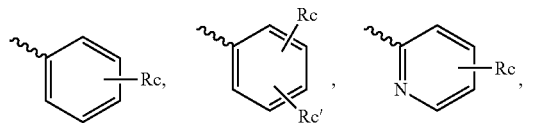

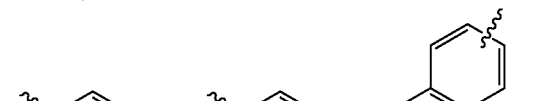

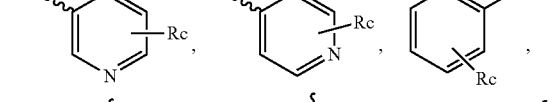

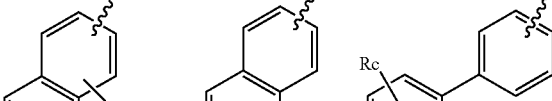

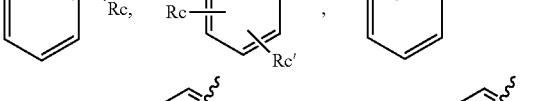

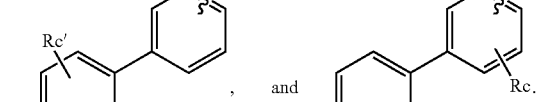

3. The compound according to claim 1, wherein R2 is selected from the group consisting of

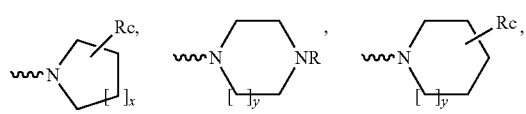

—NCH₂C(NH₂)RR',

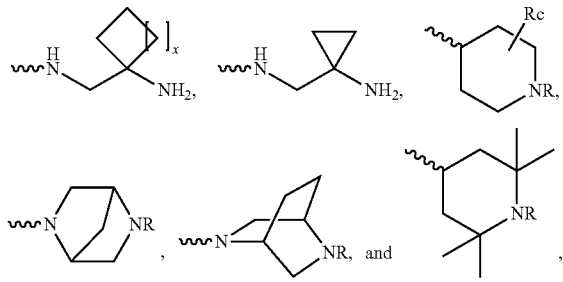

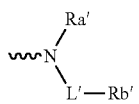

wherein x is 1-3 and y is 1-2.

4. The compound according to claim 1, wherein R2 is

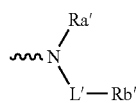

where Rb' is selected from the group consisting of an amine group, —C(NH₂)RR', —CH₂C(NH₂)RR',

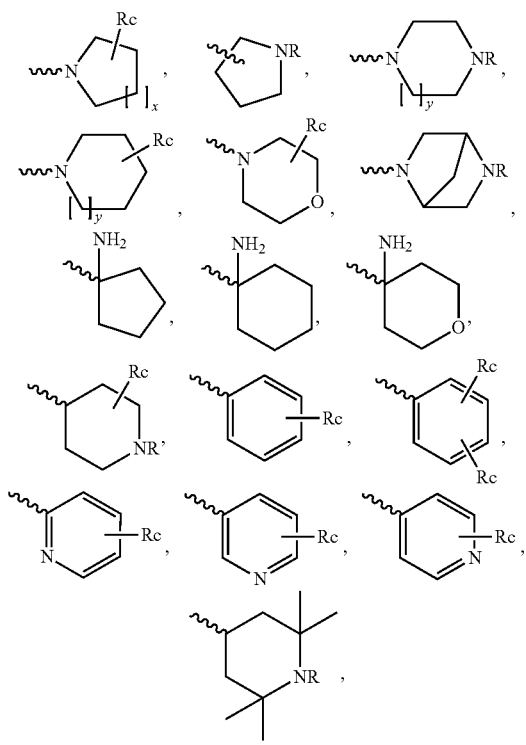

wherein x is 1-3 and y is 1-2.

5. The compound according to claim 1, wherein R2 is

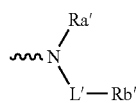

where Rb' is

6. The compound according to claim 1, wherein R2 is

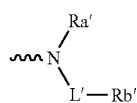

where Rb' is

7. The compound according to claim 1, wherein Rb is selected from the group consisting of

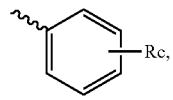

and

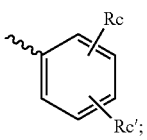

R2 is

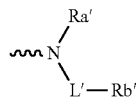

and Rb' is selected from the group consisting of an amine group, —CH₂C(NH₂)RR',

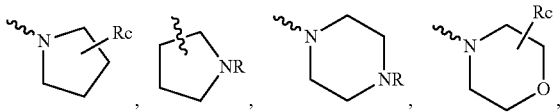

8. The compound according to claim 1, wherein Rb is selected from the group consisting of

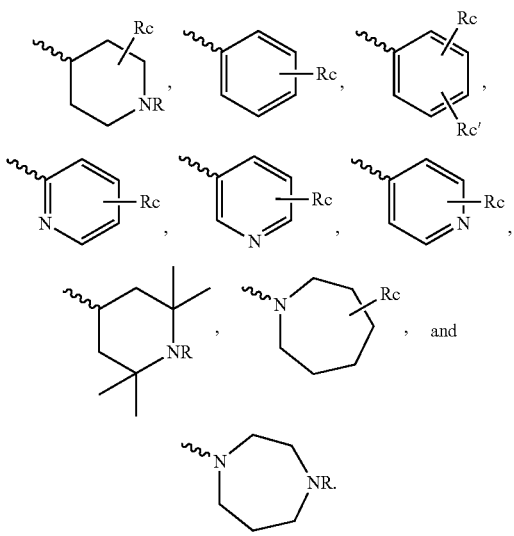

and

R2 is selected from the group consisting of

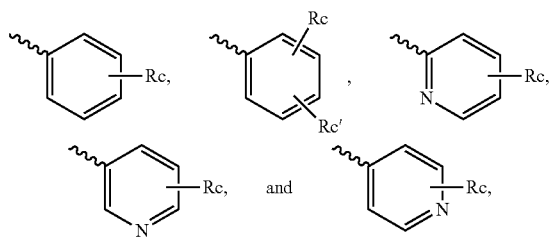

—CH₂C(NH₂)RR',

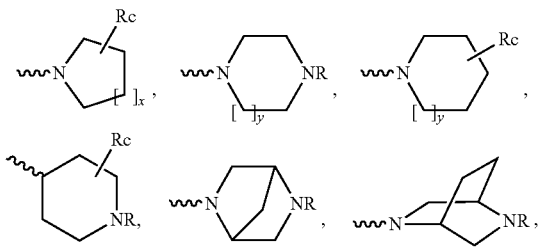

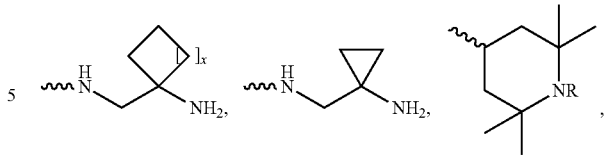

wherein x is 1-3 and y is 1-2.

9. The compound according to claim 1, wherein Rc and Rc' are each independently selected from the group consisting of t-butyl, Cl, trichloromethyl, F, trifluoromethyl, —CH₃, —NH₂, —NO₂, —(CH₂)NRR', —NHC(OR)=O, —NHC(=O)R, —NRR', —OR, —SR, —S(O)R, —S(O)₂R, —COOH, —OCF₃, and —COOR.

10. The compound according to claim 1, wherein R and R' are each independently selected from the group consisting of H, —CH₃, —C₂H₅, —C₂H₄OH, —CH(CH₃)₂, —CH₂CH(CH₃)₂, and C(=O)OC(CH₃)₃.

11. The compound according to claim 1, wherein L and L' are each independently selected from the group consisting of a bond, —CH₂—, —C₂H₄—, —C₃H₆—, —C₄H₈—, —C₅H₁₀—, —CH(CH₃)—, —CH₂CH(CH₃)—, —CH(CH₃)CH₂—, -benzene-, —CH₂-benzene—CH₂—, and -benzene—CH₂—.

12. The compound according to claim 1, wherein Rc is methyl, t-butyl, halo, trihalomethyl, —S(O)R, —S(O)₂R, —OR, —OCF₃, or —COOR.

13. The compound according to claim 1, wherein the Rc and Rc' of the R1 group are each independently halo, trihalomethyl, or —OR.

14. The compound according to claim 1, wherein R is H, methyl, ethyl, —CH₂CH(CH₃)₂, or —(CH₂)OH.

15. A pharmaceutical composition comprising one or more compounds according to claim 1 and a pharmaceutically acceptable excipient.

16. A method of treating or inhibiting an infection caused by a *Plasmodium* spp. in a subject which comprises administering to the subject a therapeutically effective amount of one or more compounds according to claim 1 or a pharmaceutical composition comprising the therapeutically effective amount of the one or more compounds, before, during, and/or after exposure to the *Plasmodium* spp.

17. A method of treating a subject suffering from malaria which comprises administering to the subject a therapeutically effective amount of one or more compounds according to claim 1 or a pharmaceutical composition comprising the therapeutically effective amount of the one or more compounds.

18. A kit comprising one or more doses of one or more compounds according to claim 1 or a pharmaceutical composition comprising the therapeutically effective amount of the one or more compounds packaged together with a supplementary active ingredient, and instructions for administration and use.

* * * * *